United States Patent
Warner et al.

(10) Patent No.: US 11,471,456 B2
(45) Date of Patent: Oct. 18, 2022

(54) FORMULATIONS COMPRISING HETEROCYCLIC PROTEIN KINASE INHIBITORS

(71) Applicant: Sumitomo Pharma Oncology, Inc., Cambridge, MA (US)

(72) Inventors: Steven L. Warner, Sandy, UT (US); Adam Siddiqui-Jain, South Jordan, UT (US); Paul Flynn, Citrus Heights, CA (US)

(73) Assignee: Sumitomo Pharma Oncology, Inc., Cambridge, MA (US)

( * ) Notice: Subject to any disclaimer, the term of this patent is extended or adjusted under 35 U.S.C. 154(b) by 98 days.

(21) Appl. No.: 16/789,342

(22) Filed: Feb. 12, 2020

(65) Prior Publication Data

US 2020/0338076 A1  Oct. 29, 2020

Related U.S. Application Data

(60) Provisional application No. 62/962,833, filed on Jan. 17, 2020, provisional application No. 62/925,153, filed on Oct. 23, 2019, provisional application No. 62/804,556, filed on Feb. 12, 2019.

(51) Int. Cl.
| | | |
|---|---|---|
| *A61K 31/5025* | (2006.01) | |
| *A61P 35/00* | (2006.01) | |
| *C07D 487/04* | (2006.01) | |
| *A61K 9/48* | (2006.01) | |
| *A61K 31/25* | (2006.01) | |
| *A61K 31/519* | (2006.01) | |

(52) U.S. Cl.
CPC ........ *A61K 31/5025* (2013.01); *A61K 9/4816* (2013.01); *A61K 31/25* (2013.01); *A61K 31/519* (2013.01); *A61P 35/00* (2018.01); *C07D 487/04* (2013.01); *C07B 2200/13* (2013.01)

(58) Field of Classification Search
CPC ... A61K 31/5025; C07D 487/04; A61P 35/00; C07B 2200/13
USPC ................ 514/248, 393; 544/236; 548/303.1
See application file for complete search history.

(56) References Cited

U.S. PATENT DOCUMENTS

| | | | |
|---|---|---|---|
| 2,779,780 A | 1/1957 | Middleton | |
| 3,935,230 A | 1/1976 | Yale | |
| 5,418,233 A | 5/1995 | Linz et al. | |
| 5,441,952 A | 8/1995 | Claremon et al. | |
| 5,587,458 A | 12/1996 | King et al. | |
| 5,621,002 A | 4/1997 | Bosslet et al. | |
| 5,747,498 A | 5/1998 | Schnur et al. | |
| 5,792,783 A | 8/1998 | Tang et al. | |
| 5,834,504 A | 11/1998 | Tang et al. | |
| 5,861,510 A | 1/1999 | Piscopio et al. | |
| 5,863,949 A | 1/1999 | Robinson et al. | |
| 5,877,305 A | 3/1999 | Huston et al. | |
| 5,883,113 A | 3/1999 | Tang et al. | |
| 5,886,020 A | 3/1999 | Tang et al. | |
| 6,169,088 B1 | 1/2001 | Matsuno et al. | |
| 6,258,824 B1 | 7/2001 | Yang | |
| 6,284,764 B1 | 9/2001 | Kath et al. | |
| 7,332,582 B2 | 2/2008 | Hardy et al. | |
| 7,488,802 B2 | 2/2009 | Collins et al. | |
| 7,695,715 B2 | 4/2010 | Hardy et al. | |
| 7,723,340 B2 | 5/2010 | Albers et al. | |
| 7,750,000 B2 * | 7/2010 | Prien .................... | C07D 487/04 514/233.2 |
| 7,750,007 B2 | 7/2010 | Bearss et al. | |
| 7,943,743 B2 | 5/2011 | Korman et al. | |
| 7,998,966 B2 | 8/2011 | Bearss et al. | |

(Continued)

FOREIGN PATENT DOCUMENTS

| | | |
|---|---|---|
| CN | 105919955 A | 9/2016 |
| DE | 10 2005 042 742 A1 | 3/2007 |

(Continued)

OTHER PUBLICATIONS

Assignment Abstract of Title of U.S. Pat. No. 10,392,392-B2 (Year: 2022).*

(Continued)

*Primary Examiner* — Joseph R Kosack
*Assistant Examiner* — Sagar Patel
(74) *Attorney, Agent, or Firm* — Honigman LLP; Lucy X. Yang; Jonathan P. O'Brien

(57) ABSTRACT

Provided is a composition comprising a polyglycolized glyceride and a compound having the following structure (I):

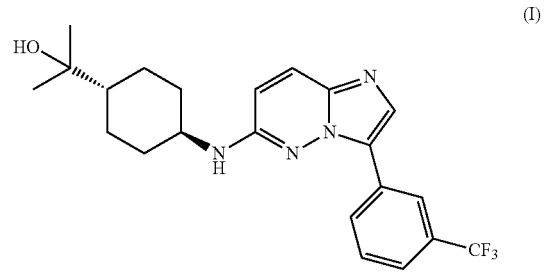

or a pharmaceutically acceptable salt thereof. Also provided are crystalline forms of the compound of structure (I), or a pharmaceutically acceptable salt thereof. Methods of making the same, and methods for using the same in the treatment of cancer, autoimmune, inflammatory and other Pim kinase-associated diseases, disorders or conditions are also disclosed.

23 Claims, 24 Drawing Sheets

(56) References Cited

U.S. PATENT DOCUMENTS

| | | |
|---|---|---|
| 8,008,449 B2 | 8/2011 | Korman et al. |
| 8,168,179 B2 | 5/2012 | Honjo et al. |
| 8,168,794 B2 | 5/2012 | Burger et al. |
| 8,217,149 B2 | 7/2012 | Irving et al. |
| 8,354,509 B2 | 1/2013 | Carven et al. |
| 8,460,927 B2 | 6/2013 | Chen |
| 8,552,154 B2 | 10/2013 | Freeman et al. |
| 8,552,156 B2 | 10/2013 | Takayanagi et al. |
| 8,686,119 B2 | 4/2014 | Rotem-Yehudar et al. |
| 8,691,546 B2 | 4/2014 | Honigberg et al. |
| 8,710,057 B2 | 4/2014 | Bearss et al. |
| 8,735,553 B1 | 5/2014 | Li et al. |
| 8,754,091 B2 | 6/2014 | Honigberg et al. |
| 8,779,108 B2 | 7/2014 | Queva et al. |
| 8,841,418 B2 | 9/2014 | Karsunky et al. |
| 8,907,053 B2 | 12/2014 | Sasikumar et al. |
| 8,927,697 B2 | 1/2015 | Davis et al. |
| 8,957,079 B2 | 2/2015 | Honigberg et al. |
| 8,969,565 B2 | 3/2015 | Bi et al. |
| 8,993,731 B2 | 3/2015 | Tyson |
| 9,096,604 B2 | 8/2015 | Chen et al. |
| 9,102,727 B2 | 8/2015 | Freeman et al. |
| 9,127,012 B2 | 9/2015 | Honigberg et al. |
| 9,133,198 B2 | 9/2015 | Honigberg et al. |
| 9,163,087 B2 | 10/2015 | Kuchroo et al. |
| 9,175,082 B2 | 11/2015 | Zhou et al. |
| 9,205,148 B2 | 12/2015 | Langermann et al. |
| 9,244,059 B2 | 1/2016 | Triebel et al. |
| 9,409,911 B2 | 8/2016 | Honigberg et al. |
| 9,416,132 B2 | 8/2016 | Xu et al. |
| 9,505,839 B2 | 11/2016 | Lonberg et al. |
| 9,801,881 B2 | 10/2017 | Buggy et al. |
| 10,047,093 B2 | 8/2018 | Xu et al. |
| 10,392,392 B2 * | 8/2019 | Xu .................. A61P 35/02 |
| 10,875,864 B2 | 12/2020 | Xu et al. |
| 2005/0227992 A1 | 10/2005 | Hurley et al. |
| 2007/0093490 A1 | 4/2007 | Prien et al. |
| 2008/0214558 A1 | 9/2008 | Vankayalapati et al. |
| 2008/0260754 A1 | 10/2008 | Li et al. |
| 2009/0093475 A1 | 4/2009 | Prien et al. |
| 2010/0227861 A1 | 9/2010 | Bearss et al. |
| 2010/0331350 A1 | 12/2010 | Honigberg et al. |
| 2011/0046127 A1 | 2/2011 | Pevarello et al. |
| 2011/0166122 A1 | 7/2011 | Andrews et al. |
| 2011/0269772 A1 | 11/2011 | Bearss et al. |
| 2012/0053208 A1 | 3/2012 | Li et al. |
| 2012/0058997 A1 | 3/2012 | Xu et al. |
| 2012/0059162 A1 | 3/2012 | Kusakabe et al. |
| 2012/0283276 A1 | 11/2012 | Honigberg et al. |
| 2012/0283277 A1 | 11/2012 | Honigberg et al. |
| 2013/0012525 A1 | 1/2013 | Honigberg et al. |
| 2013/0018034 A1 | 1/2013 | Yao et al. |
| 2013/0035334 A1 | 2/2013 | Honigberg et al. |
| 2013/0197014 A1 | 8/2013 | Chen et al. |
| 2013/0273030 A1 | 10/2013 | Buggy et al. |
| 2013/0310402 A1 | 11/2013 | Buggy et al. |
| 2013/0338172 A1 | 12/2013 | Smyth et al. |
| 2014/0039168 A1 | 2/2014 | Birau et al. |
| 2014/0057907 A1 | 2/2014 | Honigberg et al. |
| 2014/0079690 A1 | 3/2014 | Buggy et al. |
| 2014/0080844 A1 | 3/2014 | Chen et al. |
| 2014/0113919 A1 | 4/2014 | Baffert et al. |
| 2014/0135347 A1 | 5/2014 | Honigberg et al. |
| 2014/0163027 A1 | 6/2014 | Verner et al. |
| 2014/0171453 A1 | 6/2014 | Honigberg et al. |
| 2014/0187564 A1 | 7/2014 | Honigberg et al. |
| 2014/0187565 A1 | 7/2014 | Honigberg et al. |
| 2014/0200227 A1 | 7/2014 | Xue et al. |
| 2014/0212485 A1 | 7/2014 | Honigberg et al. |
| 2014/0243355 A1 | 8/2014 | Honigberg et al. |
| 2014/0329807 A1 * | 11/2014 | Xu .................. A61P 35/00 514/233.2 |
| 2014/0336206 A1 | 11/2014 | Honigberg et al. |
| 2015/0018336 A1 | 1/2015 | Chen et al. |
| 2015/0057265 A1 | 2/2015 | Li et al. |
| 2015/0210769 A1 | 7/2015 | Freeman et al. |
| 2015/0218274 A1 | 8/2015 | Sabatos-Peyton et al. |
| 2015/0259420 A1 | 9/2015 | Triebel et al. |
| 2015/0306112 A1 | 10/2015 | Wu et al. |
| 2016/0108123 A1 | 4/2016 | Freeman et al. |
| 2016/0175293 A1 | 6/2016 | Cao et al. |
| 2020/0102313 A1 | 4/2020 | Xu et al. |
| 2021/0113562 A1 | 4/2021 | Foulks et al. |
| 2021/0113576 A1 | 4/2021 | Anton et al. |

FOREIGN PATENT DOCUMENTS

| | | |
|---|---|---|
| DE | 10 2006 029 447 A1 | 12/2007 |
| EP | 0 606 046 A1 | 7/1994 |
| EP | 0 780 386 A1 | 6/1997 |
| EP | 0 818 442 A2 | 1/1998 |
| EP | 0 931 788 A2 | 7/1999 |
| EP | 1 004 578 A2 | 5/2000 |
| EP | 0 952 148 B1 | 5/2004 |
| EP | 1 900 739 A1 | 3/2008 |
| GB | 9912961.1 | 6/1999 |
| JP | 2009-541242 A | 11/2009 |
| JP | 2010-504933 A | 2/2010 |
| WO | 1990/005719 A1 | 5/1990 |
| WO | 1994/022825 A1 | 10/1994 |
| WO | 1995/019970 A1 | 7/1995 |
| WO | 1995/021613 A1 | 8/1995 |
| WO | 1996/027583 A1 | 9/1996 |
| WO | 1996/031509 A1 | 10/1996 |
| WO | 1996/033172 A1 | 10/1996 |
| WO | 1997/013760 A1 | 4/1997 |
| WO | 1997/019065 A1 | 5/1997 |
| WO | 1997/022596 A1 | 6/1997 |
| WO | 1997/023508 A1 | 7/1997 |
| WO | 1997/032856 A1 | 9/1997 |
| WO | 1998/002434 A1 | 1/1998 |
| WO | 1998/002437 A1 | 1/1998 |
| WO | 1998/002438 A1 | 1/1998 |
| WO | 1998/003516 A1 | 1/1998 |
| WO | 1998/007697 A1 | 2/1998 |
| WO | 1998/014451 A1 | 4/1998 |
| WO | 1998/030566 A1 | 7/1998 |
| WO | 1998/033768 A1 | 8/1998 |
| WO | 1998/034915 A1 | 8/1998 |
| WO | 1998/034918 A1 | 8/1998 |
| WO | 1998/050356 A1 | 11/1998 |
| WO | 1998/054093 A1 | 12/1998 |
| WO | 1999/007675 A1 | 2/1999 |
| WO | 1999/010349 A1 | 3/1999 |
| WO | 1999/016755 A1 | 4/1999 |
| WO | 1999/024440 A1 | 5/1999 |
| WO | 1999/029667 A1 | 6/1999 |
| WO | 1999/035132 A1 | 7/1999 |
| WO | 1999/035146 A1 | 7/1999 |
| WO | 1999/052889 A1 | 10/1999 |
| WO | 1999/052910 A1 | 10/1999 |
| WO | 1999/061422 A1 | 12/1999 |
| WO | 1999/062890 A1 | 12/1999 |
| WO | 2000/035436 A2 | 6/2000 |
| WO | 2001/060814 A2 | 8/2001 |
| WO | 2001/060816 A1 | 8/2001 |
| WO | 2002/006213 A2 | 1/2002 |
| WO | 2002/016351 A1 | 2/2002 |
| WO | 2002/066470 A1 | 8/2002 |
| WO | 2003/076424 A1 | 9/2003 |
| WO | 2003/077914 A1 | 9/2003 |
| WO | 2004/024895 A2 | 3/2004 |
| WO | 2004/046118 A2 | 6/2004 |
| WO | 2004/058769 A2 | 7/2004 |
| WO | 2004/058772 A1 | 7/2004 |
| WO | 2004/072072 A1 | 8/2004 |
| WO | 2004/074244 A2 | 9/2004 |
| WO | 2005/026130 A1 | 3/2005 |
| WO | 2005/037825 A2 | 4/2005 |
| WO | 2006/018718 A2 | 2/2006 |
| WO | 2006/054652 A1 | 5/2006 |
| WO | 2006/076595 A1 | 7/2006 |
| WO | 2006/116733 A2 | 11/2006 |
| WO | 2006/121168 A1 | 11/2006 |

(56) References Cited

FOREIGN PATENT DOCUMENTS

| | | |
|---|---|---|
| WO | 2007/013673 A1 | 2/2007 |
| WO | 2007/014011 A2 | 2/2007 |
| WO | 2007/020888 A1 | 2/2007 |
| WO | 2007/025090 A2 | 3/2007 |
| WO | 2007/025540 A2 | 3/2007 |
| WO | 2007/041712 A1 | 4/2007 |
| WO | 2007/084786 A1 | 7/2007 |
| WO | 2007/087068 A2 | 8/2007 |
| WO | 2007/091152 A1 | 8/2007 |
| WO | 2007/146838 A2 | 12/2007 |
| WO | 2007/147646 A1 | 12/2007 |
| WO | 2007/147647 A1 | 12/2007 |
| WO | 2008/025822 A1 | 3/2008 |
| WO | 2008/030579 A2 | 3/2008 |
| WO | 2008/037477 A1 | 4/2008 |
| WO | 2008/039218 A2 | 4/2008 |
| WO | 2008/052734 A1 | 5/2008 |
| WO | 2008/054827 A2 | 5/2008 |
| WO | 2008/055233 A1 | 5/2008 |
| WO | 2008/058126 A2 | 5/2008 |
| WO | 2008/082839 A2 | 7/2008 |
| WO | 2008/092199 A1 | 8/2008 |
| WO | 2008/106635 A1 | 9/2008 |
| WO | 2008/106692 A1 | 9/2008 |
| WO | 2008/121742 A2 | 10/2008 |
| WO | 2008/128072 A2 | 10/2008 |
| WO | 2008/132601 A1 | 11/2008 |
| WO | 2009/017954 A1 | 2/2009 |
| WO | 2009/036082 A2 | 3/2009 |
| WO | 2009/044273 A2 | 4/2009 |
| WO | 2009/055730 A1 | 4/2009 |
| WO | 2009/060197 A1 | 5/2009 |
| WO | 2009/064486 A2 | 5/2009 |
| WO | 2009/080638 A2 | 7/2009 |
| WO | 2009/085913 A1 | 7/2009 |
| WO | 2009/109576 A1 | 9/2009 |
| WO | 2009/114335 A2 | 9/2009 |
| WO | 2009/143389 A1 | 11/2009 |
| WO | 2009/155565 A1 | 12/2009 |
| WO | 2009/158571 A1 | 12/2009 |
| WO | 2010/000978 A1 | 1/2010 |
| WO | 2010/009342 A2 | 1/2010 |
| WO | 2010/017122 A2 | 2/2010 |
| WO | 2010/019570 A2 | 2/2010 |
| WO | 2010/022076 A1 | 2/2010 |
| WO | 2010/022081 A1 | 2/2010 |
| WO | 2010/026121 A1 | 3/2010 |
| WO | 2010/026122 A1 | 3/2010 |
| WO | 2010/026124 A1 | 3/2010 |
| WO | 2010/027827 A2 | 3/2010 |
| WO | 2010/071885 A1 | 6/2010 |
| WO | 2010/135581 A1 | 11/2010 |
| WO | 2010/148351 A1 | 12/2010 |
| WO | 2011/046964 A2 | 4/2011 |
| WO | 2011/057784 A1 | 5/2011 |
| WO | 2011/066342 A2 | 6/2011 |
| WO | 2011/076519 A1 | 6/2011 |
| WO | 2011/079274 A1 | 6/2011 |
| WO | 2011/101161 A1 | 8/2011 |
| WO | 2011/153514 A2 | 12/2011 |
| WO | 2012/004217 A1 | 1/2012 |
| WO | 2012/032031 A1 | 3/2012 |
| WO | 2012/080990 A1 | 6/2012 |
| WO | 2012/120415 A1 | 9/2012 |
| WO | 2012/129338 A1 | 9/2012 |
| WO | 2012/145493 A1 | 10/2012 |
| WO | 2012/154274 A1 | 11/2012 |
| WO | 2013/010136 A2 | 1/2013 |
| WO | 2013/013188 A1 | 1/2013 |
| WO | 2013/020371 A1 | 2/2013 |
| WO | 2013/059738 A2 | 4/2013 |
| WO | 2013/079174 A1 | 6/2013 |
| WO | 2013/102059 A1 | 7/2013 |
| WO | 2013/116382 A1 | 8/2013 |
| WO | 2013/134219 A1 | 9/2013 |
| WO | 2013/173518 A1 | 11/2013 |
| WO | 2013/175388 A1 | 11/2013 |
| WO | 2013/184572 A1 | 12/2013 |
| WO | 2014/018567 A1 | 1/2014 |
| WO | 2014/022758 A1 | 2/2014 |
| WO | 2014/025128 A1 | 2/2014 |
| WO | 2014/025486 A1 | 2/2014 |
| WO | 2014/026595 A1 | 2/2014 |
| WO | 2014/033530 A1 | 3/2014 |
| WO | 2014/033631 A1 | 3/2014 |
| WO | 2014/052365 A1 | 4/2014 |
| WO | 2014/055897 A2 | 4/2014 |
| WO | 2014/078578 A1 | 5/2014 |
| WO | 2014/100079 A1 | 6/2014 |
| WO | 2014/124230 A2 | 8/2014 |
| WO | 2014/130411 A1 | 8/2014 |
| WO | 2014/130693 A1 | 8/2014 |
| WO | 2014/140180 A1 | 9/2014 |
| WO | 2014/151871 A2 | 9/2014 |
| WO | 2014/159745 A1 | 10/2014 |
| WO | 2014/168975 A1 | 10/2014 |
| WO | 2014/179664 A2 | 11/2014 |
| WO | 2014/194302 A2 | 12/2014 |
| WO | 2014/200216 A1 | 12/2014 |
| WO | 2014/209804 A1 | 12/2014 |
| WO | 2015/002894 A1 | 1/2015 |
| WO | 2015/019320 A1 | 2/2015 |
| WO | 2015/048689 A1 | 4/2015 |
| WO | 2015/061668 A1 | 4/2015 |
| WO | 2015/081083 A1 | 6/2015 |
| WO | 2015/081158 A1 | 6/2015 |
| WO | 2015/085847 A1 | 6/2015 |
| WO | 2015/109124 A2 | 7/2015 |
| WO | 2015/112800 A1 | 7/2015 |
| WO | 2015/112805 A1 | 7/2015 |
| WO | 2015/116539 A1 | 8/2015 |
| WO | 2015/157257 A1 | 10/2015 |
| WO | 2015/181342 A1 | 12/2015 |
| WO | 2015/195163 A1 | 12/2015 |
| WO | 2015/200119 A1 | 12/2015 |
| WO | 2016/000619 A1 | 1/2016 |
| WO | 2016/028672 A1 | 2/2016 |
| WO | 2016/071448 A1 | 5/2016 |
| WO | 2016/092419 A1 | 6/2016 |
| WO | 2016/111947 A2 | 7/2016 |
| WO | 2016/144803 A2 | 9/2016 |
| WO | 2016/161248 A1 | 10/2016 |
| WO | 2016/161270 A1 | 10/2016 |
| WO | 2019/200254 A1 | 10/2019 |
| WO | 2020/167990 A1 | 8/2020 |

OTHER PUBLICATIONS

Wiedmann, T., and A. Naqwi, "Pharmaceutical salts: Theory, use in solid dosage forms and in situ preparation in an aerosol", Asian Journal of Pharmaceutical Sciences II (2016), pp. 722-734. (Year: 2016).*

U.S. Appl. No. 17/090,857, filed Nov. 5, 2020.

U.S. Appl. No. 17/047,383, filed Oct. 13, 2020.

Adam et al., "Targeting PIM Kinases Impairs Survival of Hematopoietic Cells Transformed by Kinase Inhibitor-Sensitive and Kinase Inhibitor-Resistant Forms of Fms-Like Tyrosine Kinase 3 and BCR/ABL," *Cancer Res* 66(7):3828-3835, Apr. 1, 2006.

Alvarado et al., "The PIM kinases in hematological cancers," *Expert Rev. Hematol.* 5(1):81-96, 2012.

Beharry et al., "The Pim protein kinases regulate energy metabolism and cell growth," *PNAS* 108(2):528-533, Jan. 11, 2011.

Blanco-Aparicio et al., "Pim 1 kinase inhibitor ETP-45299 suppresses cellular proliferation and synergizes with PI3K inhibition," *Cancer Letters* 300:145-153, 2011.

Brault et al., "PIM serine/threonine kinases in the pathogenesis and therapy of hematologic malignancies and solid cancers," *Haematologica* 95(6):1004-1015, 2010.

Bradbury et al., "Optimisation of a series of bivalent triazolopyridazine based bromodomain and extraterminal inhibitors: the discovery of (3R)-4-[2-[4-[1-(3-methoxy-[1,2,4]triazolo[4,3-b]pyridazin-6-yl)-4-

(56) References Cited

OTHER PUBLICATIONS piperidyl]phenoxy]ethyl]-1,3-dimethyl-piperazin-2-one (AZD5153)," Journal of Medicinal Chemistry 59(17):7801-7817, 2016. [journal accepted manuscript].
Brunetto et al., "First-in-human, Pharmacokinetic and Pharmacodynamic Phase I Study of Resminostat, an Oral Histone Deacetylase Inhibitor, in Patients with Advanced Solid Tumors," Clin. Cancer Res. 19(19):5494-5504, 2013.
Buggy et al., "CRA-024781: a novel synthetic inhibitor of histone deacetylase enzymes with antitumor activity in vitro and in vivo," Mol. Cancer Ther. 5(5):1309-1317, 2006.
Bullock et al., "Structural Basis of Inhibitor Specificity of the Human Protooncogene Proviral Insertion Site in Moloney Murine Leukemia Virus (PIM-1) Kinase," *J. Med. Chem.* 48:7604-7614, 2005.
CAS Registry No. 1029712-80-8, "Benzamide, 2-fluoro-N-methyl-4-[7-(6-quinolinylmethyl)imidazo[1,2-b][1,2,4]triazin-2-yl]-" Entered STN Jun. 22, 2008, 1 page.
CAS Registry No. 1035555-63-5, "Pyrido[2,3-d]pyrimidine-4,7(3H,8H)-dione, 3-[(2R)-2,3-dihydroxypropyl]-6-fluoro-5-[(2-fluoro-4-iodophenyl)amino]-8-methyl-" Entered STN Jul. 23, 2008, 1 page.
CAS Registry No. 1211441-98-3, "7H-Pyrrolo[2,3-d]pyrimidine-6-carboxamide, 7-cyclopentyl-N,N-dimethyl-2-[[5-(1-piperazinyl)-2-pyridinyl]amino]-" Entered STN Mar. 18, 2010, 1 page.
CAS Registry No. 1236699-92-5 (Deleted CAS Registry No. 1204531-26-9, "4-Pyridinecarboxamide, N-[(2S)-2,3-dihydroxypropyl]-3-[(2-fluoro-4-iodophenyl)amino]-" Entered STN Aug. 19, 2010, 1 page.
CAS Registry No. 1246560-33-7, "2-Pyrimidinamine, 5-[8-methyl-9-(1-methylethyl)-2-(4-morpholinyl)-9H-purin-6-yl]-" Entered STN Oct. 19, 2010, 1 page.
CAS Registry No. 212141-51-0, "1-Phthalazinamine, N-(4-chlorophenyl)-4-(4-pyridinylmethyl)-, hydrochloride (1:2)" Entered STN Oct. 4, 1998, 1 page.
CAS Registry No. 2457-80-9, "Adenosine, 5'-S-methyl-5'-thio-" Entered STN Nov. 16, 1984, 1 page.
CAS Registry No. 332012-40-5, "2-Pyridinecarboxamide, 4-[[[4-[(4-chlorophenyl)amino]furo[2,3-d]pyridazin-7-yl]oxy]methyl]-N-methyl-" Entered STN Apr. 22, 2001, 1 page.
CAS Registry No. 475108-18-0, "Urea, N-[2-chloro-4-[(6,7-dimethoxy-4-quinolinyl)oxy]phenyl]-N'-(5-methyl-3-isoxazolyl)-" Entered STN Dec. 4, 2002, 1 page.
CAS Registry No. 602306-29-6, "2-Pyrimidinamine, 4-[2-methyl-1-(1-methylethyl)-1H-imidazol-5-yl]-N-[4-(methylsulfonyl)phenyl]-" Entered STN Oct. 10, 2003, 1 page.
CAS Registry No. 653592-04-2, "3-Pyrrolidinol, 1-[(4-amino-5H-pyrrolo[3,2-d]pyrimidin-7-yl)methyl]-4-[(methylthio)methyl]-, (3R,4S)-" Entered STN Feb. 24, 2004, 1 page.
CAS Registry No. 656247-17-5 (Deleted STN Registry No. 928326-83-4, "1H-Indole-6-carboxylic acid, 2,3-dihydro-3-[[[4-[methyl[2-(4-methyl-1-piperazinyl)acetyl]amino]phenyl]amino]phenylmethylene]-2-oxo-, methyl ester, (3Z)-" Entered STN Mar. 1, 2004, 1 page.
CAS Registry No. 755037-03-7, "2-Pyridinecarboxamide, 4-[4-[[[[4-chloro-3-(trifluoromethyl)phenyl]amino]carbonyl]amino]-3-fluorophenoxy]-N-methyl-" Entered STN Oct. 1, 2004, 1 page.
CAS Registry No. 837364-57-5, "3-Pyridinemethanamine, 5-[3-(5,7-difluoro-1H-benzimidazol-2-yl)-1H-indazol-5-yl]-N-ethyl-4-methyl-" Entered STN Feb. 25, 2005, 1 page.
CAS Registry No. 844442-38-2, "1H-Pyrazole-3-carboxamide, 4-[(2,6-dichlorobenzoyl)amino]-N-4-piperidinyl-" Entered STN Mar. 8, 2005, 1 page.
CAS Registry No. 857876-30-3, "3-Pyridinecarboxamide, N-(2,3-dihydro-3,3-dimethyl-1H-indol-6-yl)-2-[(4-pyridinylmethyl)amino]-, phosphate (1:2)" Entered STN Aug. 1, 2005, 1 page.
CAS Registry No. 869363-13-3, "Benzoic acid, 4-[[9-chloro-7-(2,6-difluorophenyl)-5H-pyrimido[5,4-d][2]benzazepin-2-yl]amino]-" Entered STN Dec. 6, 2005, 1 page.

CAS Registry No. 877399-52-5, "2-Pyridinamine, 3-[(1R)-1-(2,6-dichloro-3-fluorophenyl)ethoxy]-5-[1-(4-piperidinyl)-1H-pyrazol-4-yl]-" Entered STN Mar. 21, 2006, 1 page.
CAS Registry No. 905281-76-7, "1H-Inden-1-one, 2,3-dihydro-5-[1-(2-hydroxyethyl)-3-(4-pyridinyl)-1H-pyrazol-4-yl]-, oxime" Entered STN Aug. 29, 2006, 1 page.
CAS Registry No. 918504-65-1, "1-Propanesulfonamide, N-[3-[[5-(4-chlorophenyl)-1H-pyrrolo[2,3-b]pyridin-3-yl]carbonyl]-2,4-difluorophenyl]-" Entered STN Jan. 26, 2007, 1 page.
CAS Registry No. 920113-03-7, "4H-1-Benzopyran-4-one, 2-(2-chlorophenyl)-5,7-dihydroxy-8-[(2R,3S)-2-(hydroxymethyl)-1-methyl-3-pyrrolidinyl]-, hydrochloride (1:1)" Entered STN Feb. 8, 2007, 1 page.
CAS Registry No. 927880-90-8, "1H-Benzimidazol-2-amine, 1-methyl-5-[[2-[5-(trifluoromethyl)-1H-imidazol-2-yl]-4-pyridinyl]oxy]-N-[4-(trifluoromethyl)phenyl]-" Entered STN Mar. 22, 2007, 1 page.
CAS Registry No. 934660-93-2 (Deleted CAS Registry No. 1029872-29-4), "Methanone, [3,4-difluoro-2-[(2-fluoro-4-iodophenyl)amino]phenyl][3-hydroxy-3-(2S)-2-piperidinyl-1-azetidinyl]-" Entered STN May 13, 2007, 1 page.
CAS Registry No. 950769-58-1, "Urea, N-[5-(1,1-dimethylethyl)-3-isoxazolyl]-N'-[4-[7-[2-(4-morpholinyl)ethoxy]imidazo[2,1-b]benzothiazol-2-yl]phenyl]-" Entered STN Oct. 16, 2007, 1 page.
CAS Registry No. 951209-71-5, "IRX 2" Entered STN Oct. 23, 2007, 1 page.
CAS Registry No. 958852-01-2, "2,4-Thiazolidinedione, 5-[[4-(4-pyridinyl)-6-quinolinyl]methylene]-, (5Z)-" Entered STN Dec. 19, 2007, 1 page.
Chang et al., "PIM Kinase Inhibitors Downregulate STAT3$^{Tyr705}$ Phosphorylation," *Mol Cancer Ther* 9(9):2478-2487, Sep. 2010.
Chen et al., "Mechanisms of cytotoxicity to Pim kinase inhibitor, SGI-1776, in acute myeloid leukemia," *Blood* 118(3):693-702, Jul. 21, 2011.
Chezal et al., "Efficient synthesis of novel dipyridoimidazoles and pyrido[1',2';1,2]imidazo[4,5-d]pyridazine derivatives," *Tetrahedron* 59:5869-5878, 2003.
Compound Summary for CID 3025986 (CAS Registry No. 345627-80-7), Pub Chem, Created Aug. 8, 2005, 25 pages.
Compound Summary for CID 50992434 (Deprecated CAS Registry No. 1204531-25-8), Pub Chem, Created Apr. 4, 2011, 24 pages.
Daigle et al., "Potent inhibition of DOT1L as treatment of MLL-fusion leukemia," Blood 122(6):1017-1025, 2013.
Dittmann et al., "The Commonly Used PI3-Kinase Probe LY294002 Is an Inhibitor of BET Bromodomains," ACS Chem. Biol. 9(2):495-502, 2014.
Ember et al., "Acetyl-lysine Binding Site of Bromodomain-Containing Protein 4 (BRD4) Interacts with Diverse Kinase Inhibitors," ACS Chem. Biol. 9:1160-1171, 2014.
Fathi et al., "A potential therapeutic target for FLT3-ITD AML: PIM1 Kinase," *Leuk Res.* 36(2):224-231, Feb. 2012.
Filippakopoulos et al., "Selective inhibition of BET bromodomains," Nature 468(7327): 1067-1073, 2010. [author manuscript].
Fish et al., "Identification of a Chemical Probe for Bromo and Extra C-Terminal Bromodomain Inhibition through Optimization of a Fragment-Derived Hit," J. Med. Chem. 55(22):9831-9837, 2012.
Giles et al., "A Phase I Study of Intravenous LBH589, a Novel Cinnamic Hydroxamic Acid Analogue Histone Deacetylase Inhibitor, in Patients with Refractory Hematologic Malignancies," Clin. Cancer Res. 12(15):4628-4635, 2006.
Gottlicher et al., "Valproic acid defines a novel class of HDAC inhibitors inducing differentiation of transformed cells," The EMBO Journal 20(24):6969-6978, 2001.
Guo et al., "Overexpression of Pim-1 in bladder cancer," *Journal of Experimental & Clinical Cancer Research* 29:161, 2010, 7 pages.
Hamid et al., "Safety and Tumor Responses with Lambrolizumab (Anti-PD-1) in Melanoma," the New England Journal of Medicine 369(2):134-144, 2013.
Hackam et al., "Translation of research evidence from animals to humans," *JAMA* 296(14):1731-1732, 2006.
Haslam et al., "Monitoring Minimal Residual Disease in the Myeloproliferative Neoplasms: Current Applications and Emerging Approaches," *BioMed Research International* 2016(7241591):1-6, 2016.

(56) References Cited

OTHER PUBLICATIONS

Jackson et al., "The role of PIM kinases in human and mouse CD4+ T cell activation and inflammatory bowel disease," *Cellular Immunology* 272:200-213, 2012.
Jacobs et al., "Pim-1 Ligand-bound Structures Reveal the Mechanism of Serine/Threonine Kinase Inhibition by LY294002," *Journal of Biological Chemistry* 280(14):13728-13734, 2005.
Jordan, "Tamoxifen: a most unlikely pioneering medicine," *Nat. Rev. Drug Discov.* 2(3):205-213, 2003.
Knutson et al., "Synergistic Anti-Tumor Activity of EZH2 Inhibitors and Glucocorticoid Receptor Agonists in Models of Germinal Center Non-Hodgkin Lymphomas," PLoS One 9(12):e111840, 2014.
Kottaridis et al., "The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials," *Blood* 98(6):1752-1759, Sep. 15, 2001.
Kumar et al., "Crystal Structures of Proto-oncogene Kinase Pim1: A Target of Aberrant Somatic Hypermutations in Diffuse Large Cell Lymphoma," *J. Mol. Biol.* 348:183-193, 2005.
Lima et al., "Bioisosterism: A Useful Strategy for Molecular Modification and Drug Design," *Current Medicinal Chemistry* 12:23-49, 2005.
Lin et al., "A small molecule inhibitor of Pim protein kinases blocks the growth of precursor T-cell lymphoblastic leukemia/lymphoma," *Blood* 115(4):824-833, Jan. 28, 2010.
Magnuson et al., "Why target PIM1 for cancer diagnosis and treatment?" *Future Oncol.* 6(9):1467-1478, 2010, 27 pages.
Maes et al., "Preclinical characterization of a potent and selective inhibitor of the histone demethylase KDM1A for MLL leukemia" Journal of Clinical Oncology 31(15)Suppl.: e13543 (Abstract), 2013.
Matsuno et al., "Potent and Selective Inhibitors of Platelet-Derived Growth Factor Receptor Phosphorylation. 1. Synthesis, Structure-Activity Relationship, and Biological Effects of a New Class of Quinazoline Derivatives," *J. Med. Chem.* 45:3057-3066, 2002.
Mazzacurati et al., "The PIM inhibitor AZD1208 synergizes with ruxolitinib to induce apoptosis of ruxolitinib sensitive and resistant JAK2-V617F-driven cells and inhibit colony formation of primary MPN cells," *Oncotarget* 6(37):40141-40157, 2015.
Millan et al., "Design and Synthesis of Inhaled p38 Inhibitors for the Treatment of Chronic Obstructive Pulmonary Disease," *Journal of Medicinal Chemistry* 54:7797-7814, 2011.
Moros et al., "Synergistic antitumor activity of lenalidomide with the BET bromodomain inhibitor CPI203 in bortezomib-resistant mantle cell lymphoma," Leukemia 28(10):2049-2059, 2014.
Mumenthaler, et al., "Pharmacologic inhibition of Pim kinases alters prostate cancer cell growth and resensitizes chemoresistant cells to taxanes," *Mol. Cancer Ther.* 8(10):2282-2893, 2009.
Nawijn et al., "For better or for worse: the role of Pim oncogenes in tumorigenesis," *Nature Reviews Cancer* 11:23-34, Jan. 2011.
Noel et al., "Abstract C244: Development of the BET bromodomain inhibitor OTX015," Mol. Cancer Ther. 12(11 Suppl.):C244, 2013.
Paquin et al., "Design and synthesis of 4-[(s-triazin-2-ylamino)methyl]-N-(2-aminophenyl)-benzamides and their analogues as a novel class of histone deacetylase inhibitors," Bioorg. Med. Chem. Lett. 18(3):1067-1071, 2008.
Philippakopoulos et al., "2C3I: Crystal Structure of Human PIM1 in Complex with Imidazopyridazin I," Protein Data Bank, URL = https://www.rcsb.org/structure/2c3i, download date Jul. 28, 2020, 6 pages.
Picaud et al., "PFI-1, a Highly Selective Protein Interaction Inhibitor, Targeting BET Bromodomains," Cancer Res. 73(11):3336-3346, 2013.
Picaud et al., "RVX-208, an inhibitor of BET transcriptional regulators with selectivity for the second bromodomain," PNAS 110(49):19754-19759, 2013.

Piekarz et al., "Inhibitor of histone deacetylation, depsipeptide (FR901228), in the treatment of peripheral and cutaneous T-cell lymphoma: a case report," Blood 98(9):2865-2868, 2001.
Pierre et al., "Novel potent dual inhibitors of CK2 and Pim kinases with antiproliferative activity against cancer cells," *Bioorganic & Medicinal Chemistry Letters* 22:3327-3331, 2012.
Plumb et al., "Pharmacodynamic Response and Inhibition of Growth of Human Tumor Xenografts by the Novel Histone Deacetylase Inhibitor PXD101," Mol. Cancer Ther. 2:721-728, 2003.
Qian et al., "Hit to Lead Account of the Discovery of a New Class of Inhibitors of Pim Kinases and Crystallographic Studies Revealing an Unusual Kinase Binding Mode," *Journal of Medicinal Chemistry* 52(7):1814-1827, 2009.
Qian et al., "Structural Basis of Constitutive Activity and a Unique Nucleotide Binding Mode of Human Pim-1 Kinase," *Journal of Biological Chemistry* 280(7):6130-6137, Feb. 18, 2005.
Raboisson et al., "Efficient preparation of imidazo[1,2-b]pyridazines under Swemrn oxidative conditions," *Tetrahedron Letters* 44:2919-2921, 2003.
Ravandi et al., "Evaluating measurable residual disease in acute myeloid leukemia," Blood Advances 2(11):1356-1366, 2018.
Ren et al., "Spatially constrained tandem bromodomain inhibition bolsters sustained repression of BRD4 transcriptional activity for TNBC cell growth," Proc. Natl. Acad. Sci. USA 115(31): 7949-7954, 2018.
Richon et al., "A class of hybrid polar inducers of transformed cell differentiation inhibits histone deacetylases," Proc. Natl. Acad. Sci. USA 95:3003-3007, 1998.
Robertson et al., "A Comparison of the Requirements for Antitumour Activity and Antibacteriophage Lambda Activity for a Series of Non-intercalative DNA-binding Agents," *Eur J Cancer Clin Oncol* 18(3):271-279, 1982.
Rosenblatt et al., "PD-1 blockade by CT-011, anti PD-1 antibody, enhances ex-vivo T cell responses to autologous dendritic/myeloma fusion vaccine," J. Immunother. 34(5):409-418, 2011.
Saito et al., "A synthetic inhibitor of histone deacetylase, MS-27-275, with marked in vivo antitumor activity against human tumors," Proc. Natl. Acad. Sci. USA 96(8):4592-4597, 1999.
Schneider et al., "Inhibition of Delta-induced Notch signaling using fucose analogs," Nat. Chem. Biol, 14(1):65-71, 2018. [author manuscript].
Schuurhuis et al., "Minimal/measureable residual disease in AML: a consensus document from the European LeukemiaNet MRD Working Party," Blood 131(12):1275-1291, 2018.
Seal et al., "Identification of a novel series of BET family bromodomain inhibitors: Binding mode and profile of I-BET151 (GSK1210151A)," Bioorganic & Medicinal Chemistry Letters 22:2968-2972, 2012.
Singh et al., "Chemotherapy of Filariasis—On the Search of New Agents Effective on the Reproductive System of Female Adult Worms," *Z. Naturforsch.* 45c:1210-1214, 1990.
Tamburini et al., "Protein synthesis is resistant to rapamycin and constitutes a promising therapeutic target in acute myeloid leukemia," Blood 114(8):1618-1627, Aug. 20, 2009.
Tefferi et al., "Revised response criteria for myelofibrosis: International Working Group-Myeloproliferative Neoplasms Research and Treatment (IWG-MRT) and European LeukemiaNet (ELN) consensus report," Blood 122(8):1395-1398, 2013.
Warner et al., "Identification of a lead small-molecule inhibitor of the Aurora kinases using a structure-assisted, fragment-based approach," Mol Cancer Ther 5(7):1764-1773, Jul. 2006.
Williamson et al., "Structure-guided design of pyrazolo[1,5-α]pyrimidines as inhibitors of human cyclin-dependent kinase 2," *Bioorganic & Medicinal Chemistry Letters* 15:863-867, 2005.
Yu et al., "Catalytic site remodeling of the DOT1L methyltransferase by selective inhibitors," Nat. Comm. 3:1288, 2012.
Xia et al., "Synthesis and Evaluation of Novel Inhibitors of Pim-1 and Pim-2 Protein Kinases," *J. Med. Chem.* 52:74-86, 2009.
Zhao et al., "The Making of I-BET762, a BET Bromodomain Inhibitor Now in Clinical Development," J. Med. Chem, 56:7498-7500, 2013.
Allred, C.A., et al., "1345-Pharmacodynamic Biomarkers for PIM Inhibition with TP-3654 in Patients with Solid Tumors", AACR

(56) References Cited

OTHER PUBLICATIONS

Annual Meeting 2021—Virtual—Poster presented during Session PO.ET06.04—Novel Targets and Pathways on Apr. 10, 2021.

Dutta, A., et al., "Genetic Ablation of Pim 1 or Pharmacologic Inhibition with TP-3654 Ameliorates Myelofibrosis in Murine Models", Leukemia, published online URL: https://doi.org/10.1038/s41375-02-01464-2, 14 pages (2021).

Dutta, A., et al., "Abstract 1874: The PIM Kinase Inhibitor TP-3654 Demonstrates Efficacy in a Murine Model of Myelofibrosis", Cancer Research, 78(Suppl 13):4 pages (2018).

Foulks, J.M., et al., "A Small-Molecule Inhibitor of PIM Kinases as a Potential Treatment for Urothelial Carcinomas", Neoplasia, 16(5):403-412 (2014).

Garrido-Laguna, I., et al., "Abstract 3586: A Phase I, First-in-human, Dose-escalation, Safety, Pharmacokinetic, and Phannacodynamic Study of Oral TP-3654, a PIM Kinase Inhibitor, in Patients with Advanced Solid Tumors", as presented during the 2020 ASCO Annual Meeting, Journal of Clinical Oncoclogy, 38(Supplement 15):3586.

Garrido-Laguna, I., et al., "Abstract P223: A Phase I, First-in-human, Open-label, Dose-escalation, Safety, Pharmacokinetic, and Pharmacodynamic Study of Oral TP-3654 Administered Daily for 28 Days to Patients with Advanced Solid Tumors", as presented during the AACR-NCI-EORTC Virtual International Conference on Molecular Targets and Cancer Therapeutis, Oct. 7-10, 2021, Molecular Cancer Therapeutics, 21(Supplement 12):4 pages.

Garrido-Laguna, I., et al., "A Phase I, First-in-Human, Open-Label, Dose Escalation, Safety, Pharmacokinetic, and Pharmacodynamic Study of Oral TP-3654 Administered Daily for 28 Days to Patients with Advanced Solid Tumors", American Society of Clinical Oncology—56th Annual Meeting. 2020; poster, 1 page.

Lebedinsky, C., et al., "A phase 1 study of TP-3654, an orally-delivered PIM kinase inhibitor, in patients with intermediate-2 or high-risk primary or secondary myelofibrosis", Blood, 136 (Supplement 1):3-4 (2020).

Lebedinsky, C., et al., "Abstract 1251: A Phase 1 Study of TP-3654, an Orally-delivered PIM kinase inhibitor, in Patients with Iintermediate-2 or High-risk Primary or Secondary Myelofibrosis", Presented during Session 634, Myeloproliferative Syndromes at the 62nd ASH Annual Meeting and Exposition Dec. 5-8, 2020, 2 pages.

Lebedinsky, C., et al., "Abstract PB1712: A Phase 1 Study of TP-3654, an Orally-delivered PIM kinase inhibitor, in Patients with Iintermediate-2 or High-risk Primary or Secondary Myelofibrosis", Presented during Myeloproliferative Neoplasm Session of the 2021 European Hematology Association 2021 virtual meeting, 2 pages.

Nath, D., et al., "The PIM Kinase Inhibitor in Combination with Ruxolitmib Exhibits Marked Improvement of Myelofibrosis in Murine Models", as presented during session 635 Myeloproliferative Syndromes: Basic Science: Identification of Novel Therapeutic Targest on Nov. 29, 2018 of the 60th Annual ASH Meeting, Blood, 132:Supplement 1 54 (4 pages) (2018).

Theisen et al., "Reversible inhibition of lysine specific demethylase 1 is a novel anti-tumor strategy for poorly differentiated endometrial carcinoma," BMC Cancer 14(752):1-12, 2014.

Venugopal et al., "A Phase I Study of Quisinostat (JNJ-26481585), an Oral Hydroxamate Histone Deacetylase Inhibitor with Evidence of Target Modulation and Antitumor Activity, in Patients with Advanced Solid Tumors," Clin. Cancer Res. 19(15):4262-4272, 2013.

Warner et al., "Identification of a lead small-molecule inhibitor of the Aurora kinases using a stiucture-assisted, fragment-based approach," *Mol Cancer Ther* 5(7):1764-1773, Jul. 2006.

\* cited by examiner

FORMULATIONS COMPRISING HETEROCYCLIC PROTEIN KINASE INHIBITORS

RELATED APPLICATIONS

This application claims the benefit of U.S. Provisional Application No. 62/962,833 filed on Jan. 17, 2020, U.S. Provisional Application No. 62/925,153, filed on Oct. 23, 2019, and U.S. Provisional Application No. 62/804,556, filed on Feb. 12, 2019. The entire teachings of the above applications are incorporated herein by reference.

FIELD

The present disclosure relates to compositions comprising compounds, and their use for the treatment of Pim-kinase mediated diseases or disorders.

BACKGROUND

Proviral insertion in murine (Pim) kinases (e.g., Pim-1 kinase, Pim-2 kinase, Pim-3 kinase) are a family of oncogenic serine/threonine kinases. Expression is seen in prostate and oral epithelial cells. Pim-1 kinase is believed to be involved in the initiation or progression of malignant transformation leading to malignancies including Burkitt's lymphoma, prostate cancer, oral cancer and diffuse large cell lymphomas, among others. Pim kinases also play a role in immune regulation. For example, enhanced Pim kinase expression has been observed in a variety of inflammatory states. Pim-2 kinase is also implicated in cytokine induced T-cell growth and survival.

SUMMARY

Various non-limiting aspects and embodiments of the invention are described below.

There remains a need for new treatments and therapies for proviral insertion in murine (Pim)-kinase related disorders or diseases. The present disclosure provides crystalline forms and pharmaceutical compositions that fulfill this need. The present disclosure further provides methods of treating disorders or diseases, comprising administering to a subject in need thereof a therapeutically effective amount of a crystalline form and/or composition of the present disclosure. Accordingly, certain embodiments of the disclosure provide a composition comprising a polyglycolized glyceride; and a compound having the following structure (I):

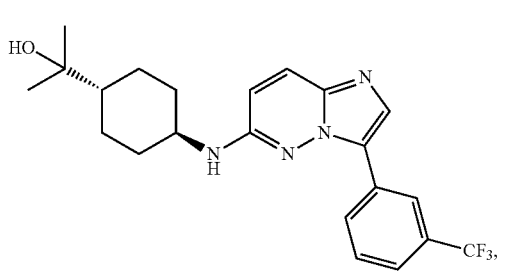

(I)

or a pharmaceutically acceptable salt thereof. Certain embodiments provide a composition comprising crystalline Form I of the hydrochloride salt of the compound of structure (I) and a pharmaceutically acceptable carrier.

Certain embodiments provide a unit dose form comprising a composition, the composition comprising a polyglycolized glyceride in an amount of about 560 mg to about 600 mg; and a compound of structure (I), or a pharmaceutically acceptable salt thereof, in an amount of about 115 mg to about 125 mg, as determined using the molecular weight of the compound of structure (I) as a free base.

Certain embodiments provide a capsule comprising a composition comprising GELUCIRE® 44/14 in an amount of about 589 mg, and a hydrochloride salt of a compound having the following structure (I) in an amount of about 130 mg, as determined using the molecular weight of the compound of structure (I) as the hydrochloride salt.

Certain embodiments provide a crystalline form of the hydrochloric acid salt of the compound of structure (I).

Certain embodiments provide crystalline forms and/or compositions that have utility over a broad range of therapeutic applications, and may be used to treat diseases, such as cancer, autoimmune diseases and various inflammatory diseases or disorders, that are mediated at least in part by protein kinase activity. Accordingly, additional embodiments of the disclosure provide methods for treating or preventing cancer (e.g., prostate cancer, colorectal cancer, or myelofibrosis), a protein kinase-mediated disease, a myeloproliferative neoplasm, or a fibrotic disease or disorder, the method comprising administering to a subject in need thereof a therapeutically effective amount of a composition or unit dose disclosed herein.

Some embodiments provide a method for treating intermediate-2 or high-risk, primary or secondary myelofibrosis in a subject in need thereof, the method comprising administering to the subject a therapeutically effective amount of a crystalline form and/or composition described herein, wherein the subject has previously received ruxolitinib, or a pharmaceutically acceptable salt thereof, or fedratinib, or a pharmaceutically acceptable salt thereof; or is ineligible to receive ruxolitinib, or a pharmaceutically acceptable salt thereof, or fedratinib, or a pharmaceutically acceptable salt thereof.

Also provided are crystalline forms and/or compositions (e.g., pharmaceutical compositions) for use in treating a disorder or disease described herein, wherein the crystalline form and/or composition is as described herein. Also provided are uses of a crystalline form and/or composition described herein for the manufacture of a medicament for the treatment of a disorder or disease described herein.

One embodiment is a method for preparing a compound of structure (I), or a pharmaceutically acceptable salt thereof, the method comprising:

(i) reacting a compound having the following structure:

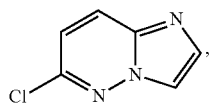

or a salt thereof, with a compound having the following structure:

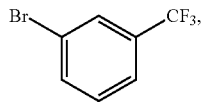

to obtain a compound having the following structure:

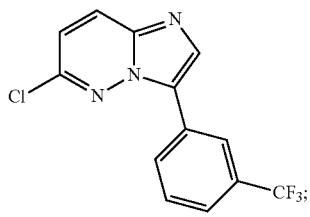 [SMILES: FC(F)(F)c1cccc(-c2cnc3ccc(Cl)nn23)c1]

and
(ii) reacting the compound having the following structure:

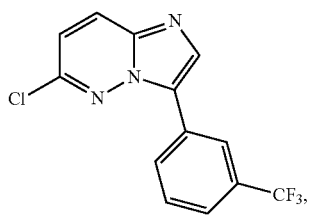 [SMILES: FC(F)(F)c1cccc(-c2cnc3ccc(Cl)nn23)c1]

or a salt thereof, with a compound having the following structure:

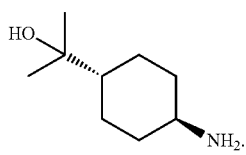

One embodiment is a method for preparing a compound of structure (I), or a pharmaceutically acceptable salt thereof, the method comprising:
reacting a compound having the following structure:

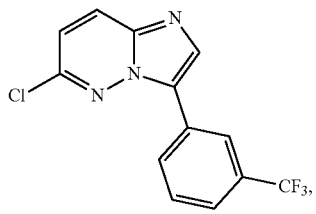 [SMILES: FC(F)(F)c1cccc(-c2cnc3ccc(Cl)nn23)c1]

or a salt thereof, with a compound having the following structure:

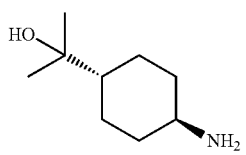

in the presence of a palladium catalyst, an alkoxide and a solvent.

One embodiment is a method for preparing a compound of structure (I), or a pharmaceutically acceptable salt thereof, the method comprising:

reacting a compound having the following structure:

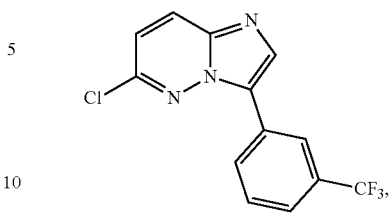

or a salt thereof, with a compound having the following structure:

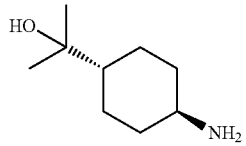

in the presence of potassium fluoride.

One embodiment provides a method for purifying a compound of structure (I), or a pharmaceutically acceptable salt thereof, the method comprising contacting a composition comprising the compound with a metal scavenging reagent.

One embodiment provides a method for preparing a compound of structure (I), or a pharmaceutically acceptable salt thereof, the method comprising:

reacting a compound having the following structure:

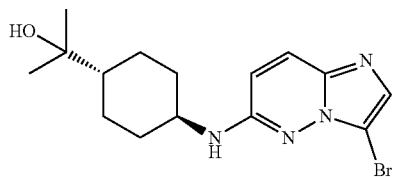 [SMILES: CC(C)(O)[C@H]1CC[C@H](Nc2ccc3ncc(Br)n3n2)CC1]

or a salt thereof, with a compound having the following structure:

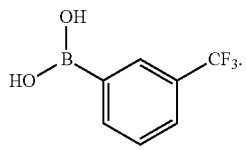 [SMILES: OB(O)c1cccc(C(F)(F)F)c1]

One embodiment provides a process for preparing a crystalline form described herein, comprising precipitating said crystalline form from a solution or suspension comprising the hydrochloric acid salt of 2-((1R,4R)-4-((3-(3-(trifluoromethyl)phenyl) imidazo[1,2-b]pyridazin-6-yl) amino)cyclohexyl)propan-2-ol and a non-aqueous medium.

DETAILED DESCRIPTION

Figure 1:
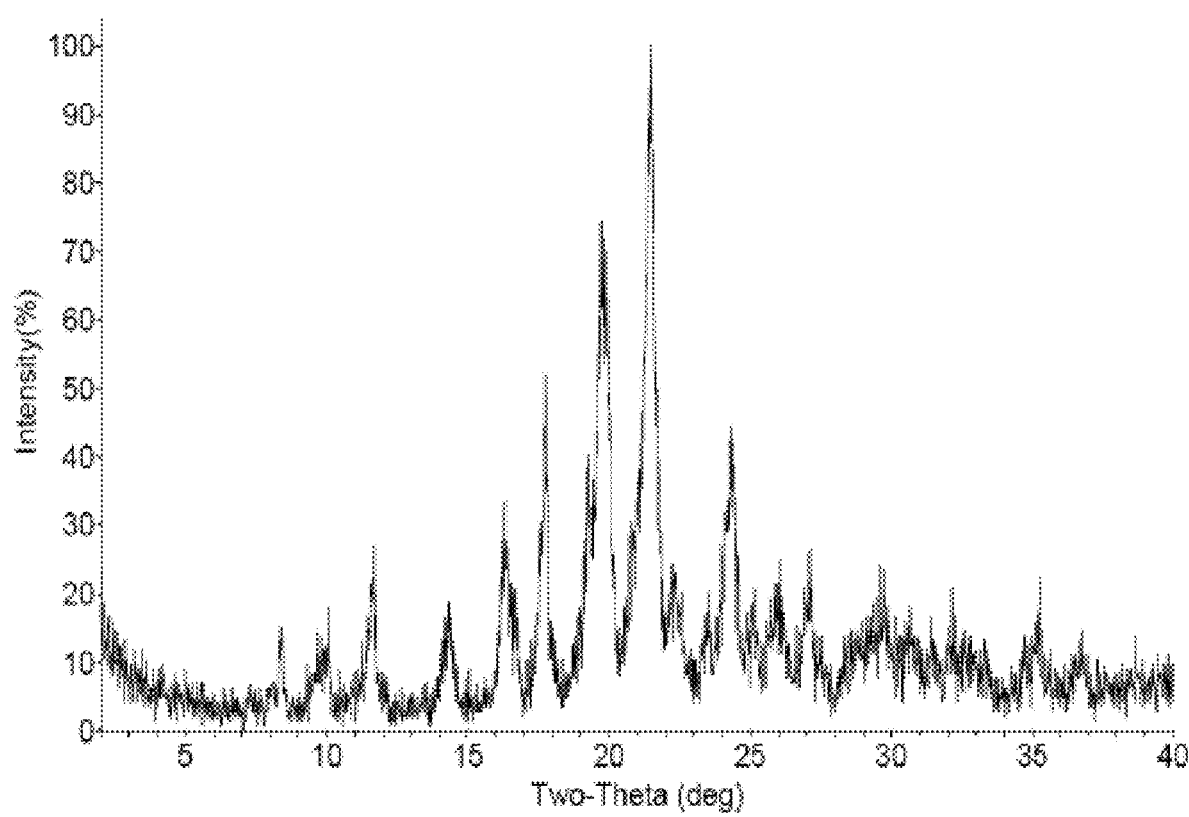
FIG. 1 is a graphical representation of the X-ray power diffraction pattern of crystalline Form I.

Various (enumerated) embodiments of the disclosure are described herein. It will be recognized that features specified in each embodiment may be combined with other specified features to provide further embodiments of the present disclosure.

Embodiment 1

A composition comprising:
a polyglycolized glyceride; and
a compound having the following structure (I):

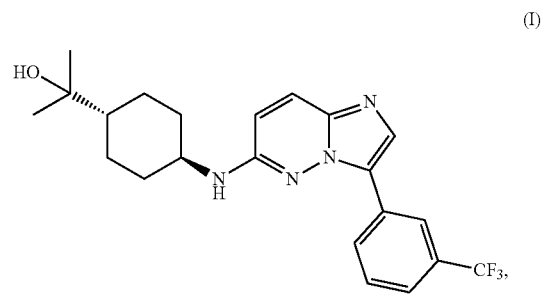 [SMILES: CC(C)(O)[C@H]1CC[C@H](Nc2ccc3ncc(-c4cccc(C(F)(F)F)c4)n3n2)CC1]

or a pharmaceutically acceptable salt thereof.

Embodiment 2

The composition of Embodiment 1, wherein the polyglycolized glyceride has a melting point ranging from about 30° C. to about 50° C.

Embodiment 3

The composition of any of the preceding Embodiments, wherein the polyglycolized glyceride has a melting point ranging from about 37° C. to about 48° C.

Embodiment 4

The composition of any of the preceding Embodiments, wherein the polyglycolized glyceride has a melting point of about 44° C.

Embodiment 5

The composition of any of the preceding Embodiments, wherein the polyglycolized glyceride has a hydrophile/lipophile balance (HLB) value ranging from about 8 to about 18.

Embodiment 6

The composition of any of the preceding Embodiments, wherein the polyglycolized glyceride has hydrophile/lipophile balance value ranging from about 10 to about 16.

Embodiment 7

The composition of any of the preceding Embodiments, wherein the polyglycolized glyceride has hydrophile/lipophile balance value of about 14.

Embodiment 8

The composition of any of the preceding Embodiments, wherein the composition further comprises a formulating agent, the formulating agent comprising polysorbate 20, polysorbate 60, polysorbate 80, glyceryl monocaprylate, glyceryl monocaprate, glyceryl monooleate, glyceryl dibehenate, propylene glycol dilaurate, propylene glycol monocaprylate, propylene glycol monolaurate, or combinations thereof.

Embodiment 9

The composition of Embodiment 8, wherein the formulating agent is polysorbate 20.

Embodiment 10

The composition of Embodiment 8, wherein the formulating agent is glyceryl monocaprylate.

Embodiment 11

The composition of any one of Embodiments 8-10, wherein the polyglycolized glyceride and formulating agent are present in a weight ratio ranging from 2:1 to 1:1.

Embodiment 12

The composition of any one of Embodiments 1-7, wherein the composition consists essentially of the compound and the polyglycolized glyceride.

Embodiment 13

The composition of any one of the preceding Embodiments, wherein the composition is a suspension.

Embodiment 14

The composition of any one of the preceding Embodiments, wherein the polyglycolized glyceride is GELUCIRE® 44/14.

Embodiment 15

The composition of any one of the preceding Embodiments, wherein the compound of structure (I) is a hydrochloride salt.

Embodiment 16

The composition of any one of the preceding Embodiments, wherein the composition comprises from about 100 mg to about 300 mg of the compound of structure (I) as determined using the molecular weight of the compound as the free base.

Embodiment 17

The composition of any one of the preceding Embodiments, wherein the composition comprises from about 100 mg to about 150 mg of the compound of structure (I) as determined using the molecular weight of the compound as the free base.

Embodiment 18

The composition of any one of the preceding Embodiments, wherein the composition comprises from about 115 mg to about 125 mg of the compound of structure (I) as determined using the molecular weight of the compound as the free base.

Embodiment 19

The composition of any one of the preceding Embodiments, wherein the composition comprises about 120 mg of the compound of structure (I) as determined using the molecular weight of the compound as the free base.

Embodiment 20

The composition of any one of Embodiments 1-16, wherein the composition comprises from about 160 mg to about 200 mg of the compound of structure (I) as determined using the molecular weight of the compound as the free base.

Embodiment 21

The composition of Embodiment 20, wherein the composition comprises from about 175 mg to about 185 mg of the compound of structure (I) as determined using the molecular weight of the compound as the free base.

Embodiment 22

The composition of Embodiment 21, wherein the composition comprises about 180 mg of the compound of structure (I) as determined using the molecular weight of the compound as the free base.

Embodiment 23

The composition of any one of Embodiments 1-16, wherein the composition comprises from about 220 mg to about 260 mg of the compound of structure (I) as determined using the molecular weight of the compound as the free base.

Embodiment 24

The composition of Embodiment 23, wherein the composition comprises from about 230 mg to about 250 mg of the compound of structure (I) as determined using the molecular weight of the compound as the free base.

Embodiment 25

The composition of Embodiment 24, wherein the composition comprises about 240 mg of the compound of structure (I) as determined using the molecular weight of the compound as the free base.

Embodiment 26

The composition of Embodiment 15, wherein the composition comprises from about 100 mg to about 160 mg of the compound of structure (I) as determined using the molecular weight of the compound as a hydrochloride salt.

Embodiment 27

The composition of Embodiment 15, wherein the composition comprises from about 120 mg to about 140 mg of the compound of structure (I) as determined using the molecular weight of the compound as a hydrochloride salt.

Embodiment 28

The composition of Embodiment 15, wherein the composition comprises about 130.44 mg of the compound of structure (I) as determined using the molecular weight of the compound as a hydrochloride salt.

Embodiment 29

The composition of any one of the preceding Embodiments, wherein the composition comprises the compound of structure (I) in a concentration ranging from about 10 wt % to about 40 wt % as determined using the molecular weight of the compound as a hydrochloride salt.

Embodiment 30

The composition of any one of the preceding Embodiments, wherein the composition comprises the compound of structure (I) in a concentration ranging from about 14 wt % to about 22 wt % as determined using the molecular weight of the compound as a hydrochloride salt.

Embodiment 31

The composition of any one of the preceding Embodiments, wherein the composition comprises the compound of structure (I) in a concentration ranging from about 18 wt % to about 19 wt % as determined using the molecular weight of the compound as a hydrochloride salt.

Embodiment 32

The composition of any one of the preceding Embodiments, wherein the composition comprises the compound in a concentration of about 18.12 wt % as determined using the molecular weight of the compound as a hydrochloride salt.

Embodiment 33

The composition of any one of the preceding Embodiments, wherein the composition comprises the compound in a concentration of about 18.38 wt % as determined using the molecular weight of the compound as a hydrochloride salt.

Embodiment 34

The composition of any one of Embodiments 1-25, wherein the composition comprises the compound of structure (I) in a concentration ranging from about 15 wt % to about 35 wt % as determined using the molecular weight of the compound as a hydrochloride salt.

Embodiment 35

The composition of Embodiment 34, wherein the composition comprises the compound of structure (I) in a concentration ranging from about 20 wt % to about 30 wt % as determined using the molecular weight of the compound as a hydrochloride salt.

Embodiment 36

The composition of Embodiment 35, wherein the composition comprises the compound in a concentration of about 25 wt % as determined using the molecular weight of the compound as a hydrochloride salt.

Embodiment 37

The composition of any one of Embodiments 1-25, wherein the composition comprises the compound of structure (I) in a concentration ranging from about 23.3 wt % to about 43.3 wt % as determined using the molecular weight of the compound as a hydrochloride salt.

Embodiment 38

The composition of Embodiment 37, wherein the composition comprises the compound of structure (I) in a concentration ranging from about 28.3 wt % to about 38.3 wt % as determined using the molecular weight of the compound as a hydrochloride salt.

Embodiment 39

The composition of Embodiment 38, wherein the composition comprises the compound in a concentration of about 33.3 wt % as determined using the molecular weight of the compound as a hydrochloride salt.

Embodiment 40

The composition of any of the preceding Embodiments, wherein the composition comprises the polyglycolized glyceride in an amount ranging from about 500 mg to about 700 mg.

Embodiment 41

The composition of any of the preceding Embodiments, wherein the composition comprises the polyglycolized glyceride in an amount ranging from about 550 mg to about 650 mg.

Embodiment 42

The composition of any of the preceding Embodiments, wherein the composition comprises the polyglycolized glyceride in an amount ranging from about 560 mg to about 600 mg.

Embodiment 43

The composition of any of the preceding Embodiments, wherein the composition comprises the polyglycolized glyceride in an amount ranging from about 585 mg to about 590 mg.

Embodiment 44

The composition of any of the preceding Embodiments, wherein the composition comprises the polyglycolized glyceride in an amount of about 587.7 mg.

Embodiment 45

The composition of any of the preceding Embodiments, wherein the composition comprises the polyglycolized glyceride in an amount of about 589.56 mg.

Embodiment 46

The composition of any one of the preceding Embodiments, wherein the composition comprises the polyglycolized glyceride in a concentration ranging from about 50 wt % to about 90 wt %.

Embodiment 47

The composition of any one of the preceding Embodiments, wherein the composition comprises the polyglycolized glyceride in a concentration ranging from about 75 wt % to about 90 wt %.

Embodiment 48

The composition of Embodiment 47, wherein the composition comprises the polyglycolized glyceride in a concentration ranging from about 78 wt % to about 84 wt %.

Embodiment 49

The composition of Embodiment 48, wherein the composition comprises the polyglycolized glyceride at a concentration of about 81 wt % to about 82 wt %.

Embodiment 50

The composition of Embodiment 49, wherein the composition comprises the polyglycolized glyceride at a concentration of about 81.62 wt %.

Embodiment 51

The composition of Embodiment 49, wherein the composition comprises the polyglycolized glyceride at a concentration of about 81.88 wt %.

Embodiment 52

The composition of any of the preceding Embodiments, wherein the composition comprises the polyglycolized glyceride in a concentration ranging from about 65 wt % to about 85 wt %.

Embodiment 53

The composition of Embodiment 52, wherein the composition comprises the polyglycolized glyceride in a concentration ranging from about 70 wt % to about 80 wt %.

Embodiment 54

The composition of Embodiment 53, wherein the composition comprises the polyglycolized glyceride at a concentration of about 75 wt %.

Embodiment 55

The composition of any one of the preceding Embodiments, wherein the composition comprises the polyglycolized glyceride in a concentration ranging from about 56.7 wt % to about 76.7 wt %.

Embodiment 56

The composition of Embodiment 55, wherein the composition comprises the polyglycolized glyceride in a concentration ranging from about 61.7 wt % to about 71.7 wt %.

Embodiment 57

The composition of Embodiment 56, wherein the composition comprises the polyglycolized glyceride at a concentration of about 66.7 wt %.

Embodiment 58

The composition of any one of the preceding Embodiments, wherein the composition is in the form of a capsule for oral administration.

Embodiment 59

The composition of any one of the preceding Embodiments, wherein the composition comprises the compound of structure (I) and the polyglycolized glyceride at a weight ratio ranging from about 1:1 to about 1:10 as determined using the molecular weight of the compound as a free base.

Embodiment 60

The composition of any one of the preceding Embodiments, wherein the composition comprises the compound of structure (I) and the polyglycolized glyceride at a weight ratio ranging from about 1:4 to about 1:6 as determined using the molecular weight of the compound as a free base.

Embodiment 61

The composition of any one of the preceding Embodiments, wherein the composition comprises the compound of structure (I) and the polyglycolized glyceride at a weight ratio of about 1:5 as determined using the molecular weight of the compound as a free base.

Embodiment 62

The composition of any one of the preceding Embodiments, wherein the composition comprises the compound of structure (I) and the polyglycolized glyceride at a weight ratio of about 1:4.9 as determined using the molecular weight of the compound as a free base.

Embodiment 63

The composition of any one of the preceding Embodiments, wherein the composition comprises the compound of structure (I) and the polyglycolized glyceride at a weight ratio ranging from about 1:4 to about 1:6 as determined using the molecular weight of the compound as a hydrochloride salt.

Embodiment 64

The composition of any one of the preceding Embodiments, wherein the composition comprises the compound of structure (I) and the polyglycolized glyceride at a weight ratio of about 1:4.5 as determined using the molecular weight of the compound as a hydrochloride salt.

Embodiment 65

The composition of any one of Embodiments 1-59, wherein the composition comprises the compound of structure (I) and the polyglycolized glyceride at a weight ratio ranging from about 1:1.6 to about 1:3.6 as determined using the molecular weight of the compound as a free base.

Embodiment 66

The composition of Embodiment 65, wherein the composition comprises the compound of structure (I) and the polyglycolized glyceride at a weight ratio ranging from about 1:2.1 to about 1:3.1 as determined using the molecular weight of the compound as a free base.

Embodiment 67

The composition of Embodiment 66, wherein the composition comprises the compound of structure (I) and the polyglycolized glyceride at a weight ratio of about 1:2.6 as determined using the molecular weight of the compound as a free base.

Embodiment 68

The composition of any one of Embodiments 1-59, wherein the composition comprises the compound of structure (I) and the polyglycolized glyceride at a weight ratio ranging from about 1:1 to about 1:2.5 as determined using the molecular weight of the compound as a free base.

Embodiment 69

The composition of Embodiment 68, wherein the composition comprises the compound of structure (I) and the polyglycolized glyceride at a weight ratio ranging from about 1:1.25 to about 1:2 as determined using the molecular weight of the compound as a free base.

Embodiment 70

The composition of Embodiment 69, wherein the composition comprises the compound of structure (I) and the polyglycolized glyceride at a weight ratio of about 1:1.76 as determined using the molecular weight of the compound as a free base.

Embodiment 71

A unit dose form comprising the composition of any one of Embodiments 1-70 in a therapeutically effective amount.

Embodiment 72

A unit dose form comprising a composition, the composition comprising:
a polyglycolized glyceride in an amount of about 560 mg to about 600 mg;
and a compound having the following structure (I):

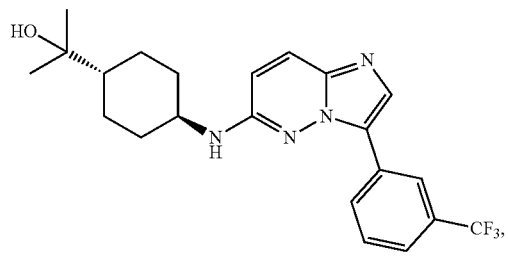

(I)

or a pharmaceutically acceptable salt thereof, in an amount of about 115 mg to about 125 mg as determined using the molecular weight of the compound as a free base.

Embodiment 73

The unit dose form of Embodiment 72, which is a capsule.

Embodiment 74

The unit dose form of Embodiment 72 or 73, wherein the compound of structure (I) is present as a hydrochloride salt.

Embodiment 75

The unit dose form of Embodiment 72, wherein the polyglycolized glyceride is GELUCIRE® 44/14 present in an amount of about 589.56 mg.

Embodiment 76

The unit dose form of Embodiment 72, wherein the compound of structure (I) is present in an amount of about 120 mg as determined using the molecular weight of the compound as a free base.

Embodiment 77

A capsule comprising a composition comprising: GELUCIRE® 44/14 in an amount of about 589.56 mg, and a hydrochloride salt of a compound having the following structure (I):

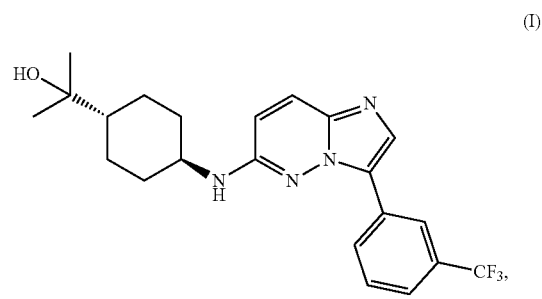 [SMILES: CC(C)(O)[C@H]1CC[C@H](Nc2ccc3ncc(-c4cccc(C(F)(F)F)c4)n3n2)CC1]

(I)

in an amount of about 130.44 mg as determined using the molecular weight of the compound as the hydrochloride salt.

Embodiment 78

A method for preparing a compound having the following structure (I):

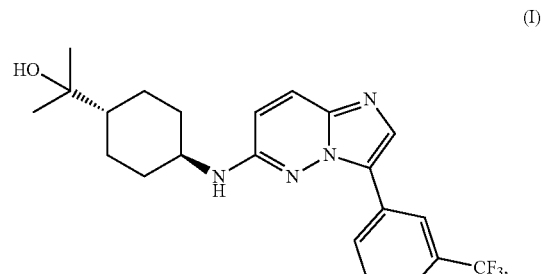

(I)

or a pharmaceutically acceptable salt thereof, the method comprising:

reacting a compound having the following structure:

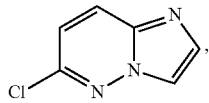

or a salt thereof, with a compound having the following structure:

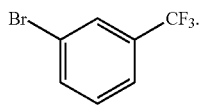

Embodiment 79

The method of Embodiment 78, wherein the method further comprises adding a base and a catalyst.

Embodiment 80

The method of any one of Embodiments 78 or 79, wherein the method further comprises reacting a compound having the following structure:

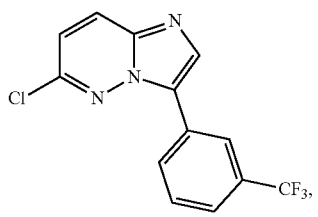 [SMILES: FC(F)(F)c1cccc(-c2cnc3ccc(Cl)nn23)c1]

or a salt thereof, with a compound having the following structure:

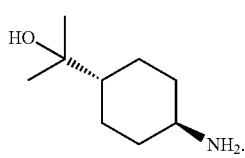

Embodiment 81

The method of any one of Embodiments 78-80, wherein the method further comprises reacting a first compound having the following structure:

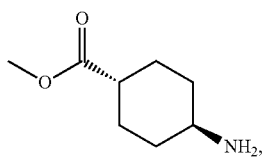

or a salt thereof, with a base and a benzyl halide reagent thereby converting the first compound to a second compound having the following structure:

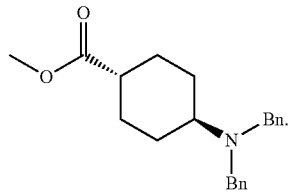 [SMILES: COC(=O)[C@H]1CC[C@H](N(Cc2ccccc2)Cc2ccccc2)CC1]

Embodiment 82

The method Embodiment 81, wherein the base is $K_2CO_3$.

Embodiment 83

A method for preparing a compound having the following structure (I):

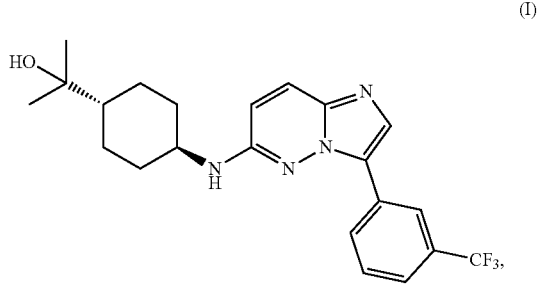 [SMILES: CC(C)(O)[C@H]1CC[C@H](Nc2ccc3ncc(-c4cccc(C(F)(F)F)c4)n3n2)CC1]

(I)

or a pharmaceutically acceptable salt thereof, the method comprising:

reacting a compound having the following structure:

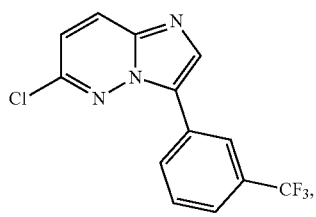 [SMILES: FC(F)(F)c1cccc(-c2cnc3ccc(Cl)nn23)c1]

or a salt thereof, with potassium fluoride and a compound having the following structure:

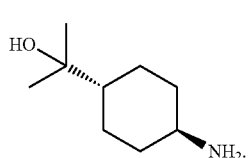

Embodiment 84

A method for purifying a compound having the following structure:

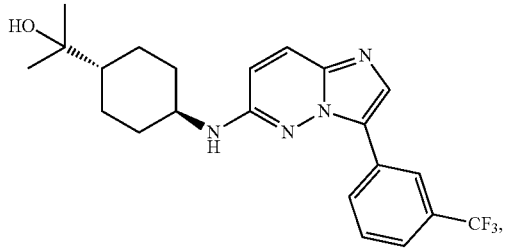 [SMILES: CC(C)(O)[C@H]1CC[C@H](Nc2ccc3ncc(-c4cccc(C(F)(F)F)c4)n3n2)CC1]

or a pharmaceutically acceptable salt thereof, the method comprising:
contacting a composition comprising the compound with a metal scavenging reagent.

Embodiment 85

The method of Embodiment 84, wherein the metal scavenging reagent is a thiol.

Embodiment 86

The method of Embodiment 84, wherein the metal scavenging reagent is thiol-functionalized silica.

Embodiment 87

A method for treating a cancer comprising administering a therapeutically effective amount of the composition of any one of Embodiments 1-70 or the unit dose of any one of Embodiments 71-76 or the capsule of Embodiment 77 to a subject in need thereof.

Embodiment 88

The method of Embodiment 87, wherein the cancer is a Pim kinase-expressing cancer.

Embodiment 89

The method of any one of Embodiments 87 or 88, wherein the cancer is prostate cancer.

Embodiment 90

The method of any one of Embodiments 87 or 88, wherein the cancer is colorectal cancer.

Embodiment 91

The method of any one of Embodiments 87 or 88, wherein the cancer is a fibrotic cancer.

Embodiment 92

The method of any one of Embodiments 87 or 88, wherein the cancer is myelofibrosis.

Embodiment 93

The method of any one of Embodiments 87 or 88, wherein the cancer is bladder cancer.

Embodiment 94

The method of any one of Embodiments 87 or 88, wherein the cancer is a hematological malignancy.

Embodiment 95

The method of Embodiment 94, wherein the hematological malignancy is acute myeloid leukemia.

Embodiment 96

The method of any one of Embodiments 87-95, wherein the method further comprises administering a therapeutically effective amount of a second anticancer agent.

Embodiment 97

The method of any one of Embodiments 87-96, wherein the method further comprises administering a therapeutically effective amount of a ruxolitinib.

Embodiment 98

A method for treating or preventing a fibrotic disease or disorder comprising administering a therapeutically effective amount of the composition of any one of Embodiments 1-70 or the unit dose of any one of Embodiments 71-76 or the capsule of Embodiment 77 to a subject in need thereof.

Embodiment 99

The method of Embodiment 98, wherein the fibrotic disease or disorder is pulmonary fibrosis, a liver fibrosis, a cardiac fibrosis, a vascular fibrosis, a renal fibrosis, a cutaneous fibrosis, a gastrointestinal fibrosis, an athrofibrosis, Dupuytren's contracture, a mediastinal fibrosis, Peyronie's disease, a retroperitoneal fibrosis, a systemic sclerosis or combination thereof.

Embodiment 100

A method for treating or preventing formation or deposition of fibrosis comprising administering a therapeutically effective amount of the composition of any one of Embodiments 1-70 or the unit dose of any one of Embodiments 71-76 or the capsule of Embodiment 77 to a subject in need thereof.

Embodiment 101

A method for inhibiting virus infection or virus replication comprising administering a therapeutically effective amount of the composition of any one of Embodiments 1-70 or the unit dose of any one of Embodiments 71-76 or the capsule of Embodiment 77 to a subject in need thereof.

Embodiment 102

A method for treating or preventing a myeloproliferative neoplasm, comprising administering a therapeutically effective amount of the composition of any one of Embodiments 1-70 or the unit dose of any one of Embodiments or the capsule of Embodiment 77 to a subject in need thereof.

Embodiment 103

The method of Embodiment 102, wherein the myeloproliferative neoplasm is polycythemia vera, essential thrombocythemia, or combinations thereof.

Embodiment 104

A method for treating or preventing an inflammatory disease or disorder, comprising administering a therapeutically effective amount of the composition of any one of Embodiments 1-70 or the unit dose of any one of Embodiments or the capsule of Embodiment 77 to a subject in need thereof.

Embodiment 105

The method of Embodiment 104, wherein the inflammatory disease or disorder is non-alcoholic fatty liver disease (NAFLD), alcoholic steatohepatitis (ASH), non-alcoholic steatohepatitis (NASH), primary biliary cholangitis, primary sclerosing cholangitis, autoimmune hepatitis, skin inflammation, psoriasis, or combinations thereof.

Embodiment 106

A method for treating or preventing an autoimmune or inflammatory disease or disorder, comprising administering a therapeutically effective amount of the composition of any one of Embodiments 1-70 or the unit dose of any one of Embodiments or the capsule of Embodiment 77 to a subject in need thereof.

Embodiment 107

The method of Embodiment 106, wherein the autoimmune or inflammatory disease or disorder is osteoarthritis, rheumatoid arthritis, pain, inflammatory bowel diseases, respiratory disorders, skin disorders or combinations thereof.

Embodiment 108

The method of any one of Embodiments 87-107, wherein the subject is human.

Embodiment 109

The method of any one of Embodiments 87-108, wherein the subject in need thereof is administered a dose of about 360 mg of the compound of structure (I), or about 480 mg of the compound of structure (I), or about 720 mg of the compound of structure (I), or about 1080 mg of the compound of structure (I), or about 1440 mg of the compound of structure (I), as determined using the molecular weight of the compound as a free base.

Embodiment 110

The method of Embodiment 109, wherein the dose is a daily dose.

Embodiment 111

A method for preparing a compound having the following structure (I):

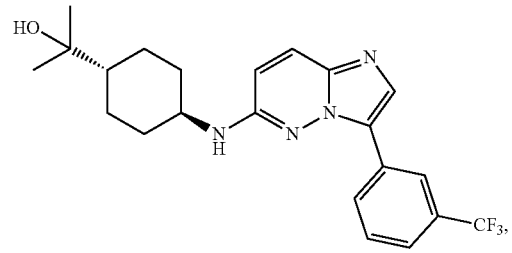

or a pharmaceutically acceptable salt thereof, the method comprising:

reacting a compound having the following structure:

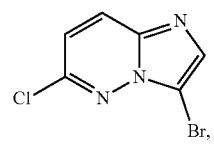 [SMILES: Clc1ccc2ncc(Br)n2n1]

or a salt thereof, with a compound having the following structure:

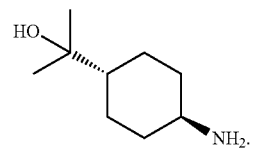

Embodiment 112

The method of Embodiment 111, wherein the method further comprises adding a first base and a catalyst.

Embodiment 113

The method of any one of Embodiments 111 or 112, wherein the first base is an amine base.

Embodiment 114

The method of any one of Embodiments 111-113, wherein the first base is diisopropylethylamine.

Embodiment 115

The method of any one of Embodiments 111-114, wherein the catalyst is cesium fluoride.

Embodiment 116

The method of any one of Embodiments 111-115, wherein the method further comprises reacting a compound having the following structure:

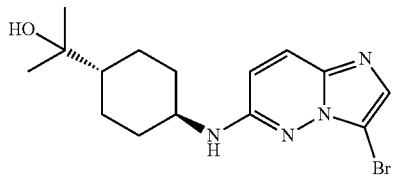 [SMILES: CC(C)(O)[C@H]1CC[C@H](Nc2ccc3ncc(Br)n3n2)CC1]

or a salt thereof, with a compound having the following structure:

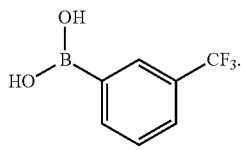

Embodiment 117

The method of Embodiment 116, wherein the method further comprises adding a palladium catalyst and a second base.

Embodiment 118

The method of Embodiment 117, wherein the palladium catalyst is $Pd(PPh_3)_2Cl_2$.

Embodiment 119

The method of any one of Embodiments 117 or 118, wherein the second base is $NaHCO_3$.

Embodiment 120

A crystalline form of the hydrochloric acid salt of the compound 2-((1R,4R)-4-((3-(3-(trifluoromethyl)phenyl)imidazo[1,2-b]pyridazin-6-yl)amino)cyclohexyl)propan-2-ol.

Embodiment 121

The crystalline form of Embodiment 120, comprising Form I.

Embodiment 122

The crystalline form of Embodiment 120 or Embodiment 121 consisting essentially of Form I.

Embodiment 123

The crystalline form of Embodiment 121, wherein Form I is in substantially pure form.

Embodiment 124

The crystalline form of any one of Embodiments 120-123, characterized by an X-ray powder diffraction pattern comprising peaks, in terms of 2-theta, at 21.5±0.2°, 19.9±0.2°, and 17.8±0.2°.

Embodiment 125

The crystalline form of Embodiment 124, further characterized by an X-ray powder diffraction pattern comprising peaks, in terms of 2-theta, at 16.3±0.2°, 19.3±0.2°, and 24.4±0.2°.

Embodiment 126

The crystalline form of Embodiment 124 or Embodiment 125, further characterized by an X-ray powder diffraction pattern comprising peaks, in terms of 2-theta, at 10.1±0.2°, 11.7±0.2°, 14.4±0.2°, and 16.7±0.2°.

Embodiment 127

The crystalline form of any one of Embodiments 120-126, having an X-ray powder diffraction pattern substantially as shown in FIG. 1.

Embodiment 128

The crystalline form of any one of Embodiments 120-127, having a differential scanning calorimetry thermogram comprising an endothermic event at 226.9±3° C.

Embodiment 129

Figure 2:
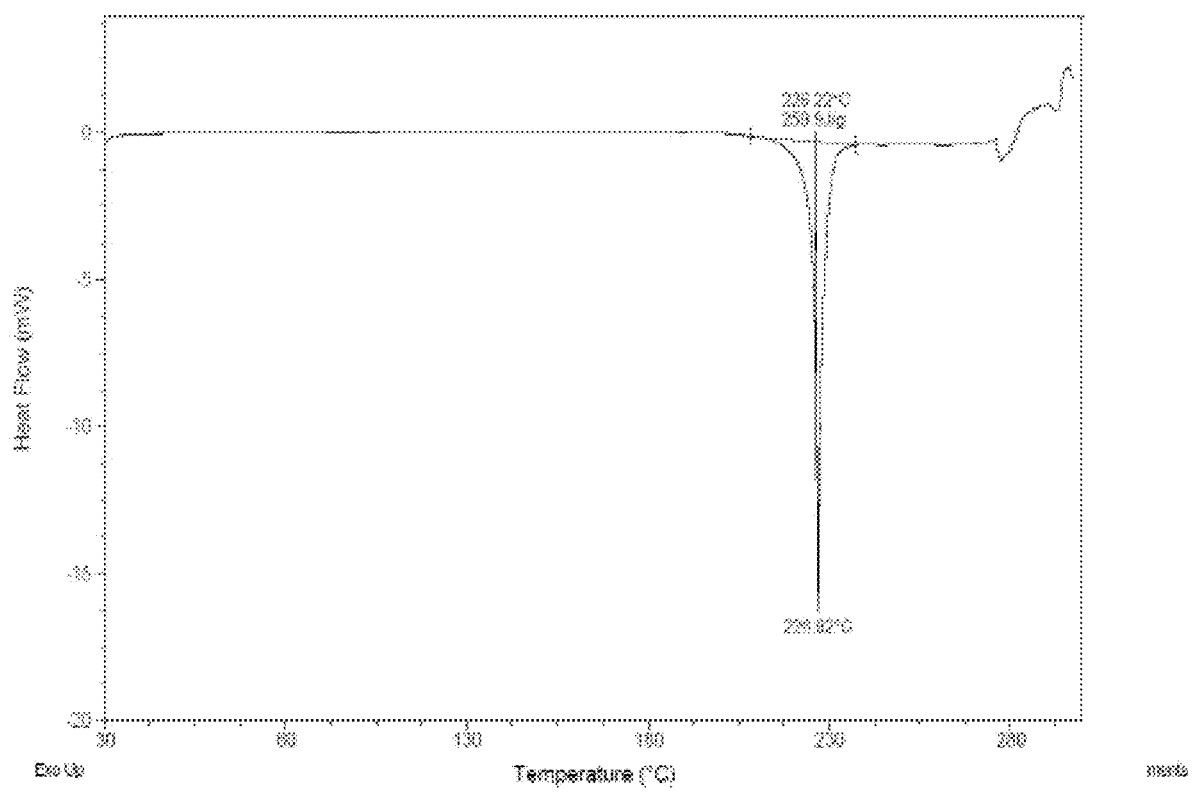
FIG. 2 is a graphical representation of the DSC thermogram of crystalline Form I.

The crystalline form of any one of Embodiments 120-128, having a differential scanning calorimetry thermogram substantially as shown in FIG. 2.

Embodiment 130

Figure 3:
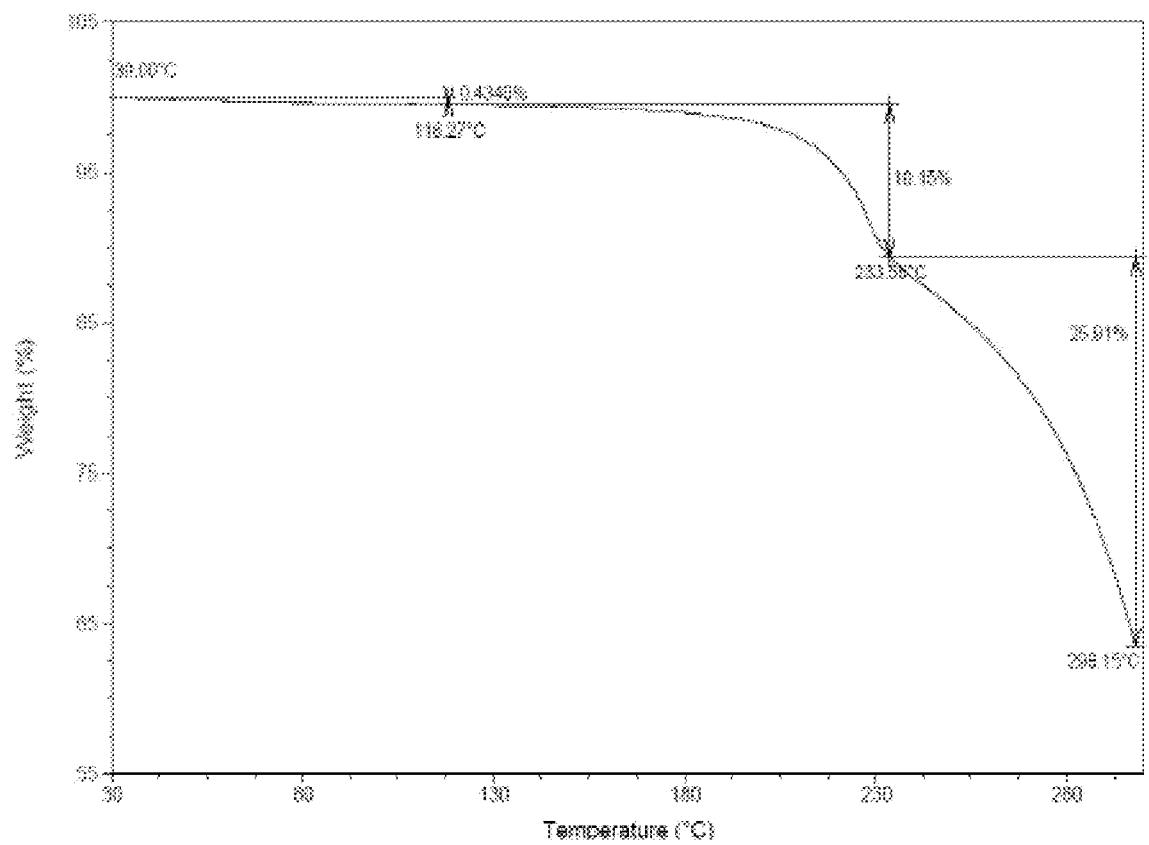
FIG. 3 is a graphical representation of the TGA thermogram of crystalline Form I.

The crystalline form of any one of Embodiments 120-129, having a thermogravimetric analysis diagram substantially as shown in FIG. 3.

Embodiment 131

The crystalline form of Embodiment 120, comprising Form II.

Embodiment 132

The crystalline form of Embodiment 120 or Embodiment 131, characterized by an X-ray powder diffraction pattern comprising peaks, in terms of 2-theta, at 15.7±0.2° and 17.0±0.2°.

Embodiment 133

Figure 5:
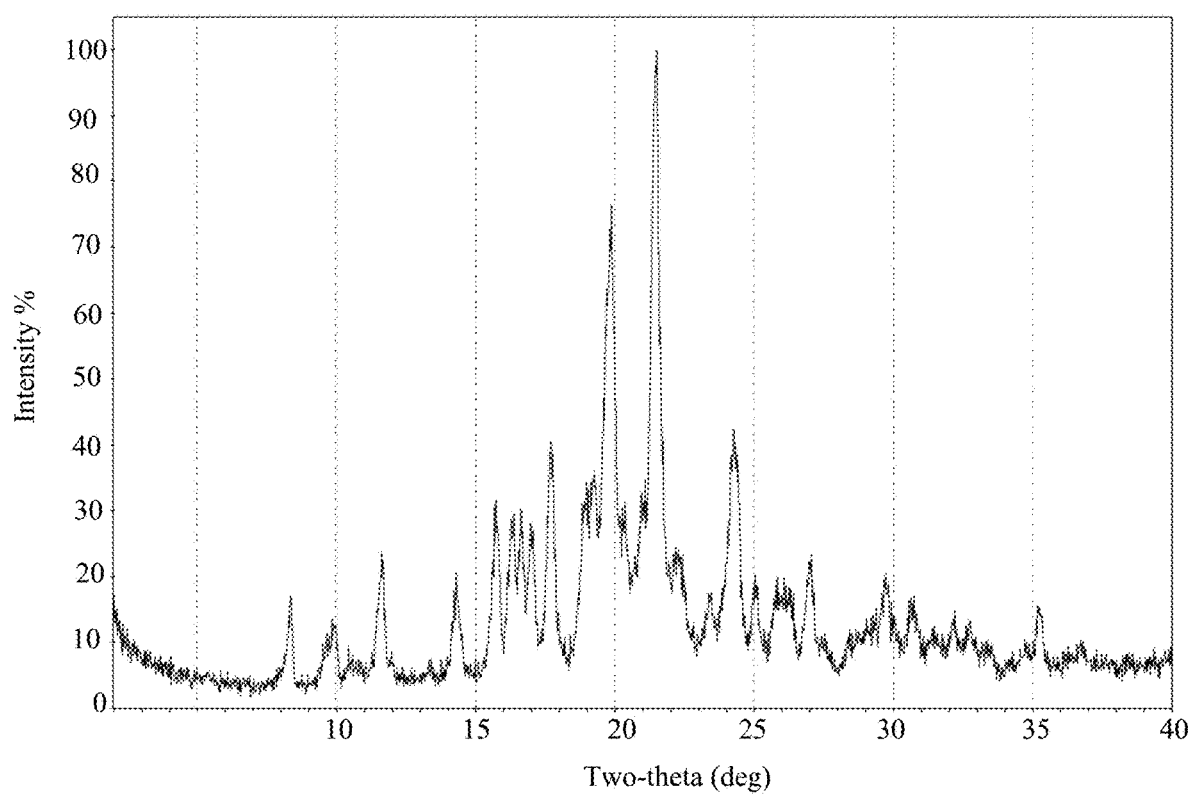
FIG. 5 is a graphical representation of the X-ray powder diffraction pattern of crystalline Form II.
Figure 6:
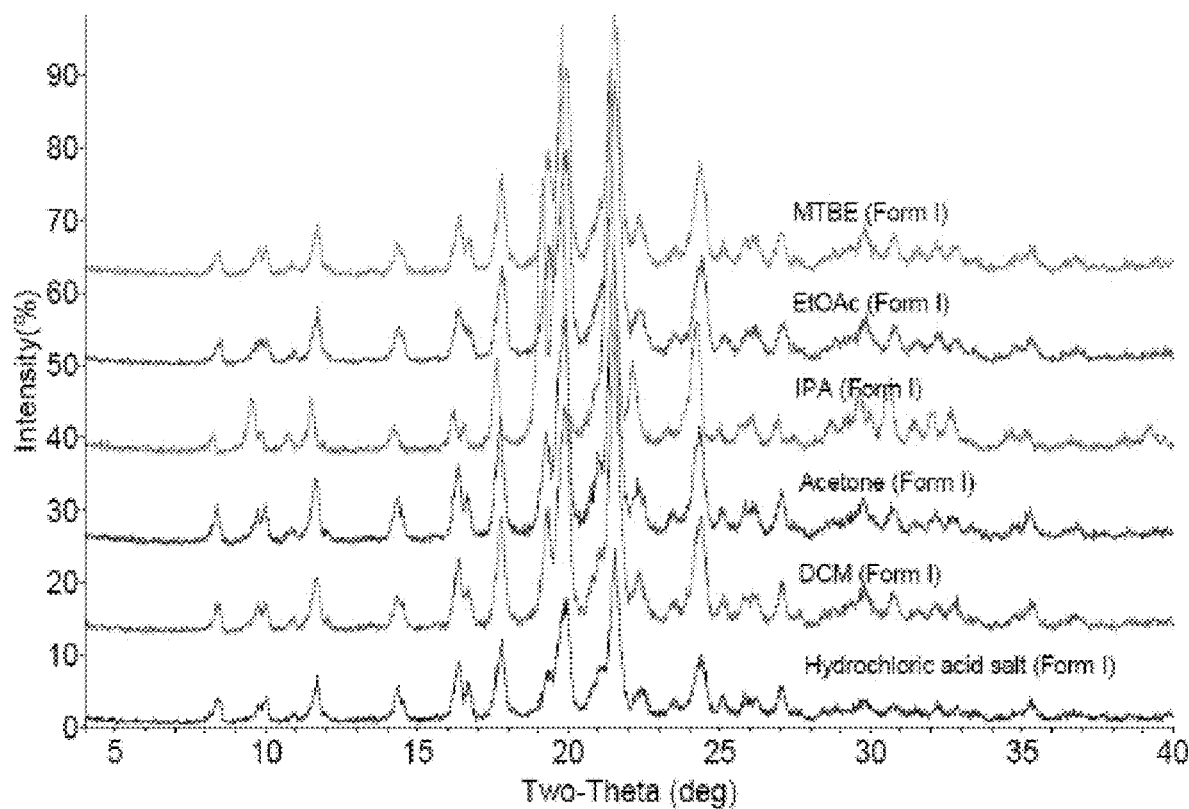
FIG. 6 is a graphical representation of the X-ray powder diffraction pattern of solids obtained in the slurry experiment described in Example 10.
Figure 7:
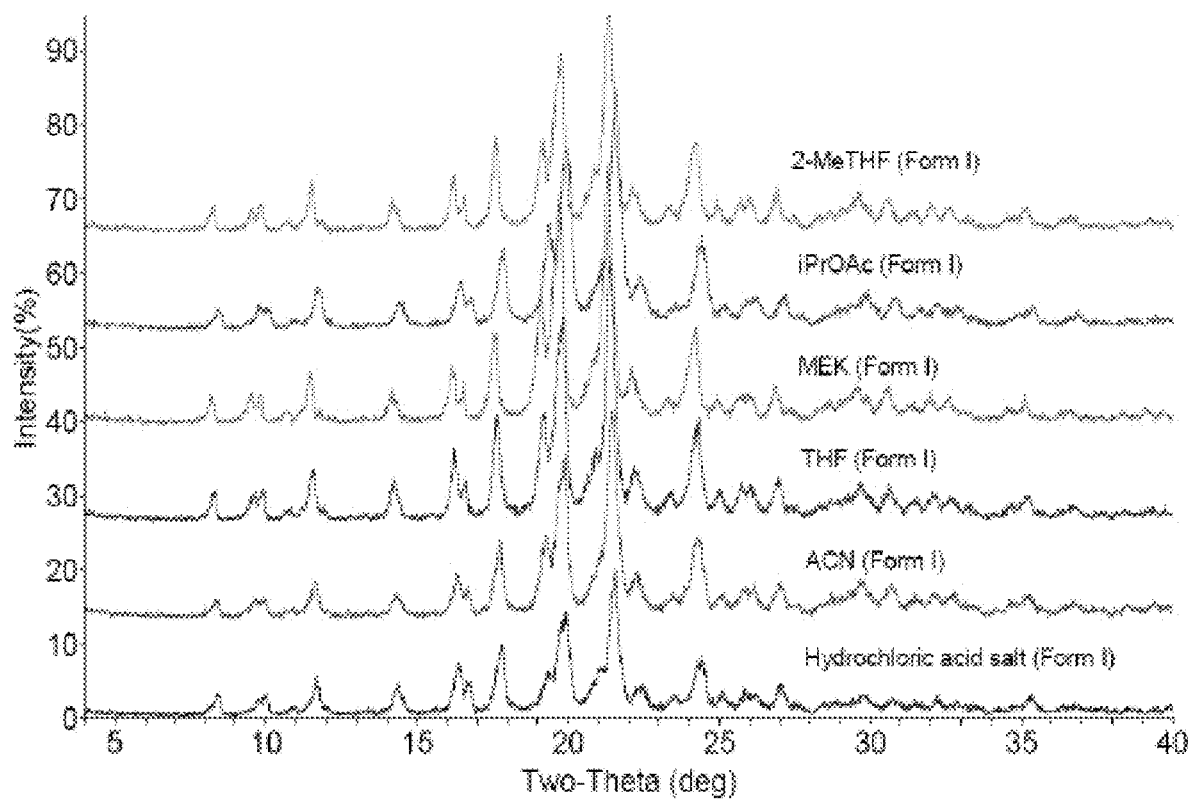
FIG. 7 is a graphical representation of the X-ray powder diffraction pattern of solids obtained in a slurry experiment described in Example 10.
Figure 8:
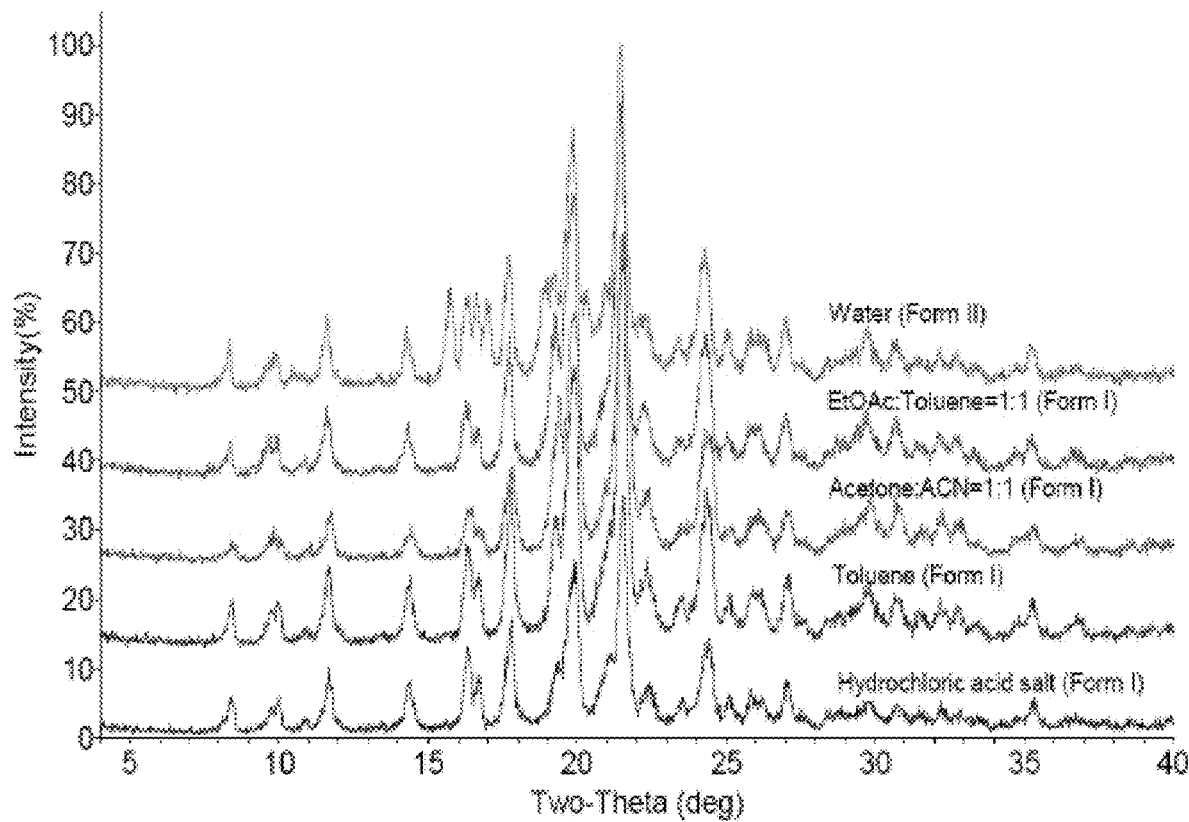
FIG. 8 is a graphical representation of the X-ray powder diffraction pattern of solids obtained in a slurry experiment described in Example 10.
Figure 9:
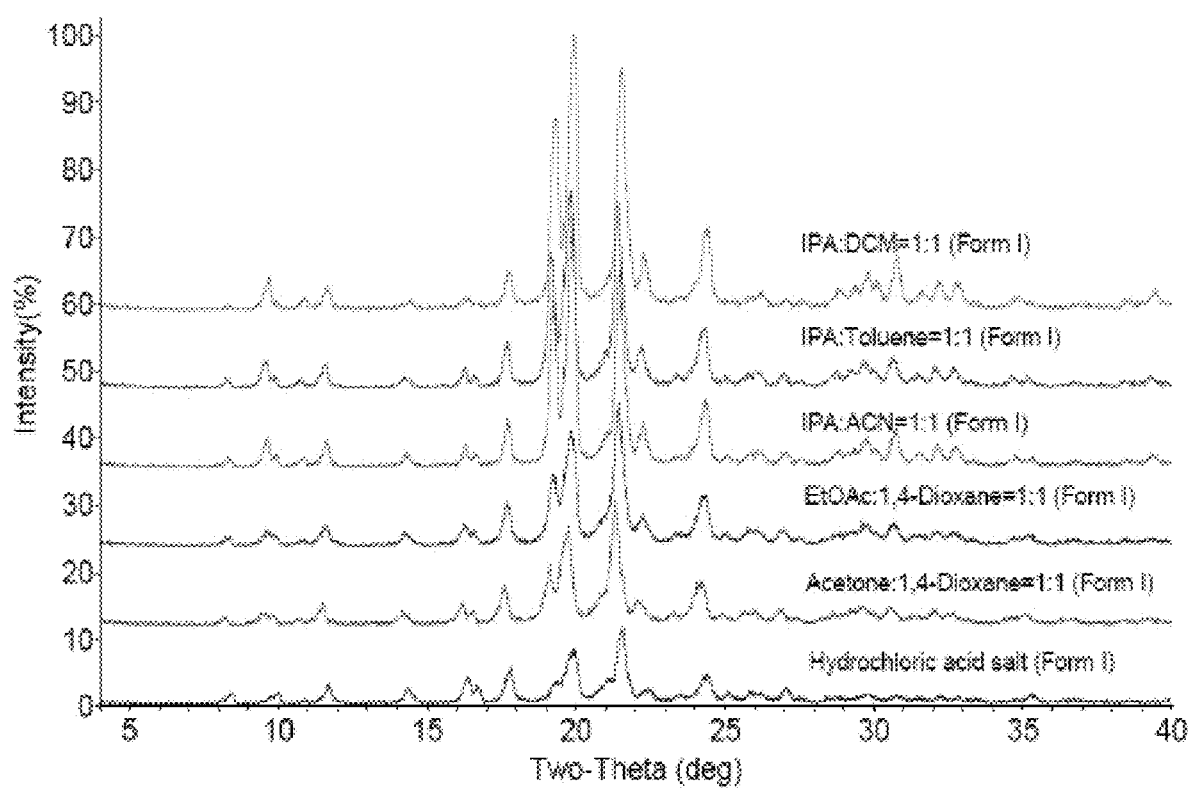
FIG. 9 is a graphical representation of the X-ray powder diffraction pattern of solids obtained in a slurry experiment described in Example 10.
Figure 10:
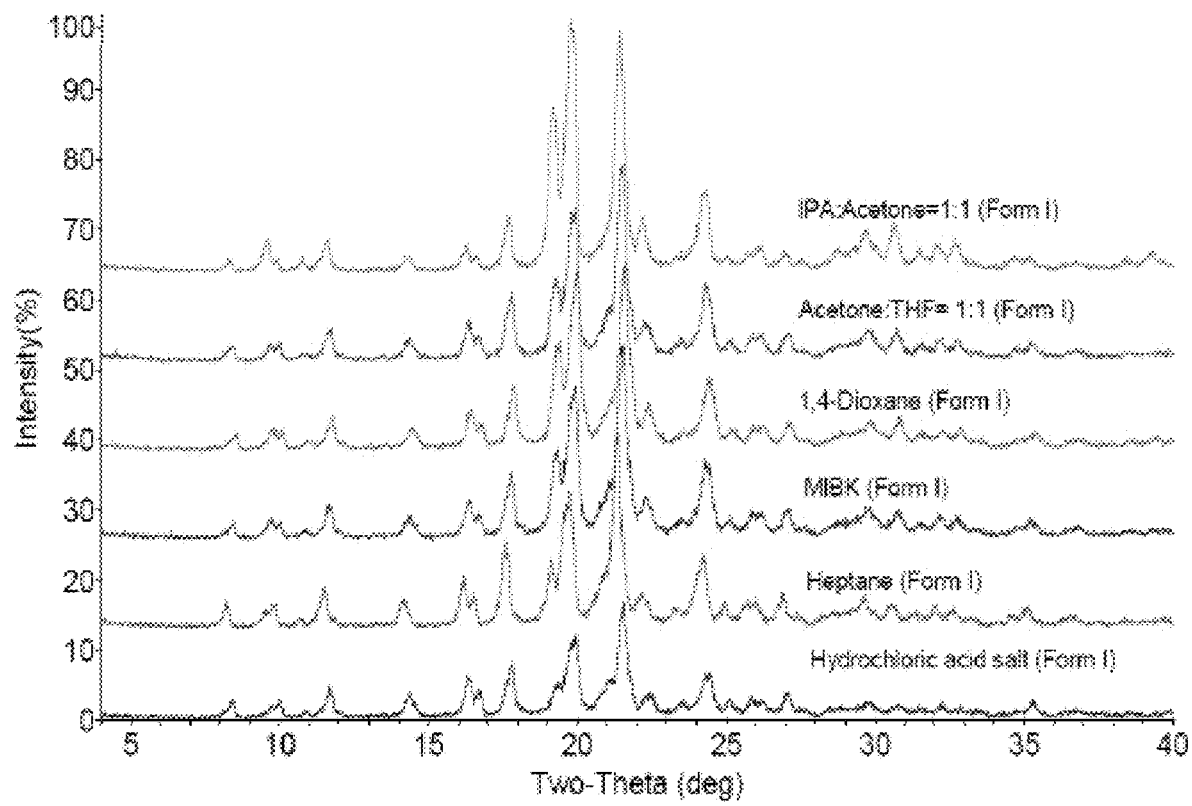
FIG. 10 is a graphical representation of the X-ray powder diffraction pattern of solids obtained in a slurry experiment described in Example 10.
Figure 11:
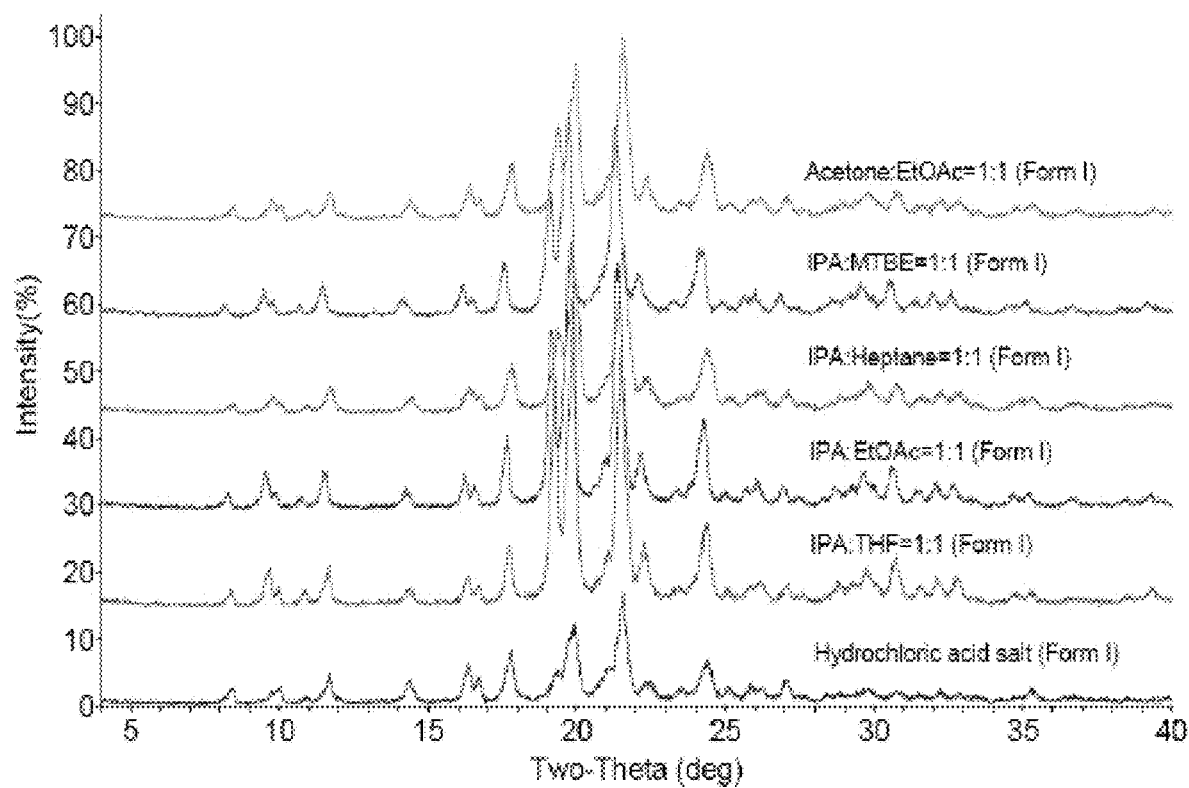
FIG. 11 is a graphical representation of the X-ray powder diffraction pattern of solids obtained in a slurry experiment described in Example 10.
Figure 12:
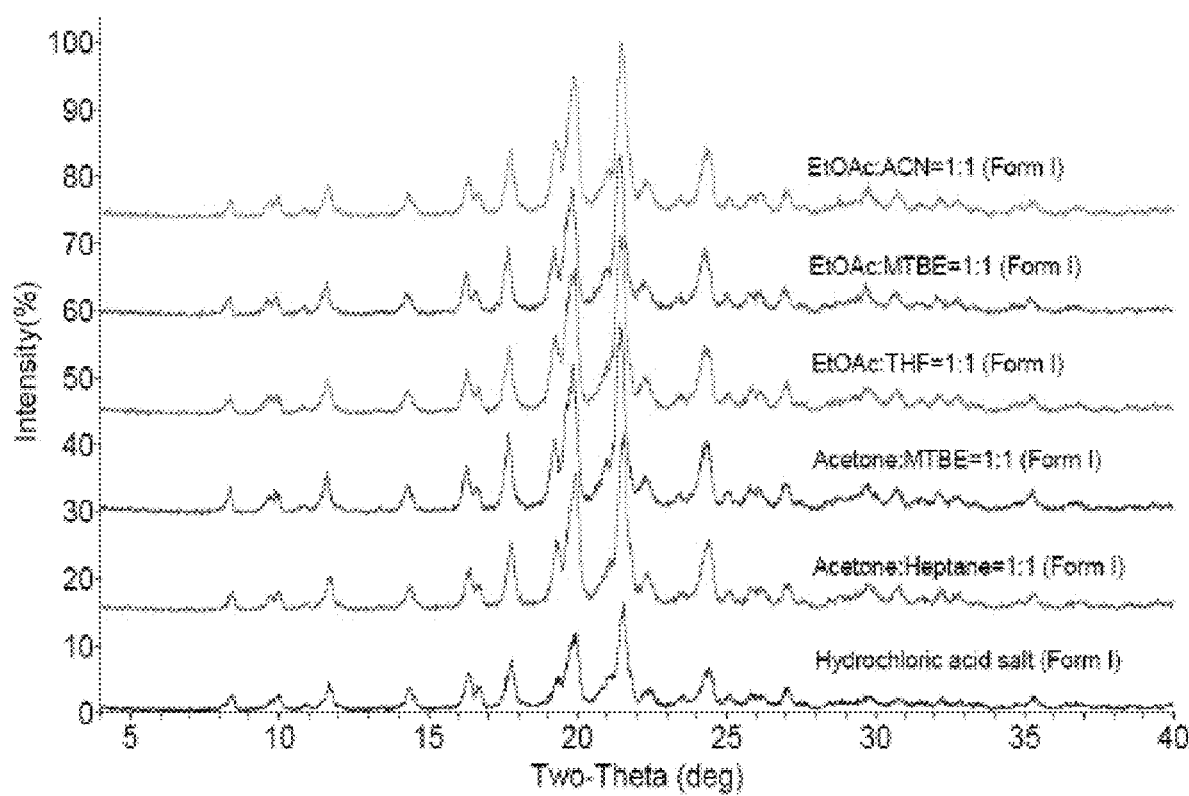
FIG. 12 is a graphical representation of the X-ray powder diffraction pattern of solids obtained in a slurry experiment described in Example 10.
Figure 13:
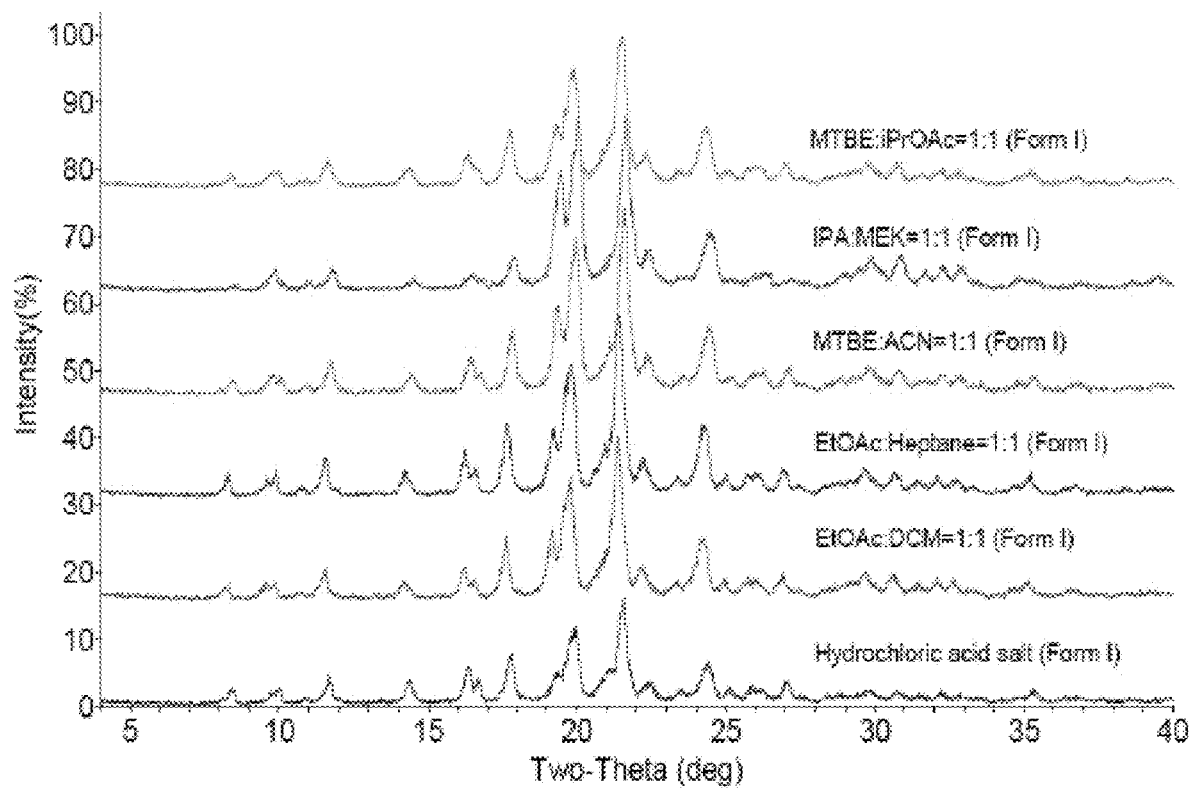
FIG. 13 is a graphical representation of the X-ray powder diffraction pattern of solids obtained in a slurry experiment described in Example 10.
Figure 14:
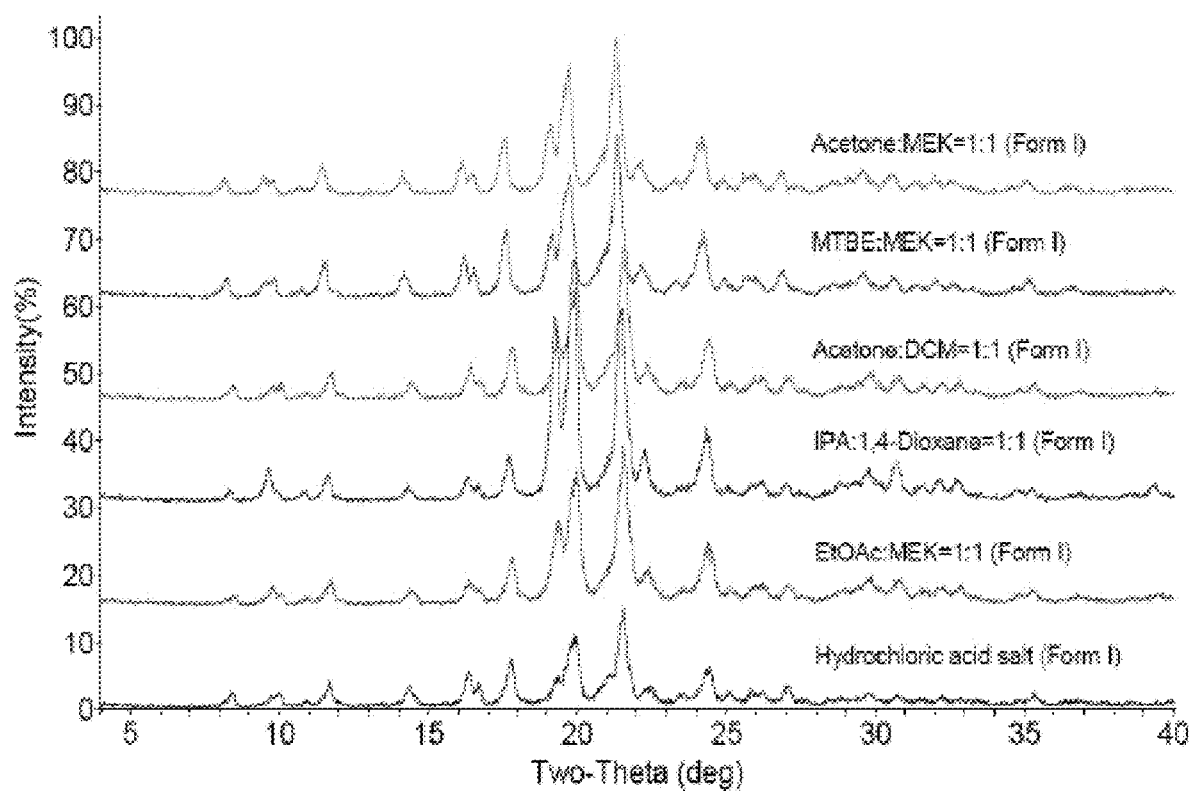
FIG. 14 is a graphical representation of the X-ray powder diffraction pattern of solids obtained in a slurry experiment described in Example 10.
Figure 15:
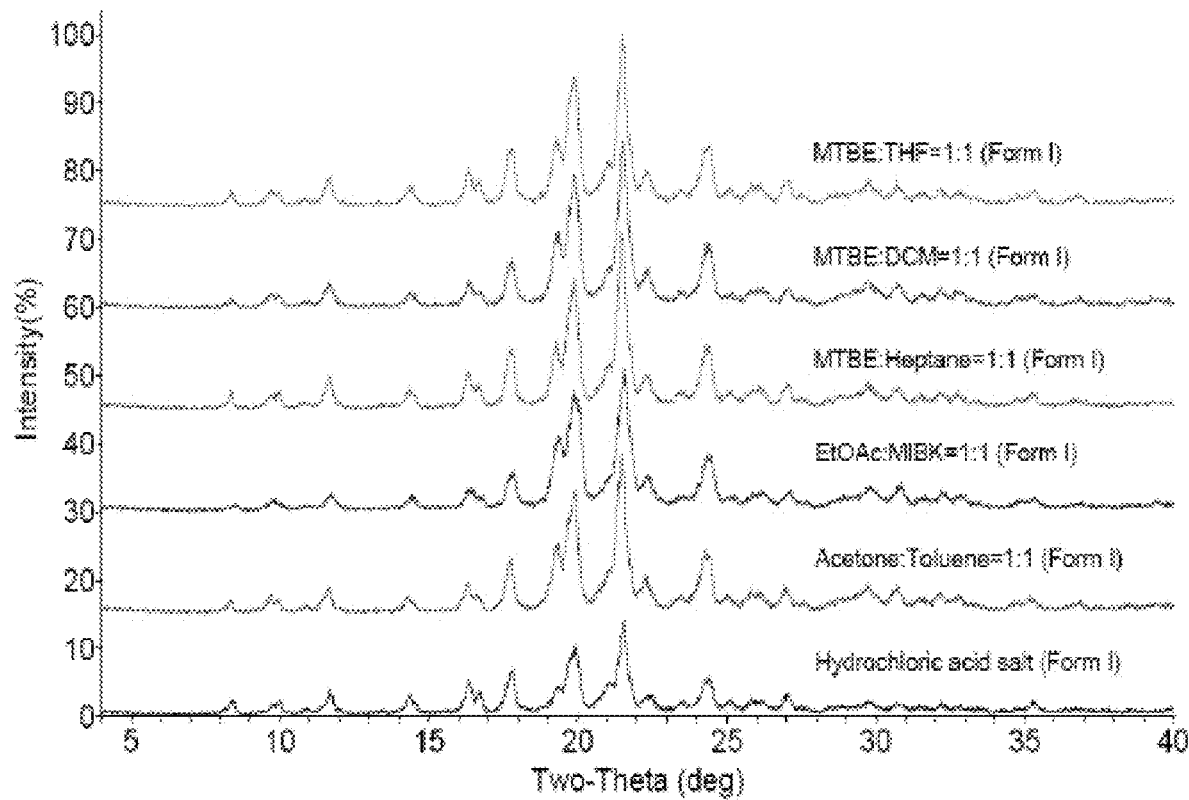
FIG. 15 is a graphical representation of the X-ray powder diffraction pattern of solids obtained in a slurry experiment described in Example 10.

The crystalline form of any one of Embodiment 131 or Embodiment 132, having an X-ray powder diffraction pattern substantially as shown in FIG. 5.

Embodiment 134

A pharmaceutical composition comprising the crystalline form of any one of Embodiments 120-133 and a pharmaceutically acceptable carrier.

Embodiment 135

A pharmaceutical composition comprising a crystalline form selected from Form I or Form II.

Embodiment 136

The pharmaceutical composition of Embodiment 134, wherein the crystalline form is Form I.

Embodiment 137

The pharmaceutical composition of Embodiment 136, wherein Form I is substantially pure.

Embodiment 138

The pharmaceutical composition of any one of Embodiments 134-137, wherein the pharmaceutically acceptable carrier comprises a formulating agent, the formulating agent comprising polysorbate 20, polysorbate 60, polysorbate 80, glyceryl monocaprylate, glyceryl monocaprate, glyceryl monooleate, glyceryl dibehenate, propylene glycol dilaurate, propylene glycol monocaprylate, propylene glycol monolaurate, or combinations thereof.

Embodiment 139

A method for treating a cancer comprising administering to a subject in need thereof a therapeutically effective amount of the crystalline form of any one of Embodiments 120-133.

Embodiment 140

The method of Embodiment 139, wherein the cancer is a Pim kinase-expressing cancer.

Embodiment 141

The method of any one of Embodiments 139 or 140, wherein the cancer is prostate cancer.

Embodiment 142

The method of any one of Embodiments 139 or 140, wherein the cancer is colorectal cancer.

Embodiment 143

The method of any one of Embodiments 139 or 140, wherein the cancer is a fibrotic cancer.

Embodiment 144

The method of any one of Embodiments 139 or 140, wherein the cancer is myelofibrosis.

Embodiment 145

The method of any one of Embodiments 139 or 140, wherein the cancer is bladder cancer.

Embodiment 146

The method of any one of Embodiments 139 or 140, wherein the cancer is a hematological malignancy.

Embodiment 147

The method of Embodiment 146, wherein the hematological malignancy is acute myeloid leukemia.

Embodiment 148

The method of any one of Embodiments 139-147, wherein the method further comprises administering a therapeutically effective amount of a second anticancer agent.

Embodiment 149

The method of any one of Embodiments 139-148, wherein the method further comprises administering a therapeutically effective amount of a ruxolitinib.

Embodiment 150

A method for treating or preventing a fibrotic disease or disorder comprising administering a therapeutically effective amount of the crystalline form of any one of Embodiments 120-133 to a subject in need thereof.

Embodiment 151

The method of Embodiment 150, wherein the fibrotic disease or disorder is pulmonary fibrosis, a liver fibrosis, a cardiac fibrosis, a vascular fibrosis, a renal fibrosis, a cutaneous fibrosis, a gastrointestinal fibrosis, an athrofibrosis, Dupuytren's contracture, a mediastinal fibrosis, Peyronie's disease, a retroperitoneal fibrosis, a systemic sclerosis or combination thereof.

Embodiment 152

A method for treating or preventing formation or deposition of fibrosis comprising administering a therapeutically effective amount of the crystalline form of any one of Embodiments 120-133 to a subject in need thereof.

Embodiment 153

A method for inhibiting virus infection or virus replication comprising administering a therapeutically effective amount of the crystalline form of any one of Embodiments 120-133 to a subject in need thereof.

Embodiment 154

A method for treating or preventing a myeloproliferative neoplasm, comprising administering a therapeutically effective amount of the crystalline form of any one of Embodiments 120-133 to a subject in need thereof.

Embodiment 155

The method of Embodiment 154, wherein the myeloproliferative neoplasm is polycythemia vera, essential thrombocythemia, or combinations thereof.

Embodiment 156

A method for treating or preventing an inflammatory disease or disorder, comprising administering a therapeutically effective amount of the crystalline form of any one of Embodiments 120-133 to a subject in need thereof.

Embodiment 157

The method of Embodiment 156, wherein the inflammatory disease or disorder is non-alcoholic fatty liver disease (NAFLD), alcoholic steatohepatitis (ASH), non-alcoholic steatohepatitis (NASH), primary biliary cholangitis, primary sclerosing cholangitis, autoimmune hepatitis, skin inflammation, psoriasis, or combinations thereof.

Embodiment 158

A method for treating or preventing an autoimmune or inflammatory disease or disorder, comprising administering a therapeutically effective amount of the crystalline form of any one of Embodiments 120-133 to a subject in need thereof.

Embodiment 159

The method of Embodiment 158, wherein the autoimmune or inflammatory disease or disorder is osteoarthritis, rheumatoid arthritis, pain, inflammatory bowel diseases, respiratory disorders, skin disorders or combinations thereof.

Embodiment 160

The method of any one of Embodiments 139-159, wherein the subject is a human subject.

Embodiment 161

A process for preparing the crystalline form of any one of Embodiments 120-130, comprising precipitating said crystalline form from a solution comprising the hydrochloric acid salt of the compound 2-((1R,4R)-4-((3-(3-(trifluoromethyl)phenyl) imidazo[1,2-b]pyridazin-6-yl)amino)cyclohexyl)propan-2-ol, methanol and ethyl acetate.

Embodiment 162

The process of Embodiment 161, wherein the precipitating involves shaking the solution for 24 hours to form a slurry.

Embodiment 163

The process of Embodiment 161 or Embodiment 162, further comprising contacting the solution with a seed crystal of the crystalline form.

Embodiment 164

A crystalline form of the hydrochloric acid salt of the compound 2-((1R,4R)-4-((3-(3-(trifluoromethyl)phenyl) imidazo[1,2-b]pyridazin-6-yl)amino)cyclohexyl)propan-2-ol prepared by the process of any one of Embodiments 161-163.

Embodiment 165

A process for preparing the crystalline form of any one of Embodiments 131-133, comprising precipitating said crystalline form from a solution comprising the hydrochloric acid salt of the compound 2-((1R,4R)-4-((3-(3-(trifluoromethyl)phenyl) imidazo[1,2-b]pyridazin-6-yl)amino)cyclohexyl)propan-2-ol and water.

Embodiment 166

The process of Embodiment 165, further comprising shaking the solution for 24 hours to form a slurry.

Embodiment 167

A crystalline form of the hydrochloric acid salt of the compound 2-((1R,4R)-4-((3-(3-(trifluoromethyl)phenyl) imidazo[1,2-b]pyridazin-6-yl)amino)cyclohexyl)propan-2-ol prepared by the process of Embodiment 165 or Embodiment 166.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Definitions

For purposes of interpreting this specification, the following definitions will apply, and whenever appropriate, terms used in the singular will also include the plural. Terms used in the specification have the following meanings unless the context clearly indicates otherwise.

All methods described herein can be performed in any suitable order unless otherwise indicated herein or otherwise clearly contradicted by context. The use of any and all examples, or exemplary language (e.g., "such as") provided herein is intended merely to better illuminate the present disclosure and does not pose a limitation on the scope of the present disclosure otherwise claimed.

The terms "a," "an," "the" and similar terms used in the context of the present disclosure (especially in the context of the claims) are to be construed to cover both the singular and plural unless otherwise indicated herein or clearly contradicted by the context.

"Polyglycolized glyceride" refers to a mixture of monoesters, diesters and triesters of glycerols and monoesters and diesters of polyethylene glycols with a mean relative molecular mass between about 200 and 6000. Polyglycolized glycerides may be obtained by partial transesterification of triglycerides with polyethylene glycol or by esterification of glycerol and polyethylene glycol with fatty acids. In some embodiments, the fatty acid component contains between 8-22 carbon atoms, for example, between 10-18 carbon atoms. Examples of natural vegetable oils from which polyglycolized glycerides can be derived include palm kernel oil and palm oil. Suitable polyol compounds generally have a molecular weight ranging from about 200 to about 6000 g/mol and preferably contain polyethylene glycol, although other polyols may be employed, such as polyglycerols or sorbitol. Polyglycolized glycerides are available on the market under the trade name GELUCIRE®. Examples of polyglycolized glycerides useful in various embodiments include WL 2514CS, LABRASOL, LABRAFIL, GELUCIRE® 44/14 (lauroyl polyoxy-32 glycerides), GELUCIRE® 33/01, GELU- CIRE® 35/10, GELUCIRE® 37/02, GELUCIRE® 50/13, GELUCIRE® 44/11 and mixtures thereof.

"GELUCIRE® 44/14" or "GELUCIRE 44/14" is a lipid-based excipient manufactured by Gattefosse Corporation, Westwood, N.J., comprising a mixture of pegylated fatty acid esters and glycerides. The number 44 denotes the melting point of the compound and 14 indicates hydrophile/lipophile balance (HLB) value. Other GELUCIRE® excipients similarly indicate values for melting point and HLB values. For example, GELUCIRE® 33/01, GELUCIRE® 35/10, GELUCIRE® 37/02, GELUCIRE® 50/13 and GELUCIRE® 44/11.

A hydrophile/lipophile balance (HLB) value can be determined by Griffin's method. The HLB value is determined according to the following equation:

$$HLB = 20 \times (M_h/M)$$

wherein, $M_h$ is the molecular mass of the hydrophilic portion of the molecule, and M is the molecular mass of the entire molecule. Thus, the value of the HLB ranges from 0 to 20, with a value of 0 corresponding to a lipophilic (i.e., hydrophobic) molecule and a value of 20 corresponding to a hydrophilic (i.e., lipophobic) molecule.

The phrase "pharmaceutically acceptable" indicates that the substance or composition must be compatible chemically and/or toxicologically with the other ingredients comprising a formulation and/or the subject (e.g., mammal) being treated therewith.

Depending on the process conditions, the end products of the present disclosure are obtained either in free (base) or salt form. Both the free form and the salts of these end products are within the scope of the present disclosure. If so desired, one form of a compound may be converted into another form. A free base may be converted into a salt; a salt may be converted into the free form or another salt.

Pharmaceutically acceptable salts are preferred. However, other salts may be useful, e.g., in isolation or purification steps which may be employed during preparation, and thus, are contemplated within the scope of the present disclosure.

As used herein, "pharmaceutically acceptable salts" refer to pharmaceutically acceptable acid or base addition salts. For example, pharmaceutically acceptable salts include, but are not limited to, acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate/hydroxymalonate, mandelate, mesylate, methylsulphate, mucate, naphthoate, napsylate, nicotinate, nitrate, octadecanoate, oleate, oxalate, palmitate, pamoate, phenylacetate, phosphate/hydrogen phosphate/dihydrogen phosphate, polygalacturonate, propionate, salicylates, stearate, succinate, sulfamate, sulfosalicylate, tartrate, tosylate, trifluoroacetate or xinafoate salt form.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the relevant disclosure of which is hereby incorporated by reference in its entirety.

Any formula given herein is intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present disclosure include isotopes of hydrogen, carbon, nitrogen, oxygen, phosphorous, fluorine, chlorine and iodine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$ $^{125}I$, respectively. The present disclosure includes various isotopically labeled compounds as defined herein, for example, those in which radioactive isotopes, such as $^3H$ and $^{14}C$, or those in which non-radioactive isotopes, such as $^2H$ and $^{13}C$, are present. Such isotopically labelled compounds are useful in metabolic studies (with $^{14}C$), reaction kinetic studies (with, for example, $^2H$ or $^3H$), detection or imaging techniques, such as positron emission tomography (PET) or single-photon emission computed tomography (SPECT), including drug or substrate tissue distribution assays, or in radioactive treatment of subjects. In particular, an $^{18}F$-labeled compound may be particularly desirable for PET or SPECT studies.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present disclosure. The concentration of such a heavier isotope, specifically deuterium, may be defined by the isotopic enrichment factor.

The term "isotopic enrichment factor," as used herein, means the ratio between the isotopic abundance and the natural abundance of a specified isotope. If a substituent in a compound of this present disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically labeled compounds of the present disclosure can generally be prepared by conventional techniques known to those skilled in the art or by processes disclosed in the schemes, examples and preparations described below (or by analogous processes to those described herein), by substituting an appropriate or readily available isotopically labeled reagent for a non-isotopically labeled reagent otherwise employed. Such compounds have a variety of potential uses, e.g., as standards and reagents in determining the ability of a potential pharmaceutical compound to bind to target proteins or receptors, or for imaging compounds of this disclosure bound to biological receptors in vivo or in vitro.

The term "malignancy", also called "cancer," refers to diseases in which abnormal cells divide without control and can invade nearby tissues. Malignant cells can also spread to other parts of the body through the blood and lymph systems. There are several main types of malignancy. Carcinoma is a malignancy that begins in the skin or in tissues that line or cover internal organs. Sarcoma is a malignancy that begins in bone, cartilage, fat, muscle, blood vessels, or other connective or supportive tissue. Leukemia is a malignancy that starts in blood-forming tissue, such as the bone marrow, and causes large numbers of abnormal blood cells to be produced and enter the blood. Lymphoma and multiple myeloma are malignancies that begin in the cells of the immune system. Central nervous system cancers are malignancies that begin in the tissues of the brain and spinal cord.

The term "solid tumor" refers to malignancies/cancers formed of abnormal masses of tissue that usually do not contain cysts or liquid areas. Solid tumors are named/classified according to the tissue/cells of origin. Examples include, but are not limited to, sarcomas and carcinomas.

The term "leukemia" refers to hematologic or blood cell malignancies/cancers that begin in blood-forming tissue, such as the bone marrow. Examples include, but are not limited to, acute myeloid leukemia (AML), chronic myeloid leukemia (CML), acute lymphocytic leukemia (ALL) and chronic lymphocytic leukemia (CLL).

The term "lymphoma" refers to lymphatic cell malignancies/cancers that begin in the cells of the immune system. Examples include, but are not limited to, non-Hodgkin's lymphoma and multiple myeloma.

As used herein, the term "subject" refers to an animal. Typically, the animal is a mammal. A subject also refers to, for example, primates (e.g., humans), cows, sheep, goats, horses, dogs, cats, rabbits, rats, mice, fish, birds and the like. In certain embodiments, the subject is a primate. In yet other embodiments, the subject is a human. Exemplary subjects include human beings of any age with risk factors for cancer.

As used herein, a subject is "in need of" a treatment if such subject would benefit biologically, medically or in quality of life from such treatment (preferably, a human).

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease/disorder refers to the treatment of the disease/disorder in a subject (e.g., a mammal), particularly in a human, and includes: (a) inhibiting the disease/disorder (e.g., slowing or arresting or reducing the development of the disease/disorder, or at least one of the clinical symptoms thereof); (b) relieving the disease/disorder (e.g., causing regression of the disease/disorder, or at least one of the clinical symptoms thereof), either physically (e.g., stabilization of a discernible symptom), physiologically (e.g., stabilization of a physical parameter), or both); (c) alleviating or ameliorating at least one physical parameter including those which may not be discernible by the subject; and/or (d) preventing or delaying the onset or development or progression of the disease or disorder from occurring in a subject (e.g., a mammal), in particular, when such a subject (e.g., a mammal) is predisposed to the disease or disorder but has not yet been diagnosed as having it.

The term "a therapeutically effective amount" (e.g., of a composition of the present disclosure) refers to an amount (e.g., of the composition of the present disclosure) that, when administered to a subject, such as a human, is sufficient to effect treatment. In one non-limiting embodiment, the term "a therapeutically effective amount" refers to the amount (e.g., of the composition of the present disclosure) that, when administered to a subject, is effective to (1) at least partially alleviate, inhibit, prevent and/or ameliorate a condition, or a disorder or a disease mediated by a Pim-kinase; or (2) reduce or inhibit the activity of a Pim-kinase. In another non-limiting embodiment, the term "a therapeutically effective amount" refers to the amount (e.g., of the composition of the present disclosure) that, when administered to a cell, or a tissue, or a non-cellular biological material, or a medium, is effective to at least partially reduce or inhibit the activity of Pim-kinase; or at least partially reduce or inhibit the expression of Pim-kinase.

The therapeutically effective amount can vary depending on such factors as the size and weight of the subject, the type of illness, or the particular composition of the present disclosure. One of ordinary skill in the art would be able to study the factors contained herein and make the determination regarding the therapeutically effective amount (e.g., of the compositions of the present disclosure) without undue experimentation.

The regimen of administration can affect what constitutes a therapeutically effective amount. A crystalline form or composition of the present disclosure can be administered to a subject either prior to or after the onset of a Pim-kinase mediated disease, disorder or condition. Further, several divided dosages, as well as staggered dosages, can be administered daily or sequentially, or the dose can be continuously infused, or can be a bolus injection. Further, the dosages of the crystalline form(s) and/or composition(s) of the present disclosure can be proportionally increased or decreased as indicated by the exigencies of the therapeutic or prophylactic situation.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e., beta emitters), conversion electron emitters (e.g., strontium-89 and samarium-153-EDTMP), or high-energy radiation, including without limitation x-rays, gamma rays, and neutrons.

"Prodrug" is meant to indicate a compound that may be converted under physiological conditions or by solvolysis to a biologically active compound used in the compositions described herein (e.g., a compound of structure (I) or pharmaceutically acceptable salt thereof). Thus, the term "prodrug" refers to a precursor of a biologically active compound that is pharmaceutically acceptable. In some aspects, a prodrug is inactive when administered to a subject, but is converted in vivo to an active compound used in embodiments (e.g., of compositions) described herein, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound (e.g., of a composition), as described herein, are typically prepared by modifying functional groups present in the active compound (e.g., of a composition) in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate, phosphate, and benzoate derivatives of a hydroxy functional group, or acetamide, formamide and benzamide derivatives of an amine functional group in the active compound and the like.

The term "in vivo" refers to an event that takes place in a subject's body.

"Optional" or "optionally" means that the subsequently described event or circumstances may or may not occur and that the description includes instances in which the event or circumstance does occur and instances in which the event does not. For example, "optionally substituted aryl" means that the aryl radical may or may not be substituted and that the description includes both substituted aryl radicals and aryl radicals having no substitution.

"Crystalline," as used herein, refers to a homogeneous solid formed by a repeating, three-dimensional pattern of atoms, ions or molecules having fixed distances between constituent parts. The unit cell is the simplest repeating unit in this pattern. Notwithstanding the homogenous nature of an ideal crystal, a perfect crystal rarely, if ever, exists. "Crystalline," as used herein, encompasses crystalline forms that include crystalline defects, for example, crystalline defects commonly formed by manipulating (e.g., preparing, purifying) the crystalline forms described herein. A person skilled in the art is capable of determining whether a sample of a compound is crystalline notwithstanding the presence of such defects.

The term "polymorph" refers to crystalline forms having the same chemical composition but different spatial arrangements of the molecules, atoms, and/or ions forming the crystal. Polymorphs can be characterized by analytical methods such as x-ray powder diffraction (XRPD), differential scanning calorimetry (DSC) and thermogravimetric analysis (TGA), for example, as described herein.

As used herein "solvate" refers to a crystalline form of a molecule, atom, and/or ion that further comprises molecules of a solvent or solvents incorporated into the crystalline lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Solvates may occur as dimers or oligomers comprising more than one molecule or compound within the crystalline lattice structure. In some embodiments, the compound of structure (I), or a pharmaceutically acceptable salt thereof, can be a solvate (e.g., hydrate).

As used herein "amorphous" refers to a solid form of a molecule, atom, and/or ion that is not crystalline. An amorphous solid does not display a definitive X-ray diffraction pattern.

As used herein, the term "substantially pure," when used in reference to a crystalline form of the compound of structure (I), means a crystalline form having a purity greater than about 90 weight %, including greater than about 91%, about 92%, about 93%, about 94%, about 95%, about 96%, about 97%, about 98%, and about 99% by weight, and also including equal to about 100% by weight, based on the weight of the compound. The remaining material comprises other form(s) of the compound, and/or reaction impurities and/or processing impurities arising from its preparation. For example, a crystalline form of the compound of structure (I), or a pharmaceutically acceptable salt thereof, may be deemed substantially pure in that it has a purity greater than 90 weight %, as measured by means that are at this time known and generally accepted in the art, where the remaining less than 10 weight % of material comprises other form(s) of the compound of structure (I), or a pharmaceutically acceptable salt thereof, and/or reaction impurities and/or processing impurities. Purity can be assessed using techniques known in the art, for example, using an HPLC assay described herein.

An XRPD pattern, DSC thermogram or TGA spectrum that is "substantially in accordance" with one or more figures herein showing an XRPD pattern or diffractogram or DSC thermogram or TGA spectrum, respectively, is one that would be considered by one skilled in the art to represent the same single crystalline form of the compound as the sample of the compound that provided the pattern or diffractogram or thermogram or spectrum of one or more figures provided herein. Thus, an XRPD pattern or DSC thermogram or TGA spectrum that is substantially in accordance may be identical to that of one of the figures or, more likely, may be somewhat different from one or more of the figures. For example, an XRPD pattern that is somewhat different from one or more of the figures may not necessarily show each of the lines of the diffraction pattern presented herein and/or may show a slight change in appearance or intensity of the lines or a shift in the position of the lines. These differences typically result from differences in the conditions involved in obtaining the data or differences in the purity of the sample used to obtain the data. A person skilled in the art is capable of determining if a sample of a crystalline compound is of the same form as or a different form from a form disclosed herein by comparison of the XRPD pattern or DSC thermogram or TGA spectrum of the sample and the corresponding XRPD pattern or DSC thermogram or TGA spectrum disclosed herein.

To this end, a person skilled in the art is capable of determining when an XRPD pattern described herein is "substantially lacking" a peak at a particular 2-theta angle. Thus, though a pattern may show a peak at a particular 2-theta angle, the pattern may still be "substantially lacking" a peak at that angle because, for example, such peak may be the result of an impurity in the sample, or may not be significant, as, for example, a peak whose intensity is below the limit of detection and/or within the background signal. In some embodiments, an XRPD pattern is substantially lacking a peak at an identified 2-theta angle if the relative intensity of a peak at the identified 2-theta angle is less than or equal to 20%, e.g., less than or equal to 15%, less than or equal to 10%, less than or equal to 9%, less than or equal to 8%, less than or equal to 7%, less than or equal to 6%, less than or equal to 5%, less than or equal to 4%, less than or equal to 3%, less than or equal to 2% or less than or equal to 1%.

It is to be understood that, unless otherwise indicated, any XRPD peak specified herein, with the exception of the XRPD peaks in Tables 1 or 2, the Figures or Examples, means the specified value±0.2 or less. For example, unless otherwise indicated, when an embodiment or a claim specifies a peak, in terms of 2-theta, at 20.0, this is to be understood to mean 20.0°±0.2° or less, that is a 2-theta angle of from 19.8° to 20.2°. In preferred embodiments, a 2-theta angle is the specified value±0.1° or less, in more preferred embodiments, ±0.05° or less.

The crystalline forms provided herein can also be identified on the basis of differential scanning calorimetry (DSC) and/or thermogravimetric analysis (TGA). DSC is a thermoanalytical technique in which the difference in the amount of heat required to increase the temperature of a sample is measured as a function of temperature. DSC can be used to detect physical transformations, such as phase transitions, of a sample. For example, DSC can be used to detect the temperature(s) at which a sample undergoes crystallization, melting or glass transition. It is to be understood that any temperature associated with DSC specified herein, with the exception of the DSC temperatures in the Figures or Examples, means the specified value±5° C. or less. For example, when an embodiment or a claim specifies an endothermic peak at 264° C., this is to be understood to mean 264° C.±5° C. or less, that is a temperature of from 259° C. to 269° C. In preferred embodiments, a DSC is the specified value±3° C. or less, in more preferred embodiments, ±2° C. or less.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is typically named before the group to which it attaches. For example, "cyclopropylethyl" comprises an ethyl backbone with a cyclopropyl substituent. All bonds are identified in the chemical structure diagrams herein, except for all bonds on some carbon atoms, which are assumed to be bonded to sufficient hydrogen atoms to complete the valency.

Preparation of the Compound of Structure (I)

The compounds and compositions of the present disclosure can be prepared in view of the novel methods, reaction schemes and examples provided herein. The compounds of the present disclosure can be synthesized using the methods described below, together with synthetic methods known in the art of synthetic organic chemistry, or by variations thereon as appreciated by those skilled in the art. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

The starting materials are generally available from commercial sources such as Sigma Aldrich or other commercial vendors, or are prepared as described in this disclosure, or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), Larock, R. C., Comprehensive Organic Transformations, $2^{nd}$-ed., Wiley-VCH Weinheim, Germany (1999), or Beilsteins Handbuch der organischen Chemie, 4, Aufl. ed. Springer-Verlag, Berlin, including supplements (also available via the Beilstein online database)).

In the preparation of the compound of structure (I), or its pharmaceutically acceptable salts, protection of remote functionality of intermediates may be necessary. The need for such protection will vary depending on the nature of the remote functionality and the conditions of the preparation methods. The need for such protection is readily determined by one skilled in the art. For a general description of protecting groups and their use, see Greene, T. W., et al., *Protecting Groups in Organic Synthesis*, 4th Ed., Wiley (2007). Protecting groups, such as the benzyl protecting group, can be incorporated in making of the compounds of the present disclosure.

As the examples herein show, it has been discovered that the compound of structure (I), or a pharmaceutically acceptable salt thereof, can be prepared according to new processes.

One embodiment provides a method for preparing a compound having the following structure:

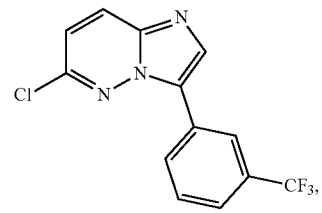 [SMILES: FC(F)(F)c1cccc(-c2cnc3ccc(Cl)nn23)c1]

or a salt thereof, comprising reacting a compound having the following structure:

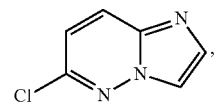

or a salt thereof, with a compound having the following structure:

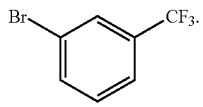

An aspect of this embodiment further comprises adding a base and a catalyst. In some more specific embodiments, the catalyst is a palladium catalyst (e.g., Pd(OAc)₂). In some embodiments, the base is K₂CO₃. In some embodiments, the method further comprises adding a phosphine reagent (e.g., tricyclohexylphosphine).

One embodiment provides a method for preparing a compound having the following structure (I):

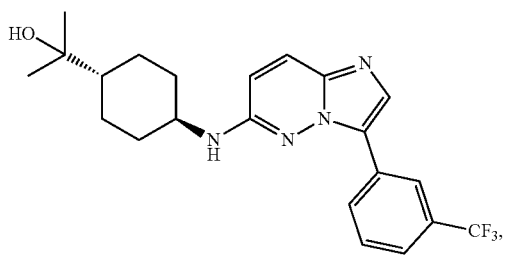

or a pharmaceutically acceptable salt thereof, the method comprising:

(i) reacting a compound having the following structure:

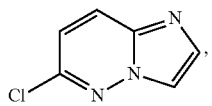

or a salt thereof, with a compound having the following structure:

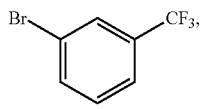

(e.g., in the presence of a base, for example, an inorganic base such as K₂CO₃, and a catalyst, for example, a palladium catalyst such as Pd(OAc)₂) to obtain a compound having the following structure:

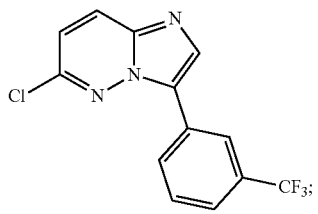 [SMILES: FC(F)(F)c1cccc(-c2cnc3ccc(Cl)nn23)c1]

and (ii) reacting the compound having the following structure:

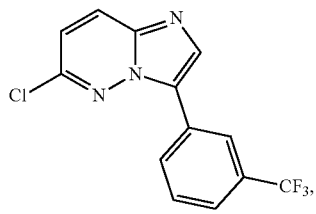 [SMILES: FC(F)(F)c1cccc(-c2cnc3ccc(Cl)nn23)c1]

or a salt thereof, with a compound having the following structure:

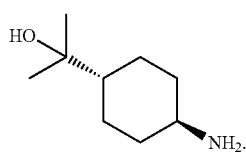

In certain embodiments, the method further comprises reacting a first compound having the following structure:

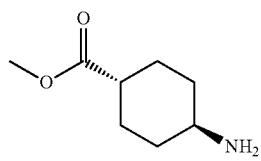

or a salt thereof, with a second base (e.g., K₂CO₃) and a benzyl halide reagent (e.g., benzyl bromide) thereby converting the first compound to a second compound having the following structure:

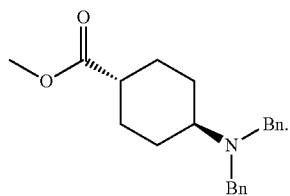 [SMILES: COC(=O)[C@H]1CC[C@H](N(Cc2ccccc2)Cc2ccccc2)CC1]

One embodiment provides a method for preparing a compound having the following structure (I):

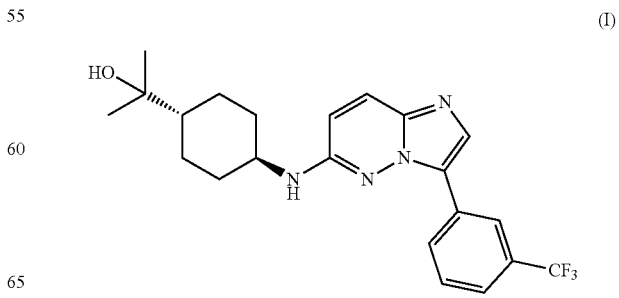

or a pharmaceutically acceptable salt thereof, the method comprising:
reacting a compound having the following structure:

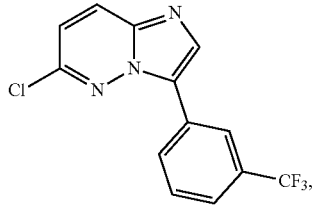

or a salt thereof, with a compound having the following structure:

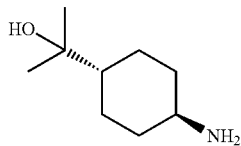

in the presence of potassium fluoride. In a more specific embodiment, the method further comprises adding a base. In certain embodiments, the base is an amine base (e.g., diisopropylethylamine).

Another embodiment provides a method for preparing a compound having the following structure (I):

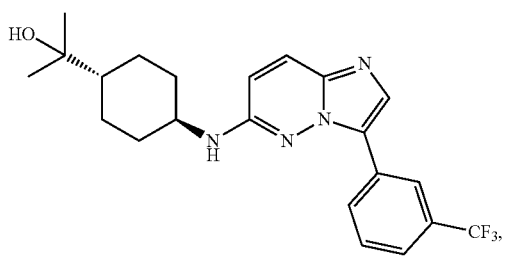

(I)

or a pharmaceutically acceptable salt thereof, the method comprising:
reacting a compound having the following structure:

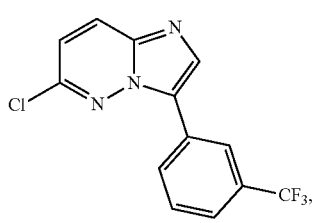 [SMILES: FC(F)(F)c1cccc(-c2cnc3ccc(Cl)nn23)c1]

or a salt thereof, with a compound having the following structure:

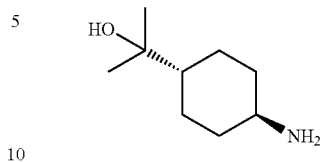

in the presence of a palladium catalyst, an alkoxide and a solvent. In some embodiments, the palladium catalyst is tris(dibenzylideneacetone)dipalladium. In some embodiments, the alkoxide is tert-butoxide (e.g., sodium tert-butoxide). In some embodiments, the solvent is toluene. In some embodiments, the reacting is conducted in the further presence of a phosphine ligand (e.g., 2,2'-bis(diphenylphosphino)-1,1'-binaphthyl) (BINAP), such as (R)-BINAP).

Another embodiment provides a method for purifying a compound having the following structure:

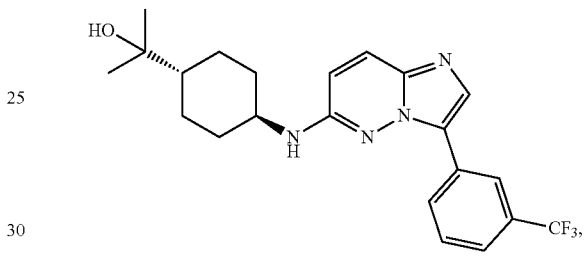

or a pharmaceutically acceptable salt thereof, the method comprising contacting a composition comprising the compound, or a pharmaceutically acceptable salt thereof, with a metal scavenging reagent. In some more specific embodiments, the metal scavenging reagent is a palladium scavenging reagent (e.g., silica thiol). In some embodiments, the method further comprises adding a solvent (e.g., a polar aprotic solvent such as ether or tetrahydrofuran). In some embodiments, the method further comprises heating the composition. In some embodiments, the method further comprises isolating the compound. In some embodiments, the method further comprises repeating the contacting step (e.g., for a total of 2-5 times).

Another embodiment provides a method for preparing a compound having the following structure:

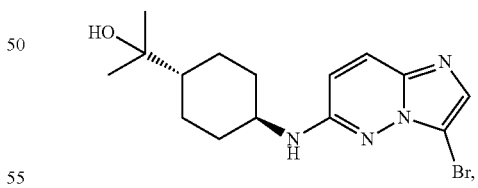

or a salt thereof, the method comprising:
reacting a compound having the following structure:

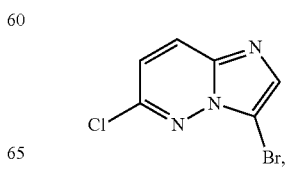

or a salt thereof, with a compound having the following structure:

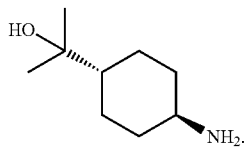

In some embodiments, the method further comprises adding a first base and a catalyst. In certain embodiments, the first base is an amine base (e.g., triethylamine or diisopropylethylamine). In some more specific embodiments, the catalyst comprises fluoride (e.g., cesium fluoride).

Another embodiment provides a method for preparing a compound having the following structure (I):

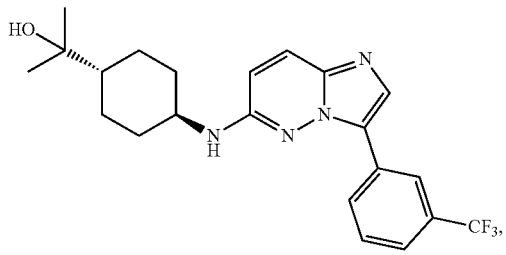
(I)

or a pharmaceutically acceptable salt thereof, the method comprising:
reacting a compound having the following structure:

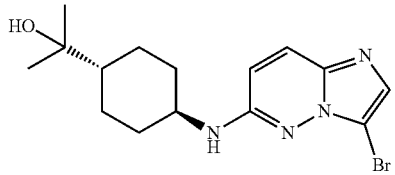
(I)

or a salt thereof, with a compound having the following structure:

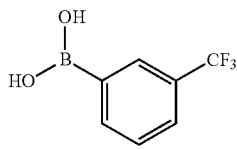

(e.g., in the presence of a palladium catalyst, such as Pd(PPh$_3$)$_2$Cl$_2$ or Pd(PPh$_3$)$_4$, and a first base, such as NaHCO$_3$ or Na$_2$CO$_3$). In some embodiments, the method further comprises adding a palladium catalyst (e.g., Pd(PPh$_3$)$_2$Cl$_2$ or Pd(PPh$_3$)$_4$) and a first base (e.g., NaHCO$_3$ or Na$_2$CO$_3$). In some embodiments, the method further comprises forming a hydrochloride salt of the compound of structure (I). In more specific embodiments, the method further comprises contacting the compound of structure (I) with hydrochloric acid. In some embodiments, the method further comprises contacting the compound of structure (I) with a seed crystal (e.g., a seed crystal of the HCl salt of the compound of structure (I)). In some embodiments, the method further comprises the method further comprises reacting a compound having the following structure:

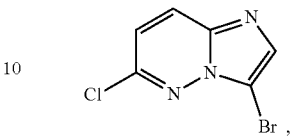

or a salt thereof, with a compound having the following structure:

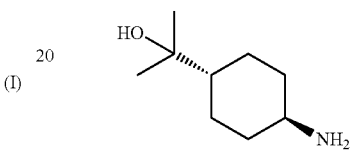

(e.g., in the presence of a second base, for example, an amine base such as diisopropylethylamine, and a catalyst, such as cesium fluoride).

Any of the methods and/or processes for preparing a compound of structure (I), or a pharmaceutically acceptable salt thereof, disclosed herein can further comprise a process for preparing a crystalline form of the compound of structure (I), or a pharmaceutically acceptable salt thereof, such as a process described herein for preparing a crystalline form of the compound of structure (I), or a pharmaceutically acceptable salt thereof, described herein.

Compositions, Combinations and Dose Forms

A "pharmaceutically acceptable carrier (diluent or excipient)" refers to media generally accepted in the art for the delivery of biologically active agents to animals, in particular, mammals, including, generally recognized as safe (GRAS) solvents, dispersion media, coatings, surfactants, antioxidants, preservatives (e.g., antibacterial agents, antifungal agents), isotonic agents, absorption delaying agents, salts, preservatives, drug stabilizers, binders, buffering agents (e.g., maleic acid, tartaric acid, lactic acid, citric acid, acetic acid, sodium bicarbonate, sodium phosphate, and the like), disintegration agents, lubricants, sweetening agents, flavoring agents, dyes, and the like and combinations thereof, as would be known to those skilled in the art (see, for example, Allen, L. V., Jr. et al., *Remington: The Science and Practice of Pharmacy* (2 Volumes), 22nd Edition, Pharmaceutical Press (2012).

Embodiments of the present disclosure are based in part on the fact that certain formulations comprising Pim kinase inhibitors unexpectedly outperform others. Specifically, embodiments of compositions comprising polyglycolized glyceride and a Pim kinase inhibitor provide higher overall exposure compared to compositions wherein other formulation agents are used in addition to or in place of polyglycolized glycerides.

Accordingly, embodiments are generally directed to a composition (e.g., a pharmaceutical composition) comprising a polyglycolized glyceride and a Pim kinase inhibitor. Certain embodiments provide a composition comprising a polyglycolized glyceride and a compound having the following structure (I):

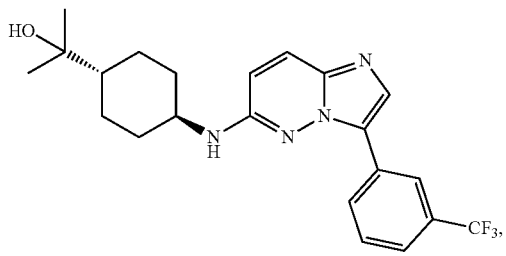 [SMILES: CC(C)(O)[C@H]1CC[C@H](Nc2ccc3ncc(-c4cccc(C(F)(F)F)c4)n3n2)CC1]

(I)

or a pharmaceutically acceptable salt thereof (e.g., the hydrochloride salt of the compound of structure (I), a crystalline form of the compound of structure (I), or a pharmaceutically acceptable salt thereof, such as Form I of the hydrochloride salt of the compound of structure (I)).

With respect to the desired application and delivery of the composition, the melting point of the polyglycolized glyceride can be selected such that the therapeutic effectiveness of the composition is optimized. Accordingly, in some embodiments, the polyglycolized glyceride has a melting point ranging from about 30 to about 50° C. In related embodiments the polyglycolized glyceride has a melting point ranging from about 31 to about 49° C., about 32 to about 48° C., about 33 to about 48° C., about 34 to about 48° C., about 35 to about 48° C., about 36 to about 48° C., about 37 to about 48° C., about 38 to about 47° C., about 39 to about 46° C., about 40 to about 45° C., about 41 to about 45° C., about 42 to about 45° C. or about 43 to about 45° C. In certain specific embodiments, the polyglycolized glyceride has a melting point of about 44° C.

Relatedly, the hydrophile/lipophile balance of the polyglycolized glyceride can also be selected to optimize embodiments of the composition. Thus, in certain embodiments, the polyglycolized glyceride has a hydrophile/lipophile balance (HLB) value ranging from about 8 to about 18, about 9 to about 17, about 9 to about 16, about 10 to about 16, about 11 to about 15, about 11 to about 15, about 12 to about 15, or about 13 to about 15. In certain specific embodiments, the polyglycolized glyceride has hydrophile/lipophile balance value of about 14.

Also provided herein are compositions (e.g., pharmaceutical compositions) comprising a crystalline form of the compound of structure (I), or a pharmaceutically acceptable salt thereof (e.g., Form I of the hydrochloride salt of the compound of structure (I)) and a pharmaceutically acceptable carrier.

Pharmaceutical compositions of the present disclosure can be formulated for particular routes of administration such as oral administration. In addition, the pharmaceutical compositions of the present disclosure can be made up in a solid form (including capsules, tablets, pills, granules, powders or suppositories). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. In some aspects, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Tablets may be either film coated or enteric coated according to methods known in the art.

Suitable compositions for oral administration include the form of tablets, lozenges, suspensions (e.g., aqueous or oily suspensions), dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients (e.g., in addition to the polyglycolized glyceride) which are suitable for the manufacture of tablets. These additional excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

In some embodiments, the composition further comprises a formulating agent, for example, a formulating agent comprising polysorbate 20, polysorbate 60, polysorbate 80, glyceryl monocaprylate, glyceryl monocaprate, glyceryl monooleate, glyceryl dibehenate, propylene glycol dilaurate, propylene glycol monocaprylate, propylene glycol monolaurate, or combinations thereof. In a specific embodiment, the formulating agent is polysorbate 20. In another specific embodiment, the formulating agent is glyceryl monocaprylate.

The ratio (e.g., weight ratio) of polyglycolized glyceride to formulating agent can be optimized to ensure effectiveness of the composition. Thus, in certain embodiments the polyglycolized glyceride and formulating agent are present in a weight ratio ranging from 2:1 to 1:1.

In some embodiments, the composition consists of the compound of structure (I) or pharmaceutically acceptable salt thereof and a polyglycolized glyceride (e.g., GELUCIRE® 44/14). In some embodiments, the composition consists essentially of the compound of structure (I) or pharmaceutically acceptable salt thereof and a polyglycolized glyceride (e.g., GELUCIRE® 44/14). In some embodiments, the composition comprises no other formulating agent, other than the polyglycolized glyceride. For example, in some embodiments, the composition comprises no other formulating agent other than polyglycolized glyceride and includes other components (e.g., sealant, such as HPMC, water, ethanol, etc.).

In some embodiments, the composition comprises the compound of structure (I) or pharmaceutically acceptable salt thereof and the polyglycolized glyceride at a weight ratio ranging from about 1:1 to about 1:10, as determined using the molecular weight of the compound of structure (I) as a free base (i.e., a molecular weight of 419.92). In some more specific embodiments, the composition comprises the compound of structure (I) or pharmaceutically acceptable salt thereof and the polyglycolized glyceride at a weight ratio ranging from about 1:1.25 to about 1:10, from about 1:1.5 to about 1:10, from about 1:1.75 to about 1:10, from about 1:2 to about 1:10, from about 1:2 to about 1:9, from about 1:2.5 to about 1:8; from about 1:3 to about 1:7, from about 1:4 to about 1:6, as determined using the molecular weight of the compound of structure (I) as a free base. In some specific embodiments, the composition comprises the compound of structure (I) or pharmaceutically acceptable salt thereof and the polyglycolized glyceride at a weight ratio of about 1:5, as determined using the molecular weight of the compound of structure (I) as a free base. In some specific embodiments, the composition comprises the compound of structure (I) or pharmaceutically acceptable salt thereof and the polyglycolized glyceride at a weight ratio of about 1:4.9, as determined using the molecular weight of the compound of structure (I) as a free base. In some specific embodiments, the composition comprises the compound of structure (I) or pharmaceutically acceptable salt thereof and the polyglycolized glyceride at a weight ratio of about 1:2.6, as determined using the molecular weight of the compound of structure (I) as a free base. In some other embodiments, the composition comprises the compound of structure (I) or pharmaceutically acceptable salt thereof and the polyglycolized glyceride at a weight ratio of about of 1:3, 1:4, 1:4.5, 1:4.9, 1:5.5, or 1:6, as determined using the molecular weight of the compound of structure (I) as a free base.

In some embodiments, the composition comprises the compound of structure (I) or pharmaceutically acceptable salt thereof and the polyglycolized glyceride at a weight ratio ranging from about 1:1.6 to about 1:3.6, as determined using the molecular weight of the compound of structure (I) as a free base. In certain embodiments, the composition comprises the compound of structure (I) or pharmaceutically acceptable salt thereof and the polyglycolized glyceride at a weight ratio ranging from about 1:2.1 to about 1:3.1, as determined using the molecular weight of the compound of structure (I) as a free base. In some more specific embodiments, the composition comprises the compound of structure (I) or pharmaceutically acceptable salt thereof and the polyglycolized glyceride at a weight ratio of about 1:2.6, as determined using the molecular weight of the compound of structure (I) as a free base.

In some embodiments, the composition comprises the compound of structure (I) or pharmaceutically acceptable salt thereof and the polyglycolized glyceride at a weight ratio ranging from about 1:1 to about 1:2.5, as determined using the molecular weight of the compound of structure (I) as a free base. In certain embodiments, the composition comprises the compound of structure (I) or pharmaceutically acceptable salt thereof and the polyglycolized glyceride at a weight ratio ranging from about 1:1.25 to about 1:2, as determined using the molecular weight of the compound of structure (I) as a free base. In some more specific embodiments, the composition comprises the compound of structure (I) or pharmaceutically acceptable salt thereof and the polyglycolized glyceride at a weight ratio of about 1:1.76, as determined using the molecular weight of the compound of structure (I) as a free base.

In some embodiments, the composition comprises the compound of structure (I) or pharmaceutically acceptable salt thereof and the polyglycolized glyceride at a weight ratio ranging from about 1:1 to about 1:10, as determined using the molecular weight of the compound of structure (I) as a hydrochloride salt (i.e., a molecular weight of 454.92). In some more specific embodiments, the composition comprises the compound of structure (I) or pharmaceutically acceptable salt thereof and the polyglycolized glyceride at a weight ratio ranging from about 1:1.25 to about 1:10, from about 1:1.5 to about 1:10, from about 1:1.75 to about 1:10, from about 1:2 to about 1:10, from about 1:2 to about 1:9, from about 1:2.5 to about 1:8; from about 1:3 to about 1:7, from about 1:4 to about 1:6, as determined using the molecular weight of the compound of structure (I) as a hydrochloride salt. In some specific embodiments, the composition comprises the compound of structure (I) or pharmaceutically acceptable salt thereof and the polyglycolized glyceride at a weight ratio of about 1:4.5, as determined using the molecular weight of the compound as a hydrochloride salt. In some other embodiments, the composition comprises the compound of structure (I) or pharmaceutically acceptable salt thereof and the polyglycolized glyceride at a weight ratio of about of 1:3, 1:4, 1:4.5, 1:5.5, or 1:6, as determined using the molecular weight of the compound as a hydrochloride salt.

In addition, the concentration of the pharmaceutically acceptable carrier(s) (e.g., polyglycolized glyceride) can be changed to suit various applications. In some embodiments the pharmaceutically acceptable carrier(s) (e.g., polyglycolized glyceride) comprises about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 50%, about 55%, about 60%, about 65%, about 70%, about 75%, about 80%, about 85%, about 90%, about 91%, about 92%, about 93%, about 94%, about 95%, about 96%, about 97%, about 98% or about 99% of the composition by v/v, w/w, v/w or w/v. In certain specific embodiments, the polyglycolized glyceride comprises 20% of the composition v/v, w/w, v/w or w/v.

One particular embodiment provides a unit dose form comprising a composition according to any one of the embodiments disclosed herein (e.g., a therapeutically effective amount of a composition according to any one of the embodiments disclosed herein). In one particular embodiment, the unit dose form is a capsule.

One particular embodiment provides a unit dose form comprising a composition, the composition comprising:

a polyglycolized glyceride (e.g., GELUCIRE® 44/14) in an amount of about 560 mg to about 600 mg (e.g., about 589 mg); and a compound having the following structure (I):

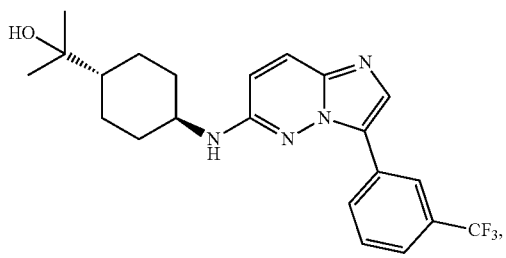

(I)

or a pharmaceutically acceptable salt thereof, in an amount of about 115 mg to about 125 mg (e.g., about 120 mg), as determined using the molecular weight of the compound of structure (I) as a free base.

In one embodiment, the unit dose form described above is a capsule. In one embodiment, the unit dosage form described above comprises the compound of structure (I) as a hydrochloride salt (e.g., Form I of the hydrochloride salt of the compound of structure (I)). In one embodiment of the unit dosage form described above, the polyglycolized glyceride is GELUCIRE® 44/14 present in an amount of about 589.56 mg. In one embodiment, the unit dosage form described above comprises the compound of structure (I), or a pharmaceutically acceptable salt thereof, in an amount of about 120 mg, as determined using the molecular weight of the compound of structure (I) as a free base.

One particular embodiment provides a capsule comprising a composition comprising:
GELUCIRE® 44/14 in an amount of about 589 mg, and
a hydrochloride salt of a compound having the following structure (I):

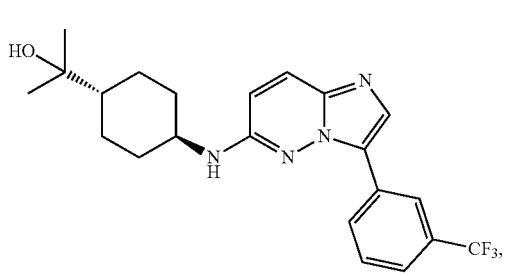

(I)

(e.g., Form I of the hydrochloride salt of the compound of structure (I)) in an amount of about 130 mg, as determined using the molecular weight of the compound as the hydrochloride salt.

The polyglycolized glyceride may be selected based on the desired characteristics and application of the composition. As such, in some embodiments, the polyglycolized glyceride comprises WL 2514CS, LABRASOL, LABRAFIL, GELUCIRE® 44/14, GELUCIRE® 33/01, GELUCIRE® 35/10, GELUCIRE® 37/02, GELUCIRE 50/13, GELUCIRE® 44/11 and mixtures thereof. In related embodiments, the polyglycolized glyceride comprises GELUCIRE® 33/01, GELUCIRE® 35/10, GELUCIRE® 37/02, GELUCIRE 50/13, GELUCIRE® 44/11 or mixtures thereof. In certain specific embodiments, the polyglycolized glyceride is GELUCIRE® 44/14.

In some embodiments, the composition is formulated for oral administration.

In still more embodiments, a composition described herein further comprises an additional therapeutic agent (e.g., anticancer agent). Non-limiting examples of such therapeutic agents are described hereinbelow.

In one particular embodiment, the present disclosure describes administration to a subject in need thereof of a unit dosage form comprising a composition, which composition comprises the compound of structure (I), or a pharmaceutically acceptable salt thereof, in an amount of about 120 mg, as determined using the molecular weight of the compound of structure (I) as a free base. In one embodiment, such unit dosage form is a capsule comprising a composition, which composition comprises the compound of structure (I), or a pharmaceutically acceptable salt thereof, in an amount of about 120 mg, as determined using the molecular weight of the compound of structure (I) as a free base.

In certain embodiments, a composition comprises a mixture of chemical components, such as carriers, stabilizers, diluents, dispersing agents, suspending agents, thickening agents, and/or excipients.

In one embodiment, the composition is formulated in aqueous solution. In specific embodiments, the aqueous solution is selected from, by way of example only, a physiologically compatible buffer, such as Hank's solution, Ringer's solution, or physiological saline buffer. In other embodiments, the composition is formulated for transmucosal administration. In specific embodiments, the composition formulated for transmucosal administration includes penetrants that are appropriate to the barrier to be permeated. In still other embodiments wherein the compositions described herein are formulated for other parenteral injection methods, appropriate formulations include aqueous or non-aqueous solutions. In specific embodiments, such compositions include physiologically compatible buffers and/or excipients.

In another embodiment, compositions described herein are formulated for oral administration. In various embodiments, the compositions described herein are formulated in oral dosage forms that include, by way of example only, tablets, powders, pills, dragees, capsules, liquids, gels, syrups, elixirs, slurries, suspensions and the like.

In one embodiment, dosage forms, such as dragee cores and tablets, are provided with one or more suitable coatings. In specific embodiments, concentrated sugar solutions are used for coating the dosage form. The sugar solutions optionally contain additional components, such as, by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active composition doses.

In certain embodiments, therapeutically effective amounts of compositions described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in ad-mixture with one or more fillers. Fillers include, by way of example only, lactose, binders such as starches, and/or lubricants such as talc or magnesium stearate and, optionally, stabilizers. In other embodiments, soft capsules contain one or more composition that is dissolved or suspended in a suitable liquid. Suitable liquids include, by way of example only, one or more fatty oil, liquid paraffin, or liquid polyethylene glycol. In addition, stabilizers are optionally added.

In one embodiment, the composition is formulated in the form of a capsule for oral administration. In more specific embodiments, the compound of structure (I) or pharmaceutically acceptable salt thereof and pharmaceutically acceptable carrier(s) (e.g., polyglycolized glyceride) are formulated into a capsule using hydroxypropyl methylcellulose (HPMC). In some specific embodiments, the compound and a polyglycolized glyceride are formulated into a capsule using hydroxypropyl methylcellulose (HPMC) at a weight ratio of 1:5 (as calculated using the molecular weight of the compound of structure (I) as a free base).

Capsules can be sealed according to methods known in the art. For example, hydroxypropyl methylcellulose (HPMC) can be dissolved in ethanol and applied as a sealant. In some embodiments, the capsule comprises a sealant (e.g., HPMC). In some more specific embodiments, the capsule comprises about 5.0±0.5 wt % of sealant. In some embodiments, the capsule comprises about 5.0±0.5 mg of sealant.

The composition may also be formulated for a route of administration other than oral. Other suitable routes of administration include intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a composition described herein is administered in a local rather than systemic manner, for example, via injection of the composition directly into an organ, often in a depot preparation or sustained release formulation. In specific embodiments, long-acting formulations are administered by implantation (for example, subcutaneously or intramuscularly) or by intramuscular injection. Furthermore, in other embodiments, the composition is delivered in the form of a targeted drug delivery system, for example, a liposome coated with organ-specific antibody. In such embodiments, the liposomes are targeted to and taken up selectively by the organ. In yet other embodiments, the composition is provided in the form of a rapid release formulation, in the form of an extended release formulation, or in the form of an intermediate release formulation. In yet other embodiments, the composition is administered topically.

In other embodiments, the composition is formulated for transmucosal administration. In specific embodiments, transmucosal formulations include penetrants that are appropriate to the barrier to be permeated. In still other embodiments, wherein the composition is formulated for other parenteral injections; appropriate formulations include aqueous or non-aqueous solutions. In specific embodiments, such solutions include physiologically compatible buffers and/or excipients.

In other embodiments, compositions described herein are formulated for buccal or sublingual administration. Formulations suitable for buccal or sublingual administration include, by way of example only, tablets, lozenges, or gels.

In still other embodiments, the composition described herein is formulated for parental injection, including bolus injection or continuous infusion. In specific embodiments, formulations for injection are presented in unit dosage form (e.g., in ampoules) or in multi-dose containers. Preservatives are, optionally, added to the injection formulations. In still other embodiments, the compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In additional embodiments, suspensions are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the active to allow for the preparation of highly concentrated solutions. Alternatively, in other embodiments, the active ingredient is in powder form for constitution with a suitable vehicle, e.g., sterile pyrogen-free water, before use.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain compositions described herein comprise a mucoadhesive polymer, selected, for example, from carboxymethylcellulose, carbomer (acrylic acid polymer), poly (methylmethacrylate), polyacrylamide, polycarbophil, acrylic acid/butyl acrylate copolymer, sodium alginate and dextran.

Useful compositions also, optionally, include solubilizing agents to aid in the solubility of the compound of structure (I) or pharmaceutically acceptable salt thereof. The term "solubilizing agent" generally includes agents that result in formation of a micellar solution or a true solution of a compound. Certain acceptable nonionic surfactants, for example, polysorbate 80, are useful as solubilizing agents, as can be ophthalmically acceptable glycols, polyglycols, e.g., polyethylene glycol 400, and glycol ethers.

Additionally, in some embodiments, the compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Still other embodiments of the composition include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In certain embodiments, the compositions described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

In some embodiments, the concentration of the compound of structure (I) or pharmaceutically acceptable salt thereof in the composition is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of the compound of structure (I) or pharmaceutically acceptable salt thereof in the composition is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of the compound of structure (I) or pharmaceutically acceptable salt thereof in the composition is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some specific embodiments, the concentration of the compound of structure (I) or pharmaceutically acceptable salt thereof in the composition ranges from about 10 wt % to about 40 wt %, as determined using the molecular weight of the compound of structure (I) as a hydrochloride salt. In some specific embodiments, the concentration of the compound of structure (I) or pharmaceutically acceptable salt thereof in the composition ranges from about 10 wt % to about 25 wt %, as determined using the molecular weight of the compound of structure (I) as a hydrochloride salt. In some other embodiments, the composition comprises the compound of structure (I) or pharmaceutically acceptable salt thereof in a concentration ranging from about 14 wt % to about 22 wt %, as determined using the molecular weight of the compound of structure (I) as a hydrochloride salt. In some other embodiments, the composition comprises the compound of structure (I) or pharmaceutically acceptable salt thereof in a concentration ranging from about 18 wt % to about 19 wt %, as determined using the molecular weight of the compound of structure (I) as a hydrochloride salt. In some other embodiments, the composition comprises the compound of structure (I) or pharmaceutically acceptable salt thereof in a concentration of about 18.38 wt %, as determined using the molecular weight of the compound of structure (I) as a hydrochloride salt. In some more specific embodiments, the composition comprises the compound of structure (I) or pharmaceutically acceptable salt thereof in a concentration of about 18.38±0.2 wt %, as determined using the molecular weight of the compound of structure (I) as a hydrochloride salt. In some more specific embodiments, the composition comprises the compound of structure (I) or pharmaceutically acceptable salt thereof in a concentration of about 18.38±0.4 wt %, as determined using the molecular weight of the compound of structure (I) as a hydrochloride salt. In some more specific embodiments, the composition comprises the compound of structure (I) or pharmaceutically acceptable salt thereof in a concentration of about 18.38±0.8 wt %, as determined using the molecular weight of the compound of structure (I) as a hydrochloride salt. In some embodiments, the composition comprises the compound of structure (I) or pharmaceutically acceptable salt thereof in a concentration of about 18.12 wt %, as determined using the molecular weight of the compound of structure (I) as a hydrochloride salt. In some more specific embodiments, the composition comprises the compound of structure (I) or pharmaceutically acceptable salt thereof in a concentration of about 18.12±0.2 wt %, as determined using the molecular weight of the compound of structure (I) as a hydrochloride salt. In some more specific embodiments, the composition comprises the compound of structure (I) or pharmaceutically acceptable salt thereof in a concentration of about 18.12±0.4 wt %, as determined using the molecular weight of the compound of structure (I) as a hydrochloride salt. In some more specific embodiments, the composition comprises the compound of structure (I) or pharmaceutically acceptable salt thereof in a concentration of about 18.12±0.8 wt %, as determined using the molecular weight of the compound of structure (I) as a hydrochloride salt.

In some embodiments, the composition comprises the polyglycolized glyceride in a concentration ranging from about 50 wt % to about 90 wt %. In some embodiments, the composition comprises the polyglycolized glyceride in a concentration ranging from about 75 wt % to about 90 wt %. In some embodiments, the composition comprises the polyglycolized glyceride in a concentration ranging from about 78 wt % to about 84 wt %. In some embodiments, the composition comprises the polyglycolized glyceride in a concentration ranging from about 81 wt % to about 82 wt %. In some more specific embodiments, the composition comprises the polyglycolized glyceride at a concentration of about 81.62 wt %. In some embodiments, the composition comprises the polyglycolized glyceride at a concentration of about 81.62±0.5 wt %. In some embodiments, the composition comprises the polyglycolized glyceride at a concentration of about 81.62±1 wt %. In some embodiments, the composition comprises the polyglycolized glyceride at a concentration of about 81.62±2 wt %. In some more specific embodiments, the composition comprises the polyglycolized glyceride at a concentration of about 81.88 wt %. In some embodiments, the composition comprises the polyglycolized glyceride at a concentration of about 81.88±0.5 wt %. In some embodiments, the composition comprises the polyglycolized glyceride at a concentration of about 81.88±1 wt %. In some embodiments, the composition comprises the polyglycolized glyceride at a concentration of about 81.88±2 wt %.

In some specific embodiments, the concentration of the compound of structure (I) or pharmaceutically acceptable salt thereof in the composition ranges from about 15 wt % to about 35 wt %, as determined using the molecular weight of the compound of structure (I) as a hydrochloride salt. In some other embodiments, the composition comprises the compound of structure (I) or pharmaceutically acceptable salt thereof in a concentration ranging from about 20 wt % to about 30 wt %, as determined using the molecular weight of the compound of structure (I) as a hydrochloride salt. In some other embodiments, the composition comprises the compound of structure (I) or pharmaceutically acceptable salt thereof in a concentration of about 25 wt %, as determined using the molecular weight of the compound of structure (I) as a hydrochloride salt. In some more specific embodiments, the composition comprises the compound of structure (I) or pharmaceutically acceptable salt thereof in a concentration of about 25±0.2 wt %, as determined using the molecular weight of the compound of structure (I) as a hydrochloride salt. In some more specific embodiments, the composition comprises the compound of structure (I) or pharmaceutically acceptable salt thereof in a concentration of about 25±0.4 wt %, as determined using the molecular weight of the compound of structure (I) as a hydrochloride salt. In some more specific embodiments, the composition comprises the compound of structure (I) or pharmaceutically acceptable salt thereof in a concentration of about 25±0.8 wt %, as determined using the molecular weight of the compound of structure (I) as a hydrochloride salt.

In some embodiments, the composition comprises the polyglycolized glyceride in a concentration ranging from about 65 wt % to about 85 wt %. In some embodiments, the composition comprises the polyglycolized glyceride in a concentration ranging from about 70 wt % to about 80 wt %. In some more specific embodiments, the composition comprises the polyglycolized glyceride at a concentration of about 75 wt %. In some embodiments, the composition comprises the polyglycolized glyceride at a concentration of about 75±0.5 wt %. In some embodiments, the composition comprises the polyglycolized glyceride at a concentration of about 75±1 wt %. In some embodiments, the composition comprises the polyglycolized glyceride at a concentration of about 75±2 wt %.

In some specific embodiments, the concentration of the compound of structure (I) or pharmaceutically acceptable salt thereof in the composition ranges from about 23.3 wt % to about 43.3 wt %, as determined using the molecular weight of the compound of structure (I) as a hydrochloride salt. In some other embodiments, the composition comprises the compound of structure (I) or pharmaceutically acceptable salt thereof in a concentration ranging from about 28.3 wt % to about 38.3 wt %, as determined using the molecular weight of the compound of structure (I) as a hydrochloride salt. In some other embodiments, the composition comprises the compound of structure (I) or pharmaceutically acceptable salt thereof in a concentration of about 33.3 wt %, as determined using the molecular weight of the compound of structure (I) as a hydrochloride salt. In some more specific embodiments, the composition comprises the compound of structure (I) or pharmaceutically acceptable salt thereof in a concentration of about 33.3±0.2 wt %, as determined using the molecular weight of the compound of structure (I) as a hydrochloride salt. In some more specific embodiments, the composition comprises the compound of structure (I) or pharmaceutically acceptable salt thereof in a concentration of about 33.3±0.4 wt %, as determined using the molecular weight of the compound of structure (I) as a hydrochloride salt. In some more specific embodiments, the composition comprises the compound of structure (I) or pharmaceutically acceptable salt thereof in a concentration of about 33.3±0.8 wt %, as determined using the molecular weight of the compound of structure (I) as a hydrochloride salt.

In some embodiments, the composition comprises the polyglycolized glyceride in a concentration ranging from about 56.7 wt % to about 76.7 wt %. In some embodiments, the composition comprises the polyglycolized glyceride in a concentration ranging from about 61.7 wt % to about 71.7 wt %. In some more specific embodiments, the composition comprises the polyglycolized glyceride at a concentration of about 66.7 wt %. In some embodiments, the composition comprises the polyglycolized glyceride at a concentration of about 66.7±0.5 wt %. In some embodiments, the composition comprises the polyglycolized glyceride at a concentration of about 66.7±1 wt %. In some embodiments, the composition comprises the polyglycolized glyceride at a concentration of about 66.7±2 wt %.

In some embodiments, the composition comprises from about 100 mg to about 300 mg of the compound of structure (I) or pharmaceutically acceptable salt thereof, as determined using the molecular weight of the hydrochloride salt of the compound of structure (I). In some embodiments, the composition comprises from about 100 mg to about 160 mg of the compound of structure (I) or pharmaceutically acceptable salt thereof, as determined using the molecular weight of the hydrochloride salt of the compound of structure (I). In some embodiments, the composition comprises from about 120 mg to about 140 mg of the compound of structure (I) or pharmaceutically acceptable salt thereof, as determined using the molecular weight of the hydrochloride salt of the compound of structure (I). In some specific embodiments, the composition comprises about 130.44 mg of the compound of structure (I) or pharmaceutically acceptable salt thereof, as determined using the molecular weight of the hydrochloride salt of the compound of structure (I). In some embodiments, the composition comprises about 130.44±0.5 mg of the compound of structure (I) or pharmaceutically acceptable salt thereof, as determined using the molecular weight of the hydrochloride salt of the compound of structure (I). In some embodiments, the composition comprises about 130.44±1 mg of the compound of structure (I) or pharmaceutically acceptable salt thereof, as determined using the molecular weight of the hydrochloride salt of the compound of structure (I). In some embodiments, the composition comprises about 130.44±3 mg of the compound of structure (I) or pharmaceutically acceptable salt thereof, as determined using the molecular weight of the hydrochloride salt of the compound of structure (I).

In some embodiments, the composition comprises from about 100 mg to about 300 mg of the compound of structure (I) or pharmaceutically acceptable salt thereof, as determined using the molecular weight of the compound of structure (I) as a free base. In some embodiments, the composition comprises from about 100 mg to about 150 mg of the compound of structure (I) or pharmaceutically acceptable salt thereof, as determined using the molecular weight of the compound of structure (I) as a free base. In some embodiments, the composition comprises from about 115 mg to about 125 mg of the compound of structure (I) or pharmaceutically acceptable salt thereof, as determined using the molecular weight of the compound of structure (I) as a free base. In some specific embodiments, the composition comprises about 120 mg of the compound of structure (I) or pharmaceutically acceptable salt thereof, as determined using the molecular weight of the compound of structure (I) as a free base. In some embodiments, the composition comprises about 120±0.5 mg of the compound of structure (I) or pharmaceutically acceptable salt thereof, as determined using the molecular weight of the compound of structure (I) as a free base. In some embodiments, the composition comprises about 120±1 mg of the compound of structure (I) or pharmaceutically acceptable salt thereof, as determined using the molecular weight of the compound of structure (I) as a free base. In some embodiments, the composition comprises about 120±3 mg of the compound of structure (I) or pharmaceutically acceptable salt thereof, as determined using the molecular weight of the compound of structure (I) as a free base.

In some embodiments, the composition comprises from about 500 mg to about 700 mg of the polyglycolized glyceride. In some embodiments, the composition comprises from about 550 mg to about 650 mg of the polyglycolized glyceride. In some embodiments, the composition comprises from about 560 mg to about 600 mg of the polyglycolized glyceride. In some embodiments, the composition comprises from about 585 mg to about 590 mg of the polyglycolized glyceride. In some embodiments, the composition comprises about 587.7 mg of the polyglycolized glyceride. In some embodiments, the composition comprises about 587.7±1 mg of the polyglycolized glyceride. In some embodiments, the composition comprises about 587.7±2 mg of the polyglycolized glyceride. In some embodiments, the composition comprises about 587.7±5 mg of the polyglycolized glyceride. In some embodiments, the composition comprises about 589.56 mg of the polyglycolized glyceride. In some embodiments, the composition comprises about 589.56±1 mg of the polyglycolized glyceride. In some embodiments, the composition comprises about 589.56±2 mg of the polyglycolized glyceride. In some embodiments, the composition comprises about 589.56±5 mg of the polyglycolized glyceride.

In some embodiments, the composition comprises from about 160 mg to about 200 mg of the compound of structure (I) or pharmaceutically acceptable salt thereof, as determined using the molecular weight of the compound of structure (I) as a free base. In some embodiments, the composition comprises from about 175 mg to about 185 mg of the compound of structure (I) or pharmaceutically acceptable salt thereof, as determined using the molecular weight of the compound of structure (I) as a free base. In some specific embodiments, the composition comprises about 180 mg of the compound of structure (I) or pharmaceutically acceptable salt thereof, as determined using the molecular weight of the compound of structure (I) as a free base. In some embodiments, the composition comprises about 180±0.5 mg of the compound of structure (I) or pharmaceutically acceptable salt thereof, as determined using the molecular weight of the compound of structure (I) as a free base. In some embodiments, the composition comprises about 180±1 mg of the compound of structure (I) or pharmaceutically acceptable salt thereof, as determined using the molecular weight of the compound of structure (I) as a free base. In some embodiments, the composition comprises about 180±3 mg of the compound of structure (I) or pharmaceutically acceptable salt thereof, as determined using the molecular weight of the compound of structure (I) as a free base.

In some embodiments, the composition comprises from about 520 mg to about 560 mg of the polyglycolized glyceride. In some embodiments, the composition comprises from about 535 mg to about 545 mg of the polyglycolized glyceride. In some embodiments, the composition comprises about 540 mg of the polyglycolized glyceride. In some embodiments, the composition comprises about 540±1 mg of the polyglycolized glyceride. In some embodiments, the composition comprises about 540±2 mg of the polyglycolized glyceride. In some embodiments, the composition comprises about 540±5 mg of the polyglycolized glyceride.

In some embodiments, the composition comprises from about 220 mg to about 260 mg of the compound of structure (I) or pharmaceutically acceptable salt thereof, as determined using the molecular weight of the compound of structure (I) as a free base. In some embodiments, the composition comprises from about 235 mg to about 245 mg of the compound of structure (I) or pharmaceutically acceptable salt thereof, as determined using the molecular weight of the compound of structure (I) as a free base. In some specific embodiments, the composition comprises about 240 mg of the compound of structure (I) or pharmaceutically acceptable salt thereof, as determined using the molecular weight of the compound of structure (I) as a free base. In some embodiments, the composition comprises about 240±0.5 mg of the compound of structure (I) or pharmaceutically acceptable salt thereof, as determined using the molecular weight of the compound of structure (I) as a free base. In some embodiments, the composition comprises about 240±1 mg of the compound of structure (I) or pharmaceutically acceptable salt thereof, as determined using the molecular weight of the compound of structure (I) as a free base. In some embodiments, the composition comprises about 240±3 mg of the compound of structure (I) or pharmaceutically acceptable salt thereof, as determined using the molecular weight of the compound of structure (I) as a free base.

In some embodiments, the composition comprises from about 440 mg to about 500 mg of the polyglycolized glyceride. In some embodiments, the composition comprises from about 475 mg to about 485 mg of the polyglycolized glyceride. In some embodiments, the composition comprises about 480 mg of the polyglycolized glyceride. In some embodiments, the composition comprises about 480±1 mg of the polyglycolized glyceride. In some embodiments, the composition comprises about 480±2 mg of the polyglycolized glyceride. In some embodiments, the composition comprises about 480±5 mg of the polyglycolized glyceride.

The compound of structure (I) used in a composition described herein may be in free base form, or in a pharmaceutically acceptable salt form, or in crystalline form, or any combination thereof. In some embodiments, the compound of structure (I) is present as a free base. In some embodiments, the compound of structure (I) is present as a salt. In some embodiments, the compound of structure (I) is present as a hydrochloride salt. In some embodiments, the compound of structure (I) is present as a crystalline, salt form. In some embodiments, the compound of structure (I) is present as Form I of the hydrochloride salt of the compound of structure (I).

Crystalline Forms

Different crystalline forms of the compound of structure (I) and its pharmaceutically acceptable salts, including the hydrochloric acid salt of the compound of structure (I), have been discovered. Accordingly, provided herein is a crystalline form of a compound of structure (I), or a pharmaceutically acceptable salt thereof (e.g., a hydrochloride salt thereof).

While crystallization is often performed on organic compounds, it is not predictable in advance as to which conditions will provide suitable conditions to lead to formation of a particular crystalline form. Further, it is not predictable as to which particular crystalline form will provide the necessary mixture of physical properties to yield a desirable drug dosage form once formulated.

Crystallization of the hydrochloric acid salt of the compound of structure (I) in selected solvents and under selected conditions resulted in the discovery of crystalline Forms I and II, with distinct physical behavior.

Experimental Instrumentation and Conditions:

X-ray powder diffraction was performed with a Rigaku D/MAS 2200 X-ray powder diffractometer. The standard measuring conditions were: X-ray generator: Cu, kα, (λ=1.54056 Å); tube voltage: 40 kV, tube current: 20 mA; DivSlit: 1 deg.; DivH.L.Slit: 10 mm; SctSlit:1 deg.; RecSlit: 0.15 mm; fixed monocromator; scanning scope: 4-40 deg.; scanning step: 10 deg/minute. Accordingly, when a crystalline form described herein is characterized by its X-ray powder diffraction pattern, for example, by listing selected peaks, the pattern and/or peaks are, in some embodiments, as measured by X-ray powder diffraction using an x-ray wavelength of 1.5406 Å.

Polarized light microscopy was performed on a Nikon LV100 Polarized Light Microscope equipped with a 5 megapixel CCD and an ocular lens of 10× and an objective lens of 20×.

Differential Scanning calorimetry (DSC) was performed with a TA Q2000 DSC with a heating rate of 10° C./minute over the range of 30° C. to 300° C. Accordingly, when a crystalline form described herein is characterized by a DSC thermogram, for example, by listing temperatures associate with various events, the temperatures and/or thermogram are, in some embodiments, as measured by DSC over a range of 30° C. to 300° C. using a heating rate of 10° C./minute.

Thermogravimetric Analysis (TGA) was performed with a TA Q5000 IR TGA, with a heating rate of 10° C./minute over the range of 30° C. to 300° C. Accordingly, when a crystalline form described herein is characterized by a TGA spectrum, the spectrum is, in some embodiments, as measured by TGA over a range of 30° C. to 300° C. using a heating rate of 10° C./minute.

Amorphous Form:

The amorphous, solid form of the hydrochloric acid salt of the compound of structure (I) was obtained, for example, using the slow evaporation method described in Example 12 by allowing a solution of the hydrochloric acid salt of the compound of structure (I) in methanol to slowly evaporate. The product thus obtained had an X-ray powder diffraction pattern with no peaks (FIG. 18), thus revealing that the reaction product was in amorphic form. Accordingly, in some embodiments, the compound of structure (I), or a pharmaceutically acceptable salt thereof (e.g., the hydrochloride salt), is in amorphous form. The compound of structure (I) is also referred to herein as 2-((1R,4R)-4-((3-(3-(trifluoromethyl)phenyl)imidazo[1,2-b]pyridazin-6-yl)amino)cyclohexyl)propan-2-ol.

Crystalline Form I:

In some embodiments of the invention, the crystalline form of the hydrochloric acid salt of the compound of structure (I) comprises, consists of or consists essentially of Form I. In some embodiments, the crystalline form of the hydrochloric acid salt of the compound of structure (I) is Form I. Form I can be generally prepared by suspending the hydrochloric acid salt of the compound of structure (I) in a solution of ethyl acetate and methanol and optionally agitating the resulting mixture.

Crystalline Form I comprises an X-ray powder diffraction pattern as shown in FIG. 1. The peak assignments corresponding to the diffraction pattern for crystalline Form I and their relative intensities are listed in Table 1.

TABLE 1

Peak Assignments and Intensities of the XRPD Pattern for Crystalline Form I.

| Angle 2-theta ° | d value Angstrom | Intensity Cps | Intensity % % |
|---|---|---|---|
| 8.5 | 10.5 | 16 | 13 |
| 10.1 | 8.8 | 21 | 17 |
| 11.7 | 7.6 | 33 | 27 |
| 14.4 | 6.2 | 19 | 15 |
| 16.3 | 5.4 | 42 | 34 |
| 16.7 | 5.3 | 19 | 15 |
| 17.8 | 5.0 | 67 | 55 |
| 19.3 | 4.6 | 45 | 37 |
| 19.9 | 4.5 | 85 | 69 |
| 21.5 | 4.1 | 123 | 100 |
| 24.4 | 3.7 | 43 | 35 |
| 27.1 | 3.3 | 25 | 20 |
| 29.7 | 3.0 | 19 | 15 |
| 35.3 | 2.5 | 24 | 20 |

In some embodiments, crystalline Form I is characterized by an X-ray powder diffraction pattern, comprising peaks, in terms of 2-theta, at 21.5±0.2°, 19.9±0.2°, and 17.8±0.2°. In some embodiments, crystalline Form I is further characterized by an X-ray powder diffraction comprising peaks, in terms of 2-theta, at 16.3±0.2°, 19.3±0.2°, and 24.4±0.2°. In some embodiments, crystalline Form I is further characterized by an X-ray powder diffraction pattern comprising peaks, in terms of 2-theta, at 10.1±0.2°, 11.7±0.2°, 14.4±0.2°, and 16.7±0.2°. In some embodiments, crystalline Form I is characterized by an X-ray powder diffraction pattern, comprising a peak, in terms of 2-theta, at 19.3±0.2°. In some embodiments, crystalline Form I is characterized by an X-ray powder diffraction pattern, comprising a peak, in terms of 2-theta, at 24.4±0.2°. In some embodiments, crystalline Form I is characterized by an X-ray powder diffraction pattern, comprising a peak, in terms of 2-theta, at 16.3±0.2°.

In some embodiments, crystalline Form I is characterized by an X-ray powder diffraction pattern comprising at least three peaks (e.g., three peaks, at least four peaks, four peaks, at least five peaks, five peaks, six peaks) at 2-theta angles selected from the group consisting of 24.4±0.2°, 21.5±0.2°, 19.9±0.2°, 19.3±0.2°, 17.8±0.2° and 16.3±0.2°.

In any of the embodiments of crystalline Form I described herein, crystalline Form I is further characterized by an X-ray diffraction pattern substantially lacking a peak, in terms of 2-theta, at 15.7±0.2°. In any of the embodiments of crystalline Form I described herein, crystalline Form I is further characterized by an X-ray diffraction pattern substantially lacking a peak, in terms of 2-theta, at 17.0±0.2°. In any of the embodiments of crystalline Form I described herein, crystalline Form I is further characterized by an X-ray diffraction pattern substantially lacking a peak, in terms of 2-theta, at 19.0±0.2°.

In some embodiments, crystalline Form I is characterized by an X-ray powder diffraction pattern substantially in accordance with that shown in FIG. 1.

The graph of differential scanning calorimetry of crystalline Form I, performed at rate of 10° C./minute with heating from 30° C. to 300° C., is shown in FIG. 2. A peak is seen at about 226.9° C., and correlates with an endothermic event. The peak onset is seen at 226.2° C., and correlates with the melting temperature of crystalline Form I. Accordingly, in some embodiments, crystalline Form I is characterized by a differential scanning calorimetry thermogram comprising an endothermic event at 226.9±3° C. In some embodiments, crystalline Form I has a melting temperature of 226±3° C. (e.g., 226.2±3° C.), for example, as measured by differential scanning calorimetry. In some embodiments, crystalline Form I has a DSC thermogram substantially in accordance with that shown in FIG. 2.

Thermogravimetric analysis graph of Form I is shown in FIG. 3. A mass loss of about 0.4% between 30° C. and 118° C. is observed. In some embodiments, crystalline Form I has a TGA diagram substantially in accordance with that shown in FIG. 3.

Figure 4:
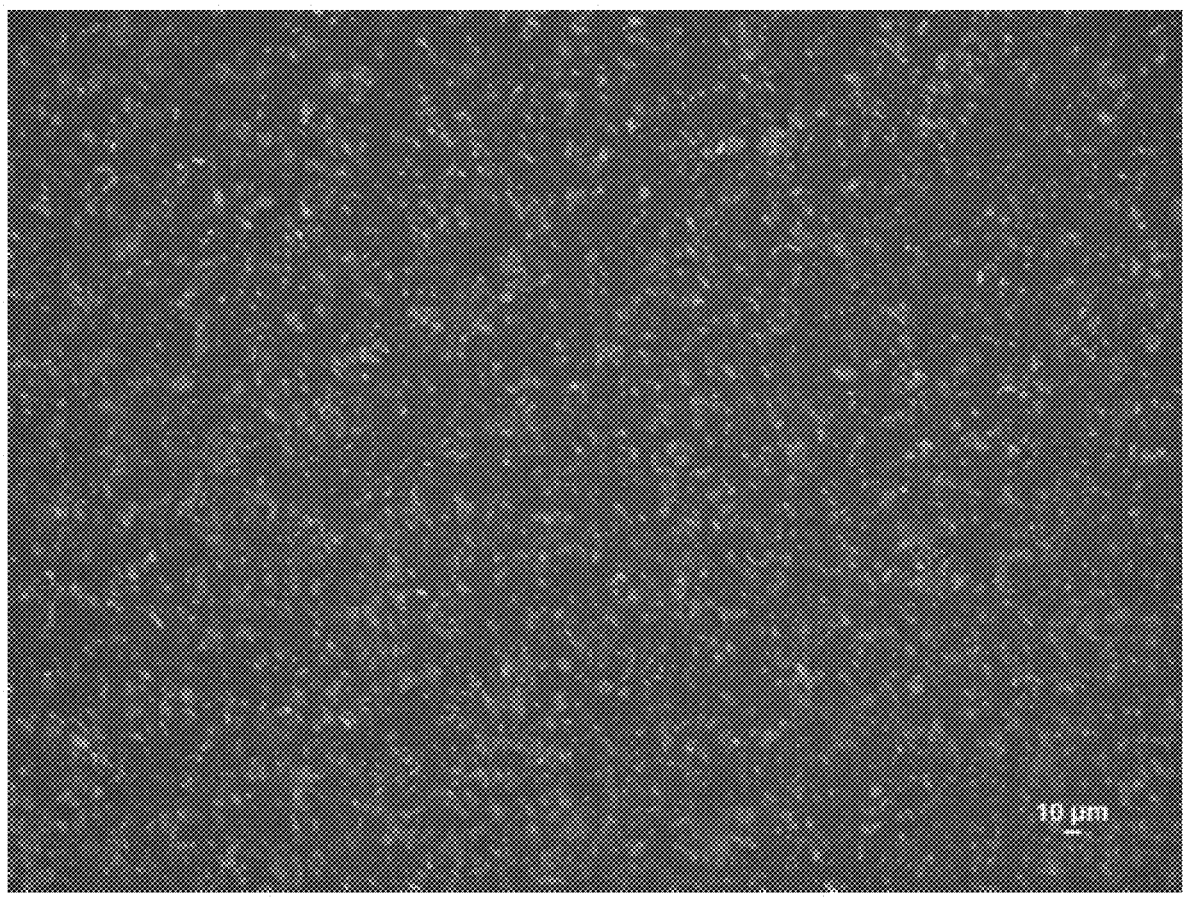
FIG. 4 is a graphical representation of a polarized light microscopy image of crystalline Form I.

The polarized light microscopy (PLM) image of crystalline Form I is shown in FIG. 4.

Form I shows good crystallinity by XRPD and birefringence by PLM.

Crystalline Form I can be prepared according to a process comprising precipitating said crystalline form from a solution or suspension comprising the hydrochloric acid salt of 2-((1R,4R)-4-((3-(3-(trifluoromethyl)phenyl) imidazo[1,2-b]pyridazin-6-yl)amino)cyclohexyl)propan-2-ol and a non-aqueous medium. In some embodiments, the non-aqueous medium comprises methanol (MeOH), ethanol (EtOH), isopropyl alcohol (IPA), 1-butanol, acetonitrile (ACN), methyl ethyl ketone (MEK), methyl isobutyl ketone (MIBK), ethyl acetate (EtOAc), isopropyl acetate (iPrOAc), methyl tert-butyl ether (MTBE), 2-methyltetrahydrofuran (2-MeTHF), dimethylformamide (DMF), N-methyl-2-pyrrolidone (NMP), dimethyl sulfoxide (DMSO), dichloromethane (DCM), 1,4-dioxane, toluene, heptane, tetrahydrofuran (THF) or acetone, or a combination thereof. In some embodiments, the non-aqueous medium is a mixture of MeOH and EtOAc.

Some embodiments of a process for preparing crystalline Form I comprise precipitating said crystalline form from a solution comprising the hydrochloric acid salt of 2-((1R,4R)-4-((3-(3-(trifluoromethyl)phenyl) imidazo[1,2-b]pyridazin-6-yl)amino)cyclohexyl)propan-2-ol and a non-aqueous medium (e.g., a solution comprising the hydrochloric acid salt of 2-((1R,4R)-4-((3-(3-(trifluoromethyl)phenyl) imidazo[1,2-b]pyridazin-6-yl)amino)cyclohexyl)propan-2-ol, methanol and ethyl acetate). Some embodiments comprise precipitating said crystalline form from a suspension comprising the hydrochloric acid salt of 2-((1R,4R)-4-((3-(3-(trifluoromethyl)phenyl) imidazo[1,2-b]pyridazin-6-yl)amino)cyclohexyl)propan-2-ol and a non-aqueous medium. Some embodiments further comprise cooling the solution or suspension to about 4° C. Some embodiments further comprise heating the solution or suspension, for example, to about 50° C. to about 75° C. (e.g., prior to cooling the solution or suspension). Some embodiments further comprise contacting the solution or suspension with a seed crystal of the crystalline form. Some embodiments further comprise contacting a solution or suspension comprising the free base of 2-((1R,4R)-4-((3-(3-(trifluoromethyl)phenyl) imidazo[1,2-b]pyridazin-6-yl)amino)cyclohexyl)propan-2-ol and a non-aqueous medium with hydrochloric acid to produce the solution or suspension comprising the hydrochloric acid salt of 2-((1R,4R)-4-((3-(3-(trifluoromethyl)phenyl) imidazo[1,2-b]pyridazin-6-yl)amino)cyclohexyl)propan-2-ol and a non-aqueous medium.

Crystalline Form II:

In some embodiments of the invention, the crystalline form of the hydrochloric acid salt of the compound of structure (I) comprises, consists of or consists essentially of Form II. In some embodiments, the crystalline form of the hydrochloric acid salt of the compound of structure (I) is Form II. Form II can be generally prepared by combining the hydrochloric acid salt of the compound of structure (I) with a solvent such as water and optionally agitating the resulting mixture.

Crystalline Form II comprises an X-ray powder diffraction pattern as shown in FIG. 5. The peak assignments corresponding to the diffraction pattern for crystalline Form II and their relative intensities are listed in Table 2.

TABLE 2

Peak Assignments and Intensities of the XRPD Pattern for Crystalline Form II.

| Angle 2-theta ° | d value Angstrom | Intensity Cps | Intensity % % |
|---|---|---|---|
| 8.4 | 10.6 | 105 | 17 |
| 10.0 | 8.9 | 63 | 10 |
| 11.6 | 7.6 | 141 | 23 |
| 14.3 | 6.2 | 118 | 19 |
| 15.7 | 5.6 | 201 | 33 |
| 16.3 | 5.4 | 152 | 25 |
| 16.6 | 5.3 | 146 | 24 |
| 17.0 | 5.2 | 129 | 21 |
| 17.7 | 5.0 | 233 | 38 |
| 19.0 | 4.7 | 186 | 30 |
| 19.3 | 4.6 | 211 | 34 |
| 19.9 | 4.5 | 392 | 63 |
| 21.0 | 4.2 | 98 | 16 |
| 21.5 | 4.1 | 619 | 100 |
| 22.4 | 4.0 | 105 | 17 |
| 23.4 | 3.8 | 45 | 7 |
| 24.3 | 3.7 | 237 | 38 |
| 25.0 | 3.6 | 77 | 12 |
| 25.8 | 3.4 | 81 | 13 |
| 26.3 | 3.4 | 71 | 12 |
| 27.1 | 3.3 | 120 | 19 |
| 29.7 | 3.0 | 67 | 11 |
| 30.7 | 2.9 | 59 | 10 |
| 32.2 | 2.8 | 46 | 7 |
| 32.7 | 2.7 | 43 | 7 |
| 35.2 | 2.6 | 70 | 11 |

In some embodiments, crystalline Form II is characterized by an X-ray powder diffraction pattern comprising peaks, in terms of 2-theta, at 21.5±0.2°, 19.9±0.2° and 17.7±0.2°. In some embodiments, crystalline Form II is further characterized by an X-ray powder diffraction pattern comprising a peak, in terms of 2-theta, at 15.7±0.2°. In some embodiments, crystalline Form II is further characterized by an X-ray powder diffraction pattern comprising a peak, in terms of 2-theta, at 17.0±0.2°. In some embodiments, crystalline Form II is further characterized by an X-ray powder diffraction pattern comprising a peak, in terms of 2-theta, at 19.0±0.2°. In some embodiments, crystalline Form II is further characterized by an X-ray powder diffraction pattern comprising a peak, in terms of 2-theta, at 24.3±0.2°.

In some embodiments, crystalline Form II is characterized by an X-ray powder diffraction pattern comprising at least three peaks (e.g., three peaks, at least four peaks, four peaks, at least five peaks, five peaks, six peaks) at 2-theta angles selected from the group consisting of 24.3±0.2°, 21.5±0.2°, 19.9±0.2°, 19.0±0.2°, 17.7±0.2°, 17.0±0.2° and 15.7±0.2°.

In some embodiments, crystalline Form II is characterized by an X-ray powder diffraction pattern substantially in accordance with that shown in FIG. 5.

Crystalline Form II can be prepared according to a process comprising precipitating said crystalline form from a suspension comprising the hydrochloric acid salt of 2-((1R,4R)-4-((3-(3-(trifluoromethyl)phenyl) imidazo[1,2-b]pyridazin-6-yl)amino)cyclohexyl)propan-2-ol and water. In some embodiments, precipitating is conducted at room temperature. Some embodiments further comprise contacting the suspension with a seed crystal of the crystalline form. Some embodiments further comprise contacting a solution or suspension comprising the free base of 2-((1R,4R)-4-((3-(3-(trifluoromethyl)phenyl) imidazo[1,2-b]pyridazin-6-yl) amino)cyclohexyl)propan-2-ol with hydrochloric acid to produce the hydrochloric acid salt of 2-((1R,4R)-4-((3-(3-(trifluoromethyl)phenyl) imidazo[1,2-b]pyridazin-6-yl) amino)cyclohexyl)propan-2-ol.

The above methods can be used to manufacture crystalline Forms I and II and the amorphic form. While the manufacture of each of crystalline Forms I and II and the amorphic form has been exemplified employing a specific solvent system and crystallization conditions, it is envisioned that each form can be obtained by employing a different solvent or combination of solvents and/or different crystallization conditions. Further, crystals of any of crystalline Forms I and II may be added to solutions or slurries of the amorphous form to seed the crystallization of that specific form. Therefore, the above description is not meant to limit the invention in any way.

Additionally, any of the crystalline Forms I and II may be treated to regenerate an amorphous form. In some embodiments of the invention, while the use of the higher level of purity of Forms I and II may be desirable, it is also desirable to utilize an amorphous form in the formulation therein to deliver therapeutically effective amounts of the hydrochloric acid salt of the compound of structure (I).

A partial list of useful solvents includes, for example, methanol (MeOH), ethanol (EtOH), isopropyl alcohol (IPA), 1-butanol, acetonitrile (ACN), methyl ethyl ketone (MEK), methyl isobutyl ketone (MIBK), ethyl acetate (EtOAc), isopropyl acetate (iPrOAc), methyl tert-butyl ether (MTBE), 2-methyltetrahydrofuran (2-MeTHF), dimethylformamide (DMF), N-methyl-2-pyrrolidone (NMP), dimethyl sulfoxide (DMSO), dichloromethane (DCM), 1, 4-dioxane, toluene, heptane, tetrahydrofuran (THF), acetone and water, and combinations thereof.

In some embodiments, a crystalline form described herein is substantially pure (e.g., as measured by high pressure liquid chromatography).

In some of the embodiments of the invention, the purity of the amorphous form of the hydrochloric acid salt of the compound of structure (I) (e.g., as measured by high pressure liquid chromatography) is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0% about 96.5%, about 97.0%, about 97.5%, about 98.0%, about 98.5%, about 99.0%, about 99.5%, or about 99.9% (e.g., total area under the curve as observed at about 220 nm). In some embodiments of the invention, the amorphous form of the hydrochloric acid salt of the compound of structure (I) is about 100.0 pure (e.g., as measured by high pressure liquid chromatography as area under the curve as observed at about 220 nm).

In some of the embodiments of the invention, the purity of crystalline Form I of the hydrochloric acid salt of the compound of structure (I) (e.g., as measured by high pressure liquid chromatography) is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% (e.g., total area under the curve as observed at about 220 nm). In some embodiments of the invention, crystalline Form I of the hydrochloric acid salt of the compound of structure (I) is about 100.0 pure (e.g., as measured by high pressure liquid chromatography as area under the curve as observed at about 220 nm).

In some of the embodiments of the invention, the purity of crystalline Form II of the hydrochloric acid salt of the compound of structure (I) (e.g., as measured by high pressure liquid chromatography) is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0% about 96.5%, about 97.0%, about 97.5%, about 98.0%, about 98.5%, about 99.0%, about 99.5%, or about 99.9% total area under the curve as observed at about 220 nm. In some embodiments of the invention, crystalline Form II of the hydrochloric acid salt of the compound of structure (I) is about 100.0 pure (e.g., as measured by high pressure liquid chromatography as area under the curve as observed at about 220 nm).

In some embodiments of the methods of manufacture of the invention, the chiral purity of the amorphous form of the hydrochloric acid salt of the compound of structure (I) (e.g., as measured by chiral chromatography, for example, at 220 nm and/or 260 nm) is greater than about 75.0%, about 75.5%, about 76.0%, about 76.5%, about 77.0%, about 77.5%, about 78.0%, about 78.5%, about 79.0%, about 79.5%, about 80.0%, about 80.5%, about 81.0%, about 81.5%, about 82.0%, about 82.5%, about 83.0%, about 83.5%, about 84.0%, about 84.5%, about 85.0%, about 85.5%, about 86.0%, about 86.5%, about 87.0%, about 87.5%, about 88.0%, about 88.5%, about 89.0%, about 89.5%, about 90.0%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% chiral purity. In some embodiments, the chiral purity of the amorphous form of the hydrochloric acid salt of the compound of structure (I) (e.g., as measured at 220 nm and/or 260 nm) is about 100%.

In some embodiments of the methods of manufacture of the invention, the chiral purity of Form I of the hydrochloric acid salt of the compound of structure (I) (e.g., as measured by chiral chromatography at 220 nm and/or 260 nm) is greater than about 75.0%, about 75.5%, about 76.0%, about 76.5%, about 77.0%, about 77.5%, about 78.0%, about 78.5%, about 79.0%, about 79.5%, about 80.0%, about 80.5%, about 81.0%, about 81.5%, about 82.0%, about 82.5%, about 83.0%, about 83.5%, about 84.0%, about 84.5%, about 85.0%, about 85.5%, about 86.0%, about 86.5%, about 87.0%, about 87.5%, about 88.0%, about 88.5%, about 89.0%, about 89.5%, about 90.0%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% chiral purity. In some embodiments, the chiral purity of Form I of the hydrochloric acid salt of the compound of structure (I) (e.g., as measured at 220 nm and/or 260 nm) is about 100%.

In some embodiments of the methods of manufacture of the invention, the chiral purity of Form II of the hydrochloric acid salt of the compound of structure (I) (e.g., as measured by chiral chromatography at 220 nm and/or 260 nm) is greater than about 75.0%, about 75.5%, about 76.0%, about 76.5%, about 77.0%, about 77.5%, about 78.0%, about 78.5%, about 79.0%, about 79.5%, about 80.0%, about 80.5%, about 81.0%, about 81.5%, about 82.0%, about 82.5%, about 83.0%, about 83.5%, about 84.0%, about 84.5%, about 85.0%, about 85.5%, about 86.0%, about 86.5%, about 87.0%, about 87.5%, about 88.0%, about 88.5%, about 89.0%, about 89.5%, about 90.0%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% chiral purity. In some embodiments, the chiral purity of Form II of the hydrochloric acid salt of the compound of structure (I) (e.g., as measured at 220 nm and/or 260 nm) is about 100%.

In some of the embodiments of the methods of manufacture of the invention, the amorphous form of the hydrochloric acid salt of the compound of structure (I) has less than about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, or about 0.009% of any one impurity introduced, obtained, or produced as a result of the chemical synthesis (e.g., as measured by chromatography at about 220 nm). In some embodiments, the impurity is a byproduct of the synthesis.

In some of the embodiments of the methods of manufacture of the invention, Form I of the hydrochloric acid salt of the compound of structure (I) has less than about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, or about 0.009% of any one impurity introduced, obtained, or produced as a result of the chemical synthesis (e.g., as measured by chromatography at about 220 nm). In some embodiments, the impurity is a byproduct of the synthesis.

In some of the embodiments of the methods of manufacture of the invention, Form II of the hydrochloric acid salt of the compound of structure (I) has less than about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, or about 0.009% of any one impurity introduced, obtained, or produced as a result of the chemical synthesis (e.g., as measured by chromatography at about 220 nm). In some embodiments, the impurity is a byproduct of the synthesis.

In some of the embodiments of the methods of manufacture of the invention, the amorphous form of the hydrochloric acid salt of the compound of structure (I) has less than about 3.0%, about 2.9%, about 2.8%, about 2.7%, about 2.6%, about 2.5%, about 2.4%, about 2.3%, about 2.2%, about 2.1%, about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09% of total impurities introduced, obtained, or produced as a result of the chemical synthesis (e.g., as measured by chromatography at about 220 nm). In some embodiments, the impurity is a byproduct of the synthesis.

In some of the embodiments of the methods of manufacture of the invention, Form I of the hydrochloric acid salt of the compound of structure (I) has less than about 3.0%, about 2.9%, about 2.8%, about 2.7%, about 2.6%, about 2.5%, about 2.4%, about 2.3%, about 2.2%, about 2.1%, about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09% of total impurities introduced, obtained, or produced as a result of the chemical synthesis (e.g., as measured by chromatography at about 220 nm). In some embodiments, the impurity is a byproduct of the synthesis.

In some of the embodiments of the methods of manufacture of the invention, Form II of the hydrochloric acid salt of the compound of structure (I) has less than about 3.0%, about 2.9%, about 2.8%, about 2.7%, about 2.6%, about 2.5%, about 2.4%, about 2.3%, about 2.2%, about 2.1%, about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09% of total impurities introduced, obtained, or produced as a result of the chemical synthesis (e.g., as measured by chromatography at about 220 nm). In some embodiments, the impurity is a byproduct of the synthesis.

Pharmacology and Utility

In certain embodiments, a method for treating a cancer is provided. The method comprises administering a therapeutically effective amount of a compound of structure (I), or a pharmaceutically acceptable salt thereof (e.g., a crystalline form of the compound of structure (I), or a pharmaceutically acceptable salt thereof, or a composition or unit dose form comprising a compound of structure (I), or a pharmaceutically acceptable salt thereof, such as a crystalline form or a composition or a unit dose disclosed herein), to a subject in need thereof.

In certain embodiments, a method for treating a disease or disorder described herein is provided, comprising administering a therapeutically effective amount of a crystalline form or a composition or a unit dose disclosed herein to a subject in need thereof.

In some embodiments, the cancer is bladder cancer, prostate cancer, colorectal cancer, a hematological malignancy, or acute myeloid leukemia. In some embodiments, the cancer is a Pim kinase-mediated cancer. In some embodiments, the cancer is bladder cancer. In some embodiments, the cancer is prostate cancer. In some embodiments, the cancer is colorectal cancer. In some embodiments, the cancer is hematological malignancy. In some embodiments, the cancer is acute myeloid leukemia. In some embodiments, the cancer is a fibrotic cancer (e.g., myelofibrosis).

As used herein, a "fibrotic cancer" is a cancer associated with fibrosis. Examples of fibrotic cancers include, but are not limited to, myelofibrosis, pancreatic cancer (e.g., pancreatic ductal adenocarcinoma), kidney cancer, liver cancer, lung cancer (e.g., large cell lung cancer, such as squamous cell carcinoma), breast cancer (e.g., inflammatory breast cancer), ovarian cancer (e.g., high grade serious ovarian carcinoma), endometrial cancer, uterine cancer, uterine sarcoma (e.g., uterine leiomyosarcoma), renal cell cancer, sarcoma (e.g., soft tissue sarcoma), malignant fibrous histiocytoma, fibrosarcoma (e.g., dermatofibrosarcoma protuberans) and hepatocellular carcinoma.

In some embodiments, the cancer treated is a hematologic cancer. Hematologic cancers that can be treated according to the methods described herein include leukemias and lymphomas (e.g., B-cell lymphoma, T-cell lymphoma). In some embodiments, the hematologic cancer is selected from acute myelogenous leukemia (AML), follicular lymphoma, acute lymphoblastic leukemia (ALL), mantle cell lymphoma, diffuse large B-cell lymphoma, lymphocytic lymphoma, mycosis fungoides, chronic lymphocytic leukemia (CLL), multiple myeloma (MM) and non-Hodgkin's lymphoma (e.g., AML, follicular lymphoma, ALL, CLL and non-Hodgkin's lymphoma). In more specific embodiments, the hematological cancer is AML. In other more specific embodiments, the hematologic cancer is CLL. In more specific embodiments, the hematologic cancer is MM. In still other specific embodiments, the hematologic cancer is myelodysplasic syndrome (MDS).

In other embodiments, the cancer comprises a solid tumor. Accordingly, in some embodiments, the cancer is a solid tumor cancer. In various embodiments, the solid tumor cancer is breast cancer, bladder cancer, liver cancer, pancreatic cancer, lung cancer, colorectal cancer, ovarian cancer, prostate cancer, or melanoma. In some embodiments, the cancer is bladder cancer. In some embodiments, the cancer is lung cancer (e.g., non-small cell lung cancer). In other embodiments, the cancer is liver cancer. In some embodiments, the cancer is a sarcoma, bladder cancer or renal cancer. In some embodiments, the cancer is prostate cancer (e.g., castration-resistant prostate cancer, castration-sensitive prostate cancer). In other embodiments, the cancer is bladder cancer, pancreatic cancer, colorectal cancer, kidney cancer, non-small cell lung carcinoma, prostate cancer, sarcoma, skin cancer, thyroid cancer, testicular cancer or vulvar cancer. In some embodiments, the cancer is endometrial cancer, pancreatic cancer, testicular cancer, renal cancer, melanoma, colorectal cancer, thyroid cancer, bladder cancer, pancreatic cancer, vulvar cancer, sarcoma, prostate cancer, lung cancer or anal cancer. In some embodiments, the cancer is a sarcoma. In some embodiments, the cancer is a renal cell carcinoma.

Further examples of cancers treatable according to the methods described herein include, but are not limited to, lung cancer, non-small cell lung cancer (NSCLC), oat-cell cancer, bone cancer, pancreatic cancer, skin cancer, dermatofibrosarcoma protuberans, cancer of the head and neck, cutaneous or intraocular melanoma, uterine cancer, ovarian cancer, colorectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (e.g., castration-resistant prostate cancer), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (e.g., pre-malignant syndrome), and mycoses fungoides.

Yet further examples of cancers treatable according to the methods described herein include, but are not limited to, Acute Lymphoblastic Leukemia (ALL); Acute Myeloid Leukemia (AML); Adrenocortical Carcinoma; Adrenocortical Carcinoma, Childhood; AIDS-Related Cancer (e.g., Kaposi Sarcoma, AIDS-Related Lymphoma, Primary CNS Lymphoma); Anal Cancer; Appendix Cancer; Astrocytomas, Childhood; Atypical Teratoid/Rhabdoid Tumor, Childhood, Central Nervous System; Basal Cell Carcinoma of the Skin; Bile Duct Cancer; Bladder Cancer; Bladder Cancer, Childhood; Bone Cancer (including Ewing Sarcoma, Osteosarcoma and Malignant Fibrous Histiocytoma); Brain Tumors/Cancer; Breast Cancer; Burkitt Lymphoma; Carcinoid Tumor (Gastrointestinal); Carcinoid Tumor, Childhood; Cardiac (Heart) Tumors, Childhood; Embryonal Tumors, Childhood; Germ Cell Tumor, Childhood; Primary CNS Lymphoma; Cervical Cancer; Childhood Cervical Cancer; Cholangiocarcinoma; Chordoma, Childhood; Chronic Lymphocytic Leukemia (CLL); Chronic Myelogenous Leukemia (CML); Chronic Myeloproliferative Neoplasms; Colorectal Cancer; Childhood Colorectal Cancer; Craniopharyngioma, Childhood; Cutaneous T-Cell Lymphoma (e.g., Mycosis Fungoides and Sézary Syndrome); Ductal Carcinoma In Situ (DCIS); Embryonal Tumors, Central Nervous System, Childhood; Endometrial Cancer (Uterine Cancer); Ependymoma, Childhood; Esophageal Cancer; Childhood Esophageal Cancer; Esthesioneuroblastoma; Ewing Sarcoma; Extracranial Germ Cell Tumor, Childhood; Extragonadal Germ Cell Tumor; Eye Cancer; Childhood Intraocular Melanoma; Intraocular Melanoma; Retinoblastoma; Fallopian Tube Cancer; Fibrous Histiocytoma of Bone, Malignant, and Osteosarcoma; Gallbladder Cancer; Gastric (Stomach) Cancer; Childhood Gastric (Stomach) Cancer; Gastrointestinal Carcinoid Tumor; Gastrointestinal Stromal Tumors (GIST); Childhood Gastrointestinal Stromal Tumors; Germ Cell Tumors; Childhood Central Nervous System Germ Cell Tumors (e.g., Childhood Extracranial Germ Cell Tumors, Extragonadal Germ Cell Tumors, Ovarian Germ Cell Tumors, Testicular Cancer); Gestational Trophoblastic Disease; Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer; Intraocular Melanoma; Childhood Intraocular Melanoma; Islet Cell Tumors, Pancreatic Neuroendocrine Tumors; Kaposi Sarcoma; Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Childhood Lung Cancer; Lymphoma; Male Breast Cancer; Malignant Fibrous Histiocytoma of Bone and Osteosarcoma; Melanoma; Childhood Melanoma; Melanoma, Intraocular (Eye); Childhood Intraocular Melanoma; Merkel Cell Carcinoma; Mesothelioma, Malignant; Childhood Mesothelioma; Metastatic Cancer; Metastatic Squamous Neck Cancer with Occult Primary; Midline Tract Carcinoma With NUT Gene Changes; Mouth Cancer; Multiple Endocrine Neoplasia Syndromes; Multiple Myeloma/Plasma Cell Neoplasms; Mycosis Fungoides; Myelodysplastic Syndromes, Myelodysplastic/Myeloproliferative Neoplasms;

Myelogenous Leukemia, Chronic (CML); Myeloid Leukemia, Acute (AML); Myeloproliferative Neoplasms, Chronic; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip and Oral Cavity Cancer and Oropharyngeal Cancer; Osteosarcoma and Malignant Fibrous Histiocytoma of Bone; Ovarian Cancer; Childhood Ovarian Cancer; Pancreatic Cancer; Childhood Pancreatic Cancer; Pancreatic Neuroendocrine Tumors; Papillomatosis (Childhood Laryngeal); Paraganglioma; Childhood Paraganglioma; Paranasal Sinus and Nasal Cavity Cancer; Parathyroid Cancer; Penile Cancer; Pharyngeal Cancer; Pheochromocytoma; Childhood Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer; Renal Cell (Kidney) Cancer; Retinoblastoma; Rhabdomyosarcoma, Childhood; Salivary Gland Cancer; Sarcoma (e.g., Childhood Rhabdomyosarcoma, Childhood Vascular Tumors, Ewing Sarcoma, Kaposi Sarcoma, Osteosarcoma (Bone Cancer), Soft Tissue Sarcoma, Uterine Sarcoma); Sézary Syndrome; Skin Cancer; Childhood Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; Childhood Stomach (Gastric) Cancer; T-Cell Lymphoma, Cutaneous (e.g., Mycosis Fungoides and Sezary Syndrome); Testicular Cancer; Childhood Testicular Cancer; Throat Cancer (e.g., Nasopharyngeal Cancer, Oropharyngeal Cancer, Hypopharyngeal Cancer); Thymoma and Thymic Carcinoma; Thyroid Cancer; Transitional Cell Cancer of the Renal Pelvis and Ureter; Ureter and Renal Pelvis, Transitional Cell Cancer; Urethral Cancer; Uterine Cancer, Endometrial; Uterine Sarcoma; Vaginal Cancer; Childhood Vaginal Cancer; Vascular Tumors; Vulvar Cancer; and Wilms Tumor and Other Childhood Kidney Tumors.

Metastases of the aforementioned cancers can also be treated in accordance with the methods described herein.

Myeloproliferative neoplasms are also amenable to the treatment methods disclosed herein. Myeloproliferative neoplasms (MPNs) refer to a group of disorders in which bone marrow stem cells grow and reproduce abnormally. MPN abnormal stem cells produce excess numbers of one or more types of blood cells (e.g., red blood cells, white blood cells, and/or platelets). As disclosed herein, myeloproliferative neoplasms include, but are not limited to, polycythemia vera (PV), primary or essential thrombocythemia (ET), primary or idiopathic myelofibrosis (MF), secondary myelofibrosis (e.g., myelofibrosis secondary to polycythemia vera or essential thrombocythemia), chronic myelogenous (myelocytic) leukemia (CIVIL), chronic myelomonocytic leukemia (CMML), chronic neutrophilic leukemia (CNL), juvenile myelomonocytic leukemia (JML), systemic mastocytosis, and chronic eosinophilic leukemia (CEL)/hyper eosinophilic syndrome (HES).

In some specific embodiments, the myeloproliferative neoplasm of the mammal treated for a myeloproliferative neoplasm according to the embodiments described herein comprises a JAK2 mutation, a thrombopoietin receptor (MPL) mutation, or a calreticulin (CALR) mutation. In some embodiments, a JAK2 mutation comprises a JAK2 V617 mutation. JAK2 V617F refers to a mutated JAK2 possessing a V→F amino acid substitution at position 617 with respect to the human, wildtype JAK2 (UniProt. 060674). In some embodiments, a MPL mutation comprises a MPL W515L mutation. MPL W515L refers to a mutated thrombopoietin receptor (MPL) possessing a W→L substitution at position 515 with respect to the human, wildtype MPL (UniProt. P40238). In some embodiments, the mutation in CALR comprises a CALR exon 9 indel.

International Prognostic Scoring System (IPSS) score is the main way that myelofibrosis patients are stratified. Risk factors using IPSS include age, constitutional symptoms (e.g., weight loss, fever, or excessive sweating), white blood cell counts, hemoglobin, peripheral blasts, complex or abnormal karyotype, transfusion dependency, and platelet counts. Patients having low-risk myelofibrosis have an IPSS score of 0. An IPSS score of 0 is typically associated with a median survival of about 180 months. In some embodiments, the myelofibrosis is low-risk myelofibrosis.

Patients having intermediate-risk myelofibrosis have an IPSS score of 1, 2 or 3. An IPSS score of 1 is also referred to as intermediate-1 risk, and is typically associated with a median survival of about 80 months. An IPSS score of 2 or 3 is also referred to as intermediate-2 risk, and is typically associated with a median survival of about 35 months. In some embodiments, the myelofibrosis is intermediate-risk myelofibrosis (e.g., intermediate-1 risk myelofibrosis, intermediate-2 risk myelofibrosis).

Patients having high-risk myelofibrosis have an IPSS score of 4 or more. An IPSS score of 4 or more is typically associated with a median survival of about 16 months. In some embodiments, the myelofibrosis is high-risk myelofibrosis.

In some embodiments, the disease or disorder (e.g., cancer, MPN) treated in accordance with the treatment methods disclosed herein is myelofibrosis. In some embodiments, the myelofibrosis is intermediate-2 or high-risk, primary or secondary MF.

In some embodiments, the MPN is a JAK inhibitor-resistant MPN (e.g., ruxolitinib-resistant and/or fedratinib-resistant MPN, such as ruxolitinib-resistant myelofibrosis, fedratinib-resistant myelofibrosis). In some embodiments, the MPN (e.g., myelofibrosis) has been previously treated with a JAK inhibitor (e.g., ruxolitinib and/or fedratinib), e.g., in the absence of a compound of structure (I), or a pharmaceutically acceptable salt thereof. In some embodiments, the subject has been previously treated with a JAK inhibitor (e.g., ruxolitib and/or fedratinib) and is intolerant, resistant, refractory or lost response to the JAK inhibitor.

In some embodiments, the subject is ineligible to receive a JAK inhibitor (e.g., ruxolitinib and/or fedratinib).

In some embodiments, the subject has been previously treated with a JAK inhibitor (e.g., ruxolitib and/or fedratinib), or is ineligible to receive a JAK inhibitor (e.g., ruxolitinib and/or fedratinib). In some aspects, the subject who has been previously treated with a JAK inhibitor is intolerant, resistant, refractory or lost response to the JAK inhibitor.

Some embodiments provide a method treating intermediate-2 or high-risk, primary or secondary myelofibrosis in a subject in need thereof, comprising administering to the subject a therapeutically effective amount of a compound of structure (I), or a pharmaceutically acceptable salt thereof (e.g., a crystalline form of the compound of structure (I), or a pharmaceutically acceptable salt thereof, or a composition or unit dose form comprising a compound of structure (I), or a pharmaceutically acceptable salt thereof, such as a crystalline form or a composition or a unit dose disclosed herein), wherein the subject has previously received ruxolitinib, or a pharmaceutically acceptable salt thereof, or fedratinib, or a pharmaceutically acceptable salt thereof; or is ineligible to receive ruxolitinib, or a pharmaceutically acceptable salt thereof, or fedratinib, or a pharmaceutically acceptable salt thereof. In some embodiments, the method further comprises administering to the subject in need thereof ruxolitinib, or a pharmaceutically acceptable salt thereof, or fedratinib, or a pharmaceutically acceptable salt thereof.

In some embodiments, treating the MPN or cancer described herein results in complete remission in the subject. When used to refer to a subject having an MPN, such as myelofibrosis, "complete remission" means a subject meets the following criteria for ≥12 weeks:
(i) bone marrow shows age-adjusted normocellularity, <5% blasts and ≤grade 1 myelofibrosis according to the European classification; and
(ii) hemoglobin≥100 g/L and <UNL, and neutrophil count≥1×10$^9$/L and <UNL in peripheral blood; and
(iii) platelet count≥100×10$^9$/L and <UNL, and <2% immature myeloid cells, except that in splenectomized patients, <5% immature myeloid cells is allowed; and
(iv) resolution of disease symptoms, non-palpable spleen and liver, and no evidence of EMH.

In some embodiments, treating the MPN or cancer described herein results in the mammal being measurable residual disease (MRD)-negative.

In the context of myeloproliferative neoplasms, such as MF, measurable residual disease, minimal residual disease and MRD refer to the presence of cells possessing acquired mutations within the JAK2, CALR and MPL genes of a subject having a myeloproliferative neoplasm, such as MF. Common mutations in JAK2 include the V617F mutation and mutations (e.g., substitutions, deletions, insertions, duplications) of exon 12. Common mutations in CALR include exon 9 mutations. Common mutations in MPL include exon 10 mutations (e.g., W515L and W515K). MRD is used diagnostically in the context of myeloproliferative neoplasms, but can also be used quantitatively to indicate the depth of response to a therapeutic intervention. MRD testing for myeloproliferative neoplasms, such as MF, is typically conducted using allele-specific quantitative PCR (qPCR), digital PCR or next-generation sequencing. The foregoing methods are reviewed in Haslam, K. and Langabeer, S. E., "Monitoring Residual Disease in the Myeloproliferative Neoplasms: Current Applications and Emerging Approaches," *Biomed. Res. Intl.* 2016:7241591, the relevant teachings of which are incorporated herein by reference in their entireties.

In some embodiments, a subject having a MPN, such as MF, is measurable residual disease negative, e.g., following administration of the compound of structure (I), or a pharmaceutically acceptable salt thereof. When a subject having a myeloproliferative neoplasm, such as MF, is described herein as being "measurable residual disease negative," "minimal residual disease negative," "MRD-negative" or "MRD$^-$," the subject lacks, or lacks to a measurable extent, cells having an acquired mutation associated with the myeloproliferative neoplasm in at least one of JAK2, CALR or MPL (e.g., the JAK2 V617F mutation, mutations of JAK2 exon 12, CALR exon 9 mutations, MPL W515K/L mutations). For example, in some embodiments, an MRD-negative subject lacks, or lacks to a measurable extent, cells having the JAK2 V617F mutation. In some embodiments, an MRD-negative subject lacks, or lacks to a measurable extent, cells having a CALR exon 9 mutation. In some embodiments, an MRD-negative subject lacks, or lacks to a measurable extent, cells having an MPL exon 10 mutation. Acquired mutations associated with myeloproliferative neoplasms are known in the art, and described in Haslam, K. and Langabeer, S. E., "Monitoring Residual Disease in the Myeloproliferative Neoplasms: Current Applications and Emerging Approaches," *Biomed. Res. Intl.* 2016:7241591, the relevant teachings of which are incorporated herein by reference in their entireties.

In some embodiments, the cancer is myelofibrosis. In some more specific embodiments, the method further comprises administering a second therapeutic agent (e.g., ruxolitinib). In some embodiments, the cancer is myelofibrosis and the method further comprises administering ruxolitinib.

Typically, the starting dose of ruxolitinib is 20 mg given orally twice daily for patients with a platelet count greater than 200×10$^9$/L, and 15 mg twice daily for patients with a platelet count between 100×10$^9$/L and 200×10$^9$/L. The dose of ruxolitinib can be increased based on patient response, up to a maximum of 25 mg twice daily. If a patient receiving ruxolitinib under these conditions for six months does not have spleen reduction or symptom improvement, ruxolitinib treatment is typically discontinued.

In embodiments involving ruxolitinib, or a pharmaceutically acceptable salt thereof, dosages of ruxolitinib, or a pharmaceutically acceptable salt thereof, range from about 1 mg to about 100 mg per day, from about 2.5 mg to about 60 mg per day, from about 5 mg to about 60 mg per day or from about 10 mg to about 50 mg per day. In some embodiments, ruxolitinib, or a pharmaceutically acceptable salt thereof, is administered in a dosage of from about 5 mg to about 100 mg per day, or from about 10 mg to about 50 mg per day. Ruxolitinib, for example, is typically given as an oral formulation twice daily in an individual dose of about 5 mg, about 10 mg, about 15 mg, about 20 mg, about 25 mg or about 30 mg.

In some embodiments, the method of the invention is particularly useful for the treatment of patients with myelofibrosis that were previously treated with JAK inhibitors (e.g., ruxolitinib or fedratinib), and became intolerant, resistant, refractory, or ineligible and/or treatment of myelofibrosis with thrombocytopenia (i.e., when platelet count is <50K and ruxolitinib cannot be used). Suitable patients may also exhibit one or more of the following characteristics: a dynamic international prognosis scoring system (DIPSS) score of intermediate-2 or high risk; a bone marrow fibrosis grade of ≥2; an absolute neutrophil count (ANC) of ≥1×10$^9$/L (without granulocyte growth factors); a platelet count of ≥50×10$^9$/L (without growth factors or platelet transfusions); a hemoglobin of ≥8 g/dL; a peripheral blood blast count of <10%; show at least 2 measurable (score≥1) symptoms using the MFSAF (v 4.0); and/or a splenomegaly as demonstrated by a splenic length of ≥5 cm by palpitation or a spleen volume of ≥450 cm$^3$ by MRI or CT scan.

Individualized treatment for patients with myelofibrosis can include an assessment of prognosis with current clinical scoring systems and an estimation of disease burden. Useful biomarker assessments for myelofibrosis treatment are summarized below:

| Analysis | Analytes |
| --- | --- |
| Gene sequencing | JAK2, MPL, CALR, ASXL1, EZH2, SRSF2, TP53, IDH1, IDH2, U2AF1, DNMT3A |
| Allele burden | JAK2V617F; CALR and MPL allele burden if assay available |

| Analysis | Analytes |
|---|---|
| Inflammatory cytokines | TGF-b1, TNF-a, IL-1a, IL-1b, IL-1Ra, IL-2, IL-2Ra, IL-6, IL-8, IL-10, IL-12, IL-15, IP-10, MIP-1b, MMP-3, MMP-9, TIMP-1, erythropoietin, GCSF |
| Bone marrow biopsy IHC | TGF-b1 |
| Peripheral hematopoietic cells | CD34 + cell counts |

In some embodiments, the disease or disorder is a fibrotic disease or disorder. In some more specific embodiments, the disease or disorder is pulmonary fibrosis (e.g., idiopathic pulmonary fibrosis (IPF), acute exacerbation of IPF, and familial pulmonary fibrosis), a liver fibrosis (e.g., liver cirrhosis and biliary cirrhosis), a cardiac fibrosis, a vascular fibrosis, a renal fibrosis, a cutaneous fibrosis, a gastrointestinal fibrosis, an athrofibrosis, Dupuytren's contracture, a mediastinal fibrosis, Peyronie's disease, a retroperitoneal fibrosis, a systemic sclerosis or combination thereof.

One embodiment provides a method for treating or preventing formation or deposition of fibrosis in or around tissue (i.e., tissue fibrosis), the method comprising administering a therapeutically effective amount of a compound of structure (I), or a pharmaceutically acceptable salt thereof (e.g., a crystalline form of the compound of structure (I), or a pharmaceutically acceptable salt thereof, or a composition or unit dose form comprising a compound of structure (I), or a pharmaceutically acceptable salt thereof, such as a crystalline form or a composition or a unit dose disclosed herein), to a subject in need thereof.

Another embodiment provides a method for inhibiting virus infection or virus replication, the method comprising administering a therapeutically effective amount of a compound of structure (I), or a pharmaceutically acceptable salt thereof (e.g., a crystalline form of the compound of structure (I), or a pharmaceutically acceptable salt thereof, or a composition or unit dose form comprising a compound of structure (I), or a pharmaceutically acceptable salt thereof, such as a crystalline form or a composition or a unit dose disclosed herein), to a subject in need thereof.

Yet another embodiment provides a method for treating myeloproliferative neoplasms (e.g., polycythemia vera, essential thrombocythemia or combinations thereof), the method comprising administering a therapeutically effective amount of a compound of structure (I), or a pharmaceutically acceptable salt thereof (e.g., a crystalline form of the compound of structure (I), or a pharmaceutically acceptable salt thereof, or a composition or unit dose form comprising a compound of structure (I), or a pharmaceutically acceptable salt thereof, such as a crystalline form or a composition or a unit dose disclosed herein), to a subject in need thereof. In some embodiments, the myeloproliferative neoplasm is polycythemia vera. In some embodiments, the myeloproliferative neoplasm is essential thrombocythemia.

Some embodiments provide a method for treating or preventing an inflammatory disease(s) or disorder(s), the method comprising administering a therapeutically effective amount of a compound of structure (I), or a pharmaceutically acceptable salt thereof (e.g., a crystalline form of the compound of structure (I), or a pharmaceutically acceptable salt thereof, or a composition or unit dose form comprising a compound of structure (I), or a pharmaceutically acceptable salt thereof, such as a crystalline form or a composition or a unit dose disclosed herein), to a subject in need thereof. In some embodiments, the inflammatory disease or disorder is non-alcoholic fatty liver disease (NAFLD), alcoholic steatohepatitis (ASH), non-alcoholic steatohepatitis (NASH), primary biliary cholangitis, primary sclerosing cholangitis, autoimmune hepatitis, skin inflammation, psoriasis, or combinations thereof.

Certain embodiments provide a method for treating or preventing an autoimmune and/or inflammatory disease(s) or disorder(s), the method comprising administering a therapeutically effective amount of a compound of structure (I), or a pharmaceutically acceptable salt thereof (e.g., a crystalline form of the compound of structure (I), or a pharmaceutically acceptable salt thereof, or a composition or unit dose form comprising a compound of structure (I), or a pharmaceutically acceptable salt thereof, such as a crystalline form or a composition or a unit dose disclosed herein), to a subject in need thereof. In some more specific embodiments, the autoimmune and/or inflammatory disease(s) or disorder(s) are mediated at least in part by protein kinase activity (e.g., Pim kinase activity). In certain embodiments, the autoimmune and/or inflammatory disease(s) or disorder(s) include osteoarthritis, rheumatoid arthritis, pain, inflammatory bowel diseases, respiratory disorders, skin disorders or combinations thereof.

A "therapeutically effective amount" means an amount of a composition sufficient to effect treatment (e.g., an amount effective to prevent, alleviate or ameliorate symptoms of disease or prolong the survival of the subject being treated). Determination of a therapeutically effective amount is well within the capability of those skilled in the art, especially in light of the detailed disclosure provided herein.

For example, for any composition described herein, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test composition which achieves a half-maximal inhibition of the protein kinase activity). Such information can then be used to more accurately determine useful doses in humans.

Toxicity and therapeutic efficacy of the compositions described herein can be determined by standard pharmaceutical procedures in cell cultures or experimental animals, e.g., by determining the $IC_{50}$ and the $LD_{50}$. The data obtained from cell culture assays and animal studies can be used in formulating a range of dosage for use in humans. The dosage may vary depending upon the dosage form employed and the route of administration utilized. The exact formulation, route of administration and dosage can be chosen by the individual physician in view of the subject's disease or disorder. (See, e.g., GOODMAN & GILMAN'S THE PHARMACOLOGICAL BASIS OF THERAPEUTICS, Ch. 3, $9^{th}$ ed., Ed. by Hardman, J., and Limbard, L., McGraw-Hill, New York City, 1996, p. 46.)

Dosage amount and interval may be adjusted individually to provide plasma levels of the active species which are sufficient to maintain the kinase modulating effects. These plasma levels are referred to as minimal effective concentrations (MECs). The MEC will vary for each composition but can be estimated from in vitro data, e.g., the concentration necessary to achieve 50-90% inhibition of a kinase. Dosages necessary to achieve the MEC will depend on individual characteristics and route of administration. HPLC assays or bioassays can be used to determine plasma concentrations.

Dosage intervals can also be determined using MEC value. Compositions should be administered using a regimen that maintains plasma levels above the MEC for about 10 to 90% of the time, preferably between about 30 to 90% of the time, and most preferably between about 50 to 90% of the time.

The amount of a composition administered will, of course, be dependent on, for example, the subject being treated, the severity of the affliction, the manner of administration, the judgment of the prescribing physician, etc.

In some embodiments, the crystalline form and/or composition and/or unit dose is administered in multiple doses. In some embodiments, dosing is about once, twice, three times, four times, five times, six times, or more than six times per day. In other embodiments, dosing is about once a month, once every two weeks, once a week, or once every other day. In another embodiment the composition further comprising another agent is administered about once per day to about 6 times per day. In another embodiment the administration of a composition further comprising another agent continues for less than about 7 days. In yet another embodiment the administration continues for more than about 6, 10, 14, 28 days, two months, six months, or one year. In some cases, continuous dosing is achieved and maintained as long as necessary.

Administration of the crystalline form and/or composition and/or unit dose (e.g., composition) may continue as long as necessary. In some embodiments, a crystalline form and/or composition and/or unit dose (e.g., composition) is administered for more than 1, 2, 3, 4, 5, 6, 7, 14, or 28 days. In some embodiments, a crystalline form and/or composition (e.g., composition) is administered for less than 28, 14, 7, 6, 5, 4, 3, 2, or 1 day. In some embodiments, a crystalline form and/or composition and/or unit dose (e.g., composition) is administered chronically on an ongoing basis, e.g., for the treatment of chronic effects.

In some embodiments, the compound of structure (I), or a pharmaceutically acceptable salt thereof, or composition comprising the compound of structure (I), or a pharmaceutically acceptable salt thereof, is administered in dosages. In some embodiments, the compound of structure (I), or a pharmaceutically acceptable salt thereof, is administered in a dosage (e.g., daily dosage) of from about 250 mg to about 2.5 g, from about 300 mg to about 1.5 g, from about 350 mg to about 2.5 g, or from about 450 mg to about 1.5 g, as determined using the molecular weight of the compound of structure (I) as a free base. In some embodiments, the subject in need thereof is administered a dose (e.g., a daily dose) of about 360 mg, or about 480 mg, or about 720 mg, or about 1,080 mg, or about 1,440 mg of the compound of structure (I), or a pharmaceutically acceptable salt thereof, as determined using the molecular weight of the compound of structure (I) as a free base.

In one embodiment, the subject in need thereof is administered a dose (e.g., a daily dose) of about 360 mg of the compound of structure (I), or a pharmaceutically acceptable salt thereof, as determined using the molecular weight of the compound of structure (I) as a free base.

In one embodiment, the subject in need thereof is administered a dose (e.g., a daily dose) of about 480 mg of the compound of structure (I), or a pharmaceutically acceptable salt thereof, as determined using the molecular weight of the compound of structure (I) as a free base.

In one embodiment, the subject in need thereof is administered a dose (e.g., a daily dose) of about 720 mg of the compound of structure (I), or a pharmaceutically acceptable salt thereof, as determined using the molecular weight of the compound of structure (I) as a free base.

In one embodiment, the subject in need thereof is administered a dose (e.g., a daily dose) of about 1,080 mg of the compound of structure (I), or a pharmaceutically acceptable salt thereof, as determined using the molecular weight of the compound of structure (I) as a free base.

In one embodiment, the subject in need thereof is administered a dose (e.g., a daily dose) of about 1,440 mg of the compound of structure (I), or a pharmaceutically acceptable salt thereof, as determined using the molecular weight of the compound of structure (I) as a free base.

In one embodiment, the subject in need thereof is administered a dose of 2 capsules, or 3 capsules, or 4 capsules, or 5 capsules, or 6 capsules, or 7 capsules, or 8 capsules, or 9 capsules, or 10 capsules, or 11 capsules, or 12 capsules, or 13 capsules, or 14 capsules, each capsule comprising a composition, which composition comprises the compound of structure (I), or a pharmaceutically acceptable salt thereof, in an amount of about 120 mg, as determined using the molecular weight of the compound of structure (I) as a free base.

In one embodiment, the subject in need thereof is administered a dose of 3 capsules, each capsule comprising a composition, which composition comprises the compound of structure (I), or a pharmaceutically acceptable salt thereof, in an amount of about 120 mg, as determined using the molecular weight of the compound of structure (I) as a free base.

In one embodiment, the subject in need thereof is administered a dose of 4 capsules, each capsule comprising a composition, which composition comprises the compound of structure (I), or a pharmaceutically acceptable salt thereof, in an amount of about 120 mg, as determined using the molecular weight of the compound of structure (I) as a free base.

In one embodiment, the subject in need thereof is administered a dose of 6 capsules, each capsule comprising a composition, which composition comprises the compound of structure (I), or a pharmaceutically acceptable salt thereof, in an amount of about 120 mg, as determined using the molecular weight of the compound of structure (I) as a free base.

In one embodiment, the subject in need thereof is administered a dose of 9 capsules, each capsule comprising a composition, which composition comprises the compound of structure (I), or a pharmaceutically acceptable salt thereof, in an amount of about 120 mg, as determined using the molecular weight of the compound of structure (I) as a free base.

In one embodiment, the subject in need thereof is administered a dose of 12 capsules, each capsule comprising a composition, which composition comprises the compound of structure (I), or a pharmaceutically acceptable salt thereof, in an amount of about 120 mg, as determined using the molecular weight of the compound of structure (I) as a free base.

In one embodiment, the administration of the crystalline form and/or compositions and/or unit dose (e.g., unit dose) is a daily administration (e.g., once daily administration). In one embodiment, the administration of the capsule is a daily administration (e.g., once daily administration). In this context, it is understood that a subject administered the compound of structure (I), or a pharmaceutically acceptable salt thereof, by capsule, for example, will likely be administered more than one capsule at a time, each of which can be quite large (e.g., size 00). Accordingly, dosing can extend over a period of time (e.g., a 1-hour period). It will be understood that a dose requiring, for example, one hour, to be completed, administered once per day is once daily dosing, notwithstanding the number of capsules or the extended period of the dosage.

It is known in the art that due to intersubject variability with respect to pharmacokinetics, individualization of dosing regimen is necessary for optimal therapy. Dosing for a composition may be found by routine experimentation in light of the instant disclosure.

The compositions may, if desired, be presented in a pack or dispenser device, such as an FDA approved kit, which may contain one or more unit dosage forms containing the active ingredient (e.g., a compound of structure (I) or a pharmaceutically acceptable salt thereof). The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions in certain embodiments optionally formulated in a compatible pharmaceutical carrier may also be prepared, placed in an appropriate container, and labeled for treatment of an indicated disease, disorder, or condition. Suitable diseases, disorders, or conditions indicated on the label may include those described herein (e.g., cancers, myeloproliferative neoplasms, fibrotic diseases or disorders, autoimmune diseases or disorders, inflammatory diseases or disorders, etc.).

In certain instances, it may be advantageous to administer a crystalline form and/or composition (e.g., composition) of the present disclosure in combination with one or more therapeutically active agents independently selected from anti-cancer agents (e.g., chemotherapeutic agents), anti-allergic agents, anti-emetics, pain relievers, immunomodulators and cytoprotective agents. Accordingly, in some embodiments, the method of treatment further comprises administering to the subject a therapeutically effective amount of one or more additional therapeutic agents (e.g., an anti-cancer agent, such as a chemotherapeutic agent, anti-allergic agent, anti-emetic, pain reliever, immunomodulator and/or cytoprotective agent).

The term "combination therapy" refers to the administration of two or more therapeutic agents to treat a therapeutic disease, disorder or condition described in the present disclosure. Such administration encompasses co-administration of the therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. A crystalline form or composition of the present disclosure and additional therapeutic agents can be administered via the same administration route or via different administration routes. Powders and/or liquids may be reconstituted or diluted to a desired dose prior to administration. In addition, such administration also encompasses use of each type of therapeutic agent in a sequential manner in separate compositions, either at approximately the same time or at different times.

General chemotherapeutic agents considered for use in combination therapies include capecitabine (Xeloda®), N4-pentoxycarbonyl-5-deoxy-5-fluorocytidine, carboplatin (Paraplatin®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), doxorubicin hydrochloride (Adriamycin®, Rubex®), fludarabine phosphate (Fludara®), 5-fluorouracil (Adrucil®, Efudex®), Gemcitabine (difluorodeoxycitidine), irinotecan (Camptosar®), L-asparaginase (ELSPAR®), 6-mercaptopurine (Purinethol®), methotrexate (Folex®), pentostatin, 6-thioguanine, thiotepa, and topotecan hydrochloride for injection (Hycamptin®).

Anti-cancer agents of particular interest for combinations with the compositions of the present disclosure include: Purine antimetabolites and/or inhibitors of de novo purine synthesis: pemetrexed (Alimta®), gemcitabine (Gemzar®), 5-fluorouracil (Adrucil®, Carac® and Efudex®), methotrexate (Trexall®), capecitabine (Xeloda®), floxuridine (FUDR®), decitabine (Dacogen®), azacitidine (Vidaza® and Azadine®), 6-mercaptopurine (Purinethol®), cladribine (Leustatin®, Litak® and Movectro®), fludarabine (Fludara®), pentostatin (Nipent®), nelarabine (Arranon®), clofarabine (Clolar® and Evoltra®), and cytarabine (Cytosar®).

MTAP inhibitors: (3R,4S)-1-((4-amino-5H-pyrrolo[3,2-d]pyrimidin-7-yl)methyl)-4-((methylthio)methyl)pyrrolidin-3-ol (MT-DADMe-Immucillin-A, CAS 653592-04-2).

Methylthioadenosine: ((2R,3R,4S,5S)-2-(6-amino-9H-purin-9-yl)-5-((methylthio)methyl)tetrahydrofuran-3,4-diol, CAS 2457-80-9).

Epidermal growth factor receptor (EGFR) inhibitors: Erlotinib hydrochloride (Tarceva®) and Gefitnib (Iressa®).

EGFR antibodies: Cetuximab (Erbitux®).

MET inhibitors: Capmatinib (INC280, CAS 1029712-80-8).

Platelet-derived Growth Factor (PDGF) receptor inhibitors: Imatinib (Gleevec®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Quizartinib (AC220, CAS 950769-58-1); Pazopanib (Votrient®); Axitinib (Inlyta®); Sorafenib (Nexavar®); Vargatef (BIBF1120, CAS 928326-83-4); Telatinib (BAY57-9352, CAS 332012-40-5); Vatalanib dihydrochloride (PTK787, CAS 212141-51-0); and Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470).

Phosphoinositide 3-kinase (PI3K) inhibitors: 4-[2-(1H-Indazol-4-yl)-6-[[4-(methylsulfonyl)piperazin-1-yl]methyl] thieno[3,2-d]pyrimidin-4-yl]morpholine (also known as GDC 0941 and described in PCT Publication Nos. WO 09/036082 and WO 09/055730); 4-(trifluoromethyl)-5-(2,6-dimorpholinopyrimidin-4-yl)pyridin-2-amine (also known as BKM120 or NVP-BKM120, and described in PCT Publication No. WO2007/084786); Alpelisib (BYL719): (5Z)-5-[[4-(4-Pyridinyl)-6-quinolinyl]methylene]-2,4-thiazolidinedione (GSK1059615, CAS 958852-01-2); 5-[8-methyl-9-(1-methylethyl)-2-(4-morpholinyl)-9H-purin-6-yl]-2-pyrimidinamine (VS-5584, CAS 1246560-33-7) and everolimus (AFINITOR®).

Cyclin-Dependent Kinase (CDK) inhibitors: Ribociclib (LEE011, CAS 1211441-98-3); Aloisine A; Alvocidib (also known as flavopiridol or HMR-1275, 2-(2-chlorophenyl)-5, 7-dihydroxy-8-[(3S,4R)-3-hydroxy-1-methyl-4-piperidinyl]-4-chromenone, and described in U.S. Pat. No. 5,621,002); Crizotinib (PF-02341066, CAS 877399-52-5); 2-(2-Chlorophenyl)-5,7-dihydroxy-8-[(2R,3S)-2-

(hydroxymethyl)-1-methyl-3-pyrrolidinyl]-4H-1-benzopyran-4-one, hydrochloride (P276-00, CAS 920113-03-7); 1-Methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265, CAS 927880-90-8); Indisulam (E7070); Roscovitine (CYC202); 6-Acetyl-8-cyclopentyl-5-methyl-2-(5-piperazin-1-yl-pyridin-2-ylamino)-8H-pyrido[2,3-d]pyrimidin-7-one, hydrochloride (PD0332991); Dinaciclib (SCH727965); N-[5-[[(5-tert-Butyloxazol-2-yl)methyl]thio]thiazol-2-yl]piperidine-4-carboxamide (BMS 387032, CAS 345627-80-7); 4-[[9-Chloro-7-(2,6-difluorophenyl)-5H-pyrimido[5,4-d][2]benzazepin-2-yl]amino]-benzoic acid (MLN8054, CAS 869363-13-3); 5-[3-(4,6-Difluoro-1H-benzimidazol-2-yl)-1H-indazol-5-yl]-N-ethyl-4-methyl-3-pyridinemethanamine (AG-024322, CAS 837364-57-5); 4-(2,6-Dichlorobenzoylamino)-1H-pyrazole-3-carboxylic acid N-(piperidin-4-yl)amide (AT7519, CAS 844442-38-2); 4-[2-Methyl-1-(1-methylethyl)-1H-imidazol-5-yl]-N-[4-(methylsulfonyl)phenyl]-2-pyrimidinamine (AZD5438,CAS 602306-29-6); Palbociclib (PD-0332991); and (2R,3R)-3-[[2-[[3-[[S(R)]—S-cyclopropylsulfonimidoyl]-phenyl]amino]-5-(trifluoromethyl)-4-pyrimidinyl]oxy]-2-butanol (BAY 10000394).

p53-MDM2 inhibitors: (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5, 6-dihydro-1H-pyrrolo[3,4-d]imidazol-4-one, [(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone (RG7112), 4-[[(2R,3S,4R,5S)-3-(3-chloro-2-fluorophenyl)-4-(4-chloro-2-fluorophenyl)-4-cyano-5-(2,2-dimethylpropyl)pyrrolidine-2-carbonyl]amino]-3-methoxybenzoic acid (RG7388), SAR299155, 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid (AMG232), {(3R,5R,6S)-5-(3-Chlorophenyl)-6-(4-chlorophenyl)-1-[(2S,3S)-2-hydroxy-3-pentanyl]-3-methyl-2-oxo-3-piperidinyl}acetic acid (AM-8553), (±)-4-[4,5-Bis(4-chlorophenyl)-2-(2-isopropoxy-4-methoxy-phenyl)-4,5-dihydro-imidazole-1-carbonyl]-piperazin-2-one (Nutlin-3), 2-Methyl-7-[Phenyl (phenylamino)methyl]-8-quinolinol (NSC 66811), 1-N-[2-(1H-indol-3-yl)ethyl]-4-N-pyridin-4-ylbenzene-1,4-diamine (JNJ-26854165), 4-[4,5-bis(3,4-chlorophenyl)-2-(2-isopropoxy-4-methoxy-phenyl)-4,5-dihydro-imidazole-1-carboxyl]-piperazin-2-one (Caylin-1), 4-[4,5-bis(4-trifluoromethyl-phenyl)-2-(2-isopropoxy-4-methoxy-phenyl)-4,5-dihydro-imidazole-1-carboxyl]-piperazin-2-one (Caylin-2), 5-[[3-Dimethylamino)propyl]amino]-3,10-dimethylpyrimido[4,5-b]quinoline-2,4(3H,10H)-dione dihydrochloride (HLI373) and trans-4-Iodo-4'-boranyl-chalcone (SC204072).

Mitogen-activated protein kinase (MEK) inhibitors: XL-518 (also known as GDC-0973, Cas No. 1029872-29-4, available from ACC Corp.); Selumetinib (5-[(4-bromo-2-chlorophenyl)amino]-4-fluoro-N-(2-hydroxyethoxy)-1-methyl-1H-benzimidazole-6-carboxamide, also known as AZD6244 or ARRY 142886, described in PCT Publication No. WO2003077914); 2-[(2-Chloro-4-iodophenyl)amino]-N-(cyclopropylmethoxy)-3,4-difluoro-benzamide (also known as CI-1040 or PD184352 and described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl)thio]methylene]-butanedinitrile (also known as U0126 and described in U.S. Pat. No. 2,779,780); N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3 S,4R,5Z,8S,9S,11E)-14-(Ethylamino)-8,9,16-trihydroxy-3,4-dimethyl-3,4,9, 19-tetrahydro-1H-2-benzoxacyclotetradecine-1,7(8H)-dione] (also known as E6201 and described in PCT Publication No. WO2003076424); 2'-Amino-3'-methoxyflavone (also known as PD98059 available from Biaffin GmbH & Co., KG, Germany); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); Pimasertib (AS-703026, CAS 1204531-26-9); Trametinib dimethyl sulfoxide (GSK-1120212, CAS 1204531-25-80); 2-(2-Fluoro-4-iodophenylamino)-N-(2-hydroxyethoxy)-1, 5-dimethyl-6-oxo-1,6-dihydropyridine-3-carboxamide (AZD 8330); 3,4-Difluoro-2-[(2-fluoro-4-iodophenyl)amino]-N-(2-hydroxyethoxy)-5-[(3-oxo-[1,2]oxazinan-2-yl)methyl] benzamide (CH 4987655 or Ro 4987655); and 5-[(4-Bromo-2-fluorophenyl)amino]-4-fluoro-N-(2-hydroxyethoxy)-1-methyl-1H-Benzimidazole-6-carboxamide (MEK162).

B-RAF inhibitors: Regorafenib (BAY73-4506, CAS 755037-03-7); Tuvizanib (AV951, CAS 475108-18-0); Vemurafenib (Zelboraf®, PLX-4032, CAS 918504-65-1); Encorafenib (also known as LGX818); 1-Methyl-5-[[2-[5-(trifluoromethyl)-1H-imidazol-2-yl]-4-pyridinyl]oxy]-N-[4-(trifluoromethyl)phenyl-1H-benzimidazol-2-amine (RAF265, CAS 927880-90-8); 5-[1-(2-Hydroxyethyl)-3-(pyridin-4-yl)-1H-pyrazol-4-yl]-2,3-dihydroinden-1-one oxime (GDC-0879, CAS 905281-76-7); 5-[2-[4-[2-(Dimethylamino)ethoxy]phenyl]-5-(4-pyridinyl)-1H-imidazol-4-yl]-2,3-dihydro-1H-Inden-1-one oxime (GSK2118436 or SB590885); (+/−)-Methyl (5-(2-(5-chloro-2-methylphenyl)-1-hydroxy-3-oxo-2,3-dihydro-1H-isoindol-1-yl)-1H-benzimidazol-2-yl)carbamate (also known as XL-281 and BMS908662), dabrafenib (Tafinlar®), and N-(3-(5-chloro-1H-pyrrolo[2,3-b]pyridine-3-carbonyl)-2,4-difluorophenyl) propane-1-sulfonamide (also known as PLX4720).

ALK inhibitors: Crizotinib (Xalkori®).

BRD inhibitors: JQ-1 (Nature 2010 Dec. 23; 468(7327): 1067-73), BI2536 (ACS Chem. Biol. 2014 May 16; 9(5): 1160-71; Boehringer Ingelheim), TG101209 (ACS Chem. Biol. 2014 May 16; 9(5):1160-71), OTX015 (Mol. Cancer Ther. November 2013/2; C244; Oncoethix), IBET762 (J Med Chem. 2013 Oct. 10; 56(19):7498-500; GlaxoSmithKline), IBET151 (Bioorg. Med. Chem. Lett. 2012 Apr. 15; 22(8):2968-72; GlaxoSmithKline), PFI-1 (J. Med. Chem. 2012 Nov. 26; 55(22):9831-7; Cancer Res. 2013 Jun. 1; 73(11):3336-46; Structural Genomics Consortium) or CPI-0610 (Constellation Pharmaceuticals). In other embodiments, the BRD inhibitor is IBET 762 (GSK525762), TEN-010 (Tensha Therapeutics), CPI-203 (*Leukemia*. 28 (10): 2049-59, 2014), RVX-208 (*Proceedings of the National Academy of Sciences of the United States of America*. 110 (49): 19754-9, 2013), LY294002 (*ACS Chemical Biology*. 9 (2): 495-502, 2014), AZD5153 (*Journal of Medicinal Chemistry*. 59 (17): 7801-17, 2016), MT-1 (*Nature Chemical Biology*. 12 (12): 1089-1096 2016) or MS645 (*Proceedings of the National Academy of Sciences of the United States of America*. 115 (31): 7949-7954, 2018).

Histone methyltransferase inhibitors: DOT1-like histone methyltransferase (DOT1L) inhibitors. DOT1L is a histone methyltransferase enzyme that targets lysine 79 in the globular domain of histone H3 for mono-, di-, or trimethylation. In some of these embodiments, the further therapeutic agent is EPZ004777, EPZ-5676 (Blood. 2013 Aug. 8; 122(6): 1017-25) or SGC0946 (Nat. Commun. 2012; 3:1288), for example, EPZ-5676. Histone deacetylase (HDAC) inhibitors. HDAC proteins may be grouped into classes based on homology to yeast HDAC proteins with Class I made up of HDAC1, HDAC2, HDAC3 and HDAC 8; Class IIa made up of HDAC4, HDAC5, HDAC7 and HDAC 9; Class IIb made up of HDAC6 and HDAC10; and Class IV made up of HDAC11. In some of these embodiments, the further therapeutic agent is trichostatin A, vorinostat (Proc. Natl. Acad. Sci. U.S.A. 1998 Mar. 17; 95(6):3003-7), givinostat, abexinostat (Mol. Cancer Ther. 2006 May; 5(5):1309-17), belinostat (Mol. Cancer Ther. 2003 August; 2(8):721-8), panobinostat (Clin. Cancer Res. 2006 Aug. 1; 12(15):4628-35), resminostat (Clin. Cancer Res. 2013 Oct. 1; 19(19): 5494-504), quisinostat (Clin. Cancer Res. 2013 Aug. 1; 19(15):4262-72), depsipeptide (Blood. 2001 Nov. 1; 98(9): 2865-8), entinostat (Proc. Natl. Acad. Sci. U.S.A. 1999 Apr. 13; 96(8):4592-7), mocetinostat (Bioorg. Med. Chem. Lett. 2008 Feb. 1; 18(3):1067-71) or valproic acid (EMBO J. 2001 Dec. 17; 20(24):6969-78). For example, in some embodiments, the further therapeutic agent is panobinostat. In other embodiments, the further therapeutic agent is panobinostat or SAHA.

Histone demethylase inhibitors. In particular embodiments, the histone demethylase inhibitor is a lysine-specific demethylase 1A (Lsdl) inhibitor. In some of these embodiments, the further therapeutic agent is HCl-2509 (BMC Cancer. 2014 Oct. 9; 14:752), tranylcypromine or ORY-1001 (J. Clin. Oncol 31, 2013 (suppl; abstr e13543). In other embodiments, the further therapeutic agent is HCl-2509.

MLL-menin inhibitors: MI-453, M-525, and MI-503.

Immunomodulators: afutuzumab (available from ROCHE®); pegfilgrastim (NEULASTA®); lenalidomide (CC-5013, REVLIMID®); thalidomide (THALOMID®); actimid (CC4047); and IRX-2 (mixture of human cytokines including interleukin 1, interleukin 2, and interferon γ, CAS 951209-71-5, available from IRX Therapeutics).

Chimeric antigen receptor T-cell (CAR-T) therapy: tisagenlecleucel (Novartis), axicabtagene ciloleucel (Kite), and tocilizumab and atlizumab (Roche).

Immune checkpoint inhibitors. In certain aspects of all embodiments, the further therapeutic agent is an immune checkpoint inhibitor (e.g., a PD-1 inhibitor, such as pembrolizumab or nivolumab; a PD-L1 inhibitor, such as atezolizumab, avelumab, or durvalumab; a CTLA-4 inhibitor; a LAG-3 inhibitor; or a Tim-3 inhibitor). Other immune checkpoint inhibitors of interest for use in combination with compounds of the present disclosure include: PD-1 inhibitors, such as pembrolizumab (KEYTRUDA®), nivolumab (OPDIVO®), cemiplimab (LIBTAYO®), spartalizumab (PDR001), pidilizumab (CureTech), MEDI0680 (Medimmune), cemiplimab (REGN2810), dostarlimab (TSR-042), PF-06801591 (Pfizer), tislelizumab (BGB-A317), camrelizumab (INCSHR1210, SHR-1210), and AMP-224 (Amplimmune); PD-L1 inhibitors, such as atezolizumab (TECENTRIQ®), avelumab (BAVENCIO®), durvalumab (IMFINZI®), FAZ053 (Novartis), and BMS-936559 (Bristol-Myers Squibb); and drugs that target CTLA-4, such as ipilimumab (YERVOY®).

In various embodiments, the immune checkpoint inhibitor is a PD-1 inhibitor. In specific embodiments, the PD-1 inhibitor is pembrolizumab, nivolumab, or a combination thereof. In particular embodiments, the PD-1 inhibitor is pembrolizumab (also known as lambrolizumab, MK-3475, MK03475, SCH-900475, or KEYTRUDA®). Pembrolizumab and other anti-PD-1 antibodies are disclosed in Hamid, O., et al. (2013) New England Journal of Medicine 369 (2): 134-44, U.S. Pat. No. 8,354,509, and WO 2009/114335, incorporated by reference in their entireties. In particular embodiments, the PD-1 inhibitor is nivolumab (also known as MDX-1106, MDX-1106-04, ONO-4538, BMS-936558, or OPDIVO®). Nivolumab (clone 5C4) and other anti-PD-1 antibodies are disclosed in U.S. Pat. No. 8,008,449 and WO 2006/121168, incorporated by reference in their entireties. In some other embodiments, the PD-1 inhibitor is AMP-224 (Amplimmune), CBT-501 (CBT Pharmaceuticals), CBT-502 (CBT Pharmaceuticals), JS001 (Junshi Biosciences), IBI308 (Innovent Biologics), INCSHR1210 (Incyte), also known as SHR-1210 (Hengrui Medicine), BGBA317 (Beigene), BGB-108 (Beigene), BAT-I306 (Bio-Thera Solutions), GLS-010 (Gloria Pharmaceuticals; WuXi Biologics), AK103, AK104, AK105 (Akesio Biopharma; Hangzhou Hansi Biologics; Hanzhong Biologics), LZMO09 (Livzon), HLX-10 (Henlius Biotech), MEDI0680 (Medimmune), PDF001 (Novartis), PF-06801591 (Pfizer), pidilizumab (CureTech), REGN2810 (Regeneron), TSR-042 (Tesaro), also known as ANB011, or CS1003 (CStone Pharmaceuticals). MEDI0680 (Medimmune) is also known as AMP-514. MEDI0680 and other anti-PD-1 antibodies are disclosed in U.S. Pat. No. 9,205,148 and WO 2012/145493, incorporated by reference in their entireties. Pidilizumab is also known as CT-011. Pidilizumab and other anti-PD-1 antibodies are disclosed in Rosenblatt, J., et al. (2011) J Immunotherapy 34(5): 409-18, U.S. Pat. Nos. 7,695,715, 7,332,582, and 8,686,119, incorporated by reference in their entireties.

In one embodiment, the anti-PD-1 antibody molecule is cemiplimab. In one embodiment, the anti-PD-1 antibody molecule is sintilimab. In one embodiment, the anti-PD-1 antibody molecule is toripalimab. In one embodiment, the anti-PD-1 antibody molecule is camrelizumab.

Further known anti-PD-1 antibody molecules include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entireties.

In one embodiment, the PD-1 inhibitor is an anti-PD-1 antibody molecule as described in US 2015/0210769. In one embodiment, the anti-PD-1 antibody molecule comprises the CDRs, variable regions, heavy chains and/or light chains of BAP049-Clone-E or BAP049-Clone-B disclosed in US 2015/0210769. The antibody molecules described herein can be made by vectors, host cells, and methods described in US 2015/0210769, incorporated by reference in its entirety.

In one embodiment, the PD-1 inhibitor is a peptide that inhibits the PD-1 signaling pathway, e.g., as described in U.S. Pat. No. 8,907,053, incorporated by reference in its entirety. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In one embodiment, the PD-1 inhibitor is AMP-224 (B7-DCIg (Amplimmune), e.g., disclosed in WO 2010/027827 and WO 2011/066342, incorporated by reference in their entireties).

In some embodiments, the immune checkpoint inhibitor is a PD-L1 inhibitor. In some such embodiments, the PD-L1 inhibitor is atezolizumab, avelumab, durvalumab, or a combination thereof. In particular embodiments, the PD-L1 inhibitor is atezolizumab, also known as MPDL3280A, RG7446, RO5541267, YW243.55.570, or TECENTRIQ™. Atezolizumab and other anti-PD-L1 antibodies are disclosed in U.S. Pat. No. 8,217,149, incorporated by reference in its entirety. In particular embodiments, the PD-L1 inhibitor is avelumab, also known as MSB0010718C. Avelumab and other anti-PD-L1 antibodies are disclosed in WO 2013/079174, incorporated by reference in its entirety. In particular embodiments, the PD-L1 inhibitor is durvalumab, also known as MEDI4736. Durvalumab and other anti-PD-L1 antibodies are disclosed in U.S. Pat. No. 8,779,108, incorporated by reference in its entirety. In certain embodiments, the PD-L1 inhibitor is KN035 (Alphamab; 3DMed), BMS 936559 (Bristol-Myers Squibb), CS1001 (CStone Pharmaceuticals), FAZ053 (Novartis), SHR-1316 (Hengrui Medicine), TQB2450 (Chiatai Tianqing), STI-A1014 (Zhaoke Pharm; Lee's Pharm), BGB-A333 (Beigene), MSB2311 (Mabspace Biosciences), or HLX-20 (Henlius Biotech). In one embodiment, the anti-PD-L1 antibody molecule is BMS-936559 (Bristol-Myers Squibb), also known as MDX-1105 or 12A4. BMS-936559 and other anti-PD-L1 antibodies are disclosed in U.S. Pat. No. 7,943,743 and WO 2015/081158, incorporated by reference in their entireties. In some embodiments, the PD-L1 inhibitor is a monoclonal antibody (e.g., as made by Hisun Pharm and applying for clinical trials).

In one embodiment, the PD-L1 inhibitor is an anti-PD-L1 antibody molecule. In one embodiment, the PD-L1 inhibitor is an anti-PD-L1 antibody molecule as disclosed in US 2016/0108123, incorporated by reference in its entirety. In one embodiment, the anti-PD-L1 antibody molecule comprises the CDRs, variable regions, heavy chains and/or light chains of BAP058-Clone O or BAP058-Clone N disclosed in US 2016/0108123.

Further known anti-PD-L1 antibodies include those described, e.g., in WO 2015/181342, WO 2014/100079, WO 2016/000619, WO 2014/022758, WO 2014/055897, WO 2015/061668, WO 2013/079174, WO 2012/145493, WO 2015/112805, WO 2015/109124, WO 2015/195163, U.S. Pat. Nos. 8,168,179, 8,552,154, 8,460,927, and 9,175,082, incorporated by reference in their entireties.

In some embodiments, the immune checkpoint inhibitor is a CTLA-4 inhibitor. In certain embodiments, the CTLA-4 inhibitor is ipilimumab. In other embodiments, the CTLA4 inhibitor is tremelimumab.

In some embodiments, the immune checkpoint inhibitor is a LAG-3 inhibitor. In some embodiments, the LAG-3 inhibitor is chosen from LAG525 (Novartis), BMS-986016 (Bristol-Myers Squibb), or TSR-033 (Tesaro). In one embodiment, the LAG-3 inhibitor is an anti-LAG-3 antibody molecule. In one embodiment, the LAG-3 inhibitor is an anti-LAG-3 antibody molecule as disclosed in US 2015/0259420, incorporated by reference in its entirety. In one embodiment, the anti-LAG-3 antibody molecule comprises the CDRs, variable regions, heavy chains and/or light chains of BAP050-Clone I or BAP050-Clone J disclosed in US 2015/0259420.

In one embodiment, the anti-LAG-3 antibody molecule is BMS-986016 (Bristol-Myers Squibb), also known as BMS986016. BMS-986016 and other anti-LAG-3 antibodies are disclosed in WO 2015/116539 and U.S. Pat. No. 9,505,839, incorporated by reference in their entireties. In one embodiment, the anti-LAG-3 antibody molecule is TSR-033 (Tesaro). In one embodiment, the anti-LAG-3 antibody molecule is IMP731 or GSK2831781 (GSK and Prima BioMed). IMP731 and other anti-LAG-3 antibodies are disclosed in WO 2008/132601 and U.S. Pat. No. 9,244,059, incorporated by reference in their entireties. In one embodiment, the anti-LAG-3 antibody molecule is IMP761 (Prima BioMed).

Further known anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839, incorporated by reference in their entireties.

In one embodiment, the anti-LAG-3 inhibitor is a soluble LAG-3 protein, e.g., IMP321 (Prima BioMed), e.g., as disclosed in WO 2009/044273, incorporated by reference in its entirety.

In some embodiments, the immune checkpoint inhibitor is a TIM-3 inhibitor. In some embodiments, the TIM-3 inhibitor is MGB453 (Novartis) or TSR-022 (Tesaro).

In one embodiment, the TIM-3 inhibitor is an anti-TIM-3 antibody molecule. In one embodiment, the TIM-3 inhibitor is an anti-TIM-3 antibody molecule as disclosed in US 2015/0218274, incorporated by reference in its entirety. In one embodiment, the anti-TIM-3 antibody molecule comprises the CDRs, variable regions, heavy chains and/or light chains of ABTIM3-hum11 or ABTIM3-hum03 disclosed in US 2015/0218274.

In one embodiment, the anti-TIM-3 antibody molecule is TSR-022 (AnaptysBio/Tesaro). In one embodiment, the anti-TIM-3 antibody molecule comprises one or more of the CDR sequences (or collectively all of the CDR sequences), the heavy chain or light chain variable region sequence, or the heavy chain or light chain sequence of APE5137 or APE5121. APE5137, APE5121, and other anti-TIM-3 antibodies are disclosed in WO 2016/161270, incorporated by reference in its entirety. In one embodiment, the anti-TIM-3 antibody molecule is the antibody clone F38-2E2.

Further known anti-TIM-3 antibodies include those described, e.g., in WO 2016/111947, WO 2016/071448, WO 2016/144803, U.S. Pat. Nos. 8,552,156, 8,841,418, and 9,163,087, incorporated by reference in their entireties.

Some subjects may experience allergic reactions to the compositions of the present disclosure and/or other anti-cancer agent(s) during or after administration; therefore, anti-allergic agents are often administered to minimize the risk of an allergic reaction. Suitable anti-allergic agents include corticosteroids (Knutson, S., et al., *PLoS One*, DOI:10.1371/journal.pone.0111840 (2014)), such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some subjects may experience nausea during and after administration of the composition of the present disclosure and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®). dexamethasone (Decadron®), prochlorperazine (Compazine®), casopitant (Rezonic® and Zunrisa®), and combinations thereof.

Medication to alleviate the pain experienced during the treatment period is often prescribed to make the subject more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

Immunomodulators of particular interest for combinations with the compositions of the present disclosure include: Afutuzumab (available from Roche®); Pegfilgrastim (Neulasta®); Lenalidomide (CC-5013, Revlimid®); Thalidomide (Thalomid®), Actimid (CC4047); and IRX-2 (mixture of human cytokines including interleukin 1, interleukin 2, and interferon γ, CAS 951209-71-5, available from IRX Therapeutics).

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy in combination with compounds of the present disclosure. Suitable cytoprotective agents include amifostine (ETHYOL®), glutamine, dimesna (TAVOCEPT®), mesna (MESNEX®), dexrazoxane (ZINECARD® or TOTECT®), xaliproden (XAPRILA®), and leucovorin (also known as calcium leucovorin, citrovorum factor and folinic acid).

Some patients may experience allergic reactions to compounds of the present disclosure and/or other therapeutic agent(s) (e.g., anti-cancer agent(s)) during or after administration. Therefore, anti-allergic agents can be administered in combination with compounds of the present disclosure and/or other therapeutic agent(s) (e.g., anti-cancer agent(s)) to minimize the risk of an allergic reaction. Suitable anti-allergic agents include corticosteroids (Knutson, S., et al., *PLoS One*, DOI:10.1371/journal.pone.0111840 (2014)), such as dexamethasone (e.g., DECADRON®), beclomethasone (e.g., BECLOVENT®), hydrocortisone (also known as cortisone, hydrocortisone sodium succinate, hydrocortisone sodium phosphate, sold under the tradenames ALACORT®, hydrocortisone phosphate, SOLU-CORTEF®, HYDROCORT ACETATE® and LANACORT®), prednisolone (sold under the tradenames DELTA-CORTEL®, ORAPRED®, PEDIAPRED® and PRELONE®), prednisone (sold under the tradenames DELTASONE®, LIQUID RED®, METICORTEN® and ORASONE®), methylprednisolone (also known as 6-methylprednisolone, methylprednisolone acetate, methylprednisolone sodium succinate, sold under the tradenames DURALONE®, MEDRALONE®, MEDROL®, M-PREDNISOL® and SOLU-MEDROL®); antihistamines, such as diphenhydramine (e.g., BENADRYL®), hydroxyzine, and cyproheptadine; and bronchodilators, such as the beta-adrenergic receptor agonists, albuterol (e.g., PROVENTIL®), and terbutaline (BRETHINE®).

Some patients may experience nausea during and after administration of the compounds described herein and/or other therapeutic agent(s) (e.g., anti-cancer agent(s)). Therefore, anti-emetics can be used in combination with compounds of the present disclosure and/or other therapeutic agent(s) (e.g., anti-cancer agent(s)) to prevent nausea (upper stomach) and vomiting. Suitable anti-emetics include aprepitant (EMEND®), ondansetron (ZOFRAN®), granisetron HCl (KYTRIL®), lorazepam (ATIVAN®, dexamethasone (DECADRON®), prochlorperazine (COMPAZINE®), casopitant (REZONIC® and ZUNRISA®), and combinations thereof.

Medication to alleviate the pain experienced during treatment is often prescribed to make the patient more comfortable. Common over-the-counter analgesics, such TYLENOL®, can also be used in combination with compounds of the present disclosure and/or other therapeutic agent(s) (e.g., anti-cancer agent(s)). Opioid analgesic drugs such as hydrocodone/paracetamol or hydrocodone/acetaminophen (e.g., VICODIN®), morphine (e.g., ASTRAMORPH® or AVINZA®), oxycodone (e.g., OXYCONTIN® or PERCOCET®), oxymorphone hydrochloride (OPANA®), and fentanyl (e.g., DURAGESIC®) can be useful for moderate or severe pain, and can be used in combination with compounds of the present disclosure and/or other therapeutic agent(s) (e.g., anti-cancer agent(s)).

The structure of the active compositions identified by code numbers, generic or trade names may be taken from the actual edition of the standard compendium "The Merck Index" or from databases, e.g. Patents International (e.g., IMS World Publications).

In one embodiment, the present disclosure provides pharmaceutical compositions either alone or together with other anti-cancer agents.

In one embodiment, an additional therapeutic agent is selected from the group consisting of mitotic inhibitors, alkylating agents, anti-metabolites, cell cycle inhibitors, enzymes, topoisomerase inhibitors such as CAMPTOSAR (irinotecan), biological response modifiers, anti-hormones, antiangiogenic agents such as MMP-2, MMP-9 and COX-2 inhibitors, anti-androgens, platinum coordination complexes (cisplatin, etc.), substituted ureas such as hydroxyurea; methylhydrazine derivatives, e.g., procarbazine; adrenocortical suppressants, e.g., mitotane, aminoglutethimide, hormone and hormone antagonists such as the adrenocorticosteriods (e.g., prednisone), progestins (e.g., hydroxyprogesterone caproate), estrogens (e.g., diethylstilbesterol), antiestrogens such as tamoxifen, androgens, e.g., testosterone propionate, and aromatase inhibitors, such as anastrozole, and AROMASIN (exemestane).

In addition, the compositions and methods of administration described herein can be used in combination with one or more JAK inhibitors. In some other embodiments, the JAK inhibitor is ruxolitinib, tofacitinib, oclacitinib, baricitinib, filgotinib, gandotinib, lestaurtinib, momelotinib, pacritinib, PF-04965842, updacitinib, perficitinib, fedratinib, cucurbitacin I, CHZ868, decernotinib, CEP-33779, R348, fibotinib, or ABT-494, which compounds are known in the art. In some embodiments, the JAK inhibitor is BMS-911543, ASN002, itacitinib, NS-018, AZD1480, gandotinib, and combinations thereof.

In some embodiments, the JAK inhibitor is a JAK1, JAK2 inhibitor, or both. For example, in some embodiments the JAK inhibitor is selected from the group consisting of ruxolitinib, gandotinib, lestaurtinib, momelotinib, pacritinib, and fedratinib. In more specific embodiments, the JAK inhibitor is ruxolitinib. In some of these embodiments, the JAK inhibitor can be optionally administered in combination with the Pim kinase inhibitor and the additional therapeutic agent(s). That is, in some embodiments, the method further comprises administering an additional therapeutic agent. In some embodiments, additional therapeutic agents include hydroxyurea, interferon alpha, cladribine, thalidomide (including derivatives thereof, e.g., pomalidomide, lenolidamide), corticosteroids (e.g., prednisone), everolimus, androgens (e.g., testosterone) and combinations thereof. In some embodiments, the additional therapeutic agent is a Pim kinase inhibitor. In some embodiments, the additional Pim kinase inhibitor is PIM447 or INCB053914.

In some embodiments, the method further comprises administering an immune checkpoint inhibitor. In some embodiments, the immune checkpoint molecule is CTLA-4, PD-1 or PD-L1. In some embodiments, the method further comprises administering a CTLA-4 inhibitor. In certain embodiments, the CTLA-4 inhibitor is ipilimumab. In other embodiments, the CTLA-4 inhibitor is tremelimumab.

In some embodiments, the method further comprises administering a PD-1 inhibitor. Exemplary PD-1 inhibitors include, but are not limited to, pembrolizumab, nivolumab, CBT-501 (CBT Pharmaceuticals), CBT-502 (CBT Pharmaceuticals), JS001 (Junshi Biosciences), IBI308 (Innovent Biologics), SHR-1210 (Hengrui Medicine), BGB-A317 (Beigene), BAT-I306 (Bio-Thera Solutions), GLS-010 (Gloria Pharmaceuticals; WuXi Biologics), AK103, AK104, AK105 (Akesio Biopharma; Hangzhou Hansi Biologics; Hanzhong Biologics), LZM009 (Livzon), HLX-10 (Henlius Biotech), CS1003 (CStone Pharmaceuticals), or combinations thereof.

In some embodiments, the PD-1 inhibitor is a monoclonal antibody (e.g., made by Genor Biopharma and in Phase I of clinical trials as of this filing; as made by Shenzhou Gongcheng and applying for clinical trials as of this filing; as made by Lunan Hope Pharmaceuticals and applying for clinical trials as of this filing).

In some embodiments, the method further comprises administering a PD-L1 inhibitor. Exemplary PD-L1 inhibitors include, but are not limited to, atezolizumab, avelumab, durvalumab, or a combination thereof. In certain embodiments, the PD-L1 inhibitor is KN035 (Alphamab; 3DMed), CS1001 (CStone Pharmaceuticals), SHR-1316 (Hengrui Medicine), TQB2450 (Chiatai Tianqing), STI-A1014 (Zhaoke Pharm; Lee's Pharm), BGB-A333 (Beigene), MSB2311 (Mabspace Biosciences), HLX-20 (Henlius Biotech) or combinations thereof. In some embodiments, the PD-L1 inhibitor is a monoclonal antibody (e.g., as made by Hisun Pharm and applying for clinical trials as of this filing).

In some embodiments, the method further comprises administering a FLT3 inhibitor, a caspase 3 activator, a BET inhibitor, an LSD1 inhibitor, a PI3K inhibitor, a PLK inhibitor, a cyclic AMP phosphodiesterase, a histone deacetylase inhibitor, an mTOR inhibitor, an iron chelator, a SYK inhibitor, an SMO antagonist or inhibitor, a hedgehog signaling pathway inhibitor, a BCR-ABL/Kit inhibitor, a BCR-ABL inhibitor, a DNA methylation inhibitor, an SMAC mimetic, an ACVR2a fusion protein, a thromopoeitin receptor agonist, a PI3K delta inhibitor, a tyrosine kinase inhibitor, a recombinant amyloid P/pentraxin 2 protein, a CDK4/6 inhibitor, a telomerase inhibitor, a TGF-β superfamily inhibitor, an LOXL2 inhibitor (e.g., an antibody), a BCL-2 inhibitor, a WNT signal inhibitor, a PD-L1 antibody, PD-1 antibody, a VEGF1/2 inhibitor, a tubulin polymerization inhibitor, an aurora kinase inhibitor, a PNP inhibitor, an AKT inhibitor or combinations thereof. In some embodiments, the method further comprises administering a hypoxia activated prodrug of bromo-isophosphoramide mustard (Br-IPM). In more specific embodiments, the method further comprises administering alvocidib, plitidepsin, INCB054329, INCB057643, INCB053914, INCB059872, rigosertib, anagrelide, givinostat, ridaforolimus, deferasirox, ASN002, LDE225/sonidegib, gleevec, dasatinib, RAD001, azacytidine, pracinostat, CPI-0610, LCL-161, sotatercept, eltrombopag, INCB050465, vismodegib, lestaurtinib (and other staurosporine analogs), PRM-151, PIM447, ribociclib, imetelstat, luspatercept, saridegib, simtuzumab, obatoclax, navitoclax, buparlisib, idelalisib, panobinostat, IMG-7289, luitpold azacitidine, CWP232291, durvalumab, vatalanib, MKC-1, TAK-901, evofosfamide, TXA127, glasdegib, AC220, forodesine (and related purine analogs), triciribine or combinations thereof.

In addition, the above methods can be carried out in combination with radiation therapy, wherein the amount of a composition in combination with the radiation therapy is effective in treating the above diseases. Techniques for administering radiation therapy are known in the art, and these techniques can be used in the combination therapy described herein.

In some embodiments, the compound of structure (I), or a pharmaceutically acceptable salt thereof (e.g., Form I of the hydrochloride salt of the compound of structure (I)), is administered on a treatment cycle, for example, a 28-day treatment cycle. In some embodiments, one or more treatment cycles (e.g., 1, 2, 3, 4, 5, 6, 7, 8, 9, 10, 11, 12, etc. cycles) of the compound of structure (I), or a pharmaceutically acceptable salt thereof (e.g., Form I of the hydrochloride salt of the compound of structure (I)), is administered. In some embodiments, the compound of structure (I), or a pharmaceutically acceptable salt thereof (e.g., Form I of the hydrochloride salt of the compound of structure (I)), is administered once or twice per day (e.g., once per day) for 28 days on a 28-day cycle.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

The following solvents were used in certain examples, for example, in the polymorph synthesis and screening experiments described below:
Acetonitrile, HPLC grade, Merck, Lot No. 1L1IF61732;
Ethanol, HPLC grade, Sigma, Lot No. 11085CH;
Methanol, HPLC grade, Merck, Lot No. SF1SF61609;
Isopropanol, AR, SCRC, Lot No. T20110623;
1-Butanol, AR, Jiangsu Enox Reagent Company, Lot No. 20110318;
Isopropyl acetate, AR, SCRC, Lot No. T20110217;
Acetone, AR, Jiangsu Enox Reagent Company, Lot No. 20110315;
MIBK, AR, Jiangsu Enox Reagent Company, Lot No. 20110216;
MEK, AR, SCRC, Lot No. T20090724;
Dichloromethane, AR, Shanghai Lingfeng Reagent Company, Lot No. 20111020;
Tetrahydrofuran, AR, Shanghai Lingfeng Reagent Company, Lot No. 20110901;
2-MeTHF, AR, Shanghai Jiachen Chemical Reagent Co. Ltd, Lot No. 100411;
N-Methylpyrrolidone, AR, Shanghai Runjie Reagent Company, Lot No. 20120116;
MTBE, HPLC grade, Scharlau, Lot No. 12670903;
1, 4-Dioxane, AR, Jiangsu Enox Reagent Company, Lot No. 20110701;
DMSO, HPLC grade, Merck, Lot No. SBOS600084;
DMF, AR, Jiangsu Enox Reagent Company, Lot No. 20110801;

Toluene, AR, SCRC, Lot No. T20100303;
Heptane, HPLC grade, Sigma-Aldrich, Lot No. 05442LH; and
Ethyl acetate, AR, Jiangsu Qiangsheng Reagent Company, Lot No. 20120201.

Example 1

Pharmacokinetic Study 1

Fasted male Sprague-Dawley rats were tested using four (4) different formulation vehicles (PO1, PO2, PO3 and PO4). The content of each formulation is summarized in Table 3a below.

TABLE 3a

Exemplary formulations

| Formulation | Components |
|---|---|
| PO1 | 100% Maisine 35-1 |
| PO2 | 90% Maisine 35-1 + 10% tween 20 |
| PO3 | 20% GELUCIRE ® 44/14 + 10% tween 20 |
| PO4 | 20% GELUCIRE ® 44/14 |

Each formulation included a nominal dosage at 21.7 mg/kg of the compound of structure (I). A summary of the pharmacokinetic profile for each different formulation is summarized in Table 3b below:

TABLE 3b

Parameters from PK Study 1

| PK Parameter | PO1 | PO2 | PO3 | PO4 |
|---|---|---|---|---|
| Nominal Dose (mg/Kg) | 21.7 | 21.7 | 21.7 | 21.7 |
| $C_{max}$ (ng/mL) | 160.57 | 98.53 | 261.00 | 633.67 |
| $T_{max}$ (h) | 6.67 | 3.00 | 2.00 | 2.00 |
| $T_{1/2}$ (h) | ND | 2.89 | 1.22 | 2.50 |
| $T_{last}$ (h) | 12.00 | 12.00 | ND | ND |
| $AUC_{0\text{-}last}$ (ng · h/mL) | 1106.59 | 455.87 | 773.24 | 1823.11 |
| $AUC_{0\text{-}inf}$ (ng · h/mL) | ND | 484.02 | 777.11 | 1846.85 |
| $MRT_{0\text{-}last}$ (h) | 5.76 | 4.43 | 2.78 | 2.81 |
| $MRT_{0\text{-}inf}$ (h) | ND | 5.56 | 2.82 | 3.18 |
| $AUC_{Extra}$ (%) | ND | 7.71 | 0.47 | 1.46 |
| AUMCExtra (%) | ND | 20.79 | 1.97 | 9.05 |
| Bioavailability (%) | 28.82 | 11.46 | 19.23 | 42.83 |

ND = not determined

The data show the bioavailability for the composition of GELUCIRE® 44/14 alone is about 1.5- to 3.7-fold higher than the compositions that contain no GELUCIRE® 44/14 or GELUCIRE® 44/14 in combination with other formulation agents.

Example 2

Pharmacokinetic Study 2

Fasted male Sprague-Dawley rats were tested using four (4) different formulation vehicles (PO5, PO6, PO7 and PO8). The content of each formulation is summarized in Table 4 below:

TABLE 4

Exemplary formulations

| Formulation | Components |
|---|---|
| PO5 | GELUCIRE ® Suspension |
| PO6 | GELUCIRE ® Suspension |
| PO7 | 1:1-Capmul MCM C8: GELUCIRE ® 44/14 |
| PO8 | 1:1-Capmul MCM C8: GELUCIRE ® 44/14 |

For each formulation type (i.e., GELUCIRE® suspension or Capmul/GELUCIRE® combination), a dosage 200 or 400 mg/kg of the compound of structure (I) was tested. A summary of the pharmacokinetic profile for each formulation is given in Table 5 below:

TABLE 5

Parameters from PK Study 2

| PK Parameter | PO5 | PO6 | PO7 | PO8 |
|---|---|---|---|---|
| Nominal Dose (mg/Kg) | 200 | 400 | 200 | 400 |
| $C_{max}$ (ng/mL) | 3843 | 6303 | 2507 | 4080 |
| $T_{max}$ (h) | 4.00 | 4.00 | 2.67 | 4.00 |
| $T_{1/2}$ (h) | 3.51 | 5.67 | 3.18 | 89.68 |
| $T_{last}$ (h) | 24.0 | 24.0 | 24.0 | 24.0 |
| $AUC_{0\text{-}last}$ (ng · h/mL) | 22690 | 60772 | 14535 | 34664 |
| $AUC_{0\text{-}inf}$ (ng · h/mL) | 23018 | 65264 | 14661 | 116350 |
| $MRT_{0\text{-}last}$ (h) | 5.82 | 8.05 | 5.07 | 8.19 |
| $MRT_{0\text{-}inf}$ (h) | 6.17 | 9.94 | 5.34 | 123.88 |
| $AUC_{Extra}$ (%) | 1.46 | 7.48 | 1.078 | 47.22 |
| $AUMC_{Extra}$ (%) | 6.7 | 23.72 | 5.804 | 63.53 |
| Bioavailability (%) | 46.7 | 62.5 | 29.9 | 35.7 |

ND = not determined

As the data show, the formulation compositions with GELUCIRE® alone (i.e., PO5 and PO6) show much better bioavailability than the formulation compositions of GELUCIRE® with Capmul MCM C8 in a 1:1 ratio (i.e., PO7 and PO8). At a dosage of 200 mg/kg, PO5 shows bioavailability that is greater than 1.5-fold better than PO7. Additionally, PO6 shows an increase in bioavailability of greater than 25% over PO8 at a dosage of 400 mg/kg.

Example 3

Pharmacokinetic Study 3

Fasted male Sprague-Dawley rats were tested using four (4) different formulation vehicles (PO9, PO10, PO11 and PO12). The content of each formulation is summarized in Table 6 below:

TABLE 6

Exemplary formulations

| Formulation | Components |
|---|---|
| PO9 | 20% GELUCIRE ® 44/14 + 10% tween 20 |
| PO10 | 20% GELUCIRE ® 44/14 |
| PO11 | 100% Capmul MCM |
| PO12 | 90% Capmul + 10% tween 20 |

Each composition was formulated with the compound of structure (I) at a dosage of 21.7 mg/kg. A summary of the pharmacokinetic profile for the different formulations is in Table 7 below:

TABLE 7

Parameters from PK Study 3

| PK Parameter | PO9 | PO10 | PO11 | PO12 |
|---|---|---|---|---|
| Nominal Dose (mg/Kg) | 21.7 | 21.7 | 21.7 | 21.7 |
| $C_{max}$ (ng/mL) | 261.00 | 633.67 | 44.80 | 36.50 |
| $T_{max}$ (h) | 2.00 | 2.00 | 8.00 | 8.00 |
| $T_{1/2}$ (h) | 1.22 | 2.50 | ND | 5.83 |
| $T_{last}$ (h) | ND | ND | 24.00 | ND |
| $AUC_{0\text{-}last}$ (ng · h/mL) | 773.24 | 1823.11 | 431.93 | 359.40 |
| $AUC_{0\text{-}inf}$ (ng · h/mL) | 777.11 | 1846.85 | ND | 397.07 |
| $MRT_{0\text{-}last}$ (h) | 2.78 | 2.81 | 10.02 | 8.81 |
| $MRT_{0\text{-}inf}$ (h) | 2.82 | 3.18 | ND | 12.36 |
| $AUC_{Extra}$ (%) | 0.47 | 1.46 | ND | 10.19 |
| $AUMC_{Extra}$ (%) | 1.97 | 9.05 | ND | 24.98 |
| Bioavailability (%) | 19.23 | 42.83 | 11.28 | 9.69 |

ND = not determined

As the data from Table 7 show, the formulation containing GELUCIRE® 44/14 alone has the best bioavailability of all the compositions tested. Specifically, the formulation with GELUCIRE® 44/14 alone shows a 2.2- to 4.4-fold greater bioavailability that the compositions with no GELUCIRE® or GELUCIRE® in combination with other formulation agents (e.g., Tween 20 or Capmul).

Example 4

Bioavailability Study

Formulation studies showed that the compound of structure (I) had poor bioavailability when administered alone (indicated as "Dry Powder (capsule)") in Table 8 below.

TABLE 8

Oral bioavailability of the compound of structure (I) in rats with different excipients

| Excipient | Oral Bioavailability (% F) |
|---|---|
| HPβCD | 11% |
| 10% EtOH/40% PG | 2% |
| 10% PS-20 | 39% |
| 10% PS-20/50% PEG400 | 15% |
| 10% EtOH/10% PEG300/20% HS15 | 38% |
| Corn Oil | 0% |
| Dry Powder (capsule) | 0% |

Accordingly, formulations were explored in order to develop improvements to the compound of structure (I)'s bioavailability. First, solubility studies were performed to determine which potential excipients would improve bioavailability. In these studies, the compound of structure (I) (HCl salt) was added to various lipid ingredients, solvents, and co-solvents and actively stirred for 24 hours. Additional drug was added to all solutions until there was un-dissolved drug remaining in all the preparations. Multi and single component excipient screens showed improved saturation solubility with GELUCIRE® 44/14, as shown in the Table 9, below.

TABLE 9

Solubility data with single component excipient screening

| Excipient (wt/wt) | Compound of structure (I) HCl added (mg) | Assay Concentration (mg/mL) |
|---|---|---|
| 20% GELUCIRE ® 44/14 | 30 | 27.49 |
| 100% GELUCIRE ® 44/14 | 30 | 2.50 |
| 2.5% Sodium Lauryl Sulfate | 23 | 11.87 |
| 10% Peceol | 5 | 0.01 |
| Propylene Glycol | 65 | 44.27 |
| PEG 400 | 4 | 1.50 |
| EtOH | 25 | 15.60 |
| 100% GELUCIRE ® 44/14 | 30 | 2.54 |
| 100% Vitamin E TPGS | 4 | 1.37 |

A rat pharmacokinetic (PK) formulation of 20 mg/kg of the compound of structure (I) (HCl salt) in GELUCIRE® 44/14 showed significant improvement to bioavailability (% F) as shown in Table 10.

TABLE 10

Rat PK result with different formulation

| Formulation | % F |
|---|---|
| 2.174 mg/mL in 5% Tween 20 | 12.2 |
| 2.174 mg/mL in 1% Tween 20 | 7.2 |
| 2.174 mg/mL in 10% Tween 20 w/2.5% SLS | 14.8 |
| 2.174 mg/mL in 2.5% SLS | 12.2 |
| 5.42 mg/mL in 20% Vitamin E TPGS | 21.6 |
| 5.42 mg/mL in 10% tween 20 + 20% Vitamin E TPGS | 19.9 |
| 4.348 mg/mL in 20% GELUCIRE ® 44/14 + 10% tween 20 in water | 19.2 |
| 4.348 mg/mL in 20% GELUCIRE ® 44/14 in water | 42.8 |

Based on this data, GELUCIRE® 44/14 shows the best performance when used as the primary and only excipient.

Example 5

Pharmacokinetic Study 4

Various formulations of the compound of structure (I) in different formulation vehicles (PO13 through PO20) were tested for their pharmacokinetic profile in rats. The content of each formulation is summarized in the table below:

TABLE 11

Exemplary formulations

| Formulation | Components | Appearance |
|---|---|---|
| PO13 | 2.174 mg/mL in 5% Tween 20 | nearly clear solution |
| PO14 | 2.174 mg/mL in 1% Tween 20 | homogenous opaque suspension |
| PO15 | 2.174 mg/mL in 10% Tween 20 w/2.5% SLS | clear solution |
| PO16 | 2.174 mg/mL in 2.5% SLS | clear solution |
| PO17 | 5.42 mg/mL in 20% Vitamin E TPGS | homogenous opaque suspension with fine particle |
| PO18 | 5.42 mg/mL in 10% tween 20 + 20% Vitamin E TPGS | homogenous hazy suspension with fine particle |
| PO19 | 4.348 mg/mL in 20% GELUCIRE ® 44/14 + 10% tween 20 in water | nearly clear solution |
| PO20 | 4.348 mg/mL in 20% GELUCIRE ® 44/14 in water | homogenous hazy suspension |

TABLE 11-continued

Exemplary formulations

| Formulation | Components | Appearance |
|---|---|---|
| PO21 | 4.348 mg/mL in Maisine 35-1 | homogenous hazy suspension |
| PO22 | 4.348 mg/mL in 90% Maisine 35-1 + 10% tween 20 | homogenous hazy suspension |

Each composition was formulated with the compound of structure (I) at a dosage of 21.7 mg/kg. A summary of the pharmacokinetic profiles for the different formulations is in Table 12 below:

TABLE 12

Parameters from PK Study 4

| Formulation | AUC | Cmax | % F | Normalized AUC |
|---|---|---|---|---|
| PO13 | 404 | 227 | 12.2 | 20.2 |
| PO14 | 256 | 195 | 7.2 | 12.8 |
| PO15 | 490 | 124 | 14.8 | 24.5 |

TABLE 12-continued

Parameters from PK Study 4

| Formulation | AUC | Cmax | % F | Normalized AUC |
|---|---|---|---|---|
| PO16 | 308 | 69.2 | 12.2 | 15.4 |
| PO17 | 803 | 264 | 21.6 | 40.15 |
| PO18 | 738 | 231 | 19.9 | 36.9 |
| PO19 | 773 | 261 | 19.2 | 38.65 |
| PO20 | 1823 | 634 | 42.8 | 91.15 |
| PO21 | 1107 | 161 | 28.8 | 55.35 |
| PO22 | 456 | 98.5 | 11.5 | 22.8 |

As the data from Table 12 show, the formulation containing GELUCIRE® 44/14 alone (PO20) is superior to all the compositions tested. Specifically, the formulation with GELUCIRE® alone (PO20) shows superior AUC, normalized AUC, highest Cmax and bioavailability (% F) as compared to all other tested formulations.

Example 6

Synthesis of Compound of Structure (I)

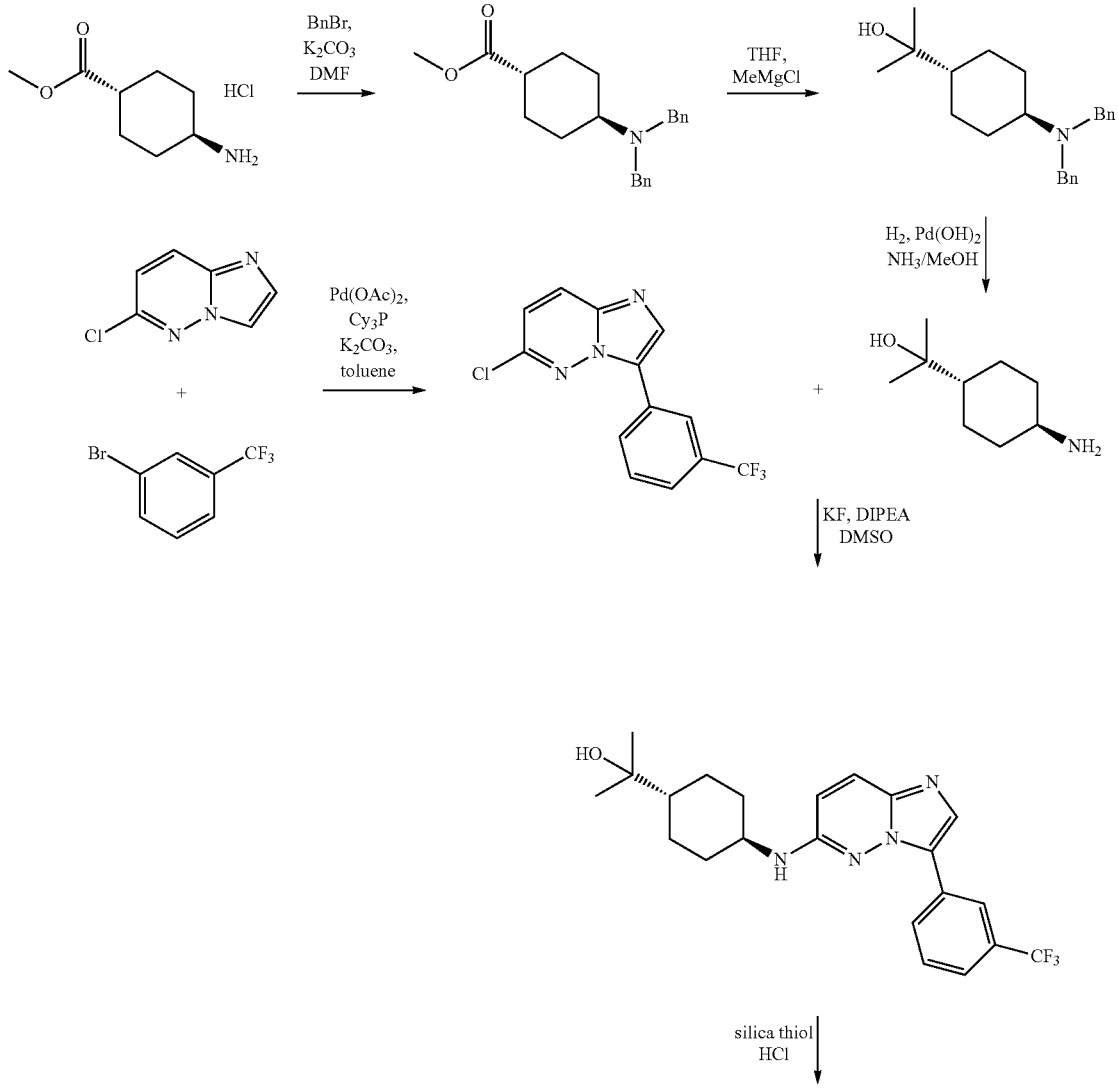

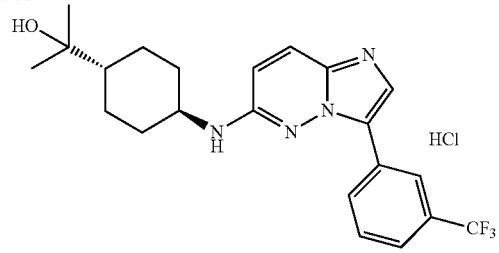

2-((1R,4R)-4-aminocyclohexyl)propan-2-ol was synthesized according to the reaction steps and under the reaction conditions depicted above. 2-((1R,4R)-4-aminocyclohexyl)propan-2-ol can also be synthesized according to the procedure described in International Publication No. WO 2013/013188, the entire contents of which are incorporated herein by reference.

In parallel, 6-chloroimidazo[1,2-b]pyridazine, potassium carbonate ($K_2CO_3$), 1-bromo-3-(trifluoromethyl)benzene, and toluene were charged into the reactor and degassed with nitrogen. Palladium acetate (Pd(OAc)$_2$) and tricyclohexylphosphine were then also charged into the reactor. The mixture was degassed with nitrogen and heated. After completion of the reaction, the mixture was cooled, and silica thiol was charged into the reactor. The mixture was stirred, filtered, and the filter cake was washed with toluene.

The filtrate was transferred back into the reactor and the organic phase was washed with water and concentrated. n-Heptane was added to the mixture dropwise with stirring, which was then cooled and filtered. The filter cake was rinsed with n-heptane and dried under reduced pressure. Representative yield of this step was 65.6% with HPLC purity of 91.4% (assay 76.8%).

6-chloro-3-(3-(trifluoromethyl)phenyl)imidazo[1,2-b]pyridazine and 2-((1R,4R)-4-aminocyclohexyl)propan-2-ol were charged into a reactor with potassium fluoride (KF), N,N-diisopropylethylamine (DIPEA), and dimethylsulfoxide (DMSO) and degassed with nitrogen. The mixture was heated, during which time additional 2-((1R,4R)-4-aminocyclohexyl)propan-2-ol, KF, and DIPEA were added to complete the reaction. The mixture was cooled and filtered through a pad of diatomite. The filter cake was washed with DMSO.

The filtrate, which included the desired product, was then transferred to a new reactor, and water was added dropwise. The mixture was stirred and then filtered, and the filter cake was washed with water. To this wet cake, silica thiol and tetrahydrofuran (THF) were added and the mixture was heated and stirred, cooled, filtered and the filter cake was washed with THF. This silica thiol treatment was repeated twice for a total of three treatments.

The filtrate was concentrated and then n-heptane was added dropwise and stirred. The resulting slurry was filtered, and the cake was washed with n-heptane.

In a new reactor, the filtrate and filter cake were added and methanol was charged. It was then heated and stirred. The mixture was then cooled and filtered. The filter cake was washed with methanol and dried under reduced pressure. Representative yield of this step was 60.8% with HPLC purity of 99.3% (assay 96.4%).

2-((1R,4R)-4-((3-(3-(trifluoromethyl)phenyl)imidazo[1,2-b]pyridazin-6-yl)amino)cyclohexyl)propan-2-ol, silica thiol, and THF were charged into a reactor and heated with stirring. The mixture was then cooled and filtered, and the filter cake was washed with THF. This was repeated twice for a total of three cycles.

A solvent switch was performed from THF to MeOH with repeated concentration and ethyl acetate was added. Ethyl acetate solution of hydrochloric acid was added dropwise to the mixture. A seed crystal of the HCl salt of the compound of structure (I) was added and resulting slurry was stirred, then filtered. The filter cake was washed with ethyl acetate, then dried under vacuum to provide Form I of 2-((1R,4R)-4-((3-(3-(trifluoromethyl)phenyl)imidazo[1,2-b]pyridazin-6-yl)amino)cyclohexyl)propan-2-ol hydrochloride salt (i.e., Form I of the compound of structure (I) HCl salt). Representative yield of this step was 82.6% with HPLC purity of 99.9%.

Compound of structure (I) was also synthesized according to the reaction steps and the reaction conditions depicted in Example 6 above, except that the step involving treatment with KF, DIPEA and DMSO was replaced with a step involving treatment with t-BuONa, (R)-BINAP, Pd$_2$(dba)$_3$ and toluene. In this procedure, 6-chloro-3-(3-(trifluoromethyl)phenyl)imidazo[1,2-b]pyridazine and 2-((1R,4R)-4-aminocyclohexyl)propan-2-ol were charged into a reactor with t-BuONa, (R)-BINAP, Pd$_2$(dba)$_3$ and toluene. Then the reaction was performed, and the resulting slurry was filtered after completion of the reaction. The filtered solid was charged into a reactor and DMSO was added. Then water was added to obtain a slurry, which was filtered, washed and dried under vacuum. Representative yield of this step was 71.5% with HPLC purity of 97.9%.

Example 7

Alternative Synthesis of Compound of Structure (I)

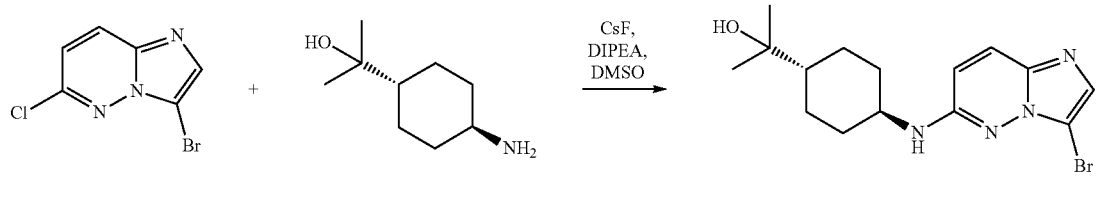

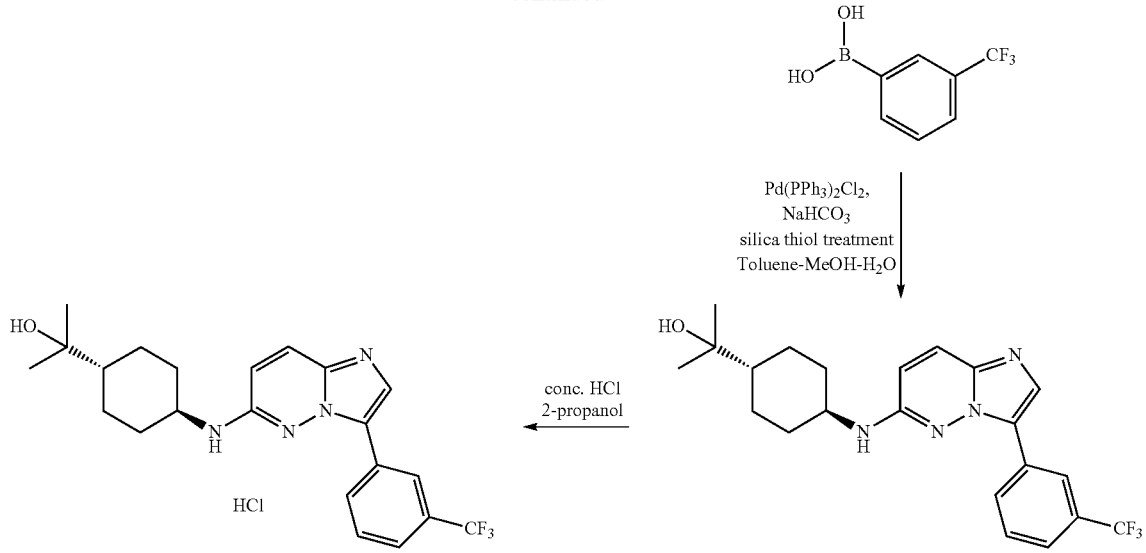

2-((1R,4R)-4-((3-(3-(trifluoromethyl)phenyl)imidazo[1,2-b]pyridazin-6-yl)amino)cyclohexyl)propan-2-ol was synthesized according to the reaction scheme and conditions depicted above.

6-chloroimidazo[1,2-b]pyridazine and 2-((1R,4R)-4-aminocyclohexyl)propan-2-ol were charged into a reactor with cesium fluoride (CsF), N,N-diisopropylethylamine (DIPEA), and dimethyl sulfoxide (DMSO). The mixture was heated at 140° C. After completion of the reaction, the mixture was filtered, and then water was added to precipitate the desired product. The slurry was filtered and dried to give 2-((1R,4R)-4-((3-bromoimidazo[1,2-b]pyridazin-6-yl)amino)cyclohexyl)propan-2-ol. Representative yield of the step was 66.3-69.8% with HPLC purity of 96.2-96.8%.

2-((1R,4R)-4-((3-bromoimidazo[1,2-b]pyridazin-6-yl)amino)cyclohexyl)propan-2-01, 3-trifluoromethyl boronic acid, sodium hydrogen carbonate, Pd(PPh$_3$)$_2$Cl$_2$ and solvent mixture (toluene-methanol-water) were added and the mixture was refluxed. After completion of the reaction, water was charged and cooled to form precipitation, and the formed solid was filtered, dried under vacuum to give 2-((1R,4R)-4-((3-(3-(trifluoromethyl)phenyl)imidazo[1,2-b]pyridazin-6-yl)amino)cyclohexyl)propan-2-ol. Above isolated product was dissolved with tetrahydrofuran (THF) and treated with silica thiol to remove residual palladium. Representative yield of the step was 89.7% with HPLC purity of 97.9%.

The free base was converted to the HCl salt using concentrated hydrochloric acid in 2-propanol. 2-((1R,4R)-4-((3-(3-(trifluoromethyl)phenyl)imidazo[1,2-b]pyridazin-6-yl)amino)cyclohexyl)propan-2-ol was suspended in 2-propanol with heating and concentrated hydrochloric acid was added. Then formed slurry was filtered and dried under reduced pressure to give 2-((1R,4R)-4-((3-(3-(trifluoromethyl)phenyl)imidazo[1,2-b]pyridazin-6-yl)amino)cyclohexyl)propan-2-ol hydrochloride. Representative yield of the step was 92% with HPLC purity of 98.9%.

Example 8

Preparation of Hydrochloric Acid Salt of the Compound of Structure (I) (Form I and Form II)

In this example, the crystalline form of the hydrochloric acid salt of the compound of structure (I) (Form I) was prepared according to the following reaction scheme:

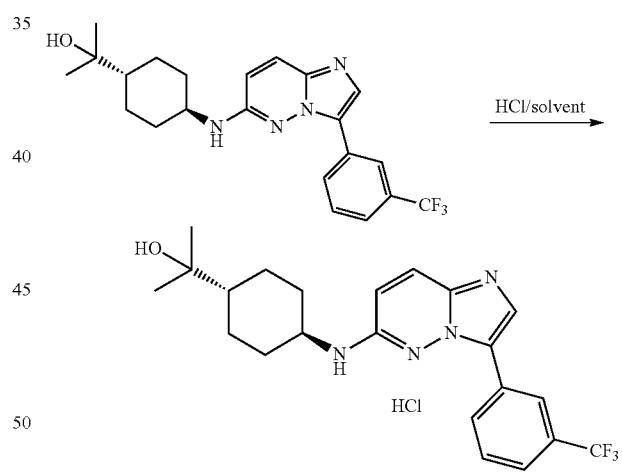

Form I was characterized by X-ray powder diffraction (XRPD) (FIG. 1), differential scanning calorimetry (FIG. 2), thermogravimetric analysis (FIG. 3) and polarized light microscopy (FIG. 4). Form I showed good crystallinity by XRPD and birefringence by polarized light microscopy. The melting point of the hydrochloric acid salt is 226.2° C. and 0.43% weight loss was detected from 30° C. to 118° C. by TGA.

A series of reactions were carried out to screen various crystallization solvents based on the solubility of the free base and the hydrochloric acid salt of the compound of structure (I). As detailed below, the solvent system of methanol (MeOH)/ethyl acetate (EA) was identified as a particularly preferred solvent system to form Form I.

As detailed in Table 13, one reaction was carried out on a 2.0 g scale to evaluate the process. 1.8 g of the hydrochloric acid salt of the compound of structure (I) was obtained with a 98.75% HPLC purity.

TABLE 13

Synthesis of Form I Using THF.

| Reaction Conditions | | | | | Product | | | |
|---|---|---|---|---|---|---|---|---|
| Free Base | THF | 4N HCl | Temp. | Time | HCl salt | Purity | XRPD | Chlorine content |
| 2.0 g (1.0 eq) | 60 mL (30 V) | 1.2 mL (1.0 eq) | 20-30° C. | 1 hr | 1.8 g | 98.75% | Form I | 7.75% |

To decrease the volume of the crystallization system, two reactions were carried out to prepare the hydrochloric acid salt of the compound of structure (I) while adding 4N of HCl/EA at 60~65° C. (Table 14). XRPD data showed that the crystallization condition was acceptable.

TABLE 14

THF Volume Screen.

| Reaction Conditions | | | | | Product | |
|---|---|---|---|---|---|---|
| Free Base | THF | 4N HCl | Temp. | Time | Purity | XRPD |
| 2.0 g (1.0 eq) | 60 mL (30 V) conc. to 13 V (60~65 C.) | 3.6 mL (3.0 equiv.) | 20-30° C. | 2 hrs | 98.76% | Form I |
| 8.0 g (1.0 eq) | 240 mL (30 V) conc. to 13 V (60~65 C.) | 10 mL (2.0 equiv.) | 20-30° C. | 2 hrs | 99.26% | Form I |

One reaction was carried out on a 30.0 g scale, to prepare a standard sample of the hydrochloric acid salt. 31 g of the hydrochloric acid salt was obtained as a light yellow product with a 98.74% HPLC purity (Table 15). However, TGA data showed that, the residual THF (1.05%) could not be removed completely even at 120° C.

TABLE 15

Scale Up Form I in THF.

| Reaction Conditions | | | | | Product | |
|---|---|---|---|---|---|---|
| Free Base | THF | 4N HCl | Temp. | Time | Purity | XRPD |
| 30.0 g (1.0 eq) | 900 mL (30 V) | 36 mL (2.0 equiv.) | 20-30° C. | 2 hrs | 98.74% | Form I |

As shown in Table 16, five reactions were carried out, to screen the reaction solvent. The analytical data showed that Me-THF and EA cannot be removed very well by drying. However, residual MeOH was acceptable; the solubility of the hydrochloric acid salt of the compound structure (I) in MeOH was 50-100 mg/mL.

TABLE 16

Crystallization Solvent Screen.

| Reaction Conditions | | | | | Product | |
|---|---|---|---|---|---|---|
| Free Base | Solvent | HCl aq. | Temp. | Time | HPLC (solid) | Residual solvent |
| 1.0 g (1.0 eq) | Me-THF 40 mL (40 V) | 4N HCl/EA 1.7 mL (2.0 eq) | 0~5° C. | 2.0 hrs | — | Me-THF: 1.38% EA: 0.03% |
| 1.0 g (1.0 eq) | MeOH 35 mL (35 V) | 4N HCl/EA 1.7 mL (2.0eq) | Conc. to~3~4 V after adding 4N HCl/EA 0~5° C. | 2.0 hrs | 99.31% | MeOH: 0.08% EA: N.D. |
| 10.0 g (1.0 eq) | EtOH 110 mL (11 V) | 10.1% HCl/EtOH 11.2 g (1.3 eq) | Added HCl/EtOH aq. at 75° C., then cooled to 0~5° C. | 8.0 hrs | 98.97% | — |
| 10.0 g (1.0 eq) | EtOH 110 mL (11 V) | 10.1% HCl/EtOH 17.3 g (2.0 eq) | Added HCl/EtOH aq. at 75° C., then cooled to 0~5° C. | 8.0 hrs | 98.64% | — |
| 1.0 g (1.0 eq) | EA 140 mL (70 V) | 4N HCl/EA 3.6 mL (3.0 eq) | Added 4N HCl/EA at 70~75° C., then cool to 20-30° C. | 1.0 hr | 98.81% | EA: 0.98% |

Two reactions were carried out, each on a 4.0 g scale, to screen the temperature using EtOH as solvent. As shown below, conditions of HCl/EA solution at 20-30° C. (Table 17) were particularly advantageous.

TABLE 17

Temperature Screen Using EtOH.

| Reaction Conditions | | | | | Product | | | |
|---|---|---|---|---|---|---|---|---|
| Free Base | EtOH | HCl soln. | Temp. | Time | HPLC | XRPD | Residual Solvent | HCl content |
| 4.0 g (1.0 eq) | 44 mL (11 V) | HCl/EA solution (1.1 eq) | Added HCl/EA soln. at 20-30° C., then stirred at 20-30° C. 0-10° C. | 4 hrs 12 hrs | 99.6% | Form I | EtOH: 0.37% EA: 0.01% | 7.86% |
| 4.0 g (1.0 eq) | 44 mL (11 V) | HCl/EA solution (1.1 eq) | Added HCl/EA solution at 40° C., then stirred at 40° C. 0-10° C. | 4 hrs 12 hrs | 99.58% | Form I | EtOH: 0.59% EA: 0.01% | 6.92% |

Although EtOH was found to be an advantageous solvent for the synthesis, pilot studies indicated that residual EtOH cannot be easily removed. For example, as shown in Table 18, two workup procedures were carried out, each on the 1.0 g scale to try to remove residual EtOH by slurry in water. Residual EtOH could not be removed very well under these conditions and the process produced a mixture of Form I and Form II.

TABLE 18

ETOH Workup Screen.

| HCl Salt | Operations | Residual solvent |
|---|---|---|
| 1.0 g EtOH: 1.16% by GC(0.83% by H-NMR) EA: 0.05% THF: 0.003% n-heptane: 0.02% | 1, Slurry at 20-30° C. in 10 V of water for 15 hrs; 4, Filtered; 5, Dried at 55-65° C. for 20 hrs. | EtOH: 0.77% EA: 0.03% |
| 1.0 g EtOH: 1.16% by GC(0.83% by H-NMR) EA: 0.05% THF: 0.003% n-heptane: 0.02% | 1, Slurry at 50-60° C. in 10 V of water for 15 hrs; 2, Cool to 20-30° C.; 3, Stirred at 20-30° C. for 2 hrs; 4, Filtered; 5, Dried at 55-65° C. for 20 hrs. | EtOH: 0.86% EA: 0.03% |

As shown in Table 19, five reactions were carried out to screen the crystallization solvent. As shown below, MeOH was found to be acceptable as a crystallization solvent.

TABLE 19

Crystalline Solvent Screening.

| Reaction Conditions | | | | | Product | | | |
|---|---|---|---|---|---|---|---|---|
| Free Base | Solvent | HCl soln. | Temp. | Time | HPLC | XRPD | Residual Solvent | HCl content |
| 0.5 g (1.0 eq) | DMF 7.5 mL (15 V) | 2 mL + 2.5 mL 2N HCl aqu | 20~30° C. | 1 hr | — | Not Form I | — | — |
| 1.0 g (1.0 eq) | Acetone 10 mL (10 V) | HCl/EA (W/W = 11.3%) 0.85 g (1.1 eq) | Added 11.3% HCl/EA at 50° C., then cool to 15-30° C. | 16 hrs | 99.20% | — | Acetone: 1.24% | 7.77% |
| 1.0 g (1.0 eq) | MTBE 10 mL (10 V) | HCl/EA (W/W = 11.3%) 0.85 g (1.1 eq) | Added 11.3% HCl/EA at 50° C., then cool to 15-30° C. | 16 hrs | 98.52% | — | MTBE: 0.82% EA: 0.21% | 6.69% |
| 1.0 g (1.0 eq) | IPAC 10 mL (10 V) | HCl/EA (W/W = 11.3%) 0.85 g (1.1 eq) | Added 11.3% HCl/EA at 70° C., then cool to 15-30° C. | 16 hrs | 98.74% | — | IPAC: 1.57% EA: 0.14% | 6.65% |

TABLE 19-continued

Crystalline Solvent Screening.

| Reaction Conditions | | | | | Product | | | |
|---|---|---|---|---|---|---|---|---|
| Free Base | Solvent | HCl soln. | Temp. | Time | HPLC | XRPD | Residual Solvent | HCl content |
| 4.0 g (1.0 eq) | MeOH 3 mL (3 V) | HCl/EA (W/W = 11.3%) 0.85 g (1.1 eq) | Added 11.3% HCl/EA at 20~30° C., then cool to −5~0° C. | 16 hrs | 99.25% | Form I | MeOH: 0.12% EA: 0.03% | 8.04% |

As shown in Table 20, two reactions were carried out on a 5.0 g scale to optimize the crystallization conditions. The data shows that the yield increases from ~70% to ~90% when 3 V of EA were added for the workup.

TABLE 20

Crystallization Conditions Optimization.

| Reaction Conditions | | | | | | | Product | | | |
|---|---|---|---|---|---|---|---|---|---|---|
| Free Base | MeOH | THF | EA | EA soln of HCl | Temp. | Time | HCl Salt | XRPD | Residual Solvent | Cl content |
| 5.28 g* 94.66% (1.0 eq) | 15 mL (3 V) | 1.7 mL (5% w/w) | 15 mL (3 V) (added before reaction) | 5.78 g (W/W = 8.3%) (1.1 eq) | 20~30° C. 0~5° C. | 5 hrs 15 hrs | 4.91 g 99.59% | Form I | EA: 0.07% THF: 0.02% MeOH: 0.08% | 7.67% |
| 5.28 g* 94.66% (1.0 eq) | 15 mL (3 V) | 1.7 mL (5% w/w) | 15 mL (3 V) (added in work up) | 5.78 g (W/W = 8.3%) (1.1 eq) | 20~30° C. 0~5° C. Add EA 15 mL (3 V) at 0~5° C., then stirred at 0~5° C. | 5 hrs 10 hrs 4 hrs | 4.83 g 99.68% | Form I | EA: 0.02% THF: 0.02% MeOH: 0.04% | 7.80% |

As shown in Table 21, two reactions were carried out, each on a 1.0 g scale, to remove residual Pd. The analytical data showed that the residual Pd can be decreased from 200 ppm to 17 ppm.

TABLE 21

Removing Residual Palladium.

| Starting Materials | | | Reaction conditions | | Product Residual |
|---|---|---|---|---|---|
| Free Base | MeOH | EA solution of HCl | Temp | Time | Pd |
| 1.0 g Residual Pd: 200 ppm | 4 mL (4 V) | 0.96 g (W/W = 10%) (1.1 eq) | Added HCl/EA at 20-30° C., then stirred at 20-30° C. 0-5° C. Added 3 V of EA dropwise at 0-5° C., the stirred at 0-5° C. | 4 hrs 16 hrs 5 hrs | Residual Pd: 17 ppm |
| 1.0 g Residual Pd: 49 ppm | 4 mL (4 V) | 0.96 g (W/W = 10%) (1.1 eq) | Added HCl/EA at 20-30° C., then stirred at 20-30° C. 0-5° C. Added 3 V of EA dropwise at 0-5° C., the stirred at 0-5° C. | 4 hrs 16 hrs 5 hrs | Residual Pd: 20 ppm |

As shown in Table 22, one reaction was carried out on a 60.0 g scale to prepare the crystal seed of Form I. 59.35 g of Form I was obtained with a 99.95% HPLC purity in 90.99% yield.

TABLE 22

Crystal Seed Preparation.

| Free Base | MeOH | EA solution of HCl | Temp | Time | HCl Salt | HPLC | XRPD | Residual solvent |
|---|---|---|---|---|---|---|---|---|
| 60.0 g | 1200 mL (20 V) Concentrated to 2.5 V | 58.15 g (W/W = 9.9%) (1.1 eq) | Added HCl/EA at 20-30° C., then stirred at 20-30° C. 0-5° C. Added 3 V of EA dropwise at 0-5° C., then stirred at 0-5° C. | 5 hrs 10 hrs 4 hrs | 59.35 g Yield: 90.99% | 99.95% | XRPD Form I | MeOH: 0.09% EA: 0.01% THF: 0.001% |

To summarize, crystalline Form I of the hydrochloric acid salt of the compound of structure (I) can be prepared, for example, by treating the THF solution of the free base with silica thiol, filtering the solution and concentrating the resulting solution to 2-3×. The solution can be transferred to MeOH to 3-4×. HCl/EA can be added dropwise at 20-30° C. A crystal seed can be added and the mixture stirred at 20-30° C. for 4-6 hours. The mixture can then be cooled to 0-5° C. and stirred at 0-5° C. for 10-15 hours. EA can be added dropwise at 0-5° C. and the resulting mixture can be stirred for 4-6 hours. The mixture can then be filtered and dried at 55-65° C. for 15-20 hours to yield Form I.

Example 9

Hydrochloric Acid Salt of Compound of Structure (I): Solubility

In this example, the solubility of the hydrochloric acid salt of the compound structure (I) was tested in different solvents at room temperature by manual dilution combined with visual observation. The solvents included: methanol (MeOH), ethanol (EtOH), isopropyl alcohol (IPA), 1-butanol, acetonitrile (ACN), methyl ethyl ketone (MEK), methyl isobutyl ketone (MIBK), ethyl acetate (EtOAc), isopropyl acetate (iPrOAc), methyl tert-butyl ether (MTBE), 2-methyltetrahydrofuran (2-MeTHF), dimethylformamide (DMF), N-methyl-2-pyrrolidone (NMP), dimethyl sulfoxide (DMSO), dichloromethane (DCM), 1, 4-dioxane, toluene, heptane, tetrahydrofuran (THF), acetone and water. The results are listed in Table 23 below.

TABLE 23

Solubility Screen.

| Solvent | Visual Solubility (mg/mL) |
|---|---|
| MeOH | >50, <100 |
| EtOH | >10, <20 |
| IPA | >2, <5 |
| 1-Butanol | >5, <10 |
| ACN | <2 |
| MEK | <2 |
| MIBK | <2 |
| EtOAc | <2 |
| iPrOAc | <2 |
| MTBE | <2 |
| 2-MeTHF | <2 |
| DMF | >10,<20 |
| NMP | >20, <25 |
| DMSO | >40,<50 |

TABLE 23-continued

Solubility Screen.

| Solvent | Visual Solubility (mg/mL) |
|---|---|
| DCM | <2 |
| Toluene | <2 |
| 1,4-Dioxane | <2 |
| Heptane | <2 |
| THF | <2 |
| Acetone | <2 |
| Water | <2 |

Example 10

Hydrochloric Acid Salt of Compound of Structure (I): Polymorph Screening (Slurry Method)

In this experiment, suspensions of the hydrochloric acid salt of the compound of structure (I) (Form I) in different solvents or solvent mixtures (Table 24) were prepared and kept shaking for 24 hours at room temperature. The residues were characterized by XRPD. The results are shown in FIGS. 6 to 15 and Table 24 below. Form II was isolated in water by the slurry method described in this example.

TABLE 24

List of Solvents Used in Slurry Method.

| Solvent | Result |
|---|---|
| IPA | Form I |
| CAN | Form I |
| MEK | Form I |
| MIBK | Form I |
| EtOAc | Form I |
| iPrOAc | Form I |
| MTBE | Form I |
| 2-MeTHF | Form I |
| DCM | Form I |
| Toluene | Form I |
| 1,4-Dioxane | Form I |
| Heptane | Form I |
| THF | Form I |
| Acetone | Form I |
| Water | Form II |
| IPA:Acetone (1:1, v/v) | Form I |
| IPA:ETOAc (1:1, v/v) | Form I |
| IPA:MTBE (1:1, v/v) | Form I |
| IPA:THF (1:1, v/v) | Form I |
| IPA:Heptane (1:1, v/v) | Form I |
| IPA:ACN (1:1, v/v) | Form I |

TABLE 24-continued

List of Solvents Used in Slurry Method.

| Solvent | Result |
| --- | --- |
| IPA:Toluene (1:1, v/v) | Form I |
| IPA:1,4-Dioxane (1:1, v/v) | Form I |
| IPA:DCM (1:1, v/v) | Form I |
| IPA:MEK (1:1, v/v) | Form I |
| Acetone:EtOAc (1:1, v/v) | Form I |
| Acetone:MTBE (1:1, v/v) | Form I |
| Acetone:THF (1:1, v/v) | Form I |
| Acetone:ACN (1:1, v/v) | Form I |
| Acetone:Toluene (1:1, v/v) | Form I |
| Acetone:MEK (1:1, v/v) | Form I |
| Acetone:1,4-Dioxane (1:1, v/v) | Form I |
| Acetone:DCM (1:1, v/v) | Form I |
| EtOAc:MTBE (1:1, v/v) | Form I |
| EtOAc:THF (1:1, v/v) | Form I |
| EtOAc:ACN (1:1, v/v) | Form I |
| EtOAc:Heptane (1:1, v/v) | Form I |
| EtOAc:Toluene (1:1, v/v) | Form I |
| EtOAc:1,4-Dioxane (1:1, v/v) | Form I |
| EtOAc:DCM (1:1, v/v) | Form I |
| EtOAc:MEK (1:1, v/v) | Form I |
| EtOAc:MIBK (1:1, v/v) | Form I |
| MTBE:ACN (1:1, v/v) | Form I |
| MTBE:MEK (1:1, v/v) | Form I |
| MTBE:THF (1:1, v/v) | Form I |
| MTBE:Heptane (1:1, v/v) | Form I |
| MTBE:DMC (1:1, v/v) | Form I |
| MTBE:iPrOAc (1:1, v/v) | Form I |
| IPA:Toluene (1:1, v/v) | Form I |

Example 11

Figure 16:
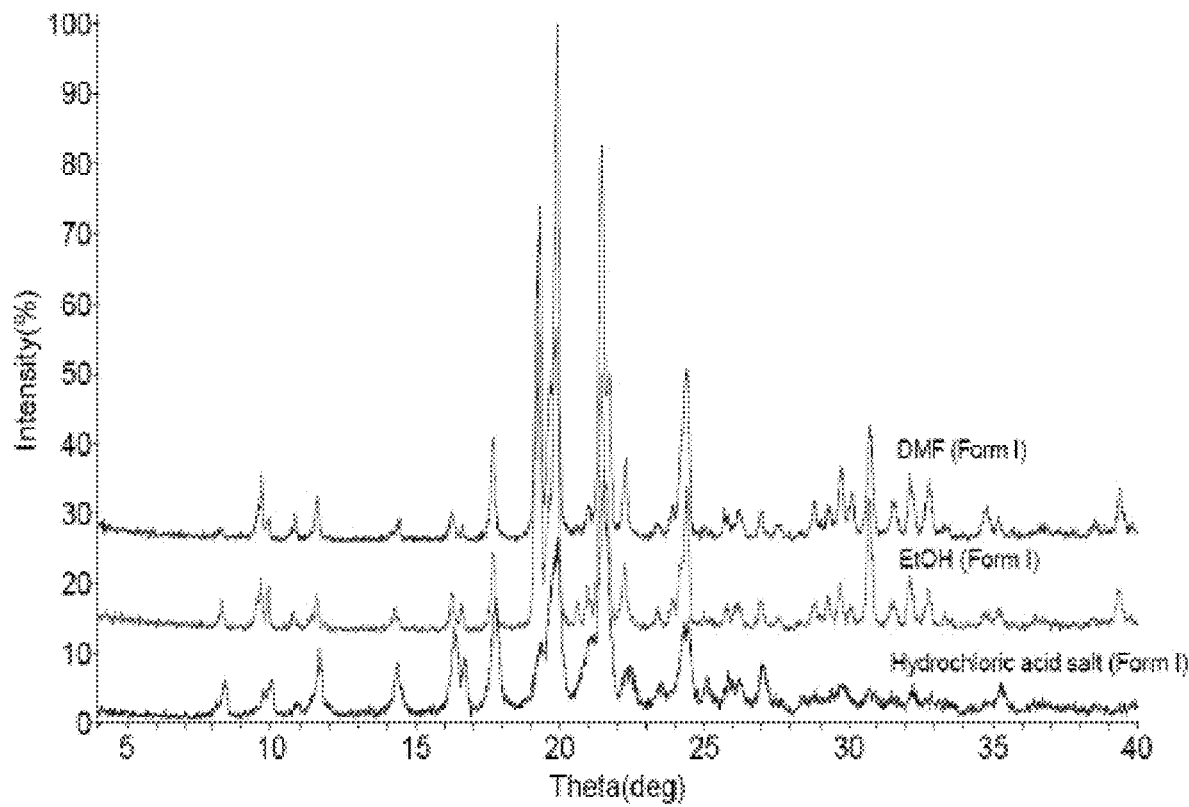
FIG. 16 is a graphical representation of solids obtained in the solvent-thermal heating/cooling experiment described in Example 11.

Hydrochloric Acid Salt of Compound of Structure (I): Solvent-Thermal Heating/Cooling Screen In this experiment, saturated solutions of the hydrochloric acid salt of the compound of structure (I) in different solvents or solvent mixtures (Table 25) were prepared at 70° C. and then cooled down to precipitate out at −20° C. The precipitations were characterized by XRPD. The results are shown in Table 25 and in FIG. 16.

TABLE 25

Solvent-Thermal Heating/Cooling Screen.

| Solvent | Results |
| --- | --- |
| EtOH | Form I |
| DMF | Form I |
| NMP | No precipitation |
| IPA:DMF (1:1, v/v) | No precipitation |
| IPA:NMP (1:1, v/v) | No precipitation |
| 1-Butanol:DMF (1:1, v/v) | No precipitation |
| 1-Butanol:NMP (1:1, v/v) | No precipitation |

Example 12

Hydrochloric Acid Salt of Compound of Structure (I): Slow Evaporation Screen

Figure 17:
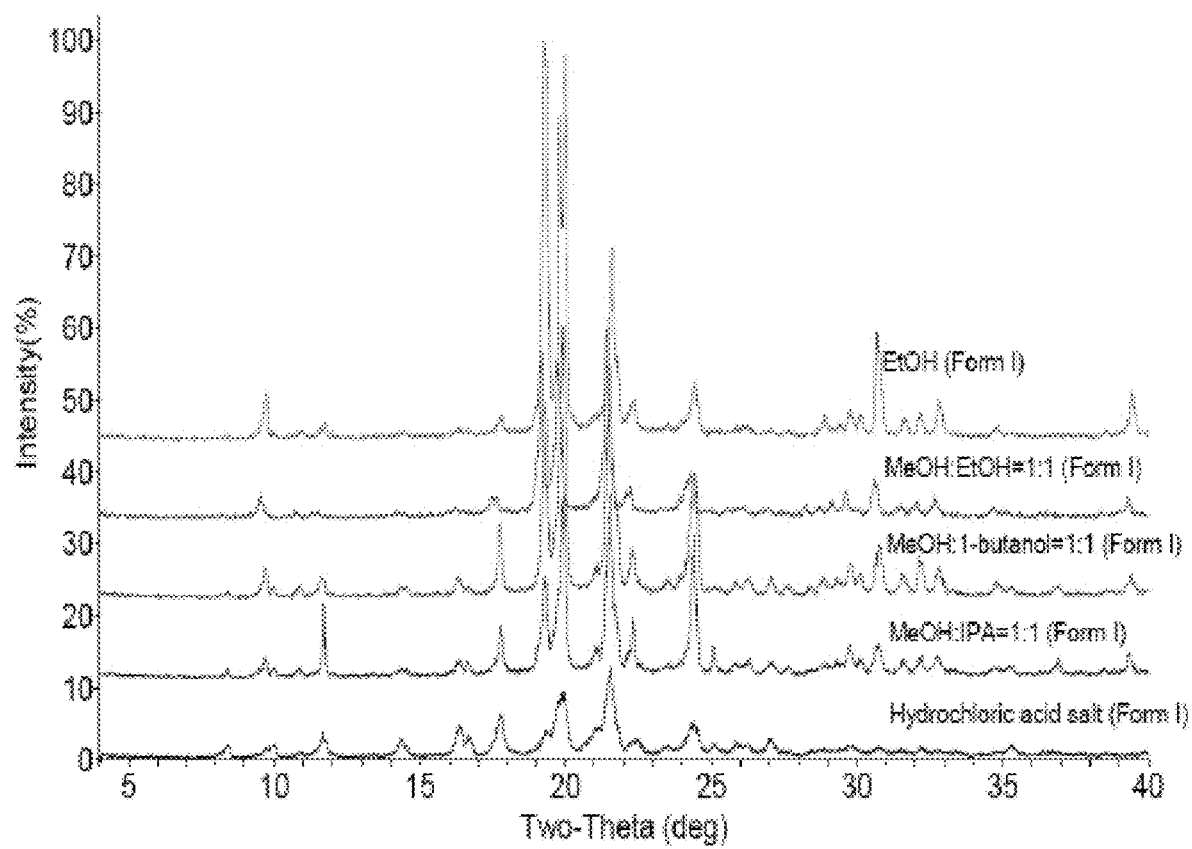
FIG. 17 is a graphical representation of solids obtained in the slow evaporation experiment described in Example 12.
Figure 18:
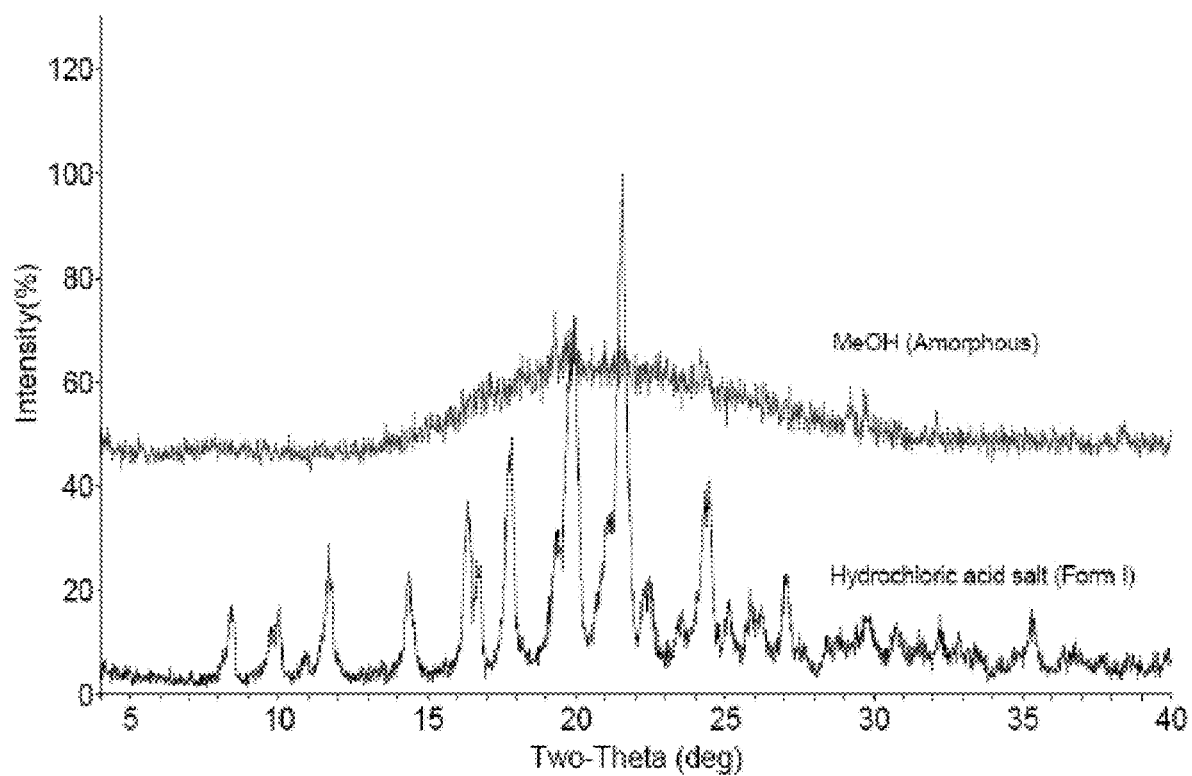
FIG. 18 is a graphical representation of solids obtained in the slow evaporation experiment described in Example 12.

Solutions of the hydrochloric acid salt of the compound of structure (I) in different solvents or solvent mixtures (Table 26) were prepared at room temperature, and then the solutions were evaporated at room temperature spontaneously (i.e., by slow evaporation in which the drug substance solution was left open to the air). The solids obtained were characterized by XRPD. The results are shown in FIG. 17, FIG. 18 and Table 26. An amorphous form was found in MeOH by slow evaporation from solution.

TABLE 26

Solvent-Thermal Heating/Cooling Screen.

| Solvent | Results |
| --- | --- |
| MeOH | Amorphous |
| EtOH | Form I |
| MeOH:EtOH (1:1, v/v) | Form I |
| MeOH:IPA (1:1, v/v) | Form I |
| MeOH:1-Butanol (1:1, v/v) | Form I |
| 1-Butanol (1:1, v/v) | No precipitation |
| MeOH:DMSO (1:1, v/v) | No precipitation |
| MeOH:NMP (1:1, v/v) | No precipitation |
| MeOH:DMF (1:1, v/v) | No precipitation |

Example 13

Manufacture of Drug Substance

Form 1 of the hydrochloride salt of the compound of structure (I) was manufactured according to the following procedure. To a reactor were added 6.00 kg of the free base of the compound of structure (I) and 157 kg of THF. The resulting mixture was heated to approximately 55-65° C. to dissolve the free base and to obtain a homogenous mixture, which was subsequently filtered. The filtrate was concentrated under reduced pressure, and the solvent was switched to methanol to obtain approximately 12 L of volume. 27 kg of ethyl acetate was added to the methanol mixture, and the resulting mixture was heated to obtain a homogeneous solution. 8.15 kg of 5 mol/L hydrochloric acid in ethyl acetate and 0.520 kg seed crystal (Form 1 of the hydrochloride salt of the compound of structure (I)), followed by 24 kg ethyl acetate were added to the homogeneous solution, and the resulting reaction mixture was cooled to 4° C. and filtered. Filtered solid was washed with ethyl acetate, and then dried at approximately 60° C. to give 5.56 kg of Form 1 of the hydrochloride salt of the compound of structure (I).

Example 14

Salt Screen

The purpose of this salt screening study was to evaluate the feasibility of forming crystalline salts of the free base of the compound of structure (I).

XRPD Method. X-ray generator: Cu, kα ($\lambda$−1.54056 Å); tube voltage: 40 kV; tube current: 40 mA; DivSlit: 1 degree; DivH.L.Slit: 10 mm; SctSlit: 1 degree; RecSlit: 0.15 mm; monochromator: fixed; scanning scope 4-40 degrees; scanning step: 10 degrees/minute.

Polarized Light Microscope Method. Nikon LV100 POL equipped with 5-megapixel CCD; ocular lens: 10×; objective lens: 10× or 20×.

DSC and TGA Methods. Heated from 30° C. to 300° C. at 10° C./minute.

HPLC Method. The chromatographic conditions for HPLC are summarized below. The typical retention time of the compound of structure (I) under these conditions was 4.08 minutes.

TABLE 27a

| | Time(Min) | A (%) | B (%) |
|---|---|---|---|
| Mobile phase gradient | 0 | 80 | 20 |
| A: 0.1% TFA in water | 8 | 5 | 95 |
| B: ACN | | | |

| | |
|---|---|
| Column temperature | 37° C. |
| Autosampler temperature | 37° C. |
| Flow rate | 1.0 mL/min |
| Inject volume | 5 μl |
| Run time | 8 min |
| Post tune | 3 min |
| Detector wavelength | 258 nm |

The free base of the compound of structure (I) (25 mg) was weighed in eleven glass sample vials, separately. The sample was dissolved with 1.0 mL THF. Appropriate amounts of hydrochloric acid, sulfuric acid, phosphoric acid, methanesulfonic acid, citric acid, tartaric acid, maleic acid, glutamic acid, succinic acid, malic acid or fumaric acid were added into vials individually according to a 1:1 molar ratio to the free base of the compound of structure (I), and stirred for 24 hours. The precipitated solids were isolated. The solvent was removed by a stream of $N_2$ for vials that had no precipitation. The solids obtained were characterized by XRPD.

Based on XRPD results, nine solids showed different XRPD patterns from the free base of the compound of structure (I). The other two samples (solids obtained from succinic acid and malic acid) did not form salts, as evidenced by their XRPD patterns, which were the same as the XRPD pattern of the free base. Four samples (solids obtained from hydrochloric acid, methanesulfonic acid, maleic acid and glutamic acid) resulted in new crystal forms, and another five samples (solids obtained from sulfuric acid, phosphoric acid, citric acid, tartaric acid, fumaric acid) resulted in amorphous solids or solids tending to be amorphous.

In order to confirm the formed salts were true salts instead of the precipitated solid acids or different polymorphs of the free base, the formed solids were compared with the solid acids by)(RFD, and the free base of the compound of structure (I) was also slurried in THF for 24 hours or evaporated by $N_2$ purge as comparison. Because only glutamic acid and maleic acid are solid acids (the other nine acids being liquid acids), glutamic acid and maleic acid were characterized by XRPD and compared with the solids obtained from glutamic acid and maleic acid treatment.

The XRPD pattern obtained from the solid obtained from glutamic acid was the same as the XRPD pattern of glutamic acid. This suggests that the solid obtained from glutamic acid did not form a salt, but a physical mixture of glutamic acid and the free base of the compound of structure (I).

The XRPD pattern obtained from the solid obtained from maleic acid was different from the XRPD pattern of maleic acid, suggesting the solid obtained from maleic acid was a crystalline, maleic acid salt of the compound of structure (I).

Based on XRPD patterns, the three salts (solids obtained from hydrochloric acid, methanesulfonic acid, maleic acid) showed relatively better crystallinity than the free base and thus were selected for further characterizations. The three salts were characterized by approximate solubility and PLM. The results of the solubility tests are shown in Table 27b. As per the results of approximate solubility, the three salts (solids obtained from hydrochloric acid salt, methanesulfonic acid salt and maleic acid) showed similar solubility in water.

TABLE 27b

Results of approximate solubility for three salts in water

| Salt Name | Visual Solubility (mg/mL) | pH |
|---|---|---|
| Hydrochloric acid salt | <0.5 | 3.08 |
| Methanesulfonic acid salt | <0.5 | 3.16 |
| Maleic acid salt | <0.5 | 3.17 |

Figure 19A:
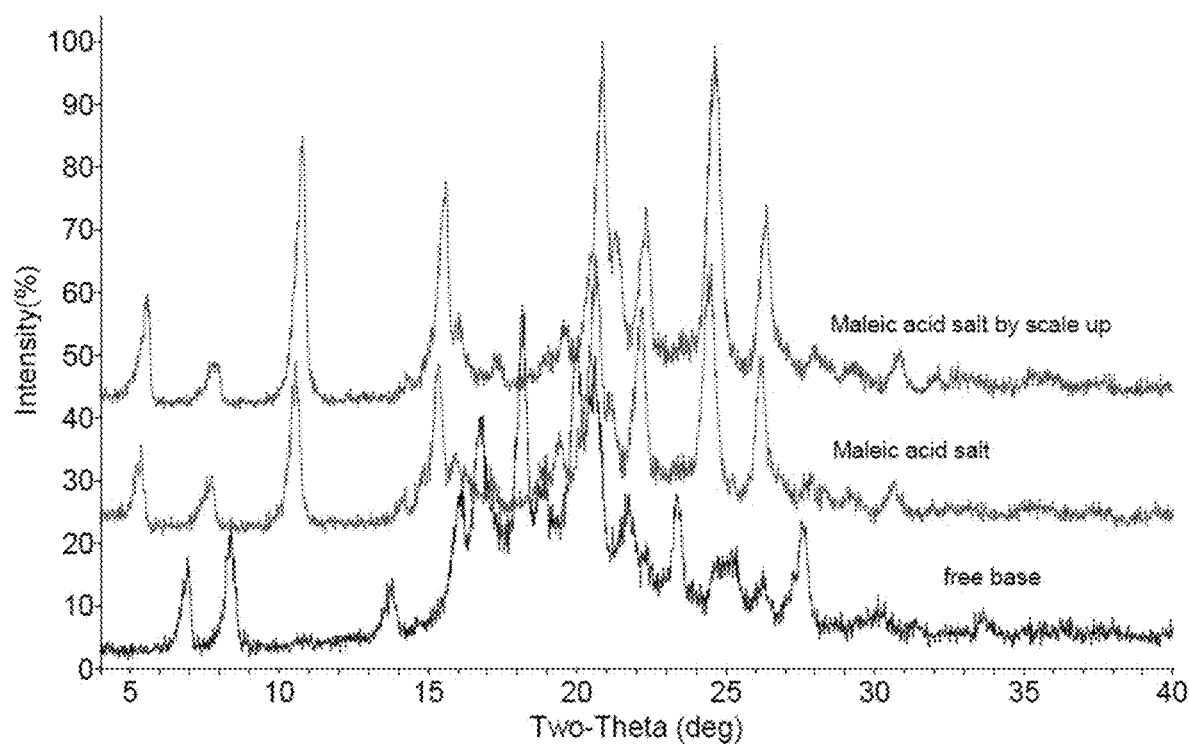
FIG. 19A is a graphical representation of the X-ray power diffraction pattern of a crystalline form of the maleic acid salt of the compound of structure (I) obtained in Example 14.
Figure 19B:
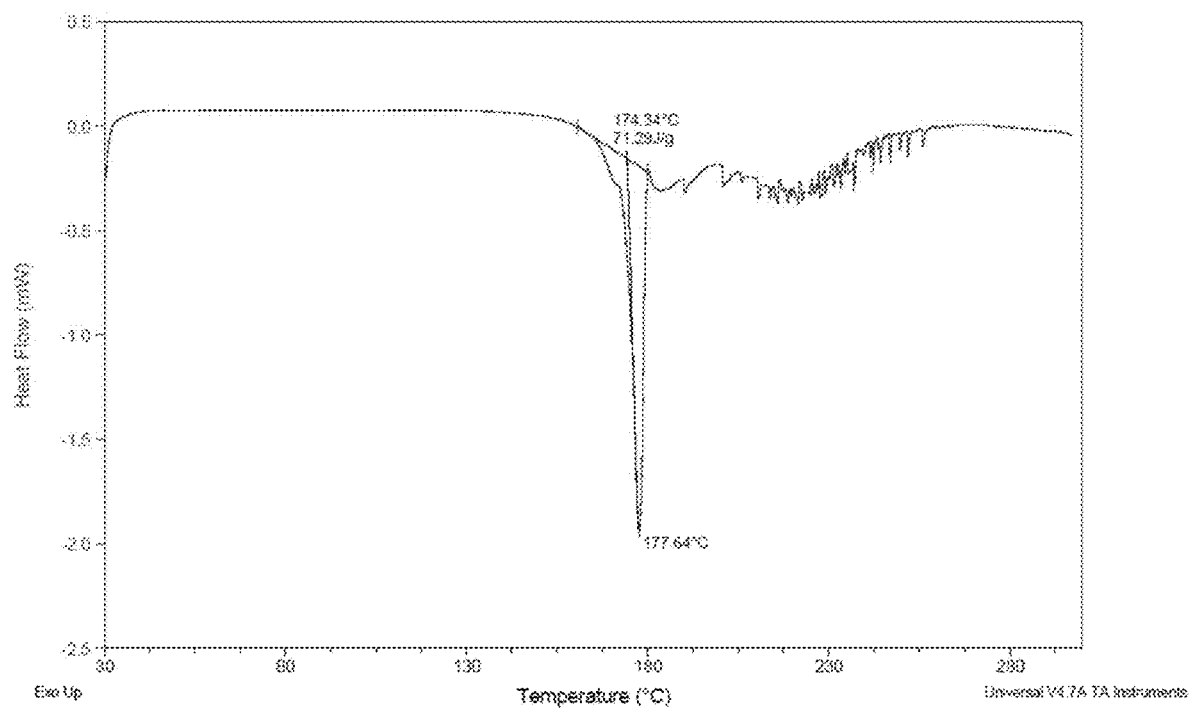
FIG. 19B is a graphical representation of the DSC thermogram of the crystalline form of the maleic acid salt of the compound of structure (I) obtained in Example 14.
Figure 19C:
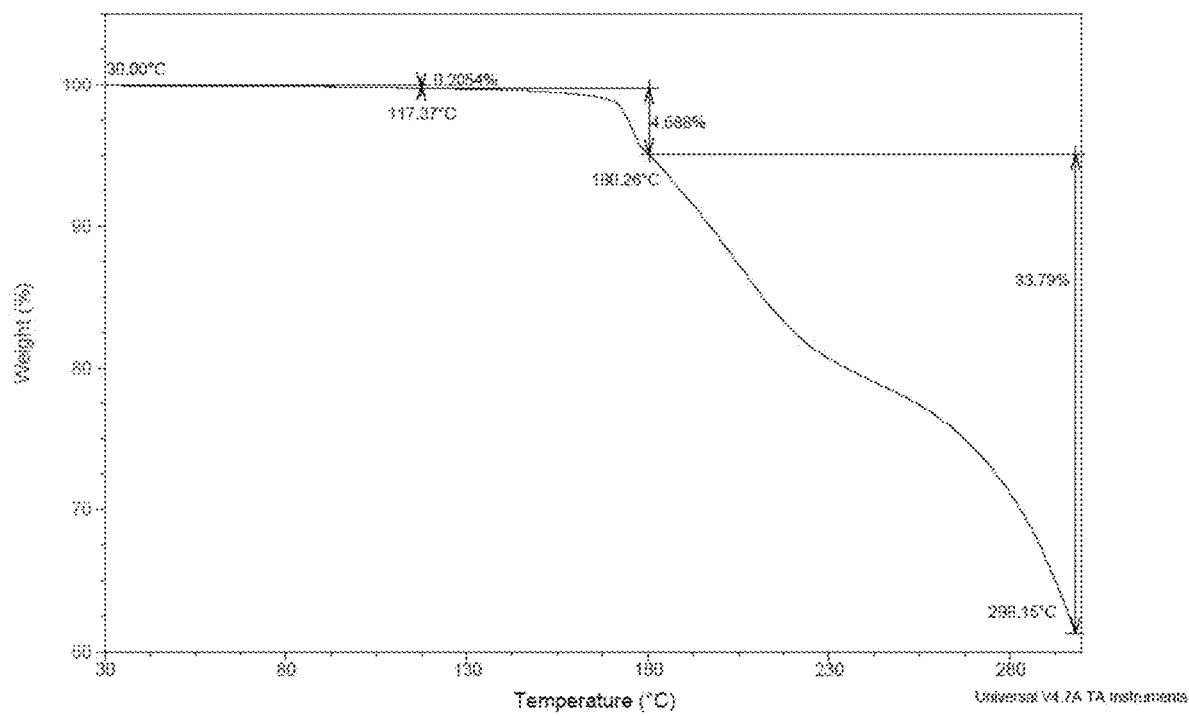
FIG. 19C is a graphical representation of the TGA thermogram of a crystalline form of the maleic acid salt of the compound of structure (I) obtained in Example 14.
Figure 20A:
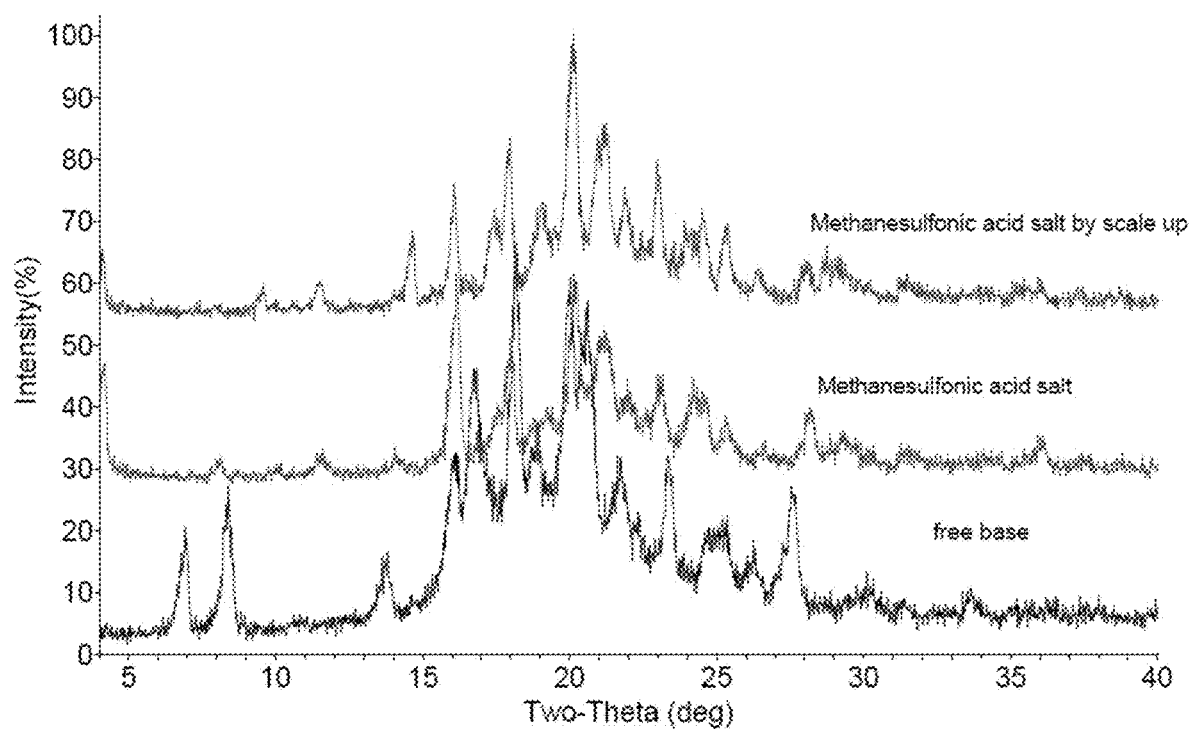
FIG. 20A is a graphical representation of the X-ray power diffraction pattern of the crystalline form of the methanesulfonic acid salt of the compound of structure (I) obtained in Example 14.
Figure 20B:
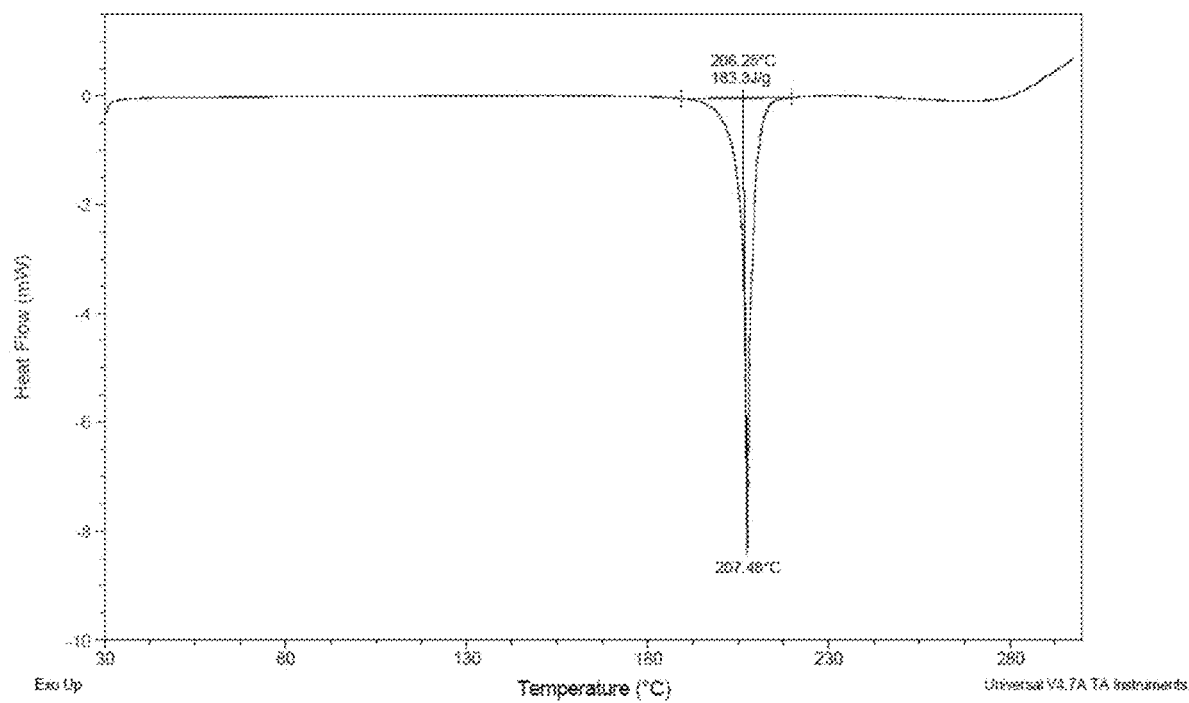
FIG. 20B is a graphical representation of the DSC thermogram of the crystalline form of the methanesulfonic acid salt of the compound of structure (I) obtained in Example 14.
Figure 20C:
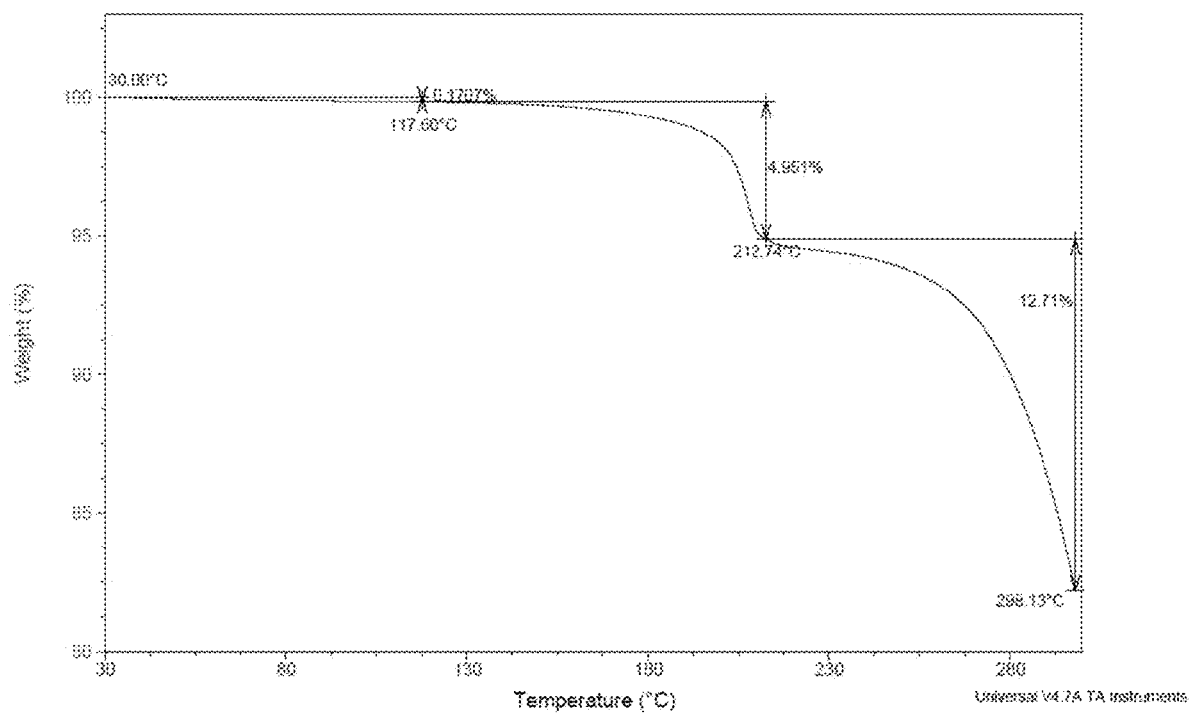
FIG. 20C is a graphical representation of the TGA thermogram of the crystalline form of the methanesulfonic acid salt of the compound of structure (I) obtained in Example 14.

Hydrochloric acid salt, maleic acid salt and methanesulfonic acid salt were scaled up and characterized by XRPD, DSC, TGA, PLM and DVS. FIGS. 19A-19C show the spectra obtained from XRPD, DSC and TGA of the maleic acid salt of the compound of structure (I), respectively. FIGS. 20A-20C show the spectra obtained from XRPD, DSC and TGA of the methanesulfonic acid salt of the compound of structure (I), respectively.

DMSO solutions of maleic acid salt (0.08 mg/ml) and methanesulfonic acid salt (0.04 mg/ml) were prepared. Solutions of maleic acid salt and methanesulfonic acid salt were injected into HPLC individually, and the purity was determined. A HPLC method was used as fit for purpose method for solubility test. The reference observed purity based on the fit for purpose method was reported. The purity by HPLC of the maleic acid salt was 99.35%. The purity by HPLC of the methanesulfonic acid salt was 99.28%.

About 10 mg solid samples of the free base of the compound of structure (I), the hydrochloric acid salt, maleic acid salt and methanesulfonic acid salt were added into 1.5 ml testing media (SGF, FaSSIF, FeSSIF), respectively, and were shaken for 0.5 hour, 2 hours and 24 hours at 37° C. The samples were then centrifuged and filtered. Saturated solutions were diluted with $MeOH:H_2O=1:2$ (v:v), and the concentrations were determined by HPLC. The final pH of the saturated solutions was tested. The solubility results are listed in Table 28.

TABLE 28

Results of solubility in relevant media of selected salts

| | | HPLC solubility (μg/mL) | | | |
|---|---|---|---|---|---|
| Salt* | Media | 0.5 hr | 2 hr | 24 hr | Final pH |
| Free base | SGF | 1358.38 | 1267.97 | 903.34 | 1.39 |
| | FaSSIF | 10.41 | 9.81 | 7.91 | 6.53 |
| | FeSSIF | 96.78 | 99.47 | 91.48 | 5.05 |
| Hydrochloric acid salt | SGF | 430.21 | 364.85 | 318.98 | 1.39 |
| | FaSSIF | 47.00 | 61.59 | 65.97 | 2.23 |
| | FeSSIF | 109.72 | 99.96 | 90.92 | 4.72 |
| Maleic acid salt | SGF | 1357.38 | 1329.33 | 774.79 | 1.32 |
| | FaSSIF | 38.33 | 49.46 | 48.58 | 2.34 |
| | FeSSIF | 114.73 | 106.13 | 96.09 | 4.69 |
| Methanesulfonic acid salt | SGF | 132.63 mg/mL | 193.76 mg/mL | 239.39 mg/mL | 1.35 |
| | FaSSIF | 89.46 | 80.81 | 63.35 | 2.12 |
| | FeSSIF | 141.56 | 182.25 | 153.20 | 4.69 |

*Particle size was not controlled.

The molar ratio of free base of compound of structure (I) to maleic acid or methanesulfonic acid in the salts was determined to be 1:1 by $^1$H NMR.

Comparisons of the free base, hydrochloric acid salt, maleic acid salt and methanesulfonic acid salt of the compound of structure (I) are listed in Table 29. As per the results of DSC, the hydrochloric acid salt showed the highest melting point compared with the free base and other two salts (maleic acid salt and methanesulfonic acid salt). This suggests better thermal stability. As per the results of DVS, hydrochloric acid salt, free base and maleic acid salt showed much lower hygroscopicity compared with methanesulfonic acid salt. Overall, hydrochloric acid salt showed better solid-state properties than free base and the other two salts (maleic acid salt and methanesulfonic acid salt).

TABLE 29

| Characterization | Free base | Hydrochloric acid salt | Maleic acid salt | Methanesulfonic acid salt |
|---|---|---|---|---|
| XRPD | Crystal | Crystal | Crystal | Crystal |
| PLM | Birefringement | Birefringement | Birefringement | Birefringement |
| DSC (melting point, ° C.) | 213.5 | 224.4 | 174.3 | 206.3 |
| TGA (weight loss) | 30.0° C.-101.9° C. 1.29% | 30.0° C.-117.6° C. 0.25% | 30.0° C.-117.4° C. 0.21% | 30.0° C.-117.6° C. 0.17% |
| | 101.9° C.-178.9° C. 0.29% | 117.6° C.-230.4° C. 9.51% | 117.4° C.-180.3° C. 0.21% | 117.6° C.-212.7° C. 4.95% |
| | 178.9° C.-300.0° C. 15.62% | 230.4° C.-300.0° C. 29.53% | 180.3° C.-300.0° C. 33.79% | 212.7° C.-300.0° C. 12.71% |
| DVS (weight gain, %) | 1.60 | 2.83 | 1.26 | 10.52 |

According to the results of solubility testing, methanesulfonic acid salt showed relatively better solubility in the three tested media (SGF, FaSSIF and FeSSIF) than the free base and the other two salts. Maleic acid salt showed relatively better solubility in SGF than hydrochloric acid salt. No significant difference in solubility was observed in FaSSIF and FeSSIF between maleic acid salt and hydrochloride acid salt.

Eleven acids were evaluated in this salt screening study. Two salts (maleic acid salt, methanesulfonic acid salt) formed true salts with 1:1 molar ratio to free base based on $^1$H-NMR. Hydrochloric acid salt, maleic acid salt, methanesulfonic acid salt were scaled up and characterized by XRPD, PLM, DSC, TGA, DVS. Maleic acid salt and methanesulfonic acid salt were further characterized by $^1$H-NMR. Based on the characterizations of three salts, hydrochloric acid salt had better physical properties such as thermal stability, crystallinity, and hygroscopicity, over the free base and the other two salts (maleic acid salt and methanesulfonic acid salt). Although in vitro solubility study results suggested that the methanesulfonic acid salt had higher solubility in biorelevant media than the hydrochloric acid and maleic acid salts, it was more hygroscopic.

Example 15

Manufacture of Drug Product for Clinical Trial

Form I of the hydrochloric acid salt of the compound of structure (I) was formulated into 120-mg doses of the free base of the compound of structure (I) in size 00 hydroxypropyl methylcellulose (HPMC) white, opaque capsules. The capsules were packaged into 120 cc high-density polyethylene (HDPE) bottles, with 50 capsules per bottle.

The formulation was composed of a 1:5 ratio of the free base of the compound of structure (I) and lauroyl polyoxy-32 glycerides (GELUCIRE® 44/14). GELUCIRE® 44/14 was the only excipient used in the formulation. METHOCEL™ E5 Premium HPMC dissolved in aqueous ethanol was applied as the capsule sealant.

GELUCIRE® 44/14 was processed before blending it with Form I of the hydrochloric acid salt of the compound of structure (I): it was heated and vigorously mixed while still in the bulk container. The required amount of GELUCIRE® 44/14 was then charged to a heated preparation vessel, and dissolved. With overhead agitation, a pre-weighed amount of Form I of the hydrochloric acid salt of the compound of structure (I) was charged to the preparation vessel containing the GELUCIRE® 44/14 through a 35 mesh screen. This drug substance blend was stirred prior to initiation of the capsule filling process.

The drug substance blend was then used to fill white, opaque, size 00 HPMC capsules. The filled capsules were collected in LDPE bags, then manually polished with gauze wiper pads and weight sorted with an automatic SADE SP440 tablet/capsule weight sorter.

The capsules were then run through a BD3000 capsule sealing machine. In this process, HPMC material was dissolved in ethanol and sprayed in a "band" onto the filled capsules, sealing them. The sealed capsules were then run through a PHARMATRON 5.1A 68/18 metal detector. The capsules were then submitted for elegance testing.

The finished drug product was manually packaged into 120 cc HDPE bottled with 38 mm HDPE caps. Each bottle was filled with 50 capsules.

The composition of the capsules at the 120-mg dose strength is provided in Table 30. The composition of the capsule banding solution used for encapsulation is shown in Table 31.

TABLE 30

Composition of 120-mg Capsules for GMP Clinical Batches

| Material Description | Percent (%) | mg/capsule (mg) |
|---|---|---|
| Form I of the hydrochloride salt of the compound of structure (I) | 18.12 | 130.44 |
| GELUCIRE ® 44/14 | 81.88 | 589.56 |
| Total | 100.0 | 720.0 |
| Capsule Shell | HPMC Capsule, Size 00, White Opaque | |
| Capsule Sealing | Percent (%) | mg/capsule (mg) |
| Capsule banding solution | n/a | q.s. |

TABLE 31

Composition of Capsule Banding Solution, 120 mg Capsules

| Material Description | Percent (%) |
|---|---|
| Hydroxypropyl Methylcellulose | 5 |
| Ethanol | q.s. |
| Purified Water | q.s. |

Example 16

Phase 1, Open-Label, Dose-Escalation, Safety, Pharmacokinetic and Pharmacodynamic Study of Oral Hydrochloride Salt of the Compound of Structure (I) (Form 1) in Patients with Intermediate-2 or High-Risk Primary or Secondary MF This study is a Phase 1, multicenter, dose-escalation, open-label trial to assess safety, tolerability, preliminary activity, pharmacokinetics and pharmacodynamics of the compound of structure (I) in patients with intermediate-2 or high-risk MF. This study will enroll approximately 21 to 50 patients, at the discretion of the investigator. The primary objective is to evaluate the safety and tolerability, and to determine the Recommended Phase 2 Dose (RP2D) of the compound of structure (I).

Patients will receive treatment with the compound of structure (I), as single agent that will be administered orally at a starting dose of 480 mg once a day (qd) on each day during consecutive 4-week treatment cycles, with no break between cycles. The dose-escalation will be performed using a two-parameter Bayesian logistic regression model (BLRM). Due to the dynamic feature of the BLRM method, the exact number of patients cannot be determined in advance.

Patients enrolled into the study will continue treatment for up to 1 year (52 weeks) unless treatment is terminated due to progression of disease or unacceptable toxicity, withdrawal of consent, or any other reason. Treatment beyond 1 year will be considered for patients deriving clinical benefit with therapy.

Patients who have completed treatment or discontinued treatment permanently will be followed for 30 days for evaluation of safety and AE parameters. A '30-day Follow-up' visit will be conducted at the end of the 30-day safety follow-up period, and within an additional window of up to 7 days (i.e., 30+<7) days, after administration of the last dose of the compound of structure (I).

Dose escalation will be performed based on a two-parameter BLRM. The BLRM method will be applied along with escalation with overdose control (EWOC) principle to control the risk of exposing patients to toxic doses. The BLRM model will be updated once all patients enrolled in newly escalated cohorts have completed the dose-limiting toxicity (DLT) evaluation period. Based on this principle, a dose level will be considered safe if the probability of excessive toxicity, i.e., the probability of a DLT rate greater than 33%, is less than or equal to 25%. After completion of a given dose cohort, a decision will be made to either adjust the dose (de-escalate the dose, escalate the dose) or stay at the same dose for the next cohort to be tested based on a risk assessment using the BLRM method. The dose recommended using the BLRM method will serve as a guide and will be integrated with clinical assessment of the toxicity information and review of other available data to determine the actual treatment dosage.

The initial dose escalation plan includes treatment with compound of structure (I) at a starting dose of 480 mg (qd, 28-day cycle). A reduction in the starting dose to 360 mg compound of structure (I) (qd, 28-day cycle) will be recommended if the initially administered starting dose is associated with unexpected or unacceptable toxicity. Escalating doses include 720 mg, 1080 mg and 1440 mg compound of structure (I) (qd, 28-day cycle). If clinically indicated, dose levels higher than 1440 mg/day may be investigated. All available data at the end of the 4-week treatment cycles will be reviewed for each dose cohort. The decision to proceed to the next dose level will depend on results observed at the previous dose level.

The exact sample size for the dose escalation design cannot be specified in advance because of the dynamic features of BLRM. It is envisioned that the study will enroll approximately 21 to 50 patients. Five dose levels of compound of structure (I) will be tested by cohort with 1-6 DLT-evaluable patients per cohort in the dose escalation assessment. The number of DLT-evaluable patients in a specific cohort must be at least 3 if there is a DLT observed in that cohort. There will be a mandatory 1-week delay between the first 2 patients in each cohort before treatment is initiated for the second patient. Patients 2 and 3, and subsequent patients of each cohort can be enrolled and treated at the same time. The first 4 weeks on treatment will be the DLT evaluation period. Only DLTs occurring in that interval will be considered in the determination of the MTD. Once a dose is tested to be safe in alignment with BLRM, additional enrichment cohorts of that dose may be enrolled to further assess the safety, PK and anti-tumor activities at that dose. The enrichment cohorts may have approximately 10 patients per cohort. The 1-week waiting period is not required for the enrichment cohorts.

The following safety event will trigger a temporary suspension of patient enrollment to study treatment: at any time, >33% (minimum of 3 patients) of the total compound of structure (I)-treated patients experience a DLT. Based on the safety review, the Sponsor will determine whether the study may continue (with or without a protocol amendment) or if it must be terminated. An ambulatory true 12-Lead ECG recording device (e.g., Holter monitor) will be supplied to study those patients receiving compound of structure (I) monotherapy. These devices will capture and digitally record continuous ECGs. Recordings are to start approximately 1 hour prior to the first drug administration on Day 1 and drug administration on Day 29. Recordings will continue through 24 hours after these two drug administrations. Patients are to be resting for 10 minutes prior to, and 10 minutes after the designated ECG capture windows, which are to precede each PK blood draw. These intensive ECGs may not be required on Day 29 if there is no evidence of drug accumulation in response to multiple dosing (i.e., exposure is the same on D1 and D29) in prior cohorts during the 4-week assessment period. The Sponsor will provide formal communication to Investigators if this decision is made. The continuous digital ECG data will be stored electronically and uploaded by the study site to the ECG core lab. Up to 10 ECGs will be extracted from the digital recordings by the ECG core lab from the 5-minutes time window preceding PK blood draws. The investigator will also evaluate 12-Lead ECGs, including QTc (preferably QTcF), for near-real-time patient safety monitoring.

Additionally, a Phase 1, first-in-human study exploring escalating dose levels of compound of structure (I) (provided in the form of the drug product of Example 15) in patients with advanced solid tumors is ongoing. This study established a range of dose levels to be tested with a starting dose of 480 mg qd, based on the molecular weight of the free base of the compound of structure (I). Preliminary data from the first two cohorts, 480 mg qd (3 patients in Cohort 1) and 720 mg qd (3 patients in Cohort 2) within the first cycle of treatment showed no marked changes in hematological parameters including platelets, WBC counts and hemoglobin. In this limited number of patients, side effects, regardless of causality, occurring with a frequency equal to 2 or greater, were diarrhea, nausea and vomiting. The events were for the most part mild in severity (all Grade 1, except one event that was Grade 2). The study is currently enrolling Cohort 3 at a dose level of 1080 mg qd.

The instant study is being conducted in patients with intermediate-2 or high-risk primary or secondary MF, who have either been pretreated and failed (patients who are intolerant, resistant, refractory or lost response to JAK inhibitors) or who are ineligible to receive ruxolitinib or fedratinib at the discretion of the investigator.

Patients must meet all of the following inclusion criteria to be eligible:
1. Adult (aged≥18 years)
2. Confirmed pathological diagnosis of primary myelofibrosis (PMF) or post-PV-MF/post-ET-MF as per WHO diagnostic criteria, and intermediate-2 or high-risk primary or secondary MF based on the Dynamic International Prognostic Scoring System (DIPSS)
3. Previously treated with a JAKi and are intolerant, resistant, refractory or lost response to the JAKi, or are ineligible to be treated with ruxolitinib or fedratinib at the discretion of the investigator
4. Grade≥2 MF23, as confirmed by bone marrow biopsy within 12 weeks prior to Screening
5. Fulfill the following laboratory parameters:
    a. Platelet count>50×109/L, without the assistance of growth factors or platelet transfusions
    b. Absolute Neutrophil Count (ANC)≥1×109/L without the assistance of granulocyte growth factors
    c. Hemoglobin≥8 g/dL
6. Peripheral blood blast count<10%
7. Eastern Cooperative Oncology Group (ECOG) performance status≤2
8. Life expectancy≥3 months
9. Adequate renal function, as determined by clinical laboratory tests (serum creatinine<1.5× upper limit of normal (ULN), and calculated creatinine clearance≥60 mL/min) (Cockcroft-Gault)
10. Adequate hepatic function (ALT/AST<2.5×ULN, bilirubin<1.5×ULN), and coagulation ([PT and PTT]<1.5× ULN)
11. Agree to provide 3 bone marrow biopsies during the study: at baseline or within 12 weeks prior to enrollment, and every 6 months post-treatment.
12. Capable of providing signed informed consent, which includes compliance with the requirements and restrictions listed in the informed consent form (ICF) and in this protocol
13. Non-fertile or agree to use an adequate method of contraception while on study and for 6 months following the study, and have a negative pregnancy test (if female of childbearing potential) and not currently nursing; males agree to use an adequate method of contraception while on study and for 3 months following the study
14. Splenomegaly during the screening period as demonstrated by splenic length≥5 cm by palpation or spleen volume of ≥450 cm3 by Magnetic Resonance Imaging (MRI) or Computerized Tomography (CT) scan
15. Show at least 2 symptoms measurable (score≥1) using the MFSAF, v4.0.
16. Able to take orally administered medication Patients meeting any one of these exclusion criteria will be prohibited from participating in this study:
1. Received previous systemic antineoplastic therapy (including unconjugated therapeutic antibodies, toxin immunoconjugates, and alpha-interferon) or any experimental therapy within 14 days or 5 half-lives, whichever is shorter, before the first dose of study treatment.
2. Major surgery within 2 weeks before the first dose of either study drug.
3. Splenic irradiation within 6 months prior to Screening or prior splenectomy.
4. AML, MDS, or peripheral blasts≥10%.
5. Prior autologous or allogeneic stem cell transplant at any time.
6. Eligible for allogeneic bone marrow or stem cell transplantation.
7. Currently receiving treatment with a prohibited medication that cannot be discontinued at least one week prior to the start of treatment.
8. Experiencing electrolyte abnormalities of NCI CTCAE Grade21≥2 (eg, serum potassium, magnesium and calcium) unless they can be corrected during screening and are deemed not clinically significant by the Investigator.
9. History of congestive heart failure, myocardial infarction within the past 6 months prior to Cycle 1/Day 1; left ventricular ejection fraction<45% by echocardiogram or MUGA, unstable arrhythmia, or evidence of ischemia on electrocardiogram (ECG) within 14 days prior to Cycle 1/Day 1.
10. Corrected QT interval (using Fridericia's correction formula) of >450 msec in men and >470 msec in women.
11. Central nervous system (CNS) cancer or metastases, meningeal carcinomatosis, malignant seizures, or a disease that either causes or threatens neurologic compromise (e.g., unstable vertebral metastases).
12. Other invasive malignancies within the last 3 years, except non-melanoma skin cancer, and localized cured prostate and cervical cancer.
13. Experienced portal hypertension or any of its complications.
14. Active, uncontrolled bacterial, viral, or fungal infections, requiring systemic therapy.
15. Known bleeding diathesis or signs of uncontrolled active bleeding (hematuria, GI bleeding) other than self-limited causes of benign etiology that have been adequately investigated at the discretion of the Investigator.
16. Requiring anticoagulation with aspirin>81 mg daily, unfractionated heparin, low molecular weight heparin (LMWH), direct anti-thrombin inhibitors, or vitamin K antagonists (e.g., warfarin).
17. Severe chronic obstructive pulmonary disease with hypoxemia (defined as resting 02 saturation of <90% breathing room air).

18. Unwilling or unable to comply with procedures required in this protocol
19. Known infection with human immunodeficiency virus, hepatitis B, or hepatitis C. Patients with history of chronic hepatitis that is currently not active are eligible.
20. Serious nonmalignant disease (e.g., hydronephrosis, liver failure, or other conditions) that could compromise protocol objectives in the opinion of the Investigator and/or the Sponsor.
21. Currently receiving any other investigational agent.
22. Exhibited allergic reactions to a similar structural compound, biological agent, or formulation.
23. Medical condition or have undergone significant surgery to the gastrointestinal tract that could impair absorption or that could result in short bowel syndrome with diarrhea due to malabsorption.

Patients enrolled in the study will be administered the drug product described in Example 15 orally, once daily in the fasting state, during each of the consecutive 4-week treatment cycles, with no breaks between cycles. The dose administered will vary depending on the dose escalation scheme and the cohort into which the patient is enrolled. The starting dose of oral compound of structure (I) will be 480 mg qd, based on the molecular weight of the free base of the compound of structure (I), and dosing will be escalated according to the BLRM; intermediate doses of compound of structure (I) may be investigated if deemed appropriate, based on review of data from each cohort.

Dosing is planned for once daily. However, compound of structure (I) capsules are very large (size 00) and it may be difficult for the patient to take all capsules at one time. Therefore, after Dose Level 2, dosing over a 1-hour period (with an even number of capsules taken every 15 minutes) will be allowed, if needed for patient comfort and tolerance.

Study drug will be taken in the morning after an overnight fast (at least 6 hours) with water, and at least 1 hour before ingesting any food or other medications. In the event a patient vomits within 30 minutes after taking the medication, he/she should not attempt to retake the dose but rather note the dose as being missed in their Dosing Diary and continue with regular dosing on the next day.

If a lower dose is recommended by the BLRM method and confirmed by the SRC, then enrollment into the next lower dose level may be initiated, and additional cohorts may be opened to enroll patients into a previously tested safe dose level to facilitate the evaluation of the dose-toxicity relationship. Dose escalation will continue until identification of the MTD or a suitable dose for the recommended phase 2 dose (the RP2D). This will occur when the following conditions are met: (1) at least 6 patients have been treated at the dose; (2) this dose satisfies one of the following conditions:
  (a) The posterior probability of targeted toxicity at this dose exceeds 50% and is the highest among potential doses, or
  (b) A minimum of 21 patients have already been treated in the Dose Escalation part of this trial; and
(3) it is the dose recommended for patients, either per the model or by review of all available clinical data in the SRC meeting.

To further assess the safety, PK and anticancer activities, approximately 10 patients may be enrolled in enrichment cohorts.

Intra-patient dose escalation for inadequate efficacy is optional if, in the expert opinion of the Investigator, less than adequate improvement (i.e., inadequate spleen reduction, inadequate symptoms improvements) has been observed. Intra-patient dose escalation is not allowed at any time within the first three cycles of treatment. After the third cycle is completed, individual patients may be considered for treatment at a dose of compound of structure (I) higher than the dose to which they were initially assigned. In order for a patient to be treated at a higher dose of compound of structure (I), the patient must have tolerated the lower dose (i.e., he or she must not have experienced any compound of structure (I)-related toxicity CTCAE grade≥2 at the lower dose originally assigned) for at least 2 cycles of therapy. Moreover, the new, higher dose with which the patient is to be treated must be a dose that has completed evaluation and has not exceeded the MTD. There is no limit to the number of times a patient may have their dose of compound of structure (I) increased. For any further increase after the initial intra-patient dose escalation, the following rules apply: the patient must have experienced no CTCAE grade≥2, compound of structure (I)-related toxicity over at least the last two cycles of therapy at the lower dose, and the higher dose being considered must have been fully evaluated and shown not to exceed the MTD. Consultation and agreement with Sponsor must occur prior to any intra-patient dose escalation occurring. The intra-patient dose escalation must be recorded on the Dosage Administration Record (DAR) Electronic Case Report Form (eCRF). Data from the first cycle of treatment at the new dose level will not be formally included into the BLRM model describing the relationship between dose and occurrence of DLT. However, this data will be incorporated into the clinical assessment of safety within a dose escalation teleconference.

The RP2D is usually the highest dose with acceptable toxicity, generally defined as the dose level producing a DLT rate of approximately 16% to 33%. Determination of the RP2D will include an evaluation of the efficacy and safety by dose and exposure analysis, an integrated dose-response and exposure-response analysis by pooling available non-clinical, pharmacokinetic, pharmacodynamic, efficacy, and safety data.

All dose modifications will need to be discussed and approved by the Medical Monitor. Dose reduction to the next lower dose level tested will be allowed. If further toxicities occur during one or more cycles at the new reduced dose level, no further reductions will be permitted, and the patient should be discontinued from the study.

Based on DLT assessments during the initial 4-week evaluation period (Cycle 1) following administration of the first dose of compound of structure (I), dose reduction in Cycle 2 and beyond will be required for patients who have a delay in treatment≥1 week due to a lack of recovery of any hematologic or nonhematologic toxicity. Subsequent retreatment of patients who are unable to be treated after a ≥2-week delay or those who experience Grade 4 thrombocytopenia and eventually recover will be discussed between Investigators and Medical Monitor, taking into account the potential benefit/risk for the individual patient. In addition, dose reductions may be permitted for patients who have toxicities that do not meet the criteria of a DLT if, following discussion between the Investigator and the Medical Monitor, it is determined to be in the best interest of the patient to continue to receive compound of structure (I) at the previous dose level. Table 32 is a guide to dose adjustments based on the severity (e.g., grade) of treatment emergent adverse events (AEs).

TABLE 32

Guide to Dose Adjustments.

| AE Severity | Course of Treatment Action |
|---|---|
| Grade 1 | Continue treatment at current does level |
| Grade 2 | Reduce dose by 1 dose level with agreement from the Investigator and Medical Monitor |
| Grade 3[a] | Withhold treatment, then reduce dose by 1 dose level upon recovery of AE to ≤ Grade 1 with agreement of the Medical Monitor |
| Grade 4[b] | Discontinue treatment[c] |

[a]Excluding brief (<72 hours) Grade 3 vomiting or diarrhea with suboptimal management
[b]Treatment will be discontinued for all patients experiencing a Grade 4 AE regardless of relatioirship to TP-3654
Abbreviations: AE = adverse event
[c]For patients who experience Grade 4 thrombocytopenia or neutropenia that do not meet DLT criteria and eventually recover to ≤ Grade 2, treatment continuation with dose reduction will be discussed between the Investigator and Medical Monitor, taking into account the potential benefit/risk for the imilvidual patient. However, if these patients experience recurrence of Grade 4 toxicity, no subsequent treatment will be permitted, even after the toxicity resolves.

Investigator and Medical Monitor determine that it is in the best interest of the patient to continue with dose reduction and only upon recovery of the toxicity to baseline or ≤Grade 1. Patients who experience a DLT suggestive of possible drug-induced liver injury (i.e., liver function test abnormalities meeting Hy's Law criteria) must be permanently discontinued from the study per the FDA Guidance on Drug-induced Liver Injury 2009.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

What is claimed is:

1. A crystalline form of the hydrochloric acid salt of a compound having the following structure (I):

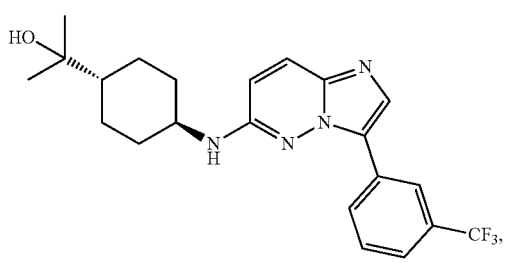

(I)

characterized by an X-ray powder diffraction pattern comprising peaks, in terms of 2-theta, at 21.5±0.2°, 19.9±0.2°, and 17.8±0.2°.

2. The crystalline form of claim 1, further characterized by an X-ray powder diffraction pattern comprising a peak, in terms of 2-theta, at 19.3±0.2°.

3. The crystalline form of claim 2, further characterized by an X-ray powder diffraction pattern comprising a peak, in terms of 2-theta, at 24.4±0.2°.

4. The crystalline form of claim 3, further characterized by an X-ray powder diffraction pattern comprising a peak, in terms of 2-theta, at 16.3±0.2°.

5. The crystalline form of claim 1, characterized by an X-ray powder diffraction pattern comprising at least three peaks at 2-theta angles selected from the group consisting of 24.4±0.2°, 21.5±0.2°, 19.9±0.2°, 19.3±0.2°, 17.8±0.2° and 16.3±0.2°.

6. The crystalline form of claim 5, further characterized by an X-ray powder diffraction pattern substantially lacking a peak, in terms of 2-theta, at 15.7±0.2°.

7. The crystalline form of claim 6, further characterized by an X-ray powder diffraction pattern substantially lacking a peak, in terms of 2-theta, at 17.0±0.2°.

8. The crystalline form of claim 7, further characterized by an X-ray powder diffraction pattern substantially lacking a peak, in terms of 2-theta, at 19.0±0.2°.

9. The crystalline form of claim 1, which is Form I having an X-ray powder diffraction pattern substantially in accordance with that shown in FIG. 1.

10. The crystalline form of claim 1, which is Form I having a differential scanning calorimetry thermogram substantially in accordance with that shown in FIG. 2.

11. The crystalline form of claim 1, which is Form I having a thermogravimetric analysis diagram substantially in accordance with that shown in FIG. 3.

12. The crystalline form of claim 1, which is Form I having a melting temperature of 226±3° C.

13. The crystalline form of claim 1, wherein the crystalline form is substantially pure.

14. A composition comprising the crystalline form of 1, and a pharmaceutically acceptable carrier.

15. A composition comprising:
a polyglycolized glyceride; and
a compound having the following structure (I):

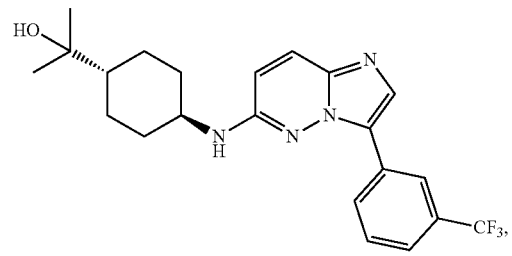

(I)

or a pharmaceutically acceptable salt thereof.

16. The composition of claim 15, wherein the polyglycolized glyceride has a melting point ranging from about 30° C. to about 50° C.

17. The composition of claim 15, wherein the polyglycolized glyceride has a hydrophile/lipophile balance (HLB) value ranging from about 8 to about 18.

18. The composition of claim 15, wherein the polyglycolized glyceride comprises lauroyl polyoxy-32 glycerides.

19. The composition of claim 15, wherein the composition comprises the compound of structure (I), or a pharmaceutically acceptable salt thereof, in a concentration ranging from about 10 weight percent (wt %) to about 40 wt %, as determined using the molecular weight of the compound of structure (I) as a hydrochloride salt.

20. The composition of claim 15, wherein the composition comprises the polyglycolized glyceride in a concentration ranging from about 50 wt % to about 90 wt %.

21. The composition of claim 15, wherein the composition comprises the compound of structure (I), or a pharmaceutically acceptable salt thereof, and the polyglycolized glyceride at a weight ratio ranging from about 1:1 to about 1:10, as determined using the molecular weight of the compound of structure (I) as a free base.

22. A unit dose form comprising the composition of claim 15 in a therapeutically effective amount.

23. A unit dose form comprising a composition, the composition comprising:

a polyglycolized glyceride in an amount of about 560 mg to about 600 mg; and a compound having the following structure (I):

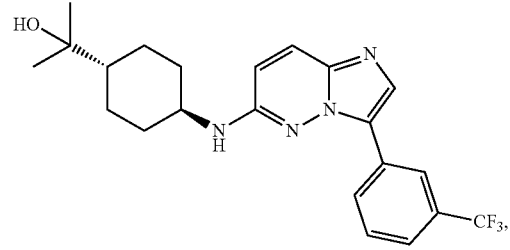

(I)

or a pharmaceutically acceptable salt thereof, in an amount of about 115 mg to about 125 mg, as determined using the molecular weight of the compound of structure (I) as a free base.

* * * * *